US008389802B2

(12) United States Patent
Hadlaczky et al.

(10) Patent No.: US 8,389,802 B2
(45) Date of Patent: Mar. 5, 2013

(54) ARTIFICIAL CHROMOSOMES, USES THEREOF AND METHODS FOR PREPARING ARTIFICIAL CHROMOSOMES

(75) Inventors: Gyula Hadlaczky, Szamos (HU); Aladar A. Szalay, Highland, CA (US)

(73) Assignees: The Biological Research Center of the Hungarian Academy of Sciences (HU); Glaxo Group Limited (GB)

( * ) Notice: Subject to any disclaimer, the term of this patent is extended or adjusted under 35 U.S.C. 154(b) by 147 days.

(21) Appl. No.: 11/284,877

(22) Filed: Nov. 21, 2005

(65) Prior Publication Data

US 2006/0095984 A1 May 4, 2006

Related U.S. Application Data

(60) Continuation of application No. 10/125,767, filed on Apr. 17, 2002, now abandoned, which is a division of application No. 09/724,693, filed on Nov. 28, 2000, now abandoned, which is a continuation of application No. 08/835,682, filed on Apr. 10, 1997, (Continued)

(51) Int. Cl.
*C12N 15/82* (2006.01)
*C12N 15/00* (2006.01)
*C12N 15/10* (2006.01)

(52) U.S. Cl. ..................... 800/278; 435/320.1; 435/468; 536/23.1

(58) Field of Classification Search ........................ None
See application file for complete search history.

(56) References Cited

U.S. PATENT DOCUMENTS

| | | | | |
|---|---|---|---|---|
| 4,441,972 | A | 4/1984 | Pohl et al. | 435/450 |
| 4,476,004 | A | 10/1984 | Pohl et al. | |
| 4,518,584 | A | 5/1985 | Mark et al. | |
| 4,608,339 | A | 8/1986 | Yoakum et al. | 435/6 |
| 4,656,134 | A | 4/1987 | Ringold et al. | 435/91 |
| 4,684,611 | A | 8/1987 | Schilperoort et al. | 435/468 |
| 4,686,186 | A | 8/1987 | Sugden | 435/243 |
| 4,736,866 | A | 4/1988 | Leder et al. | 800/10 |
| 4,784,737 | A | 11/1988 | Ray et al. | 435/455 |
| 4,801,540 | A | 1/1989 | Hiatt et al. | 435/172.3 |
| 4,806,476 | A | 2/1989 | Coons et al. | 435/451 |
| 4,873,191 | A | 10/1989 | Wagner et al. | 800/25 |
| 4,873,316 | A | 10/1989 | Meade et al. | 800/7 |
| 4,906,576 | A | 3/1990 | Marshall et al. | |
| 4,923,814 | A | 5/1990 | Marshall et al. | |
| 4,935,350 | A | 6/1990 | Patel et al. | |
| 4,946,952 | A | 8/1990 | Kiefer et al. | |
| 4,955,378 | A | 9/1990 | Grasso et al. | 607/53 |
| 4,970,162 | A | 11/1990 | Aksamit et al. | 435/346 |
| 4,997,764 | A | 3/1991 | Favera et al. | |
| 5,019,034 | A | 5/1991 | Weaver et al. | 604/20 |
| 5,021,344 | A | 6/1991 | Armau et al. | 435/473 |
| 5,063,162 | A | 11/1991 | Kiefer et al. | 435/270 |
| 5,081,018 | A | 1/1992 | Grummt et al. | |
| 5,118,620 | A | 6/1992 | Armau et al. | 435/6 |
| 5,144,019 | A | 9/1992 | Rossi et al. | |
| 5,149,796 | A | 9/1992 | Rossi et al. | |
| 5,162,215 | A | 11/1992 | Bosselman et al. | 800/23 |
| 5,215,914 | A | 6/1993 | Lo et al. | |
| 5,223,263 | A | 6/1993 | Hostetler et al. | 424/450 |
| 5,240,840 | A | 8/1993 | Feinberg et al. | 435/6 |
| 5,240,846 | A | 8/1993 | Collins et al. | 435/371 |
| 5,260,191 | A | 11/1993 | Yang et al. | 435/6 |
| 5,266,600 | A | 11/1993 | Tenmyo et al. | 514/691 |
| 5,270,201 | A * | 12/1993 | Richards et al. | 435/418 |
| 5,272,262 | A | 12/1993 | Rossi et al. | |
| 5,288,625 | A | 2/1994 | Hadlaczky et al. | 435/449 |
| 5,292,658 | A | 3/1994 | Cormier et al. | |
| 5,298,429 | A | 3/1994 | Evans et al. | 436/501 |
| 5,300,431 | A | 4/1994 | Pierce et al. | 435/6 |
| 5,324,655 | A | 6/1994 | Kriegler et al. | 435/357 |
| 5,354,674 | A | 10/1994 | Hodgson et al. | 435/6 |
| 5,358,866 | A | 10/1994 | Mullen et al. | 435/735 |
| 5,364,761 | A | 11/1994 | Ariga et al. | 435/6 |
| 5,387,742 | A | 2/1995 | Cordell et al. | 800/12 |
| 5,396,767 | A | 3/1995 | Suzuki et al. | 602/98 |
| 5,409,810 | A | 4/1995 | Larder et al. | 435/5 |
| 5,413,914 | A | 5/1995 | Franzusoff et al. | 435/23 |
| 5,418,155 | A | 5/1995 | Cormier et al. | 435/189 |
| 5,424,409 | A | 6/1995 | Ely et al. | |
| 5,434,086 | A | 7/1995 | Collins et al. | 436/125 |
| 5,434,340 | A | 7/1995 | Krimpenfort et al. | 800/11 |
| 5,436,392 | A | 7/1995 | Thomas et al. | 800/279 |
| 5,449,604 | A | 9/1995 | Schellenberg et al. | 435/6 |
| 5,453,357 | A | 9/1995 | Hogan et al. | |
| 5,457,182 | A | 10/1995 | Wiederrecht et al. | 530/402 |
| 5,461,032 | A | 10/1995 | Krapcho et al. | 514/12 |
| 5,468,615 | A | 11/1995 | Chio et al. | 435/72 |
| 5,468,634 | A | 11/1995 | Liu et al. | 435/348 |
| 5,470,708 | A | 11/1995 | Yang et al. | 435/6 |

(Continued)

FOREIGN PATENT DOCUMENTS

| | | |
|---|---|---|
| EP | 116718 | 8/1984 |
| EP | 0208491 | 1/1987 |

(Continued)

OTHER PUBLICATIONS

Borisjuk et al 2000 Nature Biotechnology 18:1303-1306.*
Donald et al 1997 Genome 40:674-681.*
Assaad et al 1992 Genetics 132:553-566.*
Yu et al 2007 Current Opinion in Biotechnology 18:425-431.*
Phan et al 2007 Transgenic Research 16:341-351.*
McClintock 1932 PNAS 18:677-681.*
"Guide to Techniques in Mouse Development", Methods in Enzymology 225:803-932 (1993).
"Transfection of DNA into eukaryotic cells", Current Protocols in Molecular Biology, vol. 1, Wiley Inter-Science, Supplement 14, Unit 9.1.1-9.1.9 (1990).
"Why are MACs in vogue", Chromos Molecular Systems—News Release (May 29, 1996), (available at http://www.chromos.com/contents.html).

(Continued)

*Primary Examiner* — Brent T Page
(74) *Attorney, Agent, or Firm* — McKenna Long & Aldridge LLP; Stephanie Seidman

(57) ABSTRACT

Methods for amplification of nucleic acids in cells are provided. Also provided are cells that contain the nucleic acids.

11 Claims, 5 Drawing Sheets

Related U.S. Application Data now abandoned, which is a continuation-in-part of application No. 08/695,191, filed on Aug. 7, 1996, now Pat. No. 6,025,155, which is a continuation-in-part of application No. 08/682,080, filed on Jul. 15, 1996, now Pat. No. 6,077,697, which is a continuation-in-part of application No. 08/629,822, filed on Apr. 10, 1996, now abandoned, application No. 11/284,877, which is a continuation of application No. 10/151,081, filed on May 16, 2002, now abandoned, which is a division of application No. 09/799,462, filed on Mar. 5, 2001, now abandoned, which is a continuation of application No. 08/835,682, which is a continuation-in-part of application No. 08/695,191, which is a continuation-in-part of application No. 08/682,080, which is a continuation-in-part of application No. 08/629,822, application No. 11/284,877, which is a continuation of application No. 09/799,462, which is a continuation of application No. 08/835,682, which is a continuation-in-part of application No. 08/695,191, which is a continuation-in-part of application No. 08/682,080, which is a continuation-in-part of application No. 08/629,822, application No. 11/284,877, which is a continuation of application No. 10/151,078, filed on May 16, 2002, which is a division of application No. 09/724,872, filed on Nov. 28, 2000, now abandoned, which is a continuation of application No. 08/835,682, which is a continuation-in-part of application No. 08/695,191, which is a continuation-in-part of application No. 08/682,080, which is a continuation-in-part of application No. 08/629,822, application No. 11/284,877, which is a continuation of application No. 10/287,313, filed on Nov. 1, 2002, now abandoned, which is a division of application No. 09/724,726, filed on Nov. 28, 2000, now abandoned, which is a division of application No. 08/835,682, which is a continuation-in-part of application No. 08/695,191, which is a continuation-in-part of application No. 08/682,080, which is a continuation-in-part of application No. 08/629,822, application No. 11/284,877, which is a continuation of application No. 10/808,689, filed on Mar. 24, 2004, now abandoned, which is a division of application No. 09/724,693, which is a continuation of application No. 08/835,682, which is a continuation-in-part of application No. 08/695,191, which is a continuation-in-part of application No. 08/682,080, which is a continuation-in-part of application No. 08/629,822, application No. 11/284,877, which is a continuation of application No. 10/219,694, filed on Aug. 14, 2002, now abandoned, which is a division of application No. 09/724,693, which is a continuation of application No. 08/835,682, which is a continuation-in-part of application No. 08/695,191, which is a continuation-in-part of application No. 08/682,080, which is a continuation-in-part of application No. 08/629,822.

U.S. PATENT DOCUMENTS

| | | | | |
|---|---|---|---|---|
| 5,470,730 | A | 11/1995 | Greenberg et al. | 435/456 |
| 5,482,928 | A | 1/1996 | De Bolle et al. | 514/12 |
| 5,489,520 | A | 2/1996 | Adams et al. | 800/293 |
| 5,491,075 | A | 2/1996 | Desnick et al. | 435/697 |
| 5,491,283 | A | 2/1996 | Groffen et al. | 800/10 |
| 5,496,731 | A | 3/1996 | Xu et al. | |
| 5,501,662 | A | 3/1996 | Hofmann et al. | 604/20 |
| 5,501,967 | A | 3/1996 | Offringa et al. | 435/469 |
| 5,503,999 | A | 4/1996 | Jilka et al. | 800/279 |
| 5,543,319 | A | 8/1996 | Fournier et al. | 435/349 |
| 5,695,967 | A | 12/1997 | Van Bokkelen et al. | 435/91.1 |
| 5,712,134 | A | 1/1998 | Hadlaczky et al. | 435/465 |
| 5,721,118 | A | 2/1998 | Scheffler et al. | |
| 5,721,367 | A | 2/1998 | Kay et al. | 800/18 |
| 5,869,294 | A | 2/1999 | Harrington et al. | 435/91.1 |
| 5,891,691 | A | 4/1999 | Hadlaczky | 435/465 |
| 6,025,155 | A | 2/2000 | Hadlaczky et al. | |
| 6,077,697 | A | 6/2000 | Hadlaczky et al. | 435/6 |
| 6,100,092 | A | 8/2000 | Borysyuk et al. | 435/468 |
| 6,133,503 | A | 10/2000 | Scheffler et al. | 800/21 |
| 6,156,953 | A | 12/2000 | Preuss et al. | 800/278 |
| 6,346,414 | B1 | 2/2002 | Jacobs | 435/320.1 |
| 6,355,860 | B1 | 3/2002 | Borysyuk et al. | 800/278 |
| 6,743,967 | B2 | 6/2004 | Hadlaczky et al. | 800/25 |
| 6,936,469 | B2 | 8/2005 | deJong et al. | 435/458 |
| 7,247,768 | B1 | 7/2007 | Klimyuk et al. | 800/278 |
| 7,521,240 | B2 | 4/2009 | Perkins et al. | 435/462 |
| 2001/0008025 | A1 | 7/2001 | Hadlaczky et al. | 800/8 |
| 2002/0160410 | A1 | 10/2002 | Hadlaczky et al. | 435/6 |
| 2002/0160970 | A1 | 10/2002 | Hadlaczky et al. | 514/44 |
| 2003/0033617 | A1 | 2/2003 | Hadlaczky et al. | |
| 2003/0059940 | A1 | 3/2003 | De Jong et al. | 435/455 |
| 2003/0083293 | A1 | 5/2003 | Hadlaczky et al. | 514/44 |
| 2003/0101480 | A1 | 5/2003 | Hadlaczky et al. | 800/278 |
| 2003/0108914 | A1 | 6/2003 | Hadlaczky et al. | 435/6 |
| 2003/0113917 | A1 | 6/2003 | De Jong et al. | 435/455 |
| 2003/0119104 | A1 | 6/2003 | Perkins et al. | 435/691 |
| 2003/0186390 | A1 | 10/2003 | De Jong et al. | 435/911 |
| 2003/0224522 | A1 | 12/2003 | De Jong et al. | 435/458 |
| 2004/0143861 | A1 | 7/2004 | Hadlaczky et al. | 800/14 |
| 2004/0163147 | A1 | 8/2004 | Hadlaczky et al. | 800/284 |
| 2004/0214290 | A1 | 10/2004 | Perez et al. | 435/911 |
| 2005/0112661 | A1 | 5/2005 | De Jong et al. | 435/6 |
| 2005/0153909 | A1 | 7/2005 | Hadlaczky et al. | 514/44 |
| 2005/0181506 | A1 | 8/2005 | Perkins et al. | 435/455 |
| 2005/0287647 | A9 | 12/2005 | Perez et al. | 435/91.1 |
| 2006/0024820 | A1 | 2/2006 | Perkins et al. | 435/320.1 |
| 2006/0095984 | A1 | 5/2006 | Hadlaczky et al. | 800/278 |
| 2006/0143732 | A1 | 6/2006 | Perez et al. | 800/278 |
| 2006/0150271 | A1 | 7/2006 | Hadlaczky et al. | 800/278 |
| 2006/0194754 | A1 | 8/2006 | deJong et al. | 514/44 |
| 2006/0246586 | A1 | 11/2006 | Perkins et al. | 435/455 |
| 2007/0061920 | A1 | 3/2007 | Hadlaczky et al. | 800/279 |
| 2009/0263898 | A1 | 10/2009 | Hadlaczky et al. | 435/419 |
| 2010/0184128 | A1 | 7/2010 | Ainley et al. | 435/41 |
| 2010/0186117 | A1 | 7/2010 | Fabijanski et al. | 800/281 |
| 2010/0221720 | A1 | 9/2010 | Perez et al. | 435/6 |

FOREIGN PATENT DOCUMENTS

| | | |
|---|---|---|
| EP | 0240373 | 10/1987 |
| EP | 249432 | 12/1987 |
| EP | 0254315 | 1/1988 |
| EP | 0264166 | 4/1988 |
| EP | 0279582 | 8/1988 |
| EP | 0338266 | 10/1989 |
| EP | 0350052 | 1/1990 |
| EP | 0375406 | 6/1990 |
| EP | 0473253 | 3/1992 |
| EP | 0532050 | 9/1992 |
| EP | 0247494 | 12/1997 |
| EP | 0838526 | 4/1998 |
| JP | 3456715 | 7/1995 |
| JP | 1999-507540 | 6/1999 |
| JP | 7-177881 | 4/2000 |
| JP | 2000-508177 | 4/2000 |
| JP | 3-503599 | 2/2002 |
| JP | 2003-102498 | 8/2003 |
| JP | A-2005-500827 | 1/2005 |
| WO | 82/04443 | 12/1982 |
| WO | 88/00239 | 1/1988 |
| WO | 88/01648 | 3/1988 |
| WO | 89/09219 | 10/1989 |
| WO | 91/00358 | 1/1991 |
| WO | 91/05044 | 4/1991 |
| WO | 92/07080 | 4/1992 |
| WO | 92/14819 | 9/1992 |
| WO | 92/17582 | 10/1992 |
| WO | 93/25567 | 12/1993 |

| | | |
|---|---|---|
| WO | 94/19456 | 9/1994 |
| WO | 94/23049 | 10/1994 |
| WO | 94/24300 | 10/1994 |
| WO | 95/00178 | 1/1995 |
| WO | 95/07643 | 3/1995 |
| WO | 95/14769 | 6/1995 |
| WO | 95/20044 | 7/1995 |
| WO | 95/22297 | 11/1995 |
| WO | 95/29992 | 11/1995 |
| WO | 95/32297 | 11/1995 |
| WO | 96/40965 | 12/1996 |
| WO | 97/07668 | 3/1997 |
| WO | 97/07669 | 3/1997 |
| WO | 97/16533 | 5/1997 |
| WO | 97/40183 | 10/1997 |
| WO | 98/08964 | 3/1998 |
| WO | 98/13505 | 4/1998 |
| WO | 98/55637 | 12/1998 |
| WO | WO 01/00858 | 1/2001 |
| WO | WO 01/07572 | 2/2001 |
| WO | WO 01/11020 | 2/2001 |
| WO | WO 02/076508 | 10/2002 |
| WO | 2002/096923 | 12/2002 |
| WO | 2002/097059 | 12/2002 |
| WO | WO 02/096923 | 12/2002 |
| WO | WO 02/097059 | 12/2002 |
| WO | 2003/093469 | 11/2003 |
| WO | WO 03/093469 | 11/2003 |
| WO | 2010/037208 | 4/2010 |
| WO | WO 2010/037209 | 4/2010 |

OTHER PUBLICATIONS

Albrecht, et al., "Cationic lipide mediated transfer of c-abl and bcr antisense oligonucleotides to immature normal myeloid cells: Uptake, biological effects and modulation of gene expression*", Ann Hematol 72:73-7, (1996).
Adam, et al., "Retrofitting YACs for direct DNA transfer into plant cells," Plant J. Jun;11(6):1349-58 (1997).
Ascenzioni, et al., "Mammalian artificial chromosomes-vectors for somatic gene therapy," Cancer Lett.; I18(2):135-42 (1997).
Avramova, "Heterochromatin in Animals and Plants", Plant Physiology 129:40-49 (2000).
Baker, et al., "Suppression of human colorectal carcinoma cell growth by wild-type p53", Science 249:912-915 (1990).
Barrett et al., "Telomere directed fragmentation of mammalian chromosomes," Nucleic Acids Res. 21 (1): 27-36 (1993).
Bartholdi, et al., "Chromosome sorting by flow cytometry," Meth. Enzy., 151:253-267, (1987).
Beck von Rodman, et al., "Expression of multiple eukaryotic cells from a single promoter," in Nicotina, Bio/Technology 13:587-591, (1995).
Berlani et al., "Genomic organization of two families of highly repeated nuclear DNA sequences of maize selected for autonomous replicating activity in yeast", Plant Molecular Biol., 11: 161-172 (1988).
Berlani et al., "Sequence analysis of three fragments of maize nuclear DNA which II replicate autonomously in yeast", Plant Molecular Biol., 11: 173-182 (1988).
Biggin, et al., "Buffer gradient gels and $^{35}$S label as an aid to rapid DNA sequence determination", Proc. Natl. Acad. Sci. USA, 80:3963-3965. (1983).
Blackburn et al., BOOK: Telomeres, Chapter 13, "Plant Telomeres", Cold Spring Harbor Laboratory Press, pp. 371-387 (1995).
Blackburn, et al., "The molecular structure of centromeres and telomeres", Ann. Rev. Biochem., 53:163-194 (1984).
Blattner, et al., "Charon phages: Safer derivatives of bacteriophage lambda for DNA cloning", Science 196:16 (1977).
Blennow, et al., Swedish survey on extra structurally abnormal chromosomes in 39 105 consecutive prenatal diagnoses: Prevalence and characterization by fluorescence in situ hybridization, Prenatal Diagnosis, 14:1019-1028, (1994).
Blumenthal, et al., "Rapid isolation of metaphase chromosome containing high molecular weight DNA," J. Cell Biol., 81:255-259 (1979).
Borisjuk, N.V. et al., "Structural analysis of rDNA in the genus*Nicotiana*," Plant Mol. Biol., 35:655-660 (1997).
Bostock and Christie, "Analysis of the frequency of sister chromatid exchange in different regions of chromosomes of the Kangaroo rat," (*Dipodomys ordii*), Chrornosoma 56: 275-287 (1976).
Bostock and Clark, "Satellite DNA in large marker chromosomes of methotrexate-resistant mouse cells", Cell 19:709-715 (1980).
Bower, "Constructing a fully defined human minichromosome: Cloning a centromere", Proc. 4th Eur. Congress Biotechnol. 3:571, (1987).
Brazolot, et al., "Efficient transfection of chicken cells by lipofection and introduction of transfected blastoderm cells into the embryo", Mol. Repro. Dev. 30:304-312 (1993).
Brewer and Fangman, "The localization of replication origins on ARS plasmids", in *S. cerevisiae*, Cell 51:463-471 (1987).
Brinster et al., "Factors affecting the efficiency of introducing foreign DNA into mice by microinjecting eggs," Proc. Natl. Acad. Sci. USA 82:4438-4442 (1985).
Brisson and Hohn, "[27] Plant virus vectors: Cauliflower mosaic vectors", Methods for Plant Molecular Biology, Weissbach et al., eds., Academic Press, N. Y., Section VIII, pp. 437-446, (1988).
Brondum-Nielsen and Mikkelsen, "A 10-year survey, 1980-1990, of prenatally diagnosed small supernumerary marker chromosomes, indentified by fish analysis. Outcome and follow-up of 14 cases diagnosed in a series of 12 699 prenatal samples," Prenatal Diagnosis, 15:615-619 (1995).
Brown et al., "Artificial chromosomes: ideal vectors?" Tibtech 18:218-223 (May 2000).
Brown et al., "Mammalian artificial chromosomes," Current Opinion: Genetics and Devt. 6: 281-288 (1996).
Brown, "Mammalian artificial chromosomes", Curr. Opin. Genes Dev. 2:479-486, (1992).
Bühler et al., "Rabbit β-Casein Promoter Directs Secretion of Human Interleukin-2 into the Milk of Transgenic Rabbits," Bio/Technology 8:140-143 (1990).
Bullock and Botchan, "Molecular events in the excision of SV40 DNA from the chromosomes of cultured mammalian cells," In: Gene Amplification., Schimke RT, ed. Cold Spring Harbor, NY: Cold Spring Harbor Laboratory Press, pp. 215-224, (1982).
Burhans and Huberman, "DNA replication origins in animal cells—a question of context?" Science 263: 639-640 (1994).
Burhans et al., "Identification of an origin of bidirectional DNA replication in mammalian chromosomes", Cell 62:955-965, (1990).
Burke, et al., "Cloning of large segments of exogenous DNA into yeast by means of artificial chromosome vectors", Science, 236:806-812, (1987).
Burki, et al., "Zonal fractionation of mammalian metaphase chromosomes and determination of their DNA content," Prep. Bioch., 3(2):157-182, (1973).
Calos, M.P., "The Potential of Extrachromosomal Replicating Vectors for Gene Therapy," TIG 12(11):463-466 (1996).
Carine, et al., "Chinese hamster cells with a minichromosome containing centromere region of human chromosome 1", Somatic Cell Molec. Genet. 12:479-491, (1986).
Carine, et al., "Molecular characterization of human minichromosomes with centromere from chromosome 1 in hamster-human hybrids", Somatic Cell Molec. Genet. 15(5):445-460, (1989).
Carrano and Wolff, "Distribution of sister chromatid exchanges in the euchromatin and heterochromatin of the Indian muntjac", Chromosoma 53:361-369, (1975).
Carrano, et al., "Measurement and purification of human chromsomes by flow cytometry and sorting," Proc. Natl. Acad. Sci. USA, 76(3): 1382-1384 (1979).
Carsience, et al., "Germline chimeric chickens from dispersed donor blastodermal cells and compromised recipient embryos", Develop 117:669-675 (1993).
Certified English translation of the Chinese article: Fu et al. "A Molecular Cytogenetic Study of an Extra Small Chromosome", Acta Genetica Sinica 19(4): 294-297 (1992).
Chalfie, et al., "Green fluorescent protein as a marker for gene expression", Science 263:802-804, (1994).
Chang, et al., "Ribozyme-mediated site-specific cleavage of the HIV-1 genome", Clin. Biotech. 2: 23-31 (1990).

Chen, et al., "Genetic mechanism of tumor suppression by the human p53 gene", Science 250:1576, (1990).
Chen, et al., "High-efficiency transformation of mammalian cells by plasmid DNA", Mol. Cell Biol. 7:2745-2752, (1987).
Chick, et al., "Beta cell culture on synthetic capillaries: an artificial endocrine pancreas", Elliot P. Joslin Research Laboratory, Harvard Medical School, p. 847-849, (1975).
Chikashige et al., "Composite motifs and repeat symmetry in *S. pombe* centromeres: Direct analysis by integration of Notl restriction sites", Cell 57:739-751, (1989).
Chisari et al., "A transgenic mouse model of the chronic hepatitis B surface antigen carrier state," Science 230: 1157-1160 (1985).
Choo, K.H.A., "Turning on the centromere," Nature Genetics 18: 3-4 (1998).
Christman et al., "Amplification of expression of hepatitis B surface antigen in 3T3 cells cotransfected with a dominant-acting gene and cloned viral DNA", Proc. Natl. Acad. Sci. U.S.A. 79:1815-1819 (1982).
Church, "Replication of chromatin in mouse mammary epithelial cells grown in vitro," Genetics 52: 843-849 (1965).
Clarke, et al., "The structure and function of yeast centromeres", Ann. Rev. Genet. 19:29-56, (1985).
Coffman, et al., "In Vitro replication of plasmids containing human ribsomal gene sequences: Origin localization and dependence on an aprotinin-binding cytosolic protein," EXP. Cell Resh., 209:123-132, (1993).
Colbère-Garapin, et al., "A new dominant hybrid selective marker for higher eukaryotic cells", J. Mol. Biol. 150:1-14, (1981).
Collard, et al., "Separation and analysis of human chromosomes by combined velocity sedimentation and flow sorting applying single- and dual-laser flow cytometry," Cytometry, 5:9-19 (1984).
Collins and Newlon, "Chromosomal DNA replication initiates at the same origins in meiosis and mitosis", Mol Cell Biol 14:3524-3534 (1994).
Conte et al., "Characterization of two extreme variants involving the short arm of chromosome 22: are they identical?," Variant Chromosome 40(3):145-149 (1997).
Cooke, "Non-programmed and engineered chromosome breakage," Cold Monograph Series 29: 219-245 (1995).
Cooper and Tyler-Smith, "The putative centromere-forming sequence of ACM8 is a single copy sequence and is not a component of most human centromeres", Hum. Mol. Gen. 7/9): 753-754 (1992).
Copenhaver et al., "Genetic definition and sequence analysis of *Arabidopsis* centromeres", Science 286:2468-2474 (1999).
Couto, et al., "Inhibition of intracellular histoplasma capsulatum replication by murine macrophages that produce human defensin", Infect. Immun. 62: 2375-2378 (1994).
Cram et al., "XVII meeting of the International Society for Analytical Cytology, Tutorial IV", Chromosome Analysis and Sorting with Commercial Flow Cytometry_1. s (1994).
Cram, et al., "Polyamine buffer for bivariate human flow cytogenetic anal, ysis and sorting", Methods in Cell Biology 33: 377-382 (1990).
Cram, et al., "Univariate analysis alf metaphase chomosomes using the hypotonic potassium chloride-propidium iodide protocol," Meth. Cell Biol., 369-376 (1990).
Cross et al., "The structure of subterminal repeated sequence present on many human chromosomes," Nucleic Acids Res. 18/221: 6649-6657 (1990).
Crystal, R.G., "Transfer of Genes to Humans: Early Lessons and Obstacles to Success," Science 270:404-410 (1995).
"Current state of the art," Chromos Molecular Systems—News Release (May 29, 1996) (available at http://www.chromos.com/contents.html).
Cuthbert et al., "Construction and characterization of a highly stable humamrodent monochromosomal hybrid panel for genetic complementation and genome mapping studies," Cytogenet Cell Genet 71: 68-76 (1995).
Cutler, "Electroporation: Being developed to transform crops", Ag Biotechnology News 7: 3, (Sep./Oct. 1990).
Davidson, et al., "Improved techniques for the induction of mammalian cell hybridization by polyethylene glycol", Somatic Cell. Genet. 2: 165-176 (1976).
de Jong et al., "Chromosome and DNA-Mediated Gene Transfer in Cultured Mammalian Cells", International Review of Cytology, 92: 133-158 (1984).
Dean, et al. , "Multiple mutations in highly conserved residues are found in mildly affected cystic fibrosis patients", Cell 67: 863-870 (1990).
deJong et al., "Mammalian artificial chromosome pilot production facility: large-scale isolation of functional satellite DNA-based artificial chromosomes", Cytometry, 35: 129-133 (1999).
DePamphilis, "Eukaryotic DNA replication: Anatomy of an origin", Annu. Rev. Biochem, 62: 29-63 (1993).
Depinet et al., "Characterization of neo-centromeres in marker chromosomes lacking detectable alpha-satellite DNA," Human Molecular Genetics 6(81): 1195-1204 (1997).
Derwert citing French patent EP 0240373 A1, published Oct. 7, 1987, for: "New DNA fragment contg. centromeric nucleotide sequence- and derived vectors, allowing foreign genes to be maintained in transgenic animals".
Dhar, et al., "Transfer of Chinese Hamster Chromosome 1 to Mouse Cells and Regional Assignment of 7 Genes: A Combination of Gene Transfer and Microcell Fusion", Somatic Cell and Molecular Genetics, 10:(6)547-559 (1984).
Dickson et al., "Human ribosomal IDNA: conserved sequence elements in a 4.3-kb region downstream from the transcription unit," Gene 84: 197-200 (1989).
Dieken, et al. , "Efficient modification of human chromosomal allesles using recombination-proficient chicken/human microcell hybrids", Nature Genet. 72: 174-1 82 (1996).
Drohan, Transgenic Animals: "Great and Small," Journal of Cellular Biochemistry, 49: 111-112 (1992).
Dunckley, et al., "Retroviral-mediated transfer of a dystrophin minigene into mdx mouse myoblasts in vitro", FEBS Lett. 296: 128-34 (1992).
Ebert et al., "Transgenic Production of a Variant of Human Tissue-type Plasminogen Activator in Goat Milk: Generation of Transgenic Goats and Analysis of Expression," Bio/Technologv 9: 835-838 (1991).
Eckdahl et al., "DNA structures associated with autonomously replicating sequences form plant", Plant molecular Biol., 12: 506-516 (1989).
Eissenberg and Elgin, "Boundary functions in the control of gene expression," Trends in Genet., 7(10): 335-340 (1991).
Erlich, et al., "Recent advances in the polymerase chain reaction", Science 252: 1643-1651 (1991).
Etches, et al., "Chimeric chickens and their use in manipulation of the chicken genome", Poultry Sci. 72: 882-889 (1993).
Eyestone, "Production and breeding of transgenic cattle using in vitro embryo production technology," Theriooenolooy 51: 509-517 (1999).
Fabb et al., "Generation of novel human MHC class II mutant B-cell lines by integrating YAC DNA into a cell line homozygously deleted for the MHC class II region," Human Molecular Genetics m 1295-1304 (1997).
Fangman and Brewer, "A question of time: replication origins of eukaryotic chromosomes", Cell 77: 363-366 (1992).
Farr, et al., "Generation of a human X-derived minichromosome using telomere associated chromosome fragmentation", EMBO J. 74: 5444-5454 (1995).
Farr, "Mammalian telomeres and chromosome fragmentation," Cell Devtl. Biol. 7:41-48 (1996).
Farrel, et al., "53 is frequently mutated in Burkitt 's lymphoma cell lines", EMBO J. 10: 2879-2887(1991).
Featherstone and Huxley, "Extrachromosomal maintenance and amplification of yeast artificial chromosomes," Genomics, 267-278 (1993).
Fechheimer, et al., "Transfection of mammalian cells with plasmid DNA by scrape loading and sonication loading", Proc. Nat. Acad. Sci. USA 84: 8463-8467 (1987).
Ferl et al., Sections 7.2.2-7.2.3 in Biochemistry & Molecular Biology of Plants, Buchanan et al., (Eds.); Rockville, MD: American Society of Plant Physiologists, p. 324-325 (2000).

Financsek et al. , "Human ribosomal RNA gene: Nucleotide sequence of the transcription initiation region and comparison of three mammalian genes," Proc. Natl. & Acad. Sci. 79: 3092-3096 (1982).
Ford and Fried, "Large inverted duplications are associated with gene amplification", Cell 45: 425-430 (1986).
Fournier, "A general high-efficiency procedure for production of microcell hybrids", Proc. Natl. Acad. Sci. USA 78: 6349-6353 (1981).
Fowler, et al., "Donor lymphoid cells of th2 cytokine phenotype reduce lethal graft versus host disease and facilitats fully allogenetic cell transfers in sublethally irradiated mice", Advances in Bone Marrow Purging and Processing: Fourth International Symposium, p. 533-540 (1994).
Frary et al., "Molecular mapping of the centromeres of tomato chromosomes 7 and 9", Mol. Gen. Genet., 295-304 (1996).
Frasier, et al., "Efficient incorporation of transfected blastodermal cells into chimeric chicken embryos". Int. J. Dev. Biol. 37: 381-385. (1993).
French, et al., "Construction of a retroviral vector incorporating mouse VL30 retrotransposon-derived, transcriptional regulatory sequences", Anal. Biochem. 228: 354-355 (1995).
Frohman and Martin, "Cut, paste, and save: new Approaches to altering :specific genes in I I mice", Cell 56: 145-147 (1989).
Fromm, et al., "Expression of genes transferred into monocot and dicot plant cells by electroporation", Proc. Nat! Acad Sci. USA 82: 5824-5828 (1985).
Ftityol, et al., "Cloning and molecular characterization of a novel chromosome specific centromere sequence of Chinese hamster", Nucl. Acids Res. 22: 3728-3736, (1994).
Fu et al., "Molecular cytogenetic study of an extra small chromosome" (China), Acta Genetica Sinica 19(4): 294-297 (1992).
Fukushige et al. "Sorting of the Human Chromosome." Cytology Engineering 7(11) 896-903 (1988). Japanese.
Fukushige et al. certified translation of: "Sorting of the Human Chromosome." Cytology Engineering 7(11) 896-903 (1988).
Garside et al., "A method for karyotyping mouse blastocyst embryos developing from in vivo and in vitro fertilized eggs," Experientia 47 :1183-1184 (1985).
Gaub, et al., "The chicken ovalbumin promoter is under negative control which is relieved by steriod hormones", The EM60 Journal, 6:(8)2313-2320 (1987).
Gillespie, et al., "Tissue-specific expression of human CD4 in transgenic: mice", Mol. Cell. Biol. 73: 2952-2958 (1993).
Gluzman, "SV40-transformed simian cells support the replication of early SV40 mutants", Gel/23: 175-182 (1981).
Gogel, et al., "Mapping of replication initiation sites in the mouse ribosomal gene cluster," Chromosoma, 104: 511-518 (1996).
Gonzales and Schmickel, "The human 18s ribosomal RNA gene: Evolution and stability," Am. J. Hum. Genet. 38: 419-427 (1986).
Gonzalez and Sylvester, "Complete sequence of the 43-kb human ribosomal DNA repeat: Analysis of the intergenic space," Genomics, 27: 320-328 (1985).
Gonzalez et al., "Variation among human 28s ribosomal RNA genes," Proc. -Natl. Acad. Sci. 82: 7666-7670 (1985).
Goodfellow, et al., "Techniques for mammalian genome transfer", in Genome Analysis a Practical Approach, K. E. Davies, ed., IRL Press, Oxford, Washington DC. pp. 1-17 (1989).
Gordon et al., "Genetic transformation of mouse embryos by microinjection of purified DNA," Proc. Natl. Acad. Sci. USA 77(12): 7380-7384 (1980).
Gordon et al., "Production of Human Tissue Plasminogen Activator in Transgenic Mouse Milk," BioTechnology 5: 1183-1187 (1987).
Gout, et al., "Prolactin-stimulated growth of cell cultures established from malignant Nb rat lymphomas," Cancer Res. 2433-2436 (1980).
Graham and van der Eb, "A new technique for the assay of infectivity of human adenovirus 5 DNA",Virology 52: 456-457, (1973).
Gravholt and Friedrich, "Molecular cyotgenetic study of supernumerary marker chromosomes in an unselected group of children," Am. J. Med. Gen., 56,: 106-111 (1995).
Gray et al., "Chromosome measurement and sorting by flow systems I," Proc: Nat. Acad. Sci. 72: 1231-1234 (1975).
Green et al., "Systematic screening of yeast artificial-chromosome libraries by use of the polymerase chain reaction",Proc. Natl. Acad. Sci. USA, 87: 1213-1217 (1990).
Green, et al. , "Chromosomal region of the cystic fibrosis gene in yeast artificial chromosomes: A model for human genome mapping",Science 250: 914-913 (1990).
Grierson, et al., *Plant Molecular Biology*, 2nd Ed., Blackie, London, Ch. 7-9(1988).
Gritz, et al., "Plasmid-encoded hygromycin B resistance: the sequence of Ihygromycin B phosphotransferase gene and its expression in *Escherichia coli* and *Saccharomyces cerevisiae*" , Gene 25: 179-188 (1983).
Gunning, et al., "A human β-actin expression vector system directs high-level accumulation of antisense transcripts", Proc. Natl. Acad. Sci. USA 84: 4831-4835 (1987).
Haaf et al., "Integration of Human cy-Satellite DNA into Simian Chromosomes: Centromere Protein Binding and Disruption of INormal Chromosome Segregation," Cell (70) 681-696 (1992).
Haas and Dowding, "Aminoglycoside-modifying enzymes," Meth. Enzymol,, 43: 611-628 (1975).
Haase, et al., "Transcription inhibits the replication of autonomously replicating plasmids in human cells", Mol. Cell. Biol. 14: 2516-2524 (1994).
Hadlacsky, "Satellite DNA-based artificial chromosomes for use in gene therapy," Curr Opin Mol Ther., 3(2):125-32 (2001).
Hadlaczky and Szalay, "Mammalian artificial chromosomes: Introduction of novel genes into mammalian artificial chromosomes", Abstract from International Symposium on Gen e Therapy of Cancer, AIDS and Genetic Disorders, Trieste (ltaly)(Apr. 1 O-1 3, 1996)(available at http://www.chromos,, com/contents. html).
Hadlaczky and Szalay, "Mammalian artificial chromosomes: Potential vectors for gene therapy", Abstract from International Symposium on Gene Therapy of Cancer, AIDS and Genetic Disorders, Trieste (Italy) (Apr. 10-13, 1996) (available at http://www. chromos. com/contents. html).
Hadlaczky er al., "DNA Synthesis and Division in Interkingdom Heterokaryons", In Vitro, 16(8): 647-650 (1980).
Hadlaczky, "Structure of metapha: se chromosomes of plants", Internatl. Rev. Cytol. 94: 57-76 (1985).
Hadlaczky, et al., "Centromere formation in mouse cells cotransformed withhuman DN A and a dominant marker gene", Proc. Nat/. Acad. Sci. USA 88: 8106-8110 (1991).
Hadlaczky, et al., "Centromere proteins", Chromosoma 97: 282-288 (1989).
Hadlaczky, et al., "Direct evidence for the non-random localization of mammalian chromosomes in the interphase nucleus", Exp. Cell Res. 167: 1-15 (1986).
Hadlaczky, et al., "Protein depleted chromosomes", Chromosoma 87: 537-555 (1981).
Hadlaczky, et al., "Structure of isolated protein-depleted chromosomes of plants", Chromosoma 86: 643-659 (1982).
Hall, et al., "Expression and regulation of *Escherichia coli* lacZ gene fusions in mammalian cells", J. Mol. Appl. Gen. 2: 101-109 (1983).
Handeli, et al., "Mapping replication units in animal cells", Cell 57: 909-920 (1989).
Hanna, et al., "Specific expression of the human CD4 gene in mature CCI4,CD8'and immature CD4+CD8+T cells and in macrophages of transgenic mice", Mol. Cell. Biol. 74: 1084-1094 (1994).
Harper, et al., "Localization of single copy DNA sequences on G-banded human chromosomes by in situ hybridization", Chromosoma 83: 431-439 (1981).
Harrington, et al. , "Formation of de novo centromeres and construction of first-generation human artificial microchromosomes," Nature Genetics, 15: 345-355 (1997).
Haskell et al., "Efficient Production of Transgenic Cattle by Retroviral Infection of Early Embryos," Molecular Reproduction and Development 40: 386-390 (1995).
Hassan, et al., "Replication and transcription sites are colocalized in human cells", J, Cell. Sci. 107:425-434 (1994).
Heller, et al., "Mini-chromosomes derived from the human Y chromosome by telomere directed chromosome breakage," Proc. Natl. Acad. Sci. USA, 93: 7125-7130 (1996).

Henikoff et al., "Position-effect variegation after 60 years," Trends in Genetics L'6. 422-426 (1990).
Hermann, et al., "High-copy expression vector based on amplification-promoting sequences," DNA Cell Biol. 13(4):437-45 (1994).
Hernandez et al., "Conserved features in the mode of replication of eukaryotic ribosomal RNA genes," EMBO J. (4): 1475-1485 (1993).
Higgins et al., "Organization of a repetitive human 1.8 kb Kpnl sequence localized in the heterochromatin of chromosome 15," Chromosoma 93: 77-86 (1985).
Hill et al., "Production of Transgenic Cattle by Pronuclear Injection," Theriogenolony 37: 222 (1992).
Hilwig and Gropp, "Decondensation of constitutive heterochromatin in L. cell chromosomes by a benzimidazole compound ("33258 Hoechst")", Exp Cell Res 81: 474-477 (1973).
Hoffman et al Lipochromosome Mediated Gene Transfer: Identification and Probable Specificity of Localization of Human chromosomal Material and Stability of the In Vitro,17(8): 735-740 (1981).
Hogan, et al., "Manipulating the Mouse Embryo: A Laboratory Manual," Cold Spring Harbor Laboratory Press, Cold Spring Harbor, NY, pp. 127 and 429 (1994).
Hogan, et al., "Manipulating the Mouse Embryo: A Laboratory Manual," Cold Spring Harbor Laboratory Press, Cold Spring Harbor, NY, pp. 253-289 see, especially pp. 255-264 and Appendix 3 (1994).
Hollo, et al., "Evidence for a megareplicon covering megabases of centrome segments", Chromosome Research 4: 240-247 (1996).
Holmen, et al., "Efficient Lipid-mediated transfection of DNA into Primary Rat Hepatocytes", In Vitro Cell, Dev. J. Biol. 30: 347-351 (1995).
Holmquist and Comings, "Sister chromatid exchange and chromosome organization based on a bromodeoxyuridine Giemsa-C-banding technique (TC-banding)", Chromosoma 52: 245-259(1975).
Houben et al. "Immunostaining and interphase arrangement of field bean kinetochores", Chrom. Res., 3: 27-31 (1995).
Houdebine, "Production of pharmaceutical proteins from transgenic animals," Journal of Biotechnology 34: 269-287 (1994).
Hsu and Markvong, "Chromosomes and DNA in Mus: Terminal DNA synthetic sequences in three species", Chromosoma 57: 311-322 (1975).
Huberman and Riggs, "On the mechanism of DNA replication in mammalian chromosomes", J Mol Biol 32: 327-341 (1968).
Huberman, et al., "The in vivo replication origin of the yeast 2 μm plasmid", Cell 57: 473-481 (1987).
Huxley, C. "Mammalian artificial chromosomes: a new tool for gene therapy" , Gene Therapy, 7: 7-12 (1994).
Huxley, C., "Mammalian artificial chromosomes and chromosome transgenics," Trends in Genetics 13(g): 345-347 (1997).
Hyde, et al., "Correction of the ion transport defect in cystic fibrosis transgenic mice by gene therapy", Nature 362: 250-255 (1993).
Hyrien, et al., "The multicopy appearance of large inverted duplication and the sequence at the inversion joint suggest a new model for gene amplification", EMBO J 7: 407-417, (1988).
Ijdo et al., "Improved telomere detection using a telomere repeat probe (TTAGGG), generated by PCR," Nucleic Acids Research 79(771) 4780 (1991).
Ikeno et al., "Construction of YAC-based mammalian artificial chromosomes", Nature Biotech., 16: 431-439 (1998).
Ioannou, et al, "A new bacteriophage P1-derived vector for the propagation of large human DNA fragments", Nature Genetics, 6: 84-89 (1994).
Ish-Horowitz, et al., "Rapid and efficient cosmid cloning", Nucleic Acids Res. 9: 2989-2998 (1981).
Jabs, et al., "Characterization of a cloned DNA sequence that is present at centromeres of all human autosomes and the X chromosome and shows polymorphic variation", Proc. Natl. Acad. 8 7: 4884-4888 (1984).
Jacob, et al., "On the regulation of DNA replication in bacteria", Cold Spring Harb Symp Quant Biol 28: 329-348 (1963).
Jiang et al., "A conserved repetitive DNA element located in the centromeres of cereal chromosomes", Proc. Nat/. Acad. Sci. U. S. A., 14210-14213 (1996).
Jiewen et al. , "Decondensation of hamster chromosomes in the nuclei of 1-cell stage mice embryo following chromosome microinjection," Therioaenolony 45: 336 (1996).
Johnson, et al., "Genetic mapping (of variable length rDNA segments to centromeric regions of mouse Chromosomes 11, 12, 15, 16, and 18," Mammalian Genome, 4: 49-52 (1993).
Joy and Gopinathan, "Expression of microinjected foreign DNA in the silkworm," 50 (1991).
Kalitsis et al., "A Chromosome 13-Specific Human Satellite I DNA Subfarnily with Minor Presence on Chromosome 21: Further Studies on Robertsonian Translocations," Genomics 16:104-112 (1993).
Kappel et al., Regulating gene expression in transgenic animals, Current Biology p. 548-553 (1992).
Kaszas et al., "Misdivision analysis of centromere structure in maize", EMBO J., 15(19): 5246-5255 (1995).
Keown, et al., "Methods for introducing DNA into mammalian cells", Meth. Enzymol. 785: 527-537 (1990).
Kerem, et al., "Identification of the cystic fibrosis gene: genetic analysis", Science 245: 1073-1080, (1989).
Kereso et al., "De novo chromosome formations by large-scale amplification of the centromeric region of mouse chromosomes," Chromosome Research 4: 2326-239 (1996).
Killary, et al. , "Microcell Fusion", Methods in Enzymology, 254: 133-151 (1995).
Kitsberg, et al., "Replication structure of the human b-globin gene domain", Nature 366:588-590 (1993).
Klotman et al. "Transgenic models of HIV-1," Current Sci Ltd. 9: 313-324 (1995).
Korenberg, et al., "Human genome organization: Alu, LINES, and the molecular structure of metaphase chromosome bands", Cell 53: 391-400 (1988).
Kornberg and Baker, *DNA Replication*. 2nd. ed., New York: W. H. Freeman and Co, p. 474 (1992).
Krimpenfort et al., "Generation of transgenic dairy cattle using 'in vitro' embryo production," Bio/Technology 9: 844-847 (1991).
Lalande, et al., "Molecular detection and differentiation of deletions in band 13q14 in human retinoblastoma," Cancer Genet Cytogenet, 23: 151-157 (1986).
Lamb and Gearhart, "YAC transgenics and the study of genetics and human disease," Curr. Opin. Gen. Dev., 5: 342-348 (1995).
Lambert, et al., "Functional complementation of ataxia-telangiectasia group D (AT-D)ceils by microcell-mediated chromosome transfer and mapping of the AT-D locus to the region 1 1q22-23", Proc. Nat. Acad. Sci. USA 88: 5907-59 (1991).
Larin et al., "De novo formation of several features of a centromere following introduction of a Y alphoid YAC into mammalian cells," Human Molecular Genetics 3/%51: 689-695 (1994).
Larsson et al. "Reduced P2-microglobulin mRNA levels in transgenic mice expressing a designed hammerhead ribozyme," Nucleic Acids Research 22: 2242-2248 (1994).
Lawrence, et al., "Sensitive, high-resolution chromatin and chromosome mapping in situ: Presence and orientation of two closely integrated copies of EBV in a lymphoma line", Cell 52: 51-61 (1988).
Le Bolc 'h, et al., "Cationic phosphonolipids as non viral vectors for DNA transfection", Tetrahedron Lett. 36: 6681-6684 (1995).
Lebo et al. , "Design and operation of a dual laser chromosome sorter," Cytometry 3: 213-219 (1982).
Ledbetter et al., "New Somatic Cell Hybrids for Physical Mapping in Distal Xq and the Fragile X Region," America/Journal of Medical Genetics 38: 418-420 (1991).
Leder, et al., "EK2 derivatives of bacteriophage lambda useful in the cloning of DNA from higher organisms: The AgtWES system", Science 796: 175-177 (1977).
Lee et al., "Human centromeric DNA," Human Genetics 100: 291-300 (1997).
Lee et al., "Human gamma X satellite DNA: an X chromosome specific centromeric DNA sequence," Chromosoma 104: 103-112 (1995).
Lehninger, *Biochemistry*, 2nd edition, Worth Publishers, New York, p. 35 and p. 864 (1976).
Li et al, "Decondensation of hamster chromosomes in the nuclei of 1-cell stage mice embryo following chromosome microinjection," Theriogenology, 45(1): 336 (1996).
Lin et al., "Isolation and identification of a novel tandemly repeated DNA sequence in the centromeric region of human chromosome 8," Chromosoma 102: 333-339 (1993).

Lindenbaum et al. A mammalian artificial chromosome engineering system (ACE System) applicable to biopharmaceutical protein production, transgenesis and gene-based cell therapy. Nucleic Acids Res. 7;32(21):e172 (2004).
Little, et al., "Intiation and termination of DNA replication in human rRNA genes," A Molec and Cell. Biol., 13 (10): 6600-6613 (1993).
Liu, et al., "The pro region of human neutrophil defensin contains a motif that is essential for normal subcellular sorting", Blood 85: 1095-1103, (1995).
Locardi, et al., "Persistent infection of normal mice with human immunodeficiency virus", J. Viral. 66: 1649-1654, (1992).
Loefler, et al., "Gene Transfer into Primary and Established Mammalian Cell Lines with Lipopolyamine-Coated DNA", Met, hods for Transforming Animal and Plant Cells 2 7 7: 599-618 (1993).
Looney, et al., "The dihydrofolate reductase amplicons in different methotrexate-resistant Chinese hamster cell lines share at least a 273-kilobase core sequence, but the amplicons in some cell lines are much larger and remarkably uniform in structure", Mol. Cell Biol. 118: 5268-5279. (1988).
Lopes et al., "Mechanism of high-copy-number integration of pMIRY-type vectors into the ribosomal DNA of *Saccharomyces cerevisiae*", Gene 105:83-90 (1991).
Lorenz, et al., "Isolation and expression of a cDNA encoding *Renilla reniformis luciferase*", Proc.Natl. Acad. Sci. USA 88: 4438-4442 (1991).
Lorenz, et al., "Expression of the *Renilla reniformis luciferase* gene in mammalian cells," J. Biolum. Chemilum. 7 7: 31-37 (1996).
Love, et al., "Transgenic birds by microinjection", Bio/Technology 72: 60-63 (1994).
Ma, et al., "Organisation and genesis of dihydrofolate reductase amplicons in the genome of a methotrexate-resistant Chinese hamster ovary cell line", Mol. Cell Biol. 8: 2316-2327 (1988).
Ma, et al., "Sister chromatid fusion initiates amplification of the dihydrofolate reductase gene in Chinese hamster cells", Genes Develop. 7: 605-620 (1993).
Madan, et al., "Fluorescence analysis of late DNA replication in mouse metaphase chromosomes using BUdR and 33258 Hoechst", Exp. Cell Res. 99: 438-444 (1976).
Maden, et al., "Clones of human ribosomal DNA containing the complete 18 S-rRNA and 28 S-rRNAgenes," J. Biochem., 2: 519-527 (1987).
Maeda et al, "Production of human a-interferon in silkworm using a baculovirus vector," Nature 315: 592-594 (1985).
Maniatis, et al., "The isolation of structural genes from libraries of eucaryotic DNA", Cell 75: 687-701 (1978).
Mansour, et al., "Disruption of r the proto-oncogene int-2 in mouse embryo-derived-stem cells: a general strategy for targeting mutations to non-selectable genes", Nature 336: 348-352 (1988).
Manuelidis, "Heterochromatic features of an 1 1-megabase transgene in brain ceils," Proc. Natl. Acad. Sci. USA, 1049-1053 (1991).
Matthews, et al., "Purification and properties of *Renilla reniformis luciferase*", Biochemistry 16:85-91 (1977).
Maxwell, et al., "Regulated expression of a diphtheria toxin A-chain gene transfected into human cells: possible strategy for inducing cancer cell suicide", Cancer Res. 46: 4660-4664, (1986).
McCallum and Maden, "Human 18s ribosomal RNA sequence inferred from DNA sequence," Biochem. J. 725-733 (1985).
McCormick et al. , "Construction of human chromosome 21-specific yeast artificial chromosomes", Proc. Nat/Acad. Sci. USA, a: 9991-9995 (1989).
McGill, et al., "λCM8, a human sequence with putative centromeric function, does not map to the centromere but is present in one or two copies at 9qter", Hum. Mol. Gen. 1(9): 749-751.
McGuigan et al, "Replication of yeast DNA and novel chromosome form &on in mouse cells," Nucleic Acids Res. 24(12): 2! 271-2280 (1996).
McLean, "Improved techniques for immortalizing animal cells", TIBTECH 11:232-238 (1993).
Meinkoth and Wahl, "Hybridization of nucleic acids immobilized on solid supports", Anal. Biochem. 738: 267-284 (1984).
Mendelsohn, et al. , "Separation of isolated Chinese hamster metaphase chromosomes into three size-groups," J. Mol. Biol., 32: 101-112 (1968).
Meyer, et al., "Inhibition of HIV-1 replication by a high-copy-number vector expressing antisense RNA for reverse transcriptase," Gene.,129(2):263-8(1993).
Meyne et al., "Chromosome localization and orientation of the simple sequence repeat of human satellite I DNA," Chromosoma 703: 99-103 (1994).
Meyne, et al., "Distribution of non-telomeric sites of the (TTAGGG), telomeric sequence in vertebrate chromosomes", Chromosoma 99: 3-10 (1990).
Miesfeld and Arnheim, "Identification of the in vivo and in vitro origin of transcription in human rDNA, Nucleic Acid Res.," vol. 10, No. 13 (1982).
Milbrandt et al., "Amplification of a cloned Chinese hamster dihydrofolate reductase gene after transfer into a dihydrofolate reductase-deficient cell line", Mol. Cell. Biol. 3:1274-1282 (1983).
Miller and Rosman, "Improved retroviral vectors for gene transfer and expression", Biotechniques 7: 980-990 (1989).
Miller et al., "High-efficiency ligation and recombination of DNA fragments by vertebrate cells", Science, 606-609 (1983).
Miller, "Is the centromeric heterochromatin of *Mus musculus* late replicating?" Chromosoma 55: 165-170 (1976).
Miller, *In Experiments in Molecular Genetics*, Cold Spring Harbor Press, pp. 352-355 (1972).
Mitani, et al., "Delivering therapeutic genes—matching approach and application", Trend s Biotech. 7 7: 162-166, (1993).
Mole-Bajer et al. , "Autoantibodies from a patient with scleroderma CREST recognized kinetochores of the higher plant *Haemanthus*", Proc. Natl. Acad. Sci. U. S. A.,87:3599-3603 (1990).
Moore et al., "Centromeric sites and cereal chromosome evolution",Chromosoma, 105: 321-323 (1997).
Moreadith et al., "Gene targeting in embryonic stem cells: the new physiology and metabolism," J. Mol. Med., z: 208-216 (1997).
Morgan and French Anderson, "Human gene therapy", Annu. Rev. Biochem. 62: 191-217, (1993).
Mukherjee et al., "Entrapment of metaphase chromosomes into phospholipid vesicles (lipochromosomes): Carrier potential in gene transfer", Proc. Natl. Acad Sci. USA, 75/3: 1361-1365 (1978).
Mulligan, "The basic science of gene therapy", Science 260:926-932 (1993).
Mullins et al. , "Perspective Series: Molecular Medicine in Genetically Engineered Animals," Transqenesis in Nonmarine Species 98(11 ): S37-S40 (1996).
Mullins et al., "Perspectives Series: Molecular medicine in genetically engineered animals; Transgenesis in the rat and larger animals," J. Clin. Invest., 9811 1 ): S37-840 (1996).
Murray, et al., "Construction of artificial chromosomes in yeast", Nature 305: 189-193, (1983).
Nabel, et al., "Site-specific gene expression in vivo by direct gene transfer into the arterial wall", Science 249: 1285-1 288, (1990).
Naider, et al., "Reversible alkylation of a methionyl residue near the active site of BGalactosidase," Biochemistry, (17): 3202-3210 (1972).
Nazar et al., "Sequence homologies in mammalian 5.8s ribosomal RNA," Biochem. s(3): 505-508 (1976).
Nikolaev, et al., "Microinjection of recombinant DNA into early embryos of the mulberry silkworm *Bombyx mori*" Mol. Biol. (Moscow) 23:1177-87 (1989).
Ohgawara et al., "Uptake of liposome-encapsulated plasmid DNA by plant protoplasts and molecular fate of foreign DNA", Protoplasma 116:145-148 (1983).
Ohnuki, "Demonstration of the spiral structure of human chromosomes," Cytology: 208: 916-917 (1965).
Ohnuki, "Structure of chromosomes," Chromosoma (Berl), 402-428 (1968).
O'Keefe, et al., "Dynamic organization of DNA replication in mammalian cell nuclei: Spatially and temporally defined replication of chromosome-specific a-satellite DNA sequences", J. Cell Biol. 7 76: 1095-1110, (1992).
Orkin, S. H., "Report and Recommendations of the Panel to Assess the NIH Investment in Research of Gene Therapy," Dec. 7, 1995 pp. 1-45. Available online at: http://www/nih.gov/news/panelrep. html.
Osborne, et al., "A mutation in the second nucleotide binding fold of the cystic fibrosis gene", Am. J. Hum. Genetics48:608-612, (1991).

Palmiter et al., "Dramatic growth of mice that develop from eggs microinjected with metallothionein-growth hormone fusion genes," Nature 300: 611-615 (1982).
Park, et al., "Modulation of Transcriptional Activity of the Chicken ovalbumin gene promoter in primary cultures of chicken oviduct cells: effects of putative regulatory elements in the 5'-flanking region", Biochem and Mol Biol International $36:(4)811-816, (1995).
Parkman et al., Abstract for: "Gene Therapy for adenosine deaminasc deficiency," Annu Rev Med 51: 33-47 (2000).
Paszowski and Saul, "[28]Direct gene transfer to plants", Methods for P/ant Molecular Biology, Weissbach et al., eds., Academic Press, N. Y., Section VIII, pp. 4.47-463, (1988).
Perez, et al., "Satellite DNA-based artificial chromosomes—chromosomal vectors," Trends Biotechnol.;18(10):402-403 (2000).
Perry and Wolff, "A new Giemsa method for the differential staining of sister chromatids", Nature 257: 156-158, (1974).
Petitte, et al. , "Production of somatic and germline chimeras in the chicken by transfer of early blastodermal cells", Development 708: 185-189, (1990).
Pierce and Sternberg, "Using Bacteriophage PI system to clone high molecular weight genomic DNA" Meth. Enzvmol., 2: 549-574 (1992).
Pierce, et al., "A positive selection1 vector for cloning high molecular weight DNA by the bacteriophage PI system: Improved cloning efficacy," Proc. Natl. Acad. Sci. USA , B: 2056-2060 (1992).
Pinkel, et al., "Cytogenetic analysis using quantitative, high-sensitivity, fluorescence hybridization", Proc. Natl. Acad. Sci. USA, 83: 2934-2938, (1986).
Pluta et al., "Structure of the human centromere at metaphase", TIBS, 15: 181-185 (1990).
Portykus, "Gene transfer to cereals: an assessment" Biotechnology 8(6):535-542 (1990).
Prasher, et al., "Primary structure of the Aequorea Victoria green-fluorescent protein", Gene 1 1 1: 229-233, (1992).
Praznovszky, et al., "De novo chromosome formation in rodent cells", Proc. Nat/. Acad. Sci. USA 88: 11042-11046. (1991).
Priest, "Cytogenetics," in Medical Technology Series. R. M. French, M. Eichman, B. Fiorella, and H. F. Weisberg, eds. (Lea and Febiger, Philadelphia) pp. 189-190 (1969).
Quastler, et al., "Cell population kinetics in the intestinal epithelium of the mouse", Exp . Cell Res. 7 7: 420-438, (1959).
Raimondi, et al., "X-ray mediated size reduction, molecular characterization and transfer in model systems of a human artificial minichromosome", Abstract from International Symposium on Gene Therapy of Cancer, AIDS and Genetic Disorders, Trieste (Italy) (Apr. 10-13, 1996).
Raimondi, "Gene targeting to the centromeric DNA of a human minichromosome." Hum. 1 1 Gene Ther. 7: 1103-1109 (1996).
Rancourt et al., "Wolffish antifreeze protein from transgenic *Drosophila*," Biotechnology;8(5):453-7. (1990).
Rasko et al., "Pattern of segregation of chicken HPRT phenotype in Chinese hamster-chick redbloodcellhybrids," Cytogenet Cell Genet 24: 129-137 (1979).
Raven et al., "The Classification of Living Things", in Botany, pp. 171-185, Worth Publishers, New York, N.Y. (1992).
Raynal et al. , "Complete nucleotide sequence of mouse 18 S rRNA gene:comparison with other available homologs," FEBS Lett. 767 (2): 263-367 (1984).
Remy, et al., "Gene Transfer with a Series of Lipophilic DNA-Binding Molecules", Bioconjugate Chem. 5: 647-654, (1994).
"Report and recommendations of the panel to assess the NIH investment in research on gene therapy," Orkin and Motulsky, co-chairs (Dec. 7, 1995)(available at http://www. nih. gov/news/panelrep. html).
Rhodes et al., "Telomere structure and function", Curr. Opin. Strut. Biol., 5: 311-322 (1995).
Richia and Lo, "Introduction of human DNA into mouse eggs by injection of dissected chromosome fragments", Science 245: 175-177, (1989).
Riego et al, "Production of Transgenic Mice and Rabbits that Carry and Express the Human Tissue Plasminogen Activator cDNA under the Control of a Bovine Alpha SI Casein Promoter," Theriogenologv 39:1 173-185 (1993).
Riordan, et al., "Identification of the cystic fibrosis gene: cloning and characterization of complementary DNA", Science 24: 5: 1066-1072, (1989).
Roberts et al., "Ribosomal RNA gene amplification: a selective advantage in tissue culture", Cancer Genet. Cytogenet. 29:119-127 (1987).
Robertson et al., "Germ-line transmission of genes introduced into cultured pluripotential cells by retroviral vector", Nature, 445-448 (1986).
Rogers, et al., "I[261 Gene transfer in plants: Production of transformed plants using Ti plasmid vectors", *Methods for Plant Molecular Biology*, Weissbach et al., eds., Academic Press, N. Y.,Section VIII, pp. 423-436, (1988).
Rommens, et al., "Identification of the cystic fibrosis gene: chromosome walking and jumping", Science 245: 1059-1065, (1989).
Rosenfeld, et al., "In vivo transfer of the human cystic fibrosis transmembrane conductance regulator gene to the airway epithelium", Cell 68: 143-1 55 (1992).
Roslaniec, et al., "Development of ,a high speed optical chromosome sorter based on photoinduced cross-linking of DNA with psoralens," International Society for Analytical Cytology Abstracts (1994).
Roth et al., "Illegitimate Recombination in Mammalian Cells", Chapter 21, 621-653.
Roth, et al., "Artifizielle chromosomen", Natur Wissenschaften 74: 78-85 (1987).
Rowe, et al. , "Genetic mapping of 18s ribosomal RNA-related loci to mouse chromosomes 5, 6, 9, 12, 17, 18, 19, and X," Mammalian Genome, 2: 886-889, 1996.
Saffery and Choo, "Strategies for engineering human chromosomes with therapeutic potential," J Gene Med., Jan.-Feb.;4(1):5-13 (2002).
Safrany and Hidvegi, "New tandem1 repeat region in the non-transcribed spacer of human ribosomal RNA gene," Nucl. Acids Res. 17(8): 3013-3023 (1989).
Sakai et al., "Human Ribosomal RNA Gene Cluster: Identification of the Proximal End Containing a Novel Tandem Repeat Sequence," Genomics 26: 521-526 (1995).
Sambrook, et al., "Molecular Cloning: A Laboratory Manual," vol. 7. 2d Ed.,Cold Spring Harbor Laboratory Press,, I Section 2.18 (1989).
Sanes, et al., "Use of a recombinant retrovirus to study post-implantation cell lineage in mouse embryos", EMBO J. 5(12): 3133-3142, (1986).
Sanford, et al., "General Protocol for Microcell-Mediated Chromosome Transfer", Somatic Cell and Molecular Genetics, 13:(3)279-284 (1987).
Sang, et al., "Transgenic chickens—methods and potential application", TIBTECH 72: 415-420.
Sanger, et al., "Cloning in single-stranded bacteriophage as an aid to rapid DNA sequencing", J. Mol. Biol. 743: 161-178, (1980).
Sart et al., "A functional neo-centralmere formed through activation of a latent human centromere and consisting of non-alpha-satellite DNA," Nature Genetic 16: 144-152 (1997).
Saxon, et al., "Selective transfer of individual human chromosomes to recipient cells", Mol. Cell. Biol. 7: 140-146 (1985).
Schedl, et al., "A method for the generation of YAC transgenic mice by pronuclear microinjection", Nut. Acids Res. 2 7: 4783-4787 (1993).
Schneider et al., "Procedure for production of hybrid genes and proteins and its use in assessing significance of amino acrid differences in homologous tryptophan synthetase CY polypeptides", Proc. Natl. Acad. Sci. USA, 78(4): 2169-2173 (1981).
"Scientists report a major step in ralizing the commercial potential of engineered artificial chromosomes in significant life sciences sectors, including gene therapy," Chromos Molecular Systems—News Release (May 29, 1996)(available at http://www. chromos. com/contents. html).
Seamark, Progress and Emerging Problems in Livestock Transgenesis: a Summary Perspective, Reprod. Fertil. Dev. 6: 653-657 (1994).

Selig, et al., "Regulation of mouse satellite DNA replication time", EMBO J. 7~419-426 (1988).
Sher, et al., "Role of T-Cell derived cytokines in the downregulation of immune responses in parasitic and retroviral infection", Immunolical Reviews (127)183-204 (?).
Shizuya, et al., "Cloning and stable /maintenance of 300-kilobase-pair fragments of human DNA in *Escherichia coli* using an F-factor-based vector," Proc. Natl. Acad. Sci. USA, a: 8794-8797 (1992).
Shwarchuk, et al., "Substructure in the radiation survival response at low dose: asynchronous and partially synchronized V79-WNRE cells," Int. J. Radial. Biol. 64(5): 601-612 (1993).
Sillar and Young, "A new method for the preparation of metaphase chromosomes for flow analysis," J. Histo. Cytoch., 29: -74-: 78 (1981).
Simons et al., "Alteration of the quality of milk by expression of sheep β-lactoglobulin in transgenic mice," Nature 328: 530-532 (1987).
Simons et al., "Gene Transfer into Sheep," Bio/Technology 6: 179-183 (1988).
Smith and Rubin, "Functional screening and complex traits: human 21q22.2 sequences affecting learning in mice," Hum. Mol. Genet. 6(10): 1729-1733 (1997).
Smith, et al. , "Amplification of large artificial chromosomes", Proc. Nat/. Acad. Sci. USA, 87: 8242-8246 (1990).
Smith, et al., "Distinctive chromosomal structures are formed very early in the amplification of CAD genes in Syrian hamster cells", Cell 63: 1219-1227 (1990).
Solus, et al., "Characterization of single-copy probe from vicinity of centromere of human chromosome I", Somatic Cell Mol. Genet. 74: 381-391 (1988).
Sternberg, "Bacteriophage PI cloning system for the isolation, amplification, and recovery of DNA fragments as large as 100 kilobase pairs", Proc. Natl. Acad. Sci. USA, 87: 103-107 (1990).
Stoehr, et al., "A reliable preparation of mono-dispersed chromosome suspensions for flow cytometry," Histochemistry, 74: 57-61 (1982).
Stolzenburg, et al., "Structural homologies and functional similarities between mammalian origins of replication and amplification promoting sequences," Chromosoma. Jun;103(3):209-14 (1994).
Strauss, "Transfection of Mammalian Cells via Lipofection", Meth Bio154: 307-327 (1996).
Strojek et al. "The use of transgenic: animal techniques for livestock improvement," Genetic Engineering: Principles and Methocls 1 A O-221-246 (1988).
Stubblefield and Pershouse, "Direct formation of microcells from mitotic cells for use in chromosome transfer" Somatic Cell & Molec. Genet.: 485-491 (1992).
Stubblefield and Wray, "Isolation of specific human metaphase chromosomes," Bioch. and Biophys. Res. Commun., 83(4): 1404-1414 (1978).
Sugden, et al., "A vector that replilcates as a plasmid and can be efficiently selected in Blymphoblast transformed by Epstein-Barr virus", Mol. Cell. Biol. 5: 410-413 (1985).
Sumner, "A simple technique for demonstrating centromeric heterochromatin", Cell Res . 75: 304-306 (1972).
Sumner, "Scanning electron microscopy of mammalian chromosomes from prophase to telophase", Chromosoma 700: 410-418, (1991).
Sun et al., "Human artificial episomal chromosomes for cloning large DNA fragments in human cells" Nature Genetics 8:33-41 (1994).
Szybalska, et al., "DNA-Mediated heritable transformation of biochemical trait", Proc. N.A.S. 48:2026-2034 (1962).
Szybalsky, et al., "Genetic studies with human cell lines", Nat/Cancer Inst. Monogr. 7: 75-89, (1982).
Takeda et al., "Expression of SV40-lacZ Gene in Mouse Preimplantation Embryos After Pronuclear Microinjection," Molecular Reproduction and Development 30: 90-94 (1991).
Tamura, et al., "Microinjection of DNA into early embryo of *Bombyx mori*", Bio Ind. 8: 26-31, (1991), (Chemical Abstracts #114 (21)(200502z).
Taylor et al. , "Analysis of extrachromosomal structures containing human centromeric alphoid satellite DNA sequences in mouse cells," Chromosoma 105: 70-81 (1996).
Teifel, et al., "New Lipid Mixture for Efficient Lipid-Mediated Transfection lof BHK Cells", Biotechniques 79: 79-82 (1995).
Telenius et al, "Stability of a functional murine satellite DNA-based artificial chromosome I I across mammalian species," Chromosome Research 7: 3-7 (1999).
Telenius et al., "Chromatid contamination can impair the purity of flow-sorted metaphase I I chromosomes," Cytometry 14: 97-101 (1993).
Thoraval et al., "A methylated human 9-kb repetitive sequence on acrocentric chromosomes is homologous to a subtelomeric repeat in chimpanzees," Proc. Natl. Acad. Sci. 93: 4442-4447 (1996).
Toledo, et al., "Co-amplified markers alternate in megabase long chromosomal inverted repeats and cluster independently in interphase nuclei at early steps of mammalian gene amplification", EMBO J. 7 7: 2665-2673 (1992).
Tomizuka et al. , "Functional expression and germline transmission of a human chromosome fragment in chimaeric mice," Nature Genetics 16: 133-143 (1997).
Tonghua, et al., "Effects of antisense epidermal growth factor and its receptor retroviral expression vectors on cell growth of human pancreatic carcinoma cell line", Chin. Med. J. (Beijing, Engl. Ed.)708: 653-659 (1995).
Tora, et al., "Cell-specific activity of a GGTCA half-palindromic oestrogerl-responsive element in the chicken ovalbumin gene promoter", The EMBO Journal 7:(12)3771-3778 (1988).
Torczynski et al., Cloning and sequencing of a human 18s ribosomal RNA gene, DNA 4 (4): 283-291 (1985).
Traver, et al., "Rapid screening of a human genomic library in yeast artificial chromosomes for single-copy sequences," Proc. Natl. Acad. Sci. USA : 5898-5902 (1989).
Tyler-Smith et al., "Mammalian chromosome structure," Curr. Opin. Genet.Devt. 3: 390-397 (1993).
Uchimiya, et al., "Transgenic plants", J. Biotechnol. 72: 1-20 (1989).
Van den Engh, et al., "Improved resolution of flow cytometric measurements of Hoechst and Chromomycin-A3-stained human chromosomes after addition of citrate and sulfite," Cytometry, 2: 266-270 (1988).
Van den Engh, et al., "Preparation and bivariate analysis of suspensions of human chromosomes" Cytometry, 6: 92-100 (1985).
Van den Engh, et al., "Preparation of chromosomes suspensions for flow cytometry," Cytometry, 5: 108-117 (1984).
Vanderbyl et al. "Transgene expression after stable transfer of a mammalian artificial chromosome into human hematopoietic cells", Exp Hematol. Dec. 2005, 33(12) 1470-1476.
Van Dilla, et al., "Human chromosome-specific DNA libraries: Construction and availability," Bio/Technology, 4: 537-552 (1986).
Velander et al, "High-level expression of a heterologous protein in the milk of transgenic swine using the cDNA encoding human protein C," Proc. Natl. Acad. Sci. USA 89: 12003-12007 (1992).
Verma, I. M. And N. Somia, "Gene Therapy-promises, problems and prospects," Nature 389: 239-42 (1997).
Vig and Richards, "Formation of primary constriction and heterochromatin in mouse does not require minor satellite Dna", Exp. Cell Res. 207: 292-298 (1992).
Vile, R. G., Abstract of: "Cancer Gene Therapy: Hard Lessons and New Courses," Gene Therapy 7(1): 2-g (2000).
Vissel et al. , "A satellite III sequence shared by human chromosomes 13,14, and 21 that is contiguous with a satellite DNA," Cytogenct Cell Genet 67: 81-86 (1992).
Voet, D. and Voet, J., Book: Biochemistry, Chapter 33, "Eukaryotic Gene Expression", John Wiley &Sons, New York, p. 1033 (1990).
Vos JM, "The Simplicity of complex MACs," Nature Biotechnology 15: 1257-1259 (1997).
Vos, "Mammalian artificial chromosomes as tools for gene therapy", Curr. Opin. Gen. Dev. 8: 351-359 (1998.
Wall et al., "High-level synthesis of a heterologous milk protein in the mammary glands of transgenic swine," Proc. Natl. Acad. Sci. USA 88: 1696-1700 (1991).
Wall et al., "Making Transgenic Livestock: Genetic Engineering on a Large Scale," Journal of Cellular Biochemistry 49: 113-120 (1992).
Wall et al., "Transgenic Dairy Cattle: Genetic Engineering on a Large Scale," J. Dairy Sci. 80(9): 2213-2224 (1997).

Wall, "Trangenic livestock: Progress and prospects for the future," Theriogenology, 45: 57-68 (1996).
Wang and Fedoroff, "Banding of human chromosomes treated with trypsin", Nature 235: 52-54, (1972).
Warburton et al., "Hamster chromosomes containing amplified human o-satellite DNA show delayed sister chromatid separation in the absence of de novo kinetochore formation," Chromosoma 706: 149-159 (1997).
Warburton, P. E., "Making CENS of Mammalian Artificial Chromosomes," Molecular Genetics and Metabolism 68: 152-160 (1999).
Waring, et al., "Nucleotide sequence repetition: A rapidly reassociating fraction of mouse DNA", Science 754: 791-794 (1966).
Waye and Willard, "Nucleotide sequence heterogeneity of alpha satellite repetitive DNA: a survey of alphoid sequences from different human chromosomes," Nucleic Acids Res. Sep. 25;15(18):7549-69 (1987).
Waye et al., "Human p satellite DNA: Genomic organization and sequence definition of a class of highly repetitive tandem DNA," Proc. Natl. Acad. Sci, 86: 6250-6254 (1989).
Weber et al., "Formation of genes coding for hybrid proteins by recombination between related, cloned genes in *E. coli*", Nut Acids Res, 11(16): 5661-5669 (1983).
Wegner, et al., "An amplification-promoting sequence from mouse genomic DNA: interaction with a trans-acting factor that also affects gene expression," DNA Cell Biol. 9(5):331-321 (1990).
Wegner, et al., "Cis-acting sequences from mouse rDNA promote plasmid DNA amplification and persistence in mouse cells: implication of HMG-1 in their function,"Nucleic Acids Res. Dec. 11;17(23):9909-32 (1989).
Weinberg, "Tumor suppressor genes", Science 254: 1138-1146 (1991).
Wells et al.,"Production of Cloned Lambs from an Established Embryonic Cell Line: A Comparison between In Vivo-and In Vitro-Matured Cytoplasts," Biology of Reproduction 57: 385-93 (1997).
White, et al., "A frame-shift mutation in the cystic fibrosis gene", Nature 344: 665-667 (1990).
Wigler, et al., "DNA-mediated transfer of the adenine phosphoribosyltransferase locus into mammalian cells", Proc. Nat/ . .4cad. Sci. USA 76: 1373-1376 (1979).
Willard and Waye, "Hierarchical order in chromosome specific human alpha satellite DNA", Trends Genet. 3: 192-198 (1987).
Willard, "Artificial Chromosomes Coming to Life", Science 290:1308-1309 (2000).
Willard, "Chromosome manipulation: a systematic approach toward understanding human chromosome structure and function," Proc. Natl. Acad. Sci. USA 93: 6847-6850—(1996).
Williams and Blattner, "Construction and characterization of the hybrid bacteriophage lambda charon vectors for DNA cloning", J. Viral. 29: 555-575, (1979).
Wilmut, et al., "Viable offspring derived from fetal and adult mammalian cells," Nature, 385: 810-813 (1997).
Wong, et al., "Sequence organization and cytological localization of the minor satellite of mouse", Nucl. Acids Res. 76: 11645-11661 (1988).
Worton et al., "Human Ribosomal RNA Genes: Orientation of the Tandem Array and Conservation of the 5 End," Science 239: 64-68 (1988).
Wright et al., "High level expression of active human alpha-I-antitrypsin in the milk of transgenic sheep," Bio/Technology 9: 830-834 (1991).
Yamada, et al., "Multiple chromosomes carrying tumor suppressor activity for a uterine endometrial carcinoma cell line identified by microcell-mediated chromosome transfer", Oncogene 5: 1141-1147 (1990).
Yates, et al., "A cis-acting element from the Epstein-Barr viral genome that permits stable replication of recombinant plasmids in latently infected cells", Proc. Nat Acad. Sci. USA 87: 3806-3810 (1984).
Yates, et al., "Stable replication of plasmids derived from Epstein-Barr virus in various mammalian cells", Nature 373: 812-815 (1985).
Yeung, et al., "Human CD4-major histocompatibility complex class II (Dqvv6)transgenic mice in an endogenous CD4/CD8_deficient background: reconstitution of phenotype and humano-restricted function," J, Exp. Med. 780: 1911-1920 (1994).
Yoon, et al., "Mapping of replication initiation sites in human ribosomal DNA by Nascent Strand abundance analysis," Mol. Cell. Bio., p. 2482-2489 (1995 ).
Yurov , "Identification and characterization of two distinct polymorphic α-satellite DNA sequences from centromeric regions of the chromosomes 13 and 21 (A2299)", Cytogenet. Cell Genet. 57: 1114 (1989).
Yurov, "Collection of a-satellite DNA probes: Highly polymorphic markers for centromeric regions of all human chromosomes (A2298)". Cytogenet, Cell Genet. 51:1114 (1989).
Zabel, et al., "NATO ASI Series, Series A: Life Sciences 83 (Mol. Form Funct. Plant Genome)" Abstract only, 609-624 (1985).
Zakian, "Telomeres: Beginning to Understand the End", Science, 270: 1601-1607 (1995).
Zang, et al., "Production of recombinant proteins in Chinese hamster ovary cells using a protein-free cell culture medium", Bio/Technology 73: 389-392 (1995).
Zemskova and Escher , "IAP DNA sequences and mouse chromosome instability," Loma Linda University APC Conference, Mar. 1997.
Zhang, et al., "T-Cell cytokine responses in human infection with Mycobacterium tuberculosis", Infection and Immunity, p. 3231-3234 (1995).
Kanda et al., "The dynamics of acentric chromosomes in cancer cells revealed by GFP-based chromosome labeling strategies," J. Chem. Biochem. Suppl. 35:107-114 (2000).
Nonomura et al., "Studies on plant artificial chromosome and nuclear organization," Recent Progress of Breeding Science 40:41-44 (1998).
Brown et al., "Mammalian artificial chromosomes," Current Opinion in Genetics & Development, 6(3):281-288, (1996).
Brown et al., "Dissecting the centromere of the human Y chromosome with cloned telomeric DNA," Human Molecular Genetics, 3(8):1227-1237, (1994).
Campbell et al., "Totipotency or multipotentiality of cultured cells: applications and progress," Theriogenology, 47:63-72, (1997).
Houdebine, "Production of pharmaceutical proteins from transgenic animals," Journal of Biotechnology, 34:269-287, (1994).
Kappell et al., "Regulating gene expression in transgenic animals," Current Opinion in Biotechnology, 3:548-553, (1992).
McGovern, "The barriers to interspecific hybridization in domestic and laboratory mammals. II. Hybrid sterility," British Veterinary Journal, 132:68-75, (1976).
Montoliu et al., "Germ line transmission of yeast artificial chromosomes in transgenic mice," Reproduction, Fertility and Development, 6:577-584, (1994).
Mullins et al., "Transgenesis in nonmurine species," Hypertension, 22(4):630-633, (1993).
Mullins et al., "Perspective Series: Molecular Medicine in Genetically Engineered Animals," Journal of Clinical Investigation, 97(7):1557-1560, (1996).
Nakahori et al., "A human Y-chromosome specific repeated DNA family (DYZ1) consists of a tandem array of pentanucleotides,"Nucleic Acids Research, 14(19):7569-7580, (1986).
Rech et al., "Introduction of a yeast artificial chromosome vector into *Saccharomyces cereviseae* cells by electroporation," Nucleic Acids Research, 18(5):1313, (1990).
Schedl et al., "Transgenic mice generated by pronuclear injection of a yeast artificial chromosome," Nucleic Acids Research, 20(12):3073-3077, (1992).
Agrisoma Biosciences, "Ag Innovation Showcase Presentation PDF," 15 pages (2010).
Applied Genetics News, "Artificial chromosomes to deliver plant genes," published Feb. 2001, Retrieved from the Internet: <URL: findarticles.com/p/articles/mi_m0DED/is_7_21/ai_70907670/, [retrieved on Aug. 27, 2010] [2 pages].
Gerontology Research Group, "Chromos artificial chromosomes inherited in mice," Retrieved from the Internet: <URL: grg.org/Chromos.htm, [retrieved on Aug. 27, 2010] [1 page].

Office Action, issued Nov. 10, 2009, in connection with U.S. Appl. No. 09/724,726 (12 pages).
Office Action, issued Mar. 17, 2010, in connection with U.S. Appl. No. 10/151,078 (13 pages).
Office Action, issued Nov. 10, 2009, in connection with U.S. Appl. No. 11/355,288 (14 pages).
Office Action, issued Jul. 8, 2010, in connection with U.S. Appl. No. 12/456,142 (24 pages).
Office Action, issued Oct. 28, 2009, in connection with U.S. Appl. No. 12/456,142 (11 pages).
Agrisoma Press Release, "Agrisoma Provides Updates on Field Trials of Soybean Engineered with Minichromosomes," Sep. 10, 2009, 3 pages.
Bioworld Today, "Spin-Out Agrisoma Focuses on Enhanced Crops, Therapeutics," retrieved from the Internet:<URL: allbusiness.com/science-technology/biochemistry-genetic-biochemistry/13400764-1.html, Nov. 3, 2009 [retrieved on Aug. 25, 2010] [2 pages].
Dow Agro Sciences Press Release, "Dow Agrosciences, Agrisoma Biosciences Announce Research and Commercial License Option Agreement for Agricultural Crops," Dec 1, 2009, 2 pages.
Agrisoma website home page, retrieved from the Internet:<URL: agrisoma.com, [retrieved on Aug. 27, 2010] [6 pages].
Agrisoma Press Release, "Agrisoma provides update on ETL-engineered Brassica Field," Sep. 10, 2009, 2 pages.
Agrisoma Press Release, "Agrisoma updates on field performance of soybean engineered with mini-chromosomes," Jul. 15, 2009, 3 pages.
Agrisoma Press Release, "Agrisoma announces field trials of soybean engineered with mini-chromosomes," Jul. 10, 2009, 2 pages.
Agrisoma Press Release, "Agrisoma announces joint venture for the development of genetically improved Jatropha varieties," 2 pages.
Ag-West Bio Inc. Bio-bulletin, "Designing new plants for biofuel," 3(2):5-6 (2008).
Search Report and Written Opinion issued Nov. 6, 2009, in connection with Singapore Patent Application Serial No. 200508623-6 (9 pages).
Search Report and Written Opinion issued Aug. 16, 2010, in connection with Singapore Patent Application Serial No. 200508623-6 (21 pages).
Hasan et al., "*Escherichia coli* genome targeting, I. Cre-Lox-Mediated in vitro generation of ori-plasmids and their in vivo chromosomal integration and retrieval," Gene 150(1):51-56 (1994).
Klinger, H. and S. Shin, "Modulation of the activity of an avian gene transferred into a mammalian cell by cell fusion," Proc. Natl. Acad. Sci. 71(4):1398-1402 (1974).
Morgenstern, J. and H. Land, "Advanced mammalian gene transfer: high titre retroviral vectors with multiple drug selection markers and a complementary helper-free packaging cell line," Nucleic Acids Research 18(12):3587-3596 (1990).
Ananiev et al., "Artificial chromosome formation in maize (*Zea mays* L.)," Chromosoma 118:157-177 (2009).
Certified English translation, Murata, M., "Studies on generation and transmission control of plant artificial chromosomes," issued on Jul. 2, 2009, retrieved from the Internet:<URL: brain.naro.affrc.go.jp/tokyo/marumoto/inv up/press090702/10murata.htm, 2 pages.
Certified English translation, Murata, M., "Molecular analysis of chromosome functional elements in plants and the construction of artificial chromosomes," issued in Jul. 2006, retrieved from the Internet:<URL: jst.go.jp/kisoken/crest/report/shheisei12/syokubutsu/murata.pdf, 32 pages.
Derwent English abstract for JP 2003-102498, published Aug. 4, 2003 entitled: "Chromosome analysis, by fixing nucleic acid sample of hybrid plant, adding labeled complementary probe, detecting probe-nucleic acid hybridization, and detecting chromosome migration by detecting probe signal," Accession Nbr. 13445276 [351], 2 pages.
Liu et al., "Complementation of plant mutants with large genomic DNA fragments by a transformation-competent artificial chromosome vector accelerates positonal cloning," Proc. Natl. Acad. Sci. USA 96:6535-6540 (1999).
Murata et al., "Functional analysis of the *Arabidopsis* centromere by T-DNA insertion-induced centromere breakage," Proc. Natl. Acad. Sci. USA 105:7511-7516 (2008).
Murata et al., "The origin, meiotic behavior, and transmission of a novel minichromosome in *Arabidopsis thaliana*," Chromosoma 115:311-319 (2006).
Murata, M., Studies on generation and transmission control of plant artificial chromosomes issued on Jul. 2, 2009, retrieved from the Internet:<URL: brain.naro.affrc.go.jp/tokyo/marumoto/inv up/press090702/10murata.htm, 2 pages [in Japanese].
Murata, M., "Molecular analysis of chromosome functional elements and construction of artificial chromosomes in plants," issued in Jul. 2006, retrieved from the Internet:<URL: jst.go.jp/kisoken/crest/report/shheisei12/syokubutsu/murata.pdf, 46 pages, [in Japanese].
Somerville, C. and S. Somerville, "Plant Functional Genomics," Science 285(5426):380-383 (1999).
Office Action, issued Aug. 31, 2010, in connection with related Japanese Patent Application No. 2003-500102, 2 pages.
Office Action, issued Sep. 14, 2010, in connection with related U.S. Appl. No. 11/082,154, 13 pages.
Notice of Allowance, issued Dec. 3, 2010, in connection with related Mexican Patent Application No. PA/a/2003/010967, 1 page.
Office Action, issued Dec. 14, 2010, in connection with corresponding Japanese Patent Application No. 2005-210480, 8 pages.
Office Action, issued Dec. 21, 2010, in connection with corresponding U.S. Appl. No. 11/355,288, 17 pages.
Response and Appeal Brief, filed Feb. 15, 2011, in connection with related Japanese Patent Application No. 2003-500102, 16 pages.
Office Action, issued Feb. 28, 2011, in connection with corresponding U.S. Appl. No. 12/456,142, 14 pages.
Notice of Acceptance, issued Feb. 18, 2011, in connection with related Australian Patent Application No. 2008203023, 3 pages.
Notice of Grant, issued May 24, 2011, in connection with related Japanese Patent Application No. 2003-500102, 1 page.
Response, filed Jun. 6, 2011, in connection with corresponding Japanese Patent Application No. 2005-210480, 16 pages.
Asahara, T., "Stem cell therapy and gene transfer for regeneration", Gene Ther. 7(6):451-457 (2000).
Bennett et al., "DNA Density in Mitotic and Meiotic Metaphase Chromosomes of Plants," J Cell Sci, 63:173-179 (1983).
Blochlinger and Diggelmann "Hygromycin B Phosphotransferase as a Selectable Marker for DNA Transfer Experiments with Higher Eucaryotic Cells," Molecular and Cellular Biology, 4(12):2929 2931 (1984).
Brown, letter to the Editor in response to "Satellite DNA-based artificial chromosomes-chromosomal vectors" , TIBTECH 18:403 (2000).
Burns, J.A. and D.U. Gerstel, "Formation of Megachromosomes from Heterochromatic Blocks of *Nicotiana tomentosiformis*," Genetics 75: 497-502 (1973).
Co et al., "Generation of transgenic mice and germline transmission of a mammalian artificial chromosome introduced into embryos by pronuclear microinjection", Chromosome Res. 8(3):183-91 (2000).
Cocking, "Plant-animal cell fusions," in *Cell fusion*, Pitman Books, London (Ciba Foundation symposium 103), pp. 119 128, (1984).
Constabel, "Somatic Hybridization in Higher Plants," In Vitro, 12(11):743 748 (1976).
Csonka et al., "Novel generation of human satellite DNA-based artificial chromosomes in mammalian cells", J. Cell. Sci. 113:3207-3216 (2000).
de Jong et al., "Efficient in-vitro transfer of a 60-Mb mammalian artificial chromosome into murine and hamster cells using cationic lipids and dendrimers", Chromosome Res. 9(6):475-85 (2001).
Fatyol et al., "Cloning and molecular characterization of a novel chromosome specific centromere sequence of Chinese hamster", Nucleic Acids Research 22(18): 3728-3736 (1994).
Fehilly et al., "Interspecific chimaerism between sheep and goat", Nature 307:634-636 (1984).
Gage, F.H., "Cell therapy", Nature 392:18-24 (1998).
Gerstel, D.U., and Burns, J.A., "Phenotypic and chromosomal abnormalities associated with the introduction of heterochromatin for *Nicotiana otophora* into *N. tabacum*," Genetics 56: 483-502 (1967).
Jiang et al. "A molecular view of plant centromeres" Trends in Plant Science 8(12): 570-575 (2003).

Kuhholzer and Prather, "Advances in Livestock Nuclear Transfer", The Society for Experimental Biology and Medicine 224:240-245 (2000).
Maluszynska and Heslop-Harrison, "Localization of tandemly repearted DNA sequences in *Arabidopsis thaliana*," The Plant Journal, 1(2):159-166 (1991).
Marschall et al., "Transfer of YACs up to 2.3 Mb intact into human cells with polyethylenimine", Gene Ther. 6(9):1634-1637 (1999).
McClintock, "The Fusion of Broken Ends of Chromosomes Following Nuclear Fusion," Genetics, 28:458-463 (1942).
Miranda et al., "Agrobacterium tumefaciens Transfers Extremely Long T-DNAs by a Unidirectional Mechanism," Journal of Bacteriology, 174(7):2288-2297, (1992).
Monteith et al., "Pronuclear microinjection of purified artificial chromosomes for generation of transgenic mice: pick-and-inject technique," Method Mol. Biol. 240:227-42 (2004).
Murata et al., "Centromeric repetitive sequences in *Arabidopsis thaliana*," Jpn. J. Genet., 69:361-370 (1994).
Oberle V, de Jong, G, Drayer, J, Hoekstra, D, "Efficient transfer of chromosome-based DNA constructs into mammalian cells," Biochimica et Biophysica Acta 1676: 223-30 (2004).
Parokonny, et al., "Genome reorganization in *Nicotiana* asymmetric somatic hybrids analysed by in situ hybridzation," The Plant Journal, 2(6):863-874 (1992).
Perez, CF, Vanderbyl SL, Mills KA, Ledebur HC, "The ACE System: A versatile chromosome engineering technology with applications for gene-based cell therapy", BioProcessing 2004; 3:61-68.
Richards, "Plant Telomeres," Cold Spring Harbor Laboratory Press, pp. 371-387 (1995).
Samstein and Platt, "Physiologic and immunologic hurdles to xenotransplantation", J. Am. Soc. Nephrol. 12:182-193 (2001).
Schmidt et al., "Physical Map and Organization of *Arabidopsis thaliana* Chromosome 4," Science, 270:480-483, 1995.
Shen et al., "A structurally defined mini-chromosome vector for the mouse germ line", Current Biology 10:31-34 (2000).
Sparvoli et al., "Replicon clusters may form structurally stable complexes of chromatin and chromosomes," Journal of Cell Science, 107:3097-3103 (1994).
Spencer et al., "Bialaphos selection of stable transformants from maize cell culture," Theor Appl Genet, 79:625-631 (1990).
Stewart et al., "Retrofitting of a satellite repeat DNA-based murine artificial chromosome (ACes) to contain loxP recombination sites", Gene Ther. Jun;9(11):719-23 (2002).
Stice et al., "Cloning: New breakthroughs leading to commercial opportunities," Therigeneology 49:129-138 (1998).
Szakal B, Cserpan I, Csonka E, Monostori E, Udvardy A, Hadlaczky G, "Cloning, characterization and localization of Chinese hamster HP1 isoforms", Chromosome Res. 12(5):483-93 (2004).
Thompson et al., "Characterization of the herbicide-resistance gene bar from *Streptomyces hygroscopicus*," The EMBO Journal, 6(9):2519 2523, 1987.
Unfried and Gruendler, "Nucleotide sequence of the 5.8S and 25S rRNA genes and of the internal transcribed spacers from *Arabidopsis thaliana*," Nucleic Acids Res., 18 (13), 4011 (1990).
Van Beusechem and Valerio, "Gene transfer into hematopoietic stem cells of nonhuman primates", Hum. Gene Ther. 7(14):1649-1668 (1996).
Vanderbyl et al., "A flow cytometry technique for measuring chromosome-mediated gene transfer", Cytometry 44(2):100-105 (2000).
Vanderbyl S, MacDonald GN, Sidhu S, Gung L, Telenius A, Perez C, Perkins E, "Transfer and stable transgene expression of a mammalian artificial chromosome into bone marrow-derived human mesenchymal stem cells", Stem Cells 22(3):324-33 (2004).
Vega et al., "Chromosome painting in plants: In situ hybridization with a DNA probe from a specific microdissected chromosome arm of common wheat," Proc. Natl. Acad. Sci. USA, 91:12041-12045 (1994).
Vickers et al., "A Protocol for the Efficient Screening of Putatively Transformed Plants for bar, the Selectable Marker Gene, Using the Polymerase Chain Reaction," Plant Molecular Biology Reporter, 14(4):363-368 (1996).
Wada et al., "HPRT yeast artificial chromosome transfer into human cells by four methods and an involvement of homologous recombination", Biochem. Biophys. Res. Commun. 200(3):1693-1700 (1994).
Wang et al., "Expression of a reporter gene after microinjection of mammalian artificial chromosomes into pronuclei of bovine zygotes," Mol Reprod Dev. Dec;60(4):433-8 (2001).
Wanner and Formanek, "Imaging of DNA in human and plant chromosomes by high-resolution scanning electron microscopy," Chromosome Research, 3:368-374 (1995).
Weldon Jones et al., "Interkingdom Fusion Between Human (HeLa) Cells and Tobacco Hybrid (GGLL) Protoplasts," Science, 193:401-403 (1976).
White et al., "A cassette containing the bar gene of *Streptomyces hygroscopicus*: a selectable marker for plant transformation," Nucleic Acids Research, 18(4):1062 (1989).
Wolf et al., "Nuclear transfer in mammals: Recent developments and future perspectives", J. Biotech. 65:99-110 (1998).
Yanagimachi, "Cloning: Experience from the mouse and other animals", Mol. Cell. Endocrin. 187:241-248 (2002).
Assaad et al., "Somatic and germinal recombination of a direct repeat in *Arabidopsis*.," Genetics 132:553-566 (1992).
Office Action, issued Aug. 9, 2011 in connection with Japanese Patent Application No. 2005-210480, with English Translation, 11 pages.
Puchta, H., "Gene replacement by homologous recombination in plants," Plant Mol. Biol. 48:173-182 (2002).
Schaefer, D., "Gene targeting in *Physcomitrella patens*," Curr. Opin. Plant Biol. 4: 143-150 (2001).
Schaefer, D. and Zryd, J., "Efficient gene targeting in the moss *Physcomitrella patens*," Plant J. 11: 1195-1206 (1997).

* cited by examiner

ARTIFICIAL CHROMOSOMES, USES THEREOF AND METHODS FOR PREPARING ARTIFICIAL CHROMOSOMES

RELATED APPLICATIONS

This application is a continuation of U.S. application Ser. No. 10/125,767, now abandoned filed Apr. 17, 2002, to GYULA HADLACZKY, entitled ARTIFICIAL CHROMOSOMES, USES THEREOF AND METHODS FOR PREPARING ARTIFICIAL CHROMOSOMES, which is a divisional of U.S. application Ser. No. 09/724,693, now abandoned, filed Nov. 28, 2000, to GYULA HADLACZKY and ALADAR SZALAY, entitled ARTIFICIAL CHROMOSOMES, USES THEREOF AND METHODS FOR PREPARING ARTIFICIAL CHROMOSOMES, which is a continuation of U.S. application Ser. No. 08/835,682, now abandoned, filed Apr. 10, 1997, to GYULA HADLACZKY and ALADAR SZALAY, entitled ARTIFICIAL CHROMOSOMES, USES THEREOF AND METHODS FOR PREPARING ARTIFICIAL CHROMOSOMES, which is a continuation-in-part of U.S. application Ser. No. 08/695,191, filed Aug. 7, 1996, now U.S. Pat. No. 6,025,155, to GYULA HADLACZKY and ALADAR SZALAY, entitled ARTIFICIAL CHROMOSOMES, USES THEREOF AND METHODS FOR PREPARING ARTIFICIAL CHROMOSOMES, which is a continuation-in-part of U.S. application Ser. No. 08/682,080, filed Jul. 15, 1996, now U.S. Pat. No. 6,077,697, to GYULA HADLACZKY and ALADAR SZALAY, entitled ARTIFICIAL CHROMOSOMES, USES THEREOF AND METHODS FOR PREPARING ARTIFICIAL CHROMOSOMES, which is a continuation-in-part of U.S. application Ser. No. 08/629,822, filed Apr. 10, 1996, now abandoned, to GYULA HADLACZKY and ALADAR SZALAY, entitled ARTIFICIAL CHROMOSOMES, USES THEREOF AND METHODS FOR PREPARING ARTIFICIAL CHROMOSOMES.

This application also is a continuation of U.S. application Ser. No. 10/151,081, now abandoned filed May 16, 2002, to GYULA HADLACZKY and ALADAR SZALAY, entitled ARTIFICIAL CHROMOSOMES, USES THEREOF AND METHODS FOR PREPARING ARTIFICIAL CHROMOSOMES, which is a divisional application of U.S. application Ser. No. 09/799,462, now abandoned filed Mar. 5, 2001, which is a continuation of U.S. application Ser. No. 08/835,682, now abandoned, which is a continuation-in-part of U.S. application Ser. No. 08/695,191, now U.S. Pat. No. 6,025,155, which is a continuation-in-part of U.S. application Ser. No. 08/682,080, now U.S. Pat. No. 6,077,697, which is a continuation-in-part of U.S. application Ser. No. 08/629,822, now abandoned.

This application also is a continuation of U.S. application Ser. No. 09/799,462, now abandoned filed Mar. 5, 2001, which is a continuation of U.S. application Ser. No. 08/835,682, now abandoned, which is a continuation-in-part of U.S. application Ser. No. 08/695,191, now U.S. Pat. No. 6,025,155, which is a continuation-in-part of U.S. application Ser. No. 08/682,080, now U.S. Pat. No. 6,077,697, which is a continuation-in-part of U.S. application Ser. No. 08/629,822, now abandoned.

This application also is a continuation of U.S. Application Ser. No. 10/151,078, now abandoned filed May 16, 2002, to GYULA HADLACZKY and ALADAR SZALAY, entitled ARTIFICIAL CHROMOSOMES, USES THEREOF AND METHODS FOR PREPARING ARTIFICIAL CHROMOSOMES, which is a divisional of U.S. application Ser. No. 09/724,872, now abandoned filed Nov. 28, 2000, to GYULA HADLACZKY and ALADAR SZALAY, entitled ARTIFICIAL CHROMOSOMES, USES THEREOF AND METHODS FOR PREPARING ARTIFICIAL CHROMOSOMES, which is a continuation of U.S. application Ser. No. 08/835,682, now abandoned, which is a continuation-in-part of U.S. application Ser. No. 08/695,191, now U.S. Pat. No. 6,025,155, which is a continuation-in-part of U.S. application Ser. No. 08/682,080, now U.S. Pat. No. 6,077,697, which is a continuation-in-part of U.S. application Ser. No. 08/629,822, now abandoned.

This application also is a continuation of U.S. application Ser. No. 10/287,313, filed Nov. 1, 2002 now abandoned, to GYULA HADLACZKY and ALADAR SZALAY, entitled ARTIFICIAL CHROMOSOMES, USES THEREOF AND METHODS FOR PREPARING ARTIFICIAL CHROMOSOMES, which is a divisional of U.S. application Ser. No. 09/724,726, filed Nov. 28, 2000 now abandoned, to GYULA HADLACZKY and ALADAR SZALAY, entitled ARTIFICIAL CHROMOSOMES, USES THEREOF AND METHODS FOR PREPARING ARTIFICIAL CHROMOSOMES, which is a divisional of U.S. application Ser. No. 08/835,682, now abandoned, which is a continuation-in-part of U.S. application Ser. No. 08/695,191, now U.S. Pat. No. 6,025,155, which is a continuation-in-part of U.S. application Ser. No. 08/682,080, now U.S. Pat. No. 6,077,697, which is a continuation-in-part of U.S. application Ser. No. 08/629,822, now abandoned.

This application also is a continuation of U.S. application Ser. No. 10/808,689, now abandoned filed Mar. 24, 2004 to GYULA HADLACZKY, entitled ARTIFICIAL CHROMOSOMES, USES THEREOF AND METHODS FOR PREPARING ARTIFICIAL CHROMOSOMES, which is a divisional of U.S. application Ser. No. 09/724,693, now abandoned, filed Nov. 28, 2000, which is a continuation of U.S. application Ser. No. 08/835,682, now abandoned, which is a continuation-in-part of U.S. application Ser. No. 08/695,191, now U.S. Pat. No. 6,025,155, which is a continuation-in-part of U.S. application Ser. No. 08/682,080, now U.S. Pat. No. 6,077,697, which is a continuation-in-part of U.S. application Ser. No. 08/629,822, now abandoned.

This application also is a continuation of U.S. application Ser. No. 10/219,694, now abandoned filed Aug. 14, 2002 to GYULA HADLACZKY, entitled ARTIFICIAL CHROMOSOMES, USES THEREOF AND METHODS FOR PREPARING ARTIFICIAL CHROMOSOMES, which is a divisional of U.S. application Ser. No. 09/724,693, now abandoned, filed Nov. 28, 2000, which is a continuation of U.S. application Ser. No. 08/835,682, now abandoned, which is a continuation-in-part of U.S. application Ser. No. 08/695,191, now U.S. Pat. No. 6,025,155, which is a continuation-in-part of U.S. application Ser. No. 08/682,080, now U.S. Pat. No. 6,077,697, which is a continuation-in-part of U.S. application Ser. No. 08/629,822, now abandoned.

Benefit of priority under 35 U.S.C. §120 is claimed to each of the above-noted applications and patents. The subject matter of each of the above-noted U.S. applications and patents is incorporated in its entirety by reference thereto.

FIELD OF THE INVENTION

The present invention relates to methods for preparing cell lines that contain artificial chromosomes, methods for isolation of the artificial chromosomes, targeted insertion of heterologous DNA into the chromosomes, delivery of the chromosomes to selected cells and tissues and methods for isolation and large-scale production of the chromosomes. Also provided are cell lines for use in the methods, and cell lines and chromosomes produced by the methods. Further provided are cell-based methods for production of heterologous proteins, gene therapy methods and methods of generating transgenic animals, particularly non-human transgenic animals, that use artificial chromosomes.

BACKGROUND OF THE INVENTION

Several viral vectors, non-viral, and physical delivery systems for gene therapy and recombinant expression of heterologous nucleic acids have been developed (see, e.g., Mitani et al. (1993) *Trends Biotech.* 11:162-166). The presently available systems, however, have numerous limitations, particularly where persistent, stable, or controlled gene expression is required. These limitations include: (1) size limitations because there is a limit, generally on order of about ten kilobases (kB), at most, to the size of the DNA insert (gene) that can be accepted by viral vectors, whereas a number of mammalian genes of possible therapeutic importance are well above this limit, especially if all control elements are included; (2) the inability to specifically target integration so that random integration occurs which carries a risk of disrupting vital genes or cancer suppressor genes; (3) the expression of randomly integrated therapeutic genes may be affected by the functional compartmentalization in the nucleus and are affected by chromatin-based position effects; (4) the copy number and consequently the expression of a given gene to be integrated into the genome cannot be controlled. Thus, improvements in gene delivery and stable expression systems are needed (see, e.g., Mulligan (1993) *Science* 260:926-932).

In addition, safe and effective vectors and gene therapy methods should have numerous features that are not assured by the presently available systems. For example, a safe vector should not contain DNA elements that can promote unwanted changes by recombination or mutation in the host genetic material, should not have the potential to initiate deleterious effects in cells, tissues, or organisms carrying the vector, and should not interfere with genomic functions. In addition, it would be advantageous for the vector to be non-integrative, or designed for site-specific integration. Also, the copy number of therapeutic gene(s) carried by the vector should be controlled and stable, the vector should secure the independent and controlled function of the introduced gene(s); and the vector should accept large (up to Mb size) inserts and ensure the functional stability of the insert.

The limitations of existing gene delivery technologies, however, argue for the development of alternative vector systems suitable for transferring large (up to Mb size or larger) genes and gene complexes together with regulatory elements that will provide a safe, controlled, and persistent expression of the therapeutic genetic material.

At the present time, none of the available vectors fulfill all these requirements. Most of these characteristics, however, are possessed by chromosomes. Thus, an artificial chromosome would be an ideal vector for gene therapy, as well as for stable, high-level, controlled production of gene products that require coordination of expression of numerous genes or that are encoded by large genes, and other uses. Artificial chromosomes for expression of heterologous genes in yeast are available, but construction of defined mammalian artificial chromosomes has not been achieved. Such construction has been hindered by the lack of an isolated, functional, mammalian centromere and uncertainty regarding the requisites for its production and stable replication. Unlike in yeast, there are no selectable genes in close proximity to a mammalian centromere, and the presence of long runs of highly repetitive pericentric heterochromatic DNA makes the isolation of a mammalian centromere using presently available methods, such as chromosome walking, virtually impossible. Other strategies are required for production of mammalian artificial chromosomes, and some have been developed. For example, U.S. Pat. No. 5,288,625 provides a cell line that contains an artificial chromosome, a minichromosome, that is about 20 to 30 megabases. Methods provided for isolation of these chromosomes, however, provide preparations of only about 10-20% purity. Thus, development of alternative artificial chromosomes and perfection of isolation and purification methods as well as development of more versatile chromosomes and further characterization of the minichromosomes is required to realize the potential of this technology.

Therefore, it is an object herein to provide mammalian artificial chromosomes and methods for introduction of foreign DNA into such chromosomes. It is also an object herein to provide methods of isolation and purification of the chromosomes. It is also an object herein to provide methods for introduction of the mammalian artificial chromosome into selected cells, and to provide the resulting cells, as well as transgenic non-human animals, birds, fish and plants that contain the artificial chromosomes. It is also an object herein to provide methods for gene therapy and expression of gene products using artificial chromosomes. It is a further object herein to provide methods for constructing species-specific artificial chromosomes de novo. Another object herein is to provide methods to generate de novo mammalian artificial chromosomes.

SUMMARY OF THE INVENTION

Mammalian artificial chromosomes (MACs) are provided. Also provided are artificial chromosomes for other higher eukaryotic species, such as insects, birds, fowl and fish, produced using the MACS and methods provided herein. Methods for generating and isolating such chromosomes are provided. Methods using the MACs to construct artificial chromosomes from other species, such as insect, bird, fowl and fish species are also provided. The artificial chromosomes are fully functional stable chromosomes. Two types of artificial chromosomes are provided. One type, herein referred to as SATACs (satellite artificial chromosomes or satellite DNA based artificial chromosomes, the terms are used interchangeably herein) are stable heterochromatic chromosomes, and the other type are minichromosomes based on amplification of euchromatin.

Artificial chromosomes provide an extra-genomic locus for targeted integration of megabase (Mb) pair size DNA fragments that contain single or multiple genes, including multiple copies of a single gene operatively linked to one promoter or each copy or several copies linked to separate promoters. Thus, methods using the MACs to introduce the genes into cells, tissues, and animals, as well as species such as birds, fowl, fish and plants, are also provided. The artificial chromosomes with integrated heterologous DNA may be used in methods of gene therapy, in methods of production of gene products, particularly products that require expression of multigenic biosynthetic pathways, and also are intended for delivery into the nuclei of germline cells, such as embryo-derived stem cells (ES cells), for production of transgenic (non-human) animals, birds, fowl and fish. Transgenic plants, including monocots and dicots, are also contemplated herein.

Mammalian artificial chromosomes provide extra-genomic specific integration sites for introduction of genes encoding proteins of interest and permit megabase size DNA integration so that, for example, genes encoding an entire metabolic pathway or a very large gene, such as the cystic fibrosis (CF; ~250 kb) genomic DNA gene, several genes, such as multiple genes encoding a series of antigens for preparation of a multivalent vaccine, can be stably introduced into a cell. Vectors for targeted introduction of such genes, including the tumor suppressor genes, such as p53, the cystic fibrosis transmembrane regulator cDNA (CFTR), and the genes for anti-HIV ribozymes, such as an anti-HIV gag ribozyme gene, into the artificial chromosomes are also provided.

The chromosomes provided herein are generated by introducing heterologous DNA that includes DNA encoding one or multiple selectable marker(s) into cells, preferably a stable cell line, growing the cells under selective conditions, and identifying from among the resulting clones those that include chromosomes with more than one centromere and/or fragments thereof. The amplification that produces the additional centromere or centromeres occurs in cells that contain chromosomes in which the heterologous DNA has integrated near the centromere in the pericentric region of the chromosome. The selected clonal cells are then used to generate artificial chromosomes.

Although non-targeted introduction of DNA, which results in some frequency of integration into appropriate loci, targeted introduction is preferred. Hence, in preferred embodiments, the DNA with the selectable marker that is introduced into cells to initiate generation of artificial chromosomes includes sequences that target it to the an amplifiable region, such as the pericentric region, heterochromatin, and particularly rDNA of the chromosome. For example, vectors, such as pTEMPUD and pHASPUD (provided herein), which include such DNA specific for mouse satellite DNA and human satellite DNA, respectively, are provided. The plasmid pHASPUD is a derivative of pTEMPUD that contains human satellite DNA sequences that specifically target human chromosomes. Preferred targeting sequences include mammalian ribosomal RNA (rRNA) gene sequences (referred to herein as rDNA) which target the heterologous DNA to integrate into the rDNA region of those chromosomes that contain rDNA. For example, vectors, such as pTERPUD, which include mouse rDNA, are provided. Upon integration into existing chromosomes in the cells, these vectors can induce the amplification that results in generation of additional centromeres.

Artificial chromosomes are generated by culturing the cells with the multicentric, typically dicentric, chromosomes under conditions whereby the chromosome breaks to form a minichromosome and formerly dicentric chromosome. Among the MACs provided herein are the SATACs, which are primarily made up of repeating units of short satellite DNA and are nearly fully heterochromatic, so that without insertion of heterologous or foreign DNA, the chromosomes preferably contain no genetic information or contain only non-protein-encoding gene sequences such as rDNA sequences. They can thus be used as "safe" vectors for delivery of DNA to mammalian hosts because they do not contain any potentially harmful genes. The SATACs are generated, not from the minichromosome fragment as, for example, in U.S. Pat. No. 5,288,625, but from the fragment of the formerly dicentric chromosome.

In addition, methods for generating euchromatic minichromosomes and the use thereof are also provided herein. Methods for generating one type of MAC, the minichromosome, previously described in U.S. Pat. No. 5,288,625, and the use thereof for expression of heterologous DNA are provided. In a particular method provided herein for generating a MAC, such as a minichromosome, heterologous DNA that includes mammalian rDNA and one or more selectable marker genes is introduced into cells which are then grown under selective conditions. Resulting cells that contain chromosomes with more than one centromere are selected and cultured under conditions whereby the chromosome breaks to form a minichromosome and a formerly multicentric (typically dicentric) chromosome from which the minichromosome was released.

Cell lines containing the minichromosome and the use thereof for cell fusion are also provided. In one embodiment, a cell line containing the mammalian minichromosome is used as recipient cells for donor DNA encoding a selected gene or multiple genes. To facilitate integration of the donor DNA into the minichromosome, the recipient cell line preferably contains the minichromosome but does not also contain the formerly dicentric chromosome. This may be accomplished by methods disclosed herein such as cell fusion and selection of cells that contain a minichromosome and no formerly dicentric chromosome. The donor DNA is linked to a second selectable marker and is targeted to and integrated into the minichromosome. The resulting chromosome is transferred by cell fusion into an appropriate recipient cell line, such as a Chinese hamster cell line (CHO). After large-scale production of the cells carrying the engineered chromosome, the chromosome is isolated. In particular, metaphase chromosomes are obtained, such as by addition of colchicine, and they are purified from the cell lysate. These chromosomes are used for cloning, sequencing and for delivery of heterologous DNA into cells.

Also provided are SATACs of various sizes that are formed by repeated culturing under selective conditions and subcloning of cells that contain chromosomes produced from the formerly dicentric chromosomes. The exemplified SATACs are based on repeating DNA units that are about 15 Mb (two ~7.5 Mb blocks). The repeating DNA unit of SATACs formed from other species and other chromosomes may vary, but typically would be on the order of about 7 to about 20 Mb. The repeating DNA units are referred to herein as megareplicons, which in the exemplified SATACs contain tandem blocks of satellite DNA flanked by non-satellite DNA, including heterologous DNA and non-satellite DNA. Amplification produces an array of chromosome segments (each called an amplicon) that contain two inverted megareplicons bordered by heterologous ("foreign") DNA. Repeated cell fusion, growth on selective medium and/or BrdU (5-bromodeoxyuridine) treatment or other treatment with other genome destabilizing reagent or agent, such as ionizing radiation, including X-rays, and subcloning results in cell lines that carry stable heterochromatic or partially heterochromatic chromosomes, including a 150-200 Mb "sausage" chromosome, a 500-1000 Mb gigachromosome, a stable 250-400 Mb megachromosome and various smaller stable chromosomes derived therefrom. These chromosomes are based on these repeating units and can include heterologous DNA that is expressed.

Thus, methods for producing MACs of both types (i.e., SATACS and minichromosomes) are provided. These methods are applicable to the production of artificial chromosomes containing centromeres derived from any higher eukaryotic cell, including mammals, birds, fowl, fish, insects and plants.

The resulting chromosomes can be purified by methods provided herein to provide vectors for introduction of heterologous DNA into selected cells for production of the gene product(s) encoded by the heterologous DNA, for production of transgenic (non-human) animals, birds, fowl, fish and plants or for gene therapy.

In addition, methods and vectors for fragmenting the minichromosomes and SATACs are provided. Such methods and vectors can be used for in vivo generation of smaller stable artificial chromosomes. Vectors for chromosome fragmentation are used to produce an artificial chromosome that contains a megareplicon, a centromere and two telomeres and will be between about 7.5 Mb and about 60 Mb, preferably between about 10 Mb-15 Mb and 30-50 Mb. As exemplified herein, the preferred range is between about 7.5 Mb and 50 Mb. Such artificial chromosomes may also be produced by other methods.

Isolation of the 15 Mb (or 30 Mb amplicon containing two 15 Mb inverted repeats) or a 30 Mb or higher multimer, such as 60 Mb, thereof should provide a stable chromosomal vector that can be manipulated in vitro. Methods for reducing the size of the MACs to generate smaller stable self-replicating artificial chromosomes are also provided.

Also provided herein, are methods for producing mammalian artificial chromosomes, including those provided herein, in vitro, and the resulting chromosomes. The methods involve in vitro assembly of the structural and functional elements to provide a stable artificial chromosome. Such elements include a centromere, two telomeres, at least one origin of replication and filler heterochromatin, e.g., satellite DNA. A selectable marker for subsequent selection is also generally included. These specific DNA elements may be obtained from the artificial chromosomes provided herein such as those that have been generated by the introduction of heterologous DNA into cells and the subsequent amplification that leads to the artificial chromosome, particularly the SATACs. Centromere sequences for use in the in vitro construction of artificial chromosomes may also be obtained by employing the centromere cloning methods provided herein. In preferred embodiments, the sequences providing the origin of replication, in particular, the megareplicator, are derived from rDNA. These sequences preferably include the rDNA origin of replication and amplification promoting sequences.

Methods and vectors for targeting heterologous DNA into the artificial chromosomes are also provided as are methods and vectors for fragmenting the chromosomes to produce smaller but stable and self-replicating artificial chromosomes.

The chromosomes are introduced into cells to produce stable transformed cell lines or cells, depending upon the source of the cells. Introduction is effected by any suitable method including, but not limited to electroporation, direct uptake, such as by calcium phosphate precipitation, uptake of isolated chromosomes by lipofection, by microcell fusion, by lipid-mediated carrier systems or other suitable method. The resulting cells can be used for production of proteins in the cells. The chromosomes can be isolated and used for gene delivery. Methods for isolation of the chromosomes based on the DNA content of the chromosomes, which differs in MACs versus the authentic chromosomes, are provided. Also provided are methods that rely on content, particularly density, and size of the MACs.

These artificial chromosomes can be used in gene therapy, gene product production systems, production of humanized genetically transformed animal organs, production of transgenic plants and animals (non-human), including mammals, birds, fowl, fish, invertebrates, vertebrates, reptiles and insects, any organism or device that would employ chromosomal elements as information storage vehicles, and also for analysis and study of centromere function, for the production of artificial chromosome vectors that can be constructed in vitro, and for the preparation of species-specific artificial chromosomes. The artificial chromosomes can be introduced into cells using microinjection, cell fusion, microcell fusion, electroporation, nuclear transfer, electrofusion, projectile bombardment, nuclear transfer, calcium phosphate precipitation, lipid-mediated transfer systems and other such methods.

Cells particularly suited for use with the artificial chromosomes include, but are not limited to plant cells, particularly tomato, *arabidopsis*, and others, insect cells, including silk worm cells, insect larvae, fish, reptiles, amphibians, arachnids, mammalian cells, avian cells, embryonic stem cells, haematopoietic stem cells, embryos and cells for use in methods of genetic therapy, such as lymphocytes that are used in methods of adoptive immunotherapy and nerve or neural cells. Thus methods of producing gene products and transgenic (non-human) animals and plants are provided. Also provided are the resulting transgenic animals and plants.

Exemplary cell lines that contain these chromosomes are also provided.

Methods for preparing artificial chromosomes for particular species and for cloning centromeres are also provided. For example, two exemplary methods provided for generating artificial chromosomes for use in different species are as follows. First, the methods herein may be applied to different species. Second, means for generating species-specific artificial chromosomes and for cloning centromeres are provided. In particular, a method for cloning a centromere from an animal or plant is provided by preparing a library of DNA fragments that contain the genome of the plant or animal and introducing each of the fragments into a mammalian satellite artificial chromosome (SATAC) that contains a centromere from a species, generally a mammal, different from the selected plant or animal, generally a non-mammal, and a selectable marker. The selected plant or animal is one in which the mammalian species centromere does not function. Each of the SATACs is introduced into the cells, which are grown under selective conditions, and cells with SATACs are identified. Such SATACS should contain a centromere encoded by the DNA from the library or should contain the necessary elements for stable replication in the selected species.

Also provided are libraries in which the relatively large fragments of DNA are contained on artificial chromosomes.

Transgenic (non-human) animals, invertebrates and vertebrates, plants and insects, fish, reptiles, amphibians, arachnids, birds, fowl, and mammals are also provided. Of particular interest are transgenic (non-human) animals and plants that express genes that confer resistance or reduce susceptibility to disease. For example, the transgene may encode a protein that is toxic to a pathogen, such as a virus, bacterium or pest, but that is not toxic to the transgenic host. Furthermore, since multiple genes can be introduced on a MAC, a series of genes encoding an antigen can be introduced, which upon expression will serve to immunize (in a manner similar to a multivalent vaccine) the host animal against the diseases for which exposure to the antigens provide immunity or some protection.

Also of interest are transgenic (non-human) animals that serve as models of certain diseases and disorders for use in studying the disease and developing therapeutic treatments and cures thereof. Such animal models of disease express genes (typically carrying a disease-associated mutation), which are introduced into the animal on a MAC and which induce the disease or disorder in the animal. Similarly, MACs carrying genes encoding antisense RNA may be introduced into animal cells to generate conditional "knock-out" transgenic (non-human) animals. In such animals, expression of the antisense RNA results in decreased or complete elimination of the products of genes corresponding to the antisense RNA. Of further interest are transgenic mammals that harbor MAC-carried genes encoding therapeutic proteins that are expressed in the animal's milk. Transgenic (non-human) animals for use in xenotransplantation, which express MAC-carried genes that serve to humanize the animal's organs, are also of interest. Genes that might be used in humanizing animal organs include those encoding human surface antigens.

Methods for cloning centromeres, such as mammalian centromeres, are also provided. In particular, in one embodiment, a library composed of fragments of SATACs are cloned into YACs (yeast artificial chromosomes) that include a detectable marker, such as DNA encoding tyrosinase, and then introduced into mammalian cells, such as albino mouse embryos. Mice produced from embryos containing such YACs that include a centromere that functions in mammals will express the detectable marker. Thus, if mice are produced from albino mouse embryos into which a functional mammalian centromere was introduced, the mice will be pigmented or have regions of pigmentation.

A method for producing repeated tandem arrays of DNA is provided. This method, exemplified herein using telomeric DNA, is applicable to any repeat sequence, and in particular, low complexity repeats. The method provided herein for synthesis of arrays of tandem DNA repeats are based in a series of extension steps in which successive doublings of a sequence of repeats results in an exponential expansion of the array of tandem repeats. An embodiment of the method of synthesizing DNA fragments containing tandem repeats may generally be described as follows. Two oligonucleotides are used as starting materials. Oligonucleotide 1 is of length k of repeated sequence (the flanks of which are not relevant) and contains a relatively short stretch (60-90 nucleotides) of the repeated sequence, flanked with appropriately chosen restriction sites:

```
5'-S1>>>>>>>>>>>>>>>>>>>>>>>>>>>S2  -3'
```

where S1 is restriction site 1 cleaved by E1, S2 is a second restriction site cleaved by E2> represents a simple repeat unit, and '_' denotes a short (8-10) nucleotide flanking sequence complementary to oligonucleotide 2:

```
3'-    S3-5'
```

where S3 is a third restriction site for enzyme E3 and which is present in the vector to be used during the construction. The method involves the following steps: (1) oligonucleotides 1 and 2 are annealed; (2) the annealed oligonucleotides are filled-in to produce a double-stranded (ds) sequence; (3) the double-stranded DNA is cleaved with restriction enzymes E1 and E3 and subsequently ligated into a vector (e.g., pUC19 or a yeast vector) that has been cleaved with the same enzymes E1 and E3; (4) the insert is isolated from a first portion of the plasmid by digesting with restriction enzymes E1 and E3, and a second portion of the plasmid is cut with enzymes E2 (treated to remove the 3'-overhang) and E3, and the large fragment (plasmid DNA plus the insert) is isolated; (5) the two DNA fragments (the S1-S3 insert fragment and the vector plus insert) are ligated; and (6) steps 4 and 5 are repeated as many times as needed to achieve the desired repeat sequence size. In each extension cycle, the repeat sequence size doubles, i.e., if m is the number of extension cycles, the size of the repeat sequence will be $k \times 2^m$ nucleotides.

DETAILED DESCRIPTION OF PREFERRED EMBODIMENTS

Definitions

Figure 1:
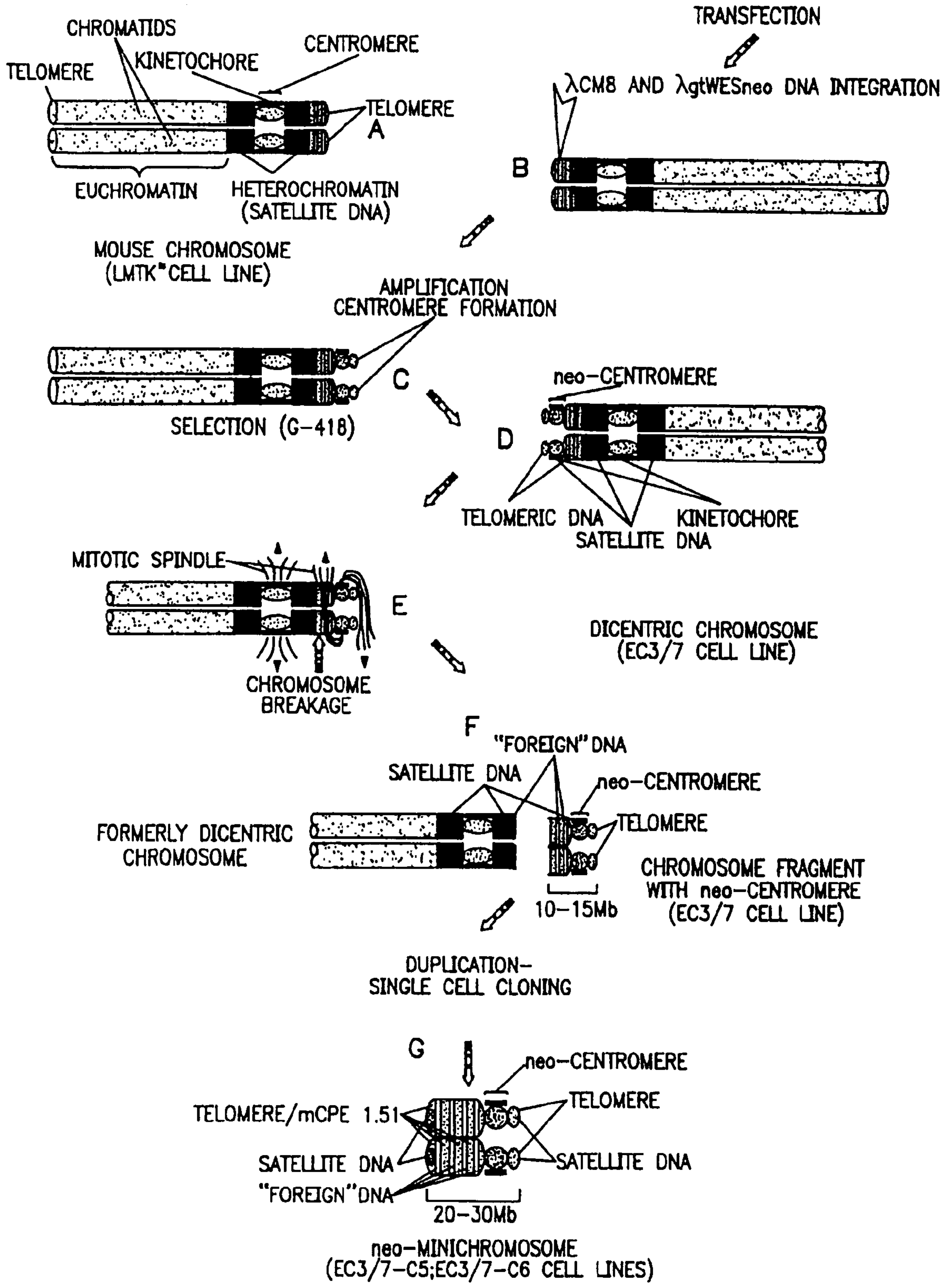
FIG. 1 is a schematic drawing depicting formation of the MMCneo (the minichromosome) chromosome. A-G represents the successive events consistent with observed data that would lead to the formation and stabilization of the minichromosome.

Unless defined otherwise, all technical and scientific terms used herein have the same meaning as is commonly understood by one of skill in the art to which this invention belongs. All patents and publications referred to herein are incorporated by reference.

As used herein, a mammalian artificial chromosome (MAC) is a piece of DNA that can stably replicate and segregate alongside endogenous chromosomes. It has the capacity to accommodate and express heterologous genes inserted therein. It is referred to as a mammalian artificial chromosome because it includes an active mammalian centromere(s). Plant artificial chromosomes, insect artificial chromosomes and avian artificial chromosomes refer to chromosomes that include plant and insect centromeres, respectively. A human artificial chromosome (HAC) refers to chromosomes that include human centromeres, BUGACs refer to insect artificial chromosomes, and AVACs refer to avian artificial chromosomes. Among the MACs provided herein are SATACs, minichromosomes, and in vitro synthesized artificial chromosomes. Methods for construction of each type are provided herein.

As used herein, in vitro synthesized artificial chromosomes are artificial chromosomes that is produced by joining the essential components (at least the centromere, and origins of replication) in vitro.

As used herein, endogenous chromosomes refer to genomic chromosomes as found in the cell prior to generation or introduction of a MAC.

As used herein, stable maintenance of chromosomes occurs when at least about 85%, preferably 90%, more preferably 95%, of the cells retain the chromosome. Stability is measured in the presence of a selective agent. Preferably these chromosomes are also maintained in the absence of a selective agent. Stable chromosomes also retain their structure during cell culturing, suffering neither intrachromosomal nor interchromosomal rearrangements.

As used herein, growth under selective conditions means growth of a cell under conditions that require expression of a selectable marker for survival.

As used herein, an agent that destabilizes a chromosome is any agent known by those of skill in the art to enhance amplification events, mutations. Such agents, which include BrdU, are well known to those of skill in the art.

As used herein, de novo with reference to a centromere, refers to generation of an excess centromere as a result of incorporation of a heterologous DNA fragment using the methods herein.

As used herein, euchromatin and heterochromatin have their recognized meanings, euchromatin refers to chromatin that stains diffusely and that typically contains genes, and heterochromatin refers to chromatin that remains unusually condensed and that has been thought to be transcriptionally inactive. Highly repetitive DNA sequences (satellite DNA), at least with respect to mammalian cells, are usually located in regions of the heterochromatin surrounding the centromere (pericentric heterochromatin). Constitutive heterochromatin refers to heterochromatin that contains the highly repetitive DNA which is constitutively condensed and genetically inactive.

As used herein, BrdU refers to 5-bromodeoxyuridine, which during replication is inserted in place of thymidine. BrdU is used as a mutagen; it also inhibits condensation of metaphase chromosomes during cell division.

As used herein, a dicentric chromosome is a chromosome that contains two centromeres. A multicentric chromosome contains more than two centromeres.

As used herein, a formerly dicentric chromosome is a chromosome that is produced when a dicentric chromosome fragments and acquires new telomeres so that two chromosomes, each having one of the centromeres, are produced. Each of the fragments are replicable chromosomes. If one of the chromosomes undergoes amplification of euchromatic DNA to produce a fully functional chromosome that contains the newly introduced heterologous DNA and primarily (at least more than 50%) euchromatin, it is a minichromosome. The remaining chromosome is a formerly dicentric chromosome. If one of the chromosomes undergoes amplification, whereby heterochromatin (satellite DNA) is amplified and a euchromatic portion (or arm) remains, it is referred to as a sausage chromosome. A chromosome that is substantially all heterochromatin, except for portions of heterologous DNA, is called a SATAC. Such chromosomes (SATACs) can be produced from sausage chromosomes by culturing the cell containing the sausage chromosome under conditions, such as BrdU treatment and/or growth under selective conditions, that destabilize the chromosome so that a satellite artificial chromosomes (SATAC) is produced. For purposes herein, it is understood that SATACs may not necessarily be produced in multiple steps, but may appear after the initial introduction of the heterologous DNA and growth under selective conditions, or they may appear after several cycles of growth under selective conditions and BrdU treatment.

As used herein, a SATAC refers to a chromosome that is substantially all heterochromatin, except for portions of heterologous DNA. Typically, SATACs are satellite DNA based artificial chromosomes, but the term encompasses any chromosome made by the methods herein that contains more heterochromatin than euchromatin.

As used herein, amplifiable, when used in reference to a chromosome, particularly the method of generating SATACs provided herein, refers to a region of a chromosome that is prone to amplification. Amplification typically occurs during replication and other cellular events involving recombination. Such regions are typically regions of the chromosome that include tandem repeats, such as satellite DNA, rDNA and other such sequences.

As used herein, amplification, with reference to DNA, is a process in which segments of DNA are duplicated to yield two or multiple copies of identical or nearly identical DNA segments that are typically joined as substantially tandem or successive repeats or inverted repeats.

As used herein an amplicon is a repeated DNA amplification unit that contains a set of inverted repeats of the megareplicon. A megareplicon represents a higher order replication unit. For example, with reference to the SATACs, the megareplicon contains a set of tandem DNA blocks each containing satellite DNA flanked by non-satellite DNA. Contained within the megareplicon is a primary replication site, referred to as the megareplicator, which may be involved in organizing and facilitating replication of the pericentric heterochromatin and possibly the centromeres. Within the megareplicon there may be smaller (e.g., 50-300 kb in some mammalian cells) secondary replicons. In the exemplified SATACS, the megareplicon is defined by two tandem ~7.5 Mb DNA blocks (see, e.g., FIG. 3). Within each artificial chromosome (AC) or among a population thereof, each amplicon has the same gross structure but may contain sequence variations. Such variations will arise as a result of movement of mobile genetic elements, deletions or insertions or mutations that arise, particularly in culture. Such variation does not affect the use of the ACs or their overall structure as described herein.

As used herein, ribosomal RNA (rRNA) is the specialized RNA that forms part of the structure of a ribosome and participates in the synthesis of proteins. Ribosomal RNA is produced by transcription of genes which, in eukaryotic cells, are present in multiple copies. In human cells, the approximately 250 copies of rRNA genes per haploid genome are spread out in clusters on at least five different chromosomes (chromosomes 13, 14, 15, 21 and 22). In mouse cells, the presence of ribosomal DNA (rDNA) has been verified on at least 11 pairs out of 20 mouse chromosomes (chromosomes 5, 6, 9, 11, 12, 15, 16, 17, 18, 19 and X ((see e.g., Rowe et al. (1996) *Mamm. Genome* 7:886-889 and Johnson et al. (1993) *Mamm. Genome* 4:49-52). In eukaryotic cells, the multiple copies of the highly conserved rRNA genes are located in a tandemly arranged series of rDNA units, which are generally about 40-45 kb in length and contain a transcribed region and a nontranscribed region known as spacer (i.e., intergenic spacer) DNA which can vary in length and sequence.

In the human and mouse, these tandem arrays of rDNA units are located adjacent to the pericentric satellite DNA sequences (heterochromatin). The regions of these chromosomes in which the rDNA is located are referred to as nucleolar organizing regions (NOR) which loop into the nucleolus, the site of ribosome production within the cell nucleus.

As used herein, the minichromosome refers to a chromosome derived from a multicentric, typically dicentric, chromosome (see, e.g., FIG. 1) that contains more euchromatic than heterochromatic DNA.

As used herein, a megachromosome refers to a chromosome that, except for introduced heterologous DNA, is substantially composed of heterochromatin. Megachromosomes are made of an array of repeated amplicons that contain two inverted megareplicons bordered by introduced heterologous DNA (see, e.g., FIG. 3 for a schematic drawing of a megachromosome). For purposes herein, a megachromosome is about 50 to 400 Mb, generally about 250-400 Mb. Shorter variants are also referred to as truncated megachromosomes (about 90 to 120 or 150 Mb), dwarf megachromosomes (~150-200 Mb) and cell lines, and a micro-megachromosome (~50-90 Mb, typically 50-60 Mb). For purposes herein, the term megachromosome refers to the overall repeated structure based on an array of repeated chromosomal segments (amplicons) that contain two inverted megareplicons bordered by any inserted heterologous DNA. The size will be specified.

As used herein, genetic therapy involves the transfer or insertion of heterologous DNA into certain cells, target cells, to produce specific gene products that are involved in correcting or modulating disease. The DNA is introduced into the selected target cells in a manner such that the heterologous DNA is expressed and a product encoded thereby is produced. Alternatively, the heterologous DNA may in some manner mediate expression of DNA that encodes the therapeutic product. It may encode a product, such as a peptide or RNA, that in some manner mediates, directly or indirectly, expression of a therapeutic product. Genetic therapy may also be used to introduce therapeutic compounds, such as TNF, that are not normally produced in the host or that are not produced in therapeutically effective amounts or at a therapeutically useful time. Expression of the heterologous DNA by the target cells within an organism afflicted with the disease thereby enables modulation of the disease. The heterologous DNA encoding the therapeutic product may be modified prior to introduction into the cells of the afflicted host in order to enhance or otherwise alter the product or expression thereof.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been exogenously introduced into the cell. Examples of heterologous DNA include, but are not limited to, DNA that encodes a gene product or gene product(s) of interest, introduced for purposes of gene therapy or for production of an encoded protein. Other examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

As used herein, a therapeutically effective product is a product that is encoded by heterologous DNA that, upon introduction of the DNA into a host, a product is expressed that effectively ameliorates or eliminates the symptoms, manifestations of an inherited or acquired disease or that cures said disease.

As used herein, transgenic plants refer to plants in which heterologous or foreign DNA is expressed or in which the expression of a gene naturally present in the plant has been altered.

As used herein, operative linkage of heterologous DNA to regulatory and effector sequences of nucleotides, such as promoters, enhancers, transcriptional and translational stop sites, and other signal sequences refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame. Preferred promoters include tissue specific promoters, such as mammary gland specific promoters, viral promoters, such TK, CMV, adenovirus promoters, and other promoters known to those of skill in the art.

As used herein, isolated, substantially pure DNA refers to DNA fragments purified according to standard techniques employed by those skilled in the art, such as that found in Maniatis et al. ((1982) *Molecular Cloning: A Laboratory Manual*, Cold Spring Harbor Laboratory Press, Cold Spring Harbor, N.Y.).

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, transformation/transfection refers to the process by which DNA or RNA is introduced into cells. Transfection refers to the taking up of exogenous nucleic acid, e.g., an expression vector, by a host cell whether or not any coding sequences are in fact expressed. Numerous methods of transfection are known to the ordinarily skilled artisan, for example, by direct uptake using calcium phosphate ($CaPO_4$; see, e.g., Wigler et al. (1979) *Proc. Natl. Acad. Sci. U.S.A.* 76:1373-1376), polyethylene glycol (PEG)-mediated DNA uptake, electroporation, lipofection (see, e.g., Strauss (1996) *Meth. Mol. Biol.* 54:307-327), microcell fusion (see, EXAMPLES, see, also Lambert (1991) *Proc. Natl. Acad. Sci. U.S.A.* 88:5907-5911; U.S. Pat. No. 5,396,767, Sanford et al. (1987) *Somatic Cell Mol. Genet.* 13:279-284; Dhar et al. (1984) *Somatic Cell Mol. Genet.* 10:547-559; and McNeill-Killary et al. (1995) *Meth. Enzymol.* 254:133-152), lipid-mediated carrier systems (see, e.g., Teifel et al. (1995) *Biotechniques* 19:79-80; Albrecht et al. (1996) *Ann. Hematol.* 72:73-79; Holmen et al. (1995) *In Vitro Cell Dev. Biol. Anim.* 31:347-351; Remy et al. (1994) *Bioconjug. Chem.* 5:647-654; Le Bolch et al. (1995) *Tetrahedron Lett.* 36:6681-6684; Loeffler et al. (1993) *Meth. Enzymol.* 217:599-618) or other suitable method. Successful transfection is generally recognized by detection of the presence of the heterologous nucleic acid within the transfected cell, such as any indication of the operation of a vector within the host cell. Transformation means introducing DNA into an organism so that the DNA is replicable, either as an extrachromosomal element or by chromosomal integration.

As used herein, injected refers to the microinjection (use of a small syringe) of DNA into a cell.

As used herein, substantially homologous DNA refers to DNA that includes a sequence of nucleotides that is sufficiently similar to another such sequence to form stable hybrids under specified conditions.

It is well known to those of skill in this art that nucleic acid fragments with different sequences may, under the same conditions, hybridize detectably to the same "target" nucleic acid. Two nucleic acid fragments hybridize detectably, under stringent conditions over a sufficiently long hybridization period, because one fragment contains a segment of at least about 14 nucleotides in a sequence which is complementary (or nearly complementary) to the sequence of at least one segment in the other nucleic acid fragment. If the time during which hybridization is allowed to occur is held constant, at a value during which, under preselected stringency conditions, two nucleic acid fragments with exactly complementary base-pairing segments hybridize detectably to each other, departures from exact complementarity can be introduced into the base-pairing segments, and base-pairing will nonetheless occur to an extent sufficient to make hybridization detectable. As the departure from complementarity between the base-pairing segments of two nucleic acids becomes larger, and as conditions of the hybridization become more stringent, the probability decreases that the two segments will hybridize detectably to each other.

Two single-stranded nucleic acid segments have "substantially the same sequence," within the meaning of the present specification, if (a) both form a base-paired duplex with the same segment, and (b) the melting temperatures of said two duplexes in a solution of 0.5×SSPE differ by less than 10° C. If the segments being compared have the same number of bases, then to have "substantially the same sequence", they will typically differ in their sequences at fewer than 1 base in 10. Methods for determining melting temperatures of nucleic acid duplexes are well known (see, e.g., Meinkoth and Wahl (1984) *Anal. Biochem.* 138:267-284 and references cited therein).

As used herein, a nucleic acid probe is a DNA or RNA fragment that includes a sufficient number of nucleotides to specifically hybridize to DNA or RNA that includes identical or closely related sequences of nucleotides. A probe may contain any number of nucleotides, from as few as about 10 and as many as hundreds of thousands of nucleotides. The conditions and protocols for such hybridization reactions are well known to those of skill in the art as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

To be used as a hybridization probe, the nucleic acid is generally rendered detectable by labelling it with a detectable moiety or label, such as $^{32}P$, $^{3}H$ and $^{14}C$, or by other means, including chemical labelling, such as by nick-translation in the presence of deoxyuridylate biotinylated at the 5'-position of the uracil moiety. The resulting probe includes the biotinylated uridylate in place of thymidylate residues and can be detected (via the biotin moieties) by any of a number of commercially available detection systems based on binding of streptavidin to the biotin. Such commercially available detection systems can be obtained, for example, from Enzo Biochemicals, Inc. (New York, N.Y.). Any other label known to those of skill in the art, including non-radioactive labels, may be used as long as it renders the probes sufficiently detectable, which is a function of the sensitivity of the assay, the time available (for culturing cells, extracting DNA, and hybridization assays), the quantity of DNA or RNA available as a source of the probe, the particular label and the means used to detect the label.

Once sequences with a sufficiently high degree of homology to the probe are identified, they can readily be isolated by standard techniques, which are described, for example, by Maniatis et al. ((1982) *Molecular Cloning: A Laboratory Manual*, Cold Spring Harbor Laboratory Press, Cold Spring Harbor, N.Y.).

As used herein, conditions under which DNA molecules form stable hybrids and are considered substantially homologous are such that DNA molecules with at least about 60% complementarity form stable hybrids. Such DNA fragments are herein considered to be "substantially homologous". For example, DNA that encodes a particular protein is substantially homologous to another DNA fragment if the DNA forms stable hybrids such that the sequences of the fragments are at least about 60% complementary and if a protein encoded by the DNA retains its activity.

For purposes herein, the following stringency conditions are defined:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

or any combination of salt and temperature and other reagents that result in selection of the same degree of mismatch or matching.

As used herein, immunoprotective refers to the ability of a vaccine or exposure to an antigen or immunity-inducing agent, to confer upon a host to whom the vaccine or antigen is administered or introduced, the ability to resist infection by a disease-causing pathogen or to have reduced symptoms. The selected antigen is typically an antigen that is presented by the pathogen.

As used herein, all assays and procedures, such as hybridization reactions and antibody-antigen reactions, unless otherwise specified, are conducted under conditions recognized by those of skill in the art as standard conditions.

A. Preparation of Cell Lines Containing MACs

1. The Megareplicon

The methods, cells and MACs provided herein are produced by virtue of the discovery of the existence of a higher-order replication unit (megareplicon) of the centromeric region. This megareplicon is delimited by a primary replication initiation site (megareplicator), and appears to facilitate replication of the centromeric heterochromatin, and most likely, centromeres. Integration of heterologous DNA into the megareplicator region or in close proximity thereto, initiates a large-scale amplification of megabase-size chromosomal segments, which leads to de novo chromosome formation in living cells.

DNA sequences that provide a preferred megareplicator are the rDNA units that give rise to ribosomal RNA (rRNA). In mammals, particularly mice and humans, these rDNA units contain specialized elements, such as the origin of replication (or origin of bidirectional replication, i.e., OBR, in mouse) and amplification promoting sequences (APS) and amplification control elements (ACE) (see, e.g., Gogel et al. (1996) *Chromosoma* 104:511-518; Coffman et al. (1993) *Exp. Cell. Res.* 209:123-132; Little et al. (1993) *Mol. Cell. Biol.* 13:6600-6613; Yoon et al. (1995) *Mol. Cell. Biol.* 15:2482-2489; Gonzalez and Sylvester (1995) *Genomics* 27:320-328;

Miesfeld and Amheim (1982) *Nuc. Acids Res.* 10:3933-3949); Maden et al. (1987) *Biochem. J.* 246:519-527).

As described herein, without being bound by any theory, these specialized elements may facilitate replication and/or amplification of megabase-size chromosomal segments in the de novo formation of chromosomes, such as those described herein, in cells. These specialized elements are typically located in the nontranscribed intergenic spacer region upstream of the transcribed region of rDNA. The intergenic spacer region may itself contain internally repeated sequences which can be classified as tandemly repeated blocks and nontandem blocks (see e.g., Gonzalez and Sylvester (1995) *Genomics* 27:320-328). In mouse rDNA, an origin of bidirectional replication may be found within a 3-kb initiation zone centered approximately 1.6 kb upstream of the transcription start site (see, e.g., Gogel et al. (1996) *Chromosoma* 104:511-518). The sequences of these specialized elements tend to have an altered chromatin structure, which may be detected, for example, by nuclease hypersensitivity or the presence of AT-rich regions that can give rise to bent DNA structures. An exemplary sequence encompassing an origin of replication is shown in SEQ ID NO. 16 and in GENBANK accession no. X82564 at about positions 2430-5435. Exemplary sequences encompassing amplification-promoting sequences include nucleotides 690-1060 and 1105-1530 of SEQ ID NO. 16.

In human rDNA, a primary replication initiation site may be found a few kilobase pairs upstream of the transcribed region and secondary initiation sites may be found throughout the nontranscribed intergenic spacer region (see, e.g., Yoon et al. (1995) *Mol. Cell. Biol.* 15:2482-2489). A complete human rDNA repeat unit is presented in GENBANK as accession no. U13369 and is set forth in SEQ ID NO. 17 herein. Another exemplary sequence encompassing a replication initiation site may be found within the sequence of nucleotides 35355-42486 in SEQ ID NO. 17 particularly within the sequence of nucleotides 37912-42486 and more particularly within the sequence of nucleotides 37912-39288 of SEQ ID NO. 17 (see Coffman et al. (1993) *Exp. Cell. Res.* 209:123-132).

Cell lines containing MACs can be prepared by transforming cells, preferably a stable cell line, with a heterologous DNA fragment that encodes a selectable marker, culturing under selective conditions, and identifying cells that have a multicentric, typically dicentric, chromosome. These cells can then be manipulated as described herein to produce the minichromosomes and other MACs, particularly the heterochromatic SATACs, as described herein.

Development of a multicentric, particularly dicentric, chromosome typically is effected through integration of the heterologous DNA in the pericentric heterochromatin, preferably in the centromeric regions of chromosomes carrying rDNA sequences. Thus, the frequency of incorporation can be increased by targeting to these regions, such as by including DNA, including, but not limited to, rDNA or satellite DNA, in the heterologous fragment that encodes the selectable marker. Among the preferred targeting sequences for directing the heterologous DNA to the pericentromeric heterochromatin are rDNA sequences that target centromeric regions of chromosomes that carry rRNA genes. Such sequences include, but are not limited to, the DNA of SEQ ID NO. 16 and GENBANK accession no. X82564 and portions thereof, the DNA of SEQ ID NO. 17 and GENBANK accession no. U13369 and portions thereof, and the DNA of SEQ ID NOS. 18-24. A particular vector incorporating from within SEQ ID NO. 16 for use in directing integration of heterologous DNA into chromosomal rDNA is pTERPUD (see Example 12). Satellite DNA sequences can also be used to direct the heterologous DNA to integrate into the pericentric heterochromatin. For example, vectors pTEMPUD and pHASPUD, which contain mouse and human satellite DNA, respectively, are provided herein (see Example 12) as exemplary vectors for introduction of heterologous DNA into cells for de novo artificial chromosome formation.

The resulting cell lines can then be treated as the exemplified cells herein to produce cells in which the dicentric chromosome has fragmented. The cells can then be used to introduce additional selective markers into the fragmented dicentric chromosome (i.e., formerly dicentric chromosome), whereby amplification of the pericentric heterochromatin will produce the heterochromatic chromosomes.

The following discussion describes this process with reference to the EC3/7 line and the resulting cells. The same procedures can be applied to any other cells, particularly cell lines to create SATACs and euchromatic minichromosomes.

2. Formation of De Novo Chromosomes

De novo centromere formation in a transformed mouse LMTK-fibroblast cell line (EC3/7) after cointegration of λ constructs (λCM8 and λgtWESneo) carrying human and bacterial DNA (Hadlaczky et al. (1991) *Proc. Natl. Acad. Sci. U.S.A.* 88:8106-8110 and U.S. application Ser. No. 08/375,271) has been shown. The integration of the "heterologous" engineered human, bacterial and phage DNA, and the subsequent amplification of mouse and heterologous DNA that led to the formation of a dicentric chromosome, occurred at the centromeric region of the short arm of a mouse chromosome. By G-banding, this chromosome was identified as mouse chromosome 7. Because of the presence of two functionally active centromeres on the same chromosome, regular breakages occur between the centromeres. Such specific chromosome breakages gave rise to the appearance (in approximately 10% of the cells) of a chromosome fragment carrying the neo-centromere. From the EC3/7 cell line (see, U.S. Pat. No. 5,288,625, deposited at the European Collection of Animal Cell Culture (hereinafter ECACC) under accession no. 90051001; see, also Hadlaczky et al. (1991) *Proc. Natl. Acad. Sci. U.S.A.* 88:8106-8110, and U.S. application Ser. No. 08/375,271 and the corresponding published European application EP 0 473 253, two sublines (EC3/7C5 and EC3/7C6) were selected by repeated single-cell cloning. In these cell lines, the neo-centromere was found exclusively on a minichromosome (neo-minichromosome), while the formerly dicentric chromosome carried traces of "heterologous" DNA.

It has now been discovered that integration of DNA encoding a selectable marker in the heterochromatic region of the centromere led to formation of the dicentric chromosome.

3. The Neo-Minichromosome

The chromosome breakage in the EC3/7 cells, which separates the neo-centromere from the mouse chromosome, occurred in the G-band positive "heterologous" DNA region. This is supported by the observation of traces of λ and human DNA sequences at the broken end of the formerly dicentric chromosome. Comparing the G-band pattern of the chromosome fragment carrying the neo-centromere with that of the stable neo-minichromosome, it is apparent that the neo-minichromosome is an inverted duplicate of the chromosome fragment that bears the neo-centromere. This is supported by the observation that although the neo-minichromosome carries only one functional centromere, both ends of the minichromosome are heterochromatic, and mouse satellite DNA sequences were found in these heterochromatic regions by in situ hybridization.

Mouse cells containing the minichromosome, which contains multiple repeats of the heterologous DNA, which in the exemplified embodiment is λ DNA and the neomycin-resistance gene, can be used as recipient cells in cell transformation. Donor DNA, such as selected heterologous DNA containing λ DNA linked to a second selectable marker, such as the gene encoding hygromycin phosphotransferase which confers hygromycin resistance (hyg), can be introduced into the mouse cells and integrated into the minichromosomes by homologous recombination of λ DNA in the donor DNA with that in the minichromosomes. Integration is verified by in situ hybridization and Southern blot analyses. Transcription and translation of the heterologous DNA is confirmed by primer extension and immunoblot analyses.

For example, DNA has been targeted into the neo-minichromosome in EC3/7C5 cells using a λ DNA-containing construct (pNem1ruc) that also contains DNA encoding hygromycin resistance and the *Renilla* luciferase gene linked to a promoter, such as the cytomegalovirus (CMV) early promoter, and the bacterial neomycin resistance-encoding DNA. Integration of the donor DNA into the chromosome in selected cells (designated PHN4) was confirmed by nucleic acid amplification (PCR) and in situ hybridization. Events that would produce a neo-minichromosome are depicted in FIG. 1.

The resulting engineered minichromosome that contains the heterologous DNA can then be transferred by cell fusion into a recipient cell line, such as Chinese hamster ovary cells (CHO) and correct expression of the heterologous DNA can be verified. Following production of the cells, metaphase chromosomes are obtained, such as by addition of colchicine, and the chromosomes purified by addition of AT- and GC-specific dyes on a dual laser beam based cell sorter (see Example 10 B for a description of methods of isolating artificial chromomsomes). Preparative amounts of chromosomes ($5\times10^4$-$5\times10^7$ chromosomes/ml) at a purity of 95% or higher can be obtained. The resulting chromosomes are used for delivery to cells by methods such as microinjection and liposome-mediated transfer.

Thus, the neo-minichromosome is stably maintained in cells, replicates autonomously, and permits the persistent long-term expression of the neo gene under non-selective culture conditions. It also contains megabases of heterologous known DNA (λ DNA in the exemplified embodiments) that serves as target sites for homologous recombination and integration of DNA of interest. The neo-minichromosome is, thus, a vector for genetic engineering of cells. It has been introduced into SCID mice, and shown to replicate in the same manner as endogenous chromosomes.

The methods herein provide means to induce the events that lead to formation of the neo-minichromosome by introducing heterologous DNA with a selective marker (preferably a dominant selectable marker) into cells and culturing the cells under selective conditions. As a result, cells that contain a multicentric, e.g., dicentric chromosome, or fragments thereof, generated by amplification are produced. Cells with the dicentric chromosome can then be treated to destabilize the chromosomes with agents, such as BrdU and/or culturing under selective conditions, resulting in cells in which the dicentric chromosome has formed two chromosomes, a so-called minichromosome, and a formerly dicentric chromosome that has typically undergone amplification in the heterochromatin where the heterologous DNA has integrated to produce a SATAC or a sausage chromosome (discussed below). These cells can be fused with other cells to separate the minichromosome from the formerly dicentric chromosome into different cells so that each type of MAC can be manipulated separately.

4. Preparation of SATACs

Figure 2:
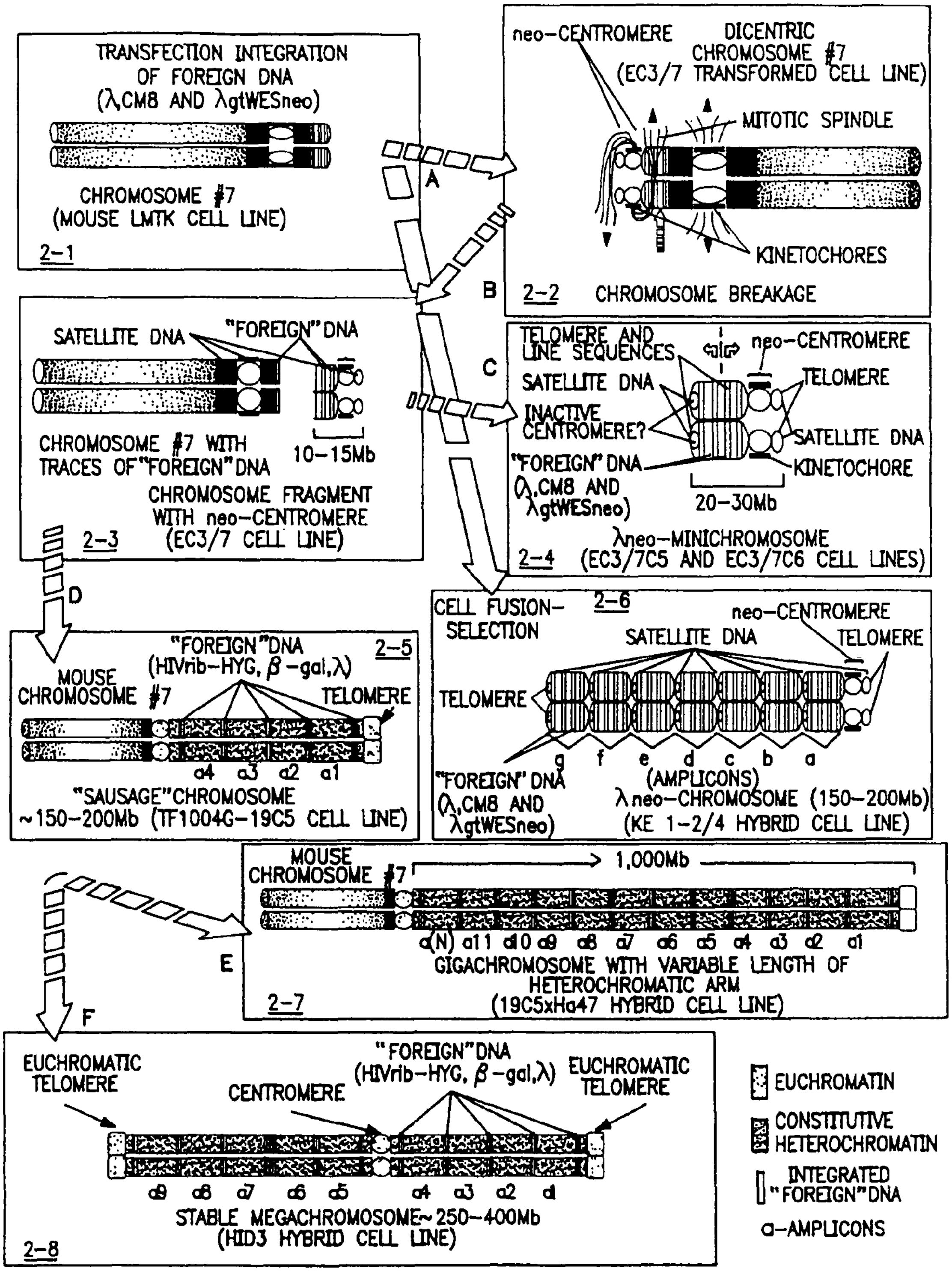
FIG. 2 shows a schematic summary of the manner in which the observed new chromosomes would form, and the relationships among the different de novo formed chromosomes. In particular, this figure shows a schematic drawing of the de novo chromosome formation initiated in the centromeric region of mouse chromosome 7. (A) A single E-type amplification in the centromeric region of chromosome 7 generates a neo-centromere linked to the integrated "foreign" DNA, and forms a dicentric chromosome. Multiple E-type amplification forms the λ neo-chromosome, which separates from the remainder of mouse chromosome 7 through a specific breakage between the centromeres of the dicentric chromosome and which was stabilized in a mouse-hamster hybrid cell line; (B) Specific breakage between the centromeres of a dicentric chromosome 7 generates a chromosome fragment with the neo-centromere, and a chromosome 7 with traces of heterologous DNA at the end; (C) Inverted duplication of the fragment bearing the neo-centromere results in the formation of a stable neo-minichromosome; (D) Integration of exogenous DNA into the heterologous DNA region of the formerly dicentric chromosome 7 initiates H-type amplification, and the formation of a heterochromatic arm. By capturing a euchromatic terminal segment, this new chromosome arm is stabilized in the form of the "sausage" chromosome; (E) BrdU (5-bromodeoxyuridine) treatment and/or drug selection induce further H-type amplification, which results in the formation of an unstable gigachromosome: (F) Repeated BrdU treatments and/or drug selection induce further H-type amplification including a centromere duplication, which leads to the formation of another heterochromatic chromosome arm. It is split off from the chromosome 7 by chromosome breakage, and by acquiring a terminal segment, the stable megachromosome is formed.
Figure 3:
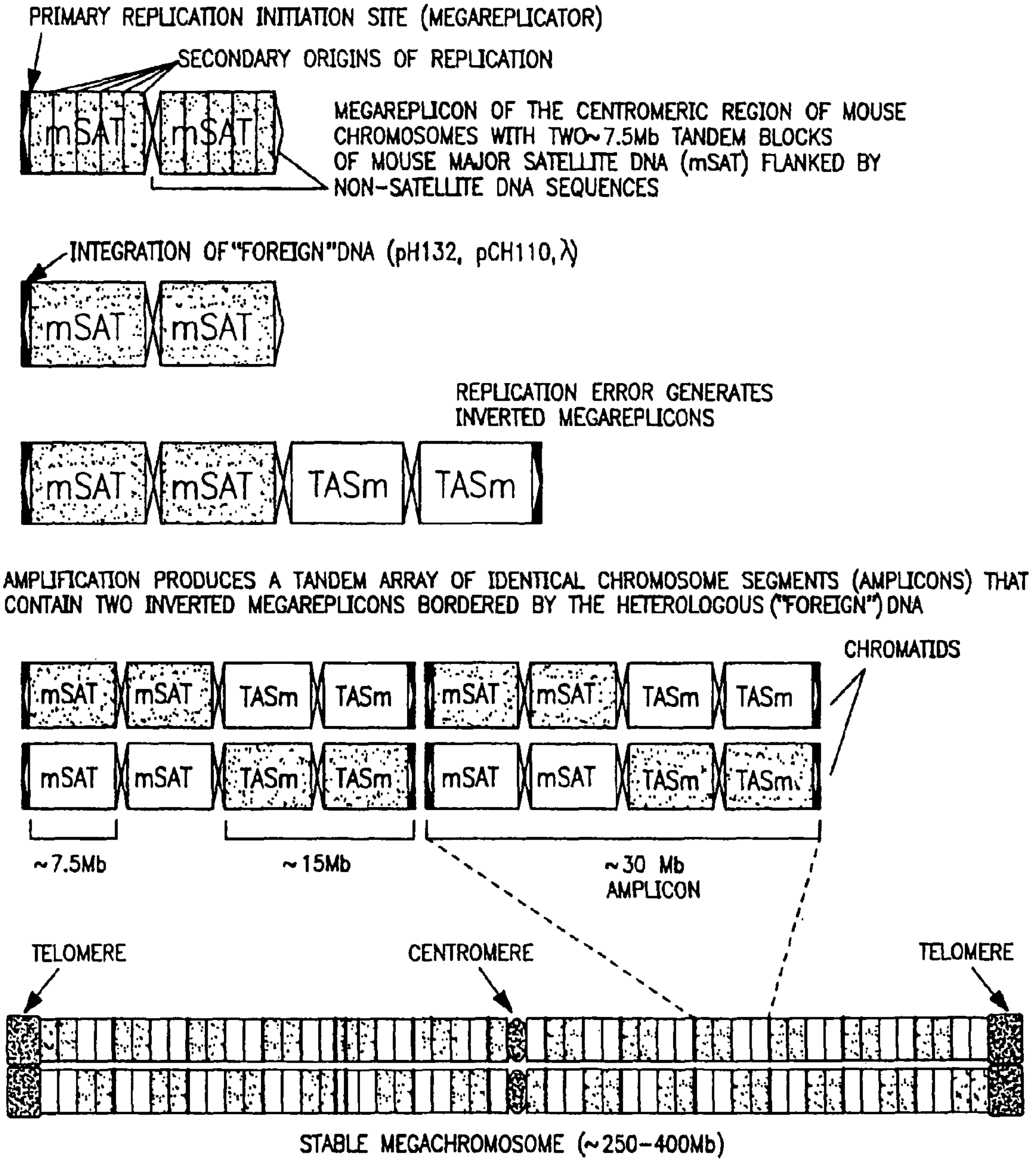
FIG. 3 is a schematic diagram of the replicon structure and a scheme by which a megachromosome could be produced.

An exemplary protocol for preparation of SATACs is illustrated in FIG. 2 (particularly D, E and F) and FIG. 3 (see, also the EXAMPLES, particularly EXAMPLES 4-7).

To prepare a SATAC, the starting materials are cells, preferably a stable cell line, such as a fibroblast cell line, and a DNA fragment that includes DNA that encodes a selective marker. The DNA fragment is introduced into the cell by methods of DNA transfer, including but not limited to direct uptake using calcium phosphate, electroporation, and lipid-mediated transfer. To insure integration of the DNA fragment in the heterochromatin, it is preferable to start with DNA that will be targeted to the pericentric heterochromatic region of the chromosome, such as λCM8 and vectors provided herein, such as pTEMPUD (FIG. 5) and pHASPUD (see Example 12) that include satellite DNA, or specifically into rDNA in the centromeric regions of chromosomes containing rDNA sequences. After introduction of the DNA, the cells are grown under selective conditions. The resulting cells are examined and any that have multicentric, particularly dicentric, chromosomes (or heterochromatic chromosomes or sausage chromosomes or other such structure; see, FIGS. 2D, 2E and 2F) are selected.

In particular, if a cell with a dicentric chromosome is selected, it can be grown under selective conditions, or, preferably, additional DNA encoding a second selectable marker is introduced, and the cells grown under conditions selective for the second marker. The resulting cells should include chromosomes that have structures similar to those depicted in FIGS. 2D, 2E, 2F. Cells with a structure, such as the sausage chromosome, FIG. 2D, can be selected and fused with a second cell line to eliminate other chromosomes that are not of interest. If desired, cells with other chromosomes can be selected and treated as described herein. If a cell with a sausage chromosome is selected, it can be treated with an agent, such as BrdU, that destabilizes the chromosome so that the heterochromatic arm forms a chromosome that is substantially heterochromatic (i.e., a megachromosome, see, FIG. 2F). Structures such as the gigachromosome in which the heterochromatic arm has amplified but not broken off from the euchromatic arm, will also be observed. The megachromosome is a stable chromosome. Further manipulation, such as fusions and growth in selective conditions and/or BrdU treatment or other such treatment, can lead to fragmentation of the megachromosome to form smaller chromosomes that have the amplicon as the basic repeating unit.

The megachromosome can be further fragmented in vivo using a chromosome fragmentation vector, such as pTEMPUD (see, FIG. 5 and EXAMPLE 12), pHASPUD or pTERPUD (see Example 12) to ultimately produce a chromosome that comprises a smaller stable replicable unit, about 15 Mb-60 Mb, containing one to four megareplicons.

Thus, the stable chromosomes formed de novo that originate from the short arm of mouse chromosome 7 have been analyzed. This chromosome region shows a capacity for amplification of large chromosome segments, and promotes de novo chromosome formation. Large-scale amplification at the same chromosome region leads to the formation of dicentric and multicentric chromosomes, a minichromosome, the 150-200 Mb size λ neo-chromosome, the "sausage" chromosome, the 500-1000 Mb gigachromosome, and the stable 250-400 Mb megachromosome.

A clear segmentation is observed along the arms of the megachromosome, and analyses show that the building units of this chromosome are amplicons of ~30 Mb composed of mouse major satellite DNA with the integrated "foreign" DNA sequences at both ends. The ~30 Mb amplicons are composed of two ~15 Mb inverted doublets of ~7.5 Mb mouse major satellite DNA blocks, which are separated from each other by a narrow band of non-satellite sequences (see, e.g., FIG. 3). The wider non-satellite regions at the amplicon borders contain integrated, exogenous (heterologous) DNA, while the narrow bands of non-satellite DNA sequences within the amplicons are integral parts of the pericentric heterochromatin of mouse chromosomes. These results indicate that the ~7.5 Mb blocks flanked by non-satellite DNA are the building units of the pericentric heterochromatin of mouse chromosomes, and the ~15 Mb size pericentric regions of mouse chromosomes contain two ~7.5 Mb units.

Apart from the euchromatic terminal segments, the whole megachromosome is heterochromatic, and has structural homogeneity. Therefore, this large chromosome offers a unique possibility for obtaining information about the amplification process, and for analyzing some basic characteristics of the pericentric constitutive heterochromatin, as a vector for heterologous DNA, and as a target for further fragmentation.

As shown herein, this phenomenon is generalizable and can be observed with other chromosomes. Also, although these de novo formed chromosome segments and chromosomes appear different, there are similarities that indicate that a similar amplification mechanism plays a role in their formation: (i) in each case, the amplification is initiated in the centromeric region of the mouse chromosomes and large (Mb size) amplicons are formed; (ii) mouse major satellite DNA sequences are constant constituents of the amplicons, either by providing the bulk of the heterochromatic amplicons (H-type amplification), or by bordering the euchromatic amplicons (E-type amplification); (iii) formation of inverted segments can be demonstrated in the λ neo-chromosome and megachromosome; (iv) chromosome arms and chromosomes formed by the amplification are stable and functional.

The presence of inverted chromosome segments seems to be a common phenomenon in the chromosomes formed de novo at the centromeric region of mouse chromosome 7. During the formation of the neo-minichromosome, the event leading to the stabilization of the distal segment of mouse chromosome 7 that bears the neo-centromere may have been the formation of its inverted duplicate. Amplicons of the megachromosome are inverted doublets of 7.5 Mb mouse major satellite DNA blocks.

5. Cell Lines

Cell lines that contain MACs, such as the minichromosome, the λ-neo chromosome, and the SATACs are provided herein or can be produced by the methods herein. Such cell lines provide a convenient source of these chromosomes and can be manipulated, such as by cell fusion or production of microcells for fusion with selected cell lines, to deliver the chromosome of interest into hybrid cell lines. Exemplary cell lines are described herein and some have been deposited with the ECACC.

a. EC3/7C5 and EC3/7C6

Cell lines EC3/7C5 and EC3/7C6 were produced by single cell cloning of EC3/7. For exemplary purposes EC3/7C5 has been deposited with the ECACC. These cell lines contain a minichromosome and the formerly dicentric chromosome from EC3/7. The stable minichromosomes in cell lines EC3/7C5 and EC3/7C6 appear to be the same and they seem to be duplicated derivatives of the ~10-15 Mb "broken-off" fragment of the dicentric chromosome. Their similar size in these independently generated cell lines might indicate that ~20-30 Mb is the minimal or close to the minimal physical size for a stable minichromosome.

b. TF1004G19

Introduction of additional heterologous DNA, including DNA encoding a second selectable marker, hygromycin phosphotransferase, i.e., the hygromycin-resistance gene, and also a detectable marker, β-galactosidase (i.e., encoded by the lacZ gene), into the EC3/7C5 cell line and growth under selective conditions produced cells designated TF1004G19. In particular, this cell line was produced from the EC3/7C5 cell line by cotransfection with plasmids pH132, which contains an anti-HIV ribozyme and hygromycin-resistance gene, pCH110 (encodes β-galactosidase) and λ phage (λcl 857 Sam 7) DNA and selection with hygromycin B.

Detailed analysis of the TF1004G19 cell line by in situ hybridization with λ phage and plasmid DNA sequences revealed the formation of the sausage chromosome. The formerly dicentric chromosome of the EC3/7C5 cell line translocated to the end of another acrocentric chromosome. The heterologous DNA integrated into the pericentric heterochromatin of the formerly dicentric chromosome and is amplified several times with megabases of mouse pericentric heterochromatic satellite DNA sequences (FIG. 2D) forming the "sausage" chromosome. Subsequently the acrocentric mouse chromosome was substituted by a euchromatic telomere.

In situ hybridization with biotin-labeled subfragments of the hygromycin-resistance and β-galactosidase genes resulted in a hybridization signal only in the heterochromatic arm of the sausage chromosome, indicating that in TF1004G19 transformant cells these genes are localized in the pericentric heterochromatin.

A high level of gene expression, however, was detected. In general, heterochromatin has a silencing effect in *Drosophila*, yeast and on the HSV-tk gene introduced into satellite DNA at the mouse centromere. Thus, it was of interest to study the TF1004G19 transformed cell line to confirm that genes located in the heterochromatin were indeed expressed, contrary to recognized dogma.

For this purpose, subclones of TF1004G19, containing a different sausage chromosome (see FIG. 2D), were established by single cell cloning. Southern hybridization of DNA isolated from the subclones with subfragments of hygromycin phosphotransferase and lacZ genes showed a close correlation between the intensity of hybridization and the length of the sausage chromosome. This finding supports the conclusion that these genes are localized in the heterochromatic arm of the sausage chromosome.

(1) TF1004G-19C5

TF1004G-19C5 is a mouse LMTK$^-$ fibroblast cell line containing neo-minichromosomes and stable "sausage" chromosomes. It is a subclone of TF1004G19 and was generated by single-cell cloning of the TF1004G19 cell line. It has been deposited with the ECACC as an exemplary cell line and exemplary source of a sausage chromosome. Subsequent fusion of this cell line with CHO K20 cells and selection with hygromycin and G418 and HAT (hypoxanthine, aminopteria, and thymidine medium; see Szybalski et al. (1962) *Proc. Natl. Acad. Sci.* 48:2026) resulted in hybrid cells (designated 19C5xHa4) that carry the sausage chromosome and the neo-minichromosome. BrdU treatment of the hybrid cells, followed by single cell cloning and selection with G418 and/or hygromycin produced various cells that carry chromosomes of interest, including GB43 and G3D5.

(2) Other Subclones

Cell lines GB43 and G3D5 were obtained by treating 19C5xHa4 cells with BrdU followed by growth in G418-containing selective medium and retreatment with BrdU. The two cell lines were isolated by single cell cloning of the selected cells.

GB43 cells contain the neo-minichromosome only. G3D5, which has been deposited with the ECACC, carries the neo-minichromosome and the megachromosome. Single cell cloning of this cell line followed by growth of the subclones in G418- and hygromycin-containing medium yielded subclones such as the GHB42 cell line carrying the neo-minichromosome and the megachromosome. H1D3 is a mouse-hamster hybrid cell line carrying the megachromosome, but no neo-minichromosome, and was generated by treating 19C5xHa4 cells with BrdU followed by growth in hygromycin-containing selective medium and single cell subcloning of selected cells. Fusion of this cell line with the $CD4^+$ HeLa cell line that also carries DNA encoding an additional selection gene, the neomycin-resistance gene, produced cells (designated H1xHE41 cells) that carry the megachromosome as well as a human chromosome that carries CD4neo. Further BrdU treatment and single cell cloning produced cell lines, such as 1B3, that include cells with a truncated megachromosome.

6. DNA Constructs Used to Transform the Cells

Figure 4:
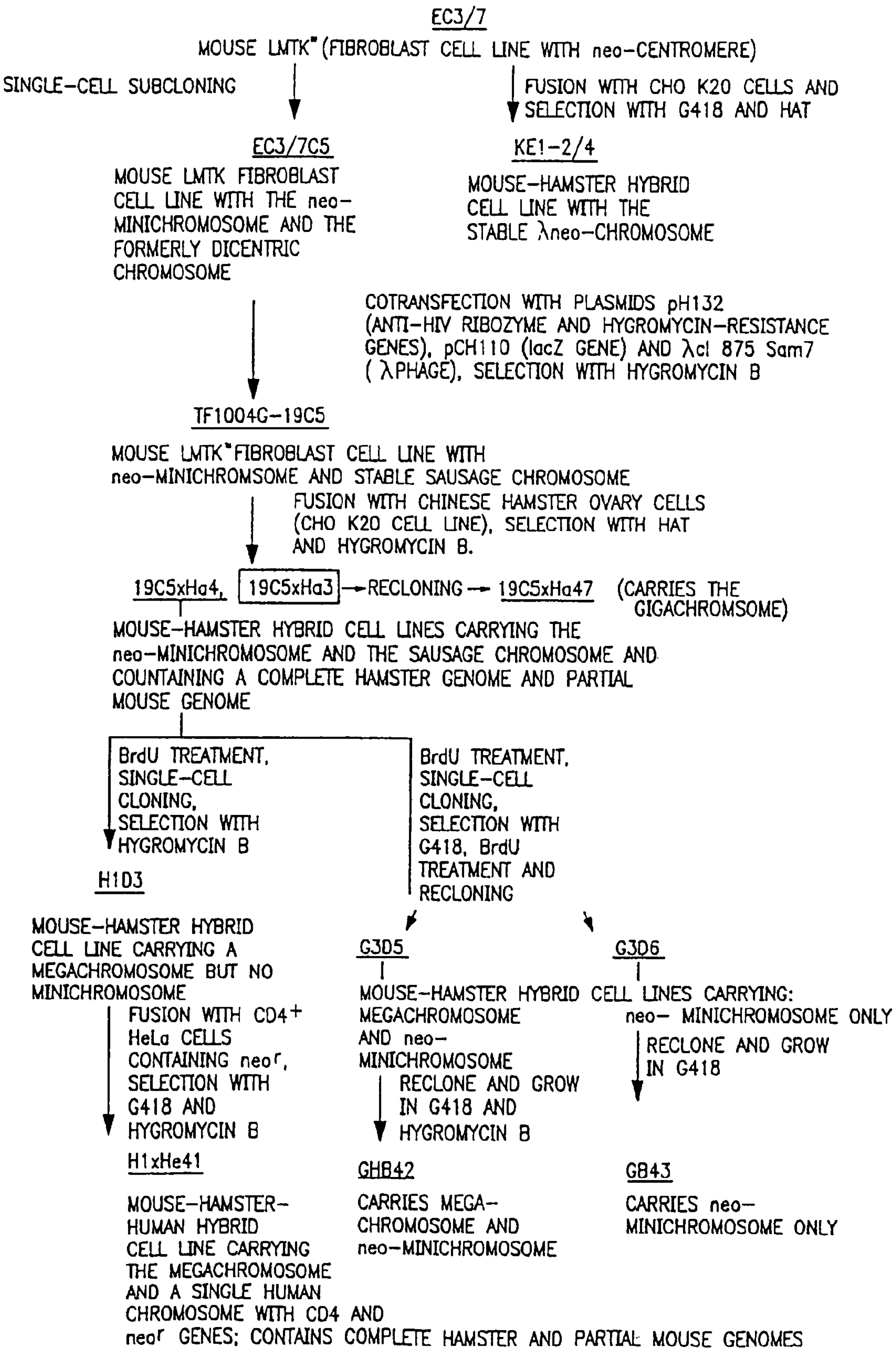
FIG. 4 sets forth the relationships among some of the exemplary cell lines described herein.

Heterologous DNA can be introduced into the cells by transfection or other suitable method at any stage during preparation of the chromosomes (see, e.g., FIG. 4). In general, incorporation of such DNA into the MACs is assured through site-directed integration, such as may be accomplished by inclusion of λ-DNA in the heterologous DNA (for the exemplified chromosomes), and also an additional selective marker gene. For example, cells containing a MAC, such as the minichromosome or a SATAC, can be cotransfected with a plasmid carrying the desired heterologous DNA, such as DNA encoding an HIV ribozyme, the cystic fibrosis gene, and DNA encoding a second selectable marker, such as hygromycin resistance. Selective pressure is then applied to the cells by exposing them to an agent that is harmful to cells that do not express the new selectable marker. In this manner, cells that include the heterologous DNA in the MAC are identified. Fusion with a second cell line can provide a means to produce cell lines that contain one particular type of chromosomal structure or MAC.

Various vectors for this purpose are provided herein (see, Examples) and others can be readily constructed. The vectors preferably include DNA that is homologous to DNA contained within a MAC in order to target the DNA to the MAC for integration therein. The vectors also include a selectable marker gene and the selected heterologous gene(s) of interest. Based on the disclosure herein and the knowledge of the skilled artisan, one of skill can construct such vectors.

Of particular interest herein is the vector pTEMPUD and derivatives thereof that can target DNA into the heterochromatic region of selected chromosomes. These vectors can also serve as fragmentation vectors (see, e.g., Example 12).

Heterologous genes of interest include any gene that encodes a therapeutic product and DNA encoding gene products of interest. These genes and DNA include, but are not limited to: the cystic fibrosis gene (CF), the cystic fibrosis transmembrane regulator (CFTR) gene (see, e.g., U.S. Pat. No. 5,240,846; Rosenfeld et al. (1992) *Cell* 68:143-155; Hyde et al. (1993) *Nature* 362: 250-255; Kerem et al. (1989) *Science* 245:1073-1080; Riordan et al. (1989) *Science* 245: 1066-1072; Rommens et al. (1989) *Science* 245:1059-1065; Osborne et al. (1991) *Am. J. Hum. Genetics* 48:6089-6122; White et al. (1990) *Nature* 344:665-667; Dean et al. (1990) *Cell* 61:863-870; Erlich et al. (1991) *Science* 252:1643; and U.S. Pat. Nos. 5,453,357, 5,449,604, 5,434,086, and 5,240,846, which provides a retroviral vector encoding the normal CFTR gene).

B. Isolation of Artificial Chromosomes

The MACs provided herein can be isolated by any suitable method known to those of skill in the art. Also, methods are provided herein for effecting substantial purification, particularly of the SATACs. SATACs have been isolated by fluorescence-activated cell sorting (FACS). This method takes advantage of the nucleotide base content of the SATACs, which, by virtue of their high heterochromatic DNA content, will differ from any other chromosomes in a cell. In particular embodiment, metaphase chromosomes are isolated and stained with base-specific dyes, such as Hoechst 33258 and chromomycin A3. Fluorescence-activated cell sorting will separate the SATACs from the endogenous chromosomes. A dual-laser cell sorter (FACS Vantage Becton Dickinson Immunocytometry Systems) in which two lasers were set to excite the dyes separately, allowed a bivariate analysis of the chromosomes by base-pair composition and size. Cells containing such SATACs can be similarly sorted.

Additional methods provided herein for isolation of artificial chromosomes from endogenous chromosomes include procedures that are particularly well suited for large-scale isolation of artificial chromosomes such as SATACs. In these methods, the size and density differences between SATACs and endogenous chromosomes are exploited to effect separation of these two types of chromosomes. Such methods involve techniques such as swinging bucket centrifugation, zonal rotor centrifugation, and velocity sedimentation. Affinity-, particularly immunoaffinity-, based methods for separation of artificial from endogenous chromosomes are also provided herein. For example, SATACs, which are predominantly heterochromatin, may be separated from endogenous chromosomes through immunoaffinity procedures involving antibodies that specifically recognize heterochromatin, and/or the proteins associated therewith, when the endogenous chromosomes contain relatively little heterochromatin, such as in hamster cells.

C. In Vitro Construction of Artificial Chromosomes

Artificial chromosomes can be constructed in vitro by assembling the structural and functional elements that contribute to a complete chromosome capable of stable replication and segregation alongside endogenous chromosomes in cells. The identification of the discrete elements that in combination yield a functional chromosome has made possible the in vitro generation of artificial chromosomes. The process of in vitro construction of artificial chromosomes, which can be rigidly controlled, provides advantages that may be desired in the generation of chromosomes that, for example, are required in large amounts or that are intended for specific use in transgenic animal systems.

For example, in vitro construction may be advantageous when efficiency of time and scale are important considerations in the preparation of artificial chromosomes. Because in vitro construction methods do not involve extensive cell culture procedures, they may be utilized when the time and labor required to transform, feed, cultivate, and harvest cells used in in vivo cell-based production systems is unavailable.

In vitro construction may also be rigorously controlled with respect to the exact manner in which the several elements of the desired artificial chromosome are combined and in what sequence and proportions they are assembled to yield a chromosome of precise specifications. These aspects may be of significance in the production of artificial chromosomes that will be used in live animals where it is desirable to be certain that only very pure and specific DNA sequences in specific amounts are being introduced into the host animal.

The following describes the processes involved in the construction of artificial chromosomes in vitro, utilizing a megachromosome as exemplary starting material.

1. Identification and Isolation of the Components of the Artificial Chromosome

The MACs provided herein, particularly the SATACs, are elegantly simple chromosomes for use in the identification and isolation of components to be used in the in vitro construction of artificial chromosomes. The ability to purify MACs to a very high level of purity, as described herein, facilitates their use for these purposes. For example, the megachromosome, particularly truncated forms thereof (i.e. cell lines, such as 1B3 and mM2C1, which are derived from H1D3 (deposited at the European Collection of Animal Cell Culture (ECACC) under Accession No. 96040929, see EXAMPLES below) serve as starting materials.

For example, the mM2C1 cell line contains a micro-megachromosome (~50-60 kB), which advantageously contains only one centromere, two regions of integrated heterologous DNA with adjacent rDNA sequences, with the remainder of the chromosomal DNA being mouse major satellite DNA. Other truncated megachromosomes can serve as a source of telomeres, or telomeres can be provided (see, Examples below regarding construction of plasmids containing tandemly repeated telomeric sequences). The centromere of the mM2C1 cell line contains mouse minor satellite DNA, which provides a useful tag for isolation of the centromeric DNA.

Additional features of particular SATACs provided herein, such as the micro-megachromosome of the mM2C1 cell line, that make them uniquely suited to serve as starting materials in the isolation and identification of chromosomal components include the fact that the centromeres of each megachromosome within a single specific cell line are identical. The ability to begin with a homogeneous centromere source (as opposed to a mixture of different chromosomes having differing centromeric sequences) greatly facilitates the cloning of the centromere DNA. By digesting purified megachromosomes, particularly truncated megachromosomes, such as the micro-megachromosome, with appropriate restriction endonucleases and cloning the fragments into the commercially available and well known YAC vectors (see, e.g., Burke et al. (1987) *Science* 236:806-812), BAC vectors (see, e.g., Shizuya et al. (1992) *Proc. Natl. Acad. Sci. U.S.A.* 89: 8794-8797 bacterial artificial chromosomes which have a capacity of incorporating 0.9-1 Mb of DNA) or PAC vectors (the P1 artificial chromosome vector which is a P1 plasmid derivative that has a capacity of incorporating 300 kb of DNA and that is delivered to *E. coli* host cells by electroporation rather than by bacteriophage packaging; see, e.g., Ioannou et al. (1994) *Nature Genetics* 6:84-89; Pierce et al. (1992) *Meth. Enzymol.* 216:549-574; Pierce et al. (1992) *Proc. Natl. Acad. Sci. U.S.A.* 89:2056-2060; U.S. Pat. No. 5,300,431 and International PCT application No. WO 92/14819) vectors, it is possible for as few as 50 clones to represent the entire micro-megachromosome.

a. Centromeres

An exemplary centromere for use in the construction of a mammalian artificial chromosome is that contained within the megachromosome of any of the megachromosome-containing cell lines provided herein, such as, for example, H1D3 and derivatives thereof, such as mM2C1 cells. Megachromosomes are isolated from such cell lines utilizing, for example, the procedures described herein, and the centromeric sequence is extracted from the isolated megachromosomes. For example, the megachromosomes may be separated into fragments utilizing selected restriction endonucleases that recognize and cut at sites that, for instance, are primarily located in the replication and/or heterologous DNA integration sites and/or in the satellite DNA. Based on the sizes of the resulting fragments, certain undesired elements may be separated from the centromere-containing sequences. The centromere-containing DNA, which could be as large as 1 Mb.

Probes that specifically recognize the centromeric sequences, such as mouse minor satellite DNA-based probes (see, e.g., Wong et al. (1988) *Nucl. Acids Res.* 16:11645-11661), may be used to isolate the centromere-containing YAC, BAC or PAC clones derived from the megachromosome. Alternatively, or in conjunction with the direct identification of centromere-containing megachromosomal DNA, probes that specifically recognize the non-centromeric elements, such as probes specific for mouse major satellite DNA, the heterologous DNA and/or rDNA, may be used to identify and eliminate the non-centromeric DNA-containing clones.

Additionally, centromere cloning methods described herein may be utilized to isolate the centromere-containing sequence of the megachromosome. For example, Example 12 describes the use of YAC vectors in combination with the murine tyrosinase gene and NMRI/Han mice for identification of the centromeric sequence.

Once the centromere fragment has been isolated, it may be sequenced and the sequence information may in turn be used in PCR amplification of centromere sequences from megachromosomes or other sources of centromeres. Isolated centromeres may also be tested for function in vivo by transferring the DNA into a host mammalian cell. Functional analysis may include, for example, examining the ability of the centromere sequence to bind centromere-binding proteins. The cloned centromere will be transferred to mammalian cells with a selectable marker gene and the binding of a centromere-specific protein, such as anti-centromere antibodies (e.g., LU851, see, Hadlaczky et al. (1986) *Exp. Cell Res.* 167:1-15) can be used to assess function of the centromeres.

b. Telomeres

Preferred telomeres are the 1 kB synthetic telomere provided herein (see, Examples). A double synthetic telomere construct, which contains a 1 kB synthetic telomere linked to a dominant selectable marker gene that continues in an inverted orientation may be used for ease of manipulation. Such a double construct contains a series of TTAGGG repeats 3' of the marker gene and a series of repeats of the inverted sequence, i.e., GGGATT, 5' of the marker gene as follows: $(GGGATTT)_n$—dominant marker gene—$(TTAGGG)_n$. Using an inverted marker provides an easy means for insertion, such as by blunt end ligation, since only properly oriented fragments will be selected.

c. Megareplicator

The megareplicator sequences, such as the rDNA, provided herein are preferred for use in in vitro constructs. The rDNA provides an origin of replication and also provides sequences that facilitate amplification of the artificial chromosome in vivo to increase the size of the chromosome to, for example accommodate increasing copies of a heterologous gene of interest as well as continuous high levels of expression of the heterologous genes.

d. Filler Heterochromatin

Filler heterochromatin, particularly satellite DNA, is included to maintain structural integrity and stability of the artificial chromosome and provide a structural base for carrying genes within the chromosome. The satellite DNA is typically A/T-rich DNA sequence, such as mouse major satellite DNA, or G/C-rich DNA sequence, such as hamster natural satellite DNA. Sources of such DNA include any eukaryotic organisms that carry non-coding satellite DNA with sufficient A/T or G/C composition to promote ready separation by sequence, such as by FACS, or by density gradients. The satellite DNA may also be synthesized by generating sequence containing monotone, tandem repeats of highly A/T- or G/C-rich DNA units.

The most suitable amount of filler heterochromatin for use in construction of the artificial chromosome may be empirically determined by, for example, including segments of various lengths, increasing in size, in the construction process. Fragments that are too small to be suitable for use will not provide for a functional chromosome, which may be evaluated in cell-based expression studies, or will result in a chromosome of limited functional lifetime or mitotic and structural stability.

e. Selectable Marker

Any convenient selectable marker may be used and at any convenient locus in the MAC.

2. Combination of the Isolated Chromosomal Elements

Once the isolated elements are obtained, they may be combined to generate the complete, functional artificial chromosome. This assembly can be accomplished for example, by in vitro ligation either in solution, LMP agarose or on microbeads. The ligation is conducted so that one end of the centromere is directly joined to a telomere. The other end of the centromere, which serves as the gene-carrying chromosome arm, is built up from a combination of satellite DNA and rDNA sequence and may also contain a selectable marker gene. Another telomere is joined to the end of the gene-carrying chromosome arm. The gene-carrying arm is the site at which any heterologous genes of interest, for example, in expression of desired proteins encoded thereby, are incorporated either during in vitro construction of the chromosome or sometime thereafter.

3. Analysis and Testing of the Artificial Chromosome

Artificial chromosomes constructed in vitro may be tested for functionality in in vivo mammalian cell systems, using any of the methods described herein for the SATACs, minichromosomes, or known to those of skill in the art.

4. Introduction of Desired Heterologous DNA into the In Vitro Synthesized Chromosome Heterologous DNA may be introduced into the in vitro synthesized chromosome using routine methods of molecular biology, may be introduced using the methods described herein for the SATACs, or may be incorporated into the in vitro synthesized chromosome as part of one of the synthetic elements, such as the heterochromatin. The heterologous DNA may be linked to a selected repeated fragment, and then the resulting construct may be amplified in vitro using the methods for such in vitro amplification provided herein (see the Examples).

D. Introduction of Artificial Chromosomes into Cells, Tissues, Animals and Plants Suitable hosts for introduction of the MACs provided herein, include, but are not limited to, any animal or plant, cell or tissue thereof, including, but not limited to: mammals, birds, reptiles, amphibians, insects, fish, arachnids, tobacco, tomato, wheat, plants and algae. The MACs, if contained in cells, may be introduced by cell fusion or microcell fusion or, if the MACs have been isolated from cells, they may be introduced into host cells by any method known to those of skill in this art, including but not limited to: direct DNA transfer, electroporation, lipid-mediated transfer, e.g., lipofection and liposomes, microprojectile bombardment, microinjection in cells and embryos, protoplast regeneration for plants, and any other suitable method (see, e.g., Weissbach et al. (1988) Methods for Plant Molecular Biology, Academic Press, N.Y., Section VIII, pp. 421-463; Grierson et al. (1988) Plant Molecular Biology, 2d Ed., Blackie, London, Ch. 7-9; see, also U.S. Pat. Nos. 5,491,075; 5,482,928; and 5,424,409; see, also, e.g., U.S. Pat. No. 5,470,708, which describes particle-mediated transformation of mammalian unattached cells).

Other methods for introducing DNA into cells include nuclear microinjection and bacterial protoplast fusion with intact cells. Polycations, such as polybrene and polyornithine, may also be used. For various techniques for transforming mammalian cells, see e.g., Keown et al. *Methods in Enzymology* (1990) Vol. 185, pp. 527-537; and Mansour et al. (1988) *Nature* 336:348-352.

For example, isolated, purified artificial chromosomes can be injected into an embryonic cell line such as a human kidney primary embryonic cell line (ATCC accession number CRL 1573) or embryonic stem cells (see, e.g., Hogan et al. (1994) *Manipulating the Mouse Embryo: A Laboratory Manual*, Cold Spring Harbor Laboratory Press, Cold Spring Harbor, N.Y., see, especially, pages 255-264 and Appendix 3).

Preferably the chromosomes are introduced by microinjection, using a system such as the Eppendorf automated microinjection system, and grown under selective conditions, such as in the presence of hygromycin B or neomycin.

1. Methods for Introduction of Chromosomes into Hosts

Depending on the host cell used, transformation is done using standard techniques appropriate to such cells. These methods include any, including those described herein, known to those of skill in the art.

a. DNA Uptake

For mammalian cells that do not have cell walls, the calcium phosphate precipitation method for introduction of exogenous DNA (see, e.g., Graham et al. (1978) *Virology* 52:456-457; Wigler et al. (1979) *Proc. Natl. Acad. Sci. U.S.A.* 76:1373-1376; and *Current Protocols in Molecular Biology Vol.* 1, Wiley Inter-Science, Supplement 14, Unit 9.1.1-9.1.9 (1990)) is often preferred. DNA uptake can be accomplished by DNA alone or in the presence of polyethylene glycol (PEG-mediated gene transfer), which is a fusion agent, or by any variations of such methods known to those of skill in the art (see, e.g., U.S. Pat. No. 4,684,611).

Lipid-mediated carrier systems are also among the preferred methods for introduction of DNA into cells (see, e.g., Teifel et al. (1995) *Biotechniques* 19:79-80; Albrecht et al. (1996) *Ann. Hematol.* 72:73-79; Holmen et al. (1995) *In Vitro Cell Dev. Biol. Anim.* 31:347-351; Remy et al. (1994) *Bioconjug. Chem.* 5:647-654; Le Bolc'h et al. (1995) *Tetrahedron Lett.* 36:6681-6684; Loeffler et al. (1993) *Meth. Enzymol.* 217:599-618). Lipofection (see, e.g., Strauss (1996) *Meth. Mol. Biol.* 54:307-327) may also be used to introduce DNA into cells. This method is particularly well-suited for transfer of exogenous DNA into chicken cells (e.g., chicken blastodermal cells and primary chicken fibroblasts; see Brazolot et al. (1991) *Mol. Repro. Dev.* 30:304-312). In particular, DNA of interest can be introduced into chickens in operative linkage with promoters from genes, such as lysozyme and ovalbumin, that are expressed in the egg, thereby permitting expression of the heterologous DNA in the egg.

Additional methods useful in the direct transfer of DNA into cells include particle gun electrofusion (see, e.g., U.S. Pat. Nos. 4,955,378, 4,923,814, 4,476,004, 4,906,576 and 4,441,972) and virion-mediated gene transfer.

A commonly used approach for gene transfer in land plants involves the direct introduction of purified DNA into protoplasts. The three basic methods for direct gene transfer into plant cells include: 1) polyethylene glycol (PEG)-mediated DNA uptake, 2) electroporation-mediated DNA uptake and 3) microinjection. In addition, plants may be transformed using ultrasound treatment (see, e.g., International PCT application publication No. WO 91/00358).

b. Electroporation

Electroporation involves providing high-voltage electrical pulses to a solution containing a mixture of protoplasts and foreign DNA to create reversible pores in the membranes of plant protoplasts as well as other cells. Electroporation is generally used for prokaryotes or other cells, such as plants that contain substantial cell-wall barriers. Methods for effecting electroporation are well known (see, e.g., U.S. Pat. Nos. 4,784,737, 5,501,967, 5,501,662, 5,019,034, 5,503,999; see, also Fromm et al. (1985) *Proc. Natl. Acad. Sci. U.S.A.* 82:5824-5828).

For example, electroporation is often used for transformation of plants (see, e.g., *Ag Biotechnology News* 7:3 and 17 (September/October 1990)). In this technique, plant protoplasts are electroporated in the presence of the DNA of interest that also includes a phenotypic marker. Electrical impulses of high field strength reversibly permeabilize biomembranes allowing the introduction of the plasmids. Electroporated plant protoplasts reform the cell wall, divide, and form plant callus. Transformed plant cells will be identified by virtue of the expressed phenotypic marker. The exogenous DNA may be added to the protoplasts in any form such as, for example, naked linear, circular or supercoiled DNA, DNA encapsulated in liposomes, DNA in spheroplasts, DNA in other plant protoplasts, DNA complexed with salts, and other methods.

c. Microcells

The chromosomes can be transferred by preparing microcells containing an artificial chromosome and then fusing with selected target cells. Methods for such preparation and fusion of microcells are well known (see the Examples and also see, e.g., U.S. Pat. Nos. 5,240,840, 4,806,476, 5,298,429, 5,396,767, Fournier (1981) *Proc. Natl. Acad. Sci. U.S.A.* 78:6349-6353; and Lambert et al. (1991) *Proc. Natl. Acad. Sci. U.S.A.* 88:5907-59). Microcell fusion, using microcells that contain an artificial chromosome, is a particularly useful method for introduction of MACs into avian cells, such as DT40 chicken pre-B cells (for a description of DT40 cell fusion, see, e.g., Dieken et al. (1996) *Nature Genet.* 12:174-182).

2. Hosts

Suitable hosts include any host known to be useful for introduction and expression of heterologous DNA. Of particular interest herein, animal and plant cells and tissues, including, but not limited to insect cells and larvae, plants, and animals, particularly transgenic (non-human) animals, and animal cells. Other hosts include, but are not limited to mammals, birds, particularly fowl such as chickens, reptiles, amphibians, insects, fish, arachnids, tobacco, tomato, wheat, monocots, dicots and algae, and any host into which introduction of heterologous DNA is desired. Such introduction can be effected using the MACs provided herein, or, if necessary by using the MACs provided herein to identify species-specific centromeres and/or functional chromosomal units and then using the resulting centromeres or chromosomal units as artificial chromosomes, or alternatively, using the methods exemplified herein for production of MACs to produce species-specific artificial chromosomes.

a. Introduction of DNA into Embryos for Production of Transgenic (Non-Human) Animals and Introduction of DNA into Animal Cells Transgenic (non-human) animals can be produced by introducing exogenous genetic material into a pronucleus of a mammalian zygote by microinjection (see, e.g., U.S. Pat. Nos. 4,873,191 and 5,354,674; see, also, International PCT application publication No. WO 95/14769, which is based on U.S. application Ser. No. 08/159,084). The zygote is capable of development into a mammal. The embryo or zygote is transplanted into a host female uterus and allowed to develop. Detailed protocols and examples are set forth below.

Nuclear transfer (see, Wilmut et al. (1997) *Nature* 385:810-813, International PCT application Nos. WO 97/07669 and WO 97/07668). Briefly in this method, the SATAC containing the genes of interest is introduced by any suitable method, into an appropriate donor cell, such as a mammary gland cell, that contains totipotent nuclei. The diploid nucleus of the cell, which is either in G0 or G1 phase, is then introduced, such as by cell fusion or microinjection, into an unactivated oocyte, preferably enucleated cell, which is arrested in the metaphase of the second meiotic division. Enucleation may be effected by any suitable method, such as actual removal, or by treating with means, such as ultraviolet light, that functionally remove the nucleus. The oocyte is then activated, preferably after a period of contact, about 6-20 hours for cattle, of the new nucleus with the cytoplasm, while maintaining correct ploidy, to produce a reconstituted embryo, which is then introduced into a host. Ploidy is maintained during activation, for example, by incubating the reconstituted cell in the presence of a microtubule inhibitor, such as nocodazole, colchicine, colcemid, and TAXOL, whereby the DNA replicates once.

Transgenic chickens can be produced by injection of dispersed blastodermal cells from Stage X chicken embryos into recipient embryos at a similar stage of development (see e.g., Etches et al. (1993) *Poultry Sci.* 72:882-889; Petitte et al. (1990) *Development* 108:185-189). Heterologous DNA is first introduced into the donor blastodermal cells using methods such as, for example, lipofection (see, e.g., Brazolot et al. (1991) *Mol. Repro. Dev.* 30:304-312) or microcell fusion (see, e.g., Dieken et al. (1996) *Nature Genet.* 12:174-182). The transfected donor cells are then injected into recipient chicken embryos (see e.g., Carsience et al. (1993) *Development* 117: 669-675). The recipient chicken embryos within the shell are candled and allowed to hatch to yield a germline chimeric chicken.

DNA can be introduced into animal cells using any known procedure, including, but not limited to: direct uptake, incubation with polyethylene glycol (PEG), microinjection, electroporation, lipofection, cell fusion, microcell fusion, particle bombardment, including microprojectile bombardment (see, e.g., U.S. Pat. No. 5,470,708, which provides a method for transforming unattached mammalian cells via particle bombardment), and any other such method. For example, the transfer of plasmid DNA in liposomes directly to human cells in situ has been approved by the FDA for use in humans (see, e.g., Nabel, et al. (1990) *Science* 249:1285-1288 and U.S. Pat. No. 5,461,032).

b. Introduction of Heterologous DNA into Plants

Numerous methods for producing or developing transgenic plants are available to those of skill in the art. The method used is primarily a function of the species of plant. These methods include, but are not limited to: direct transfer of DNA by processes, such as PEG-induced DNA uptake, protoplast fusion, microinjection, electroporation, and microprojectile bombardment (see, e.g., Uchimiya et al. (1989) *J. of Biotech.* 12: 1-20 for a review of such procedures, see, also, e.g., U.S. Pat. Nos. 5,436,392 and 5,489,520 and many others). For purposes herein, when introducing a MAC, microinjection, protoplast fusion and particle gun bombardment are preferred.

Plant species, including tobacco, rice, maize, rye, soybean, *Brassica napus*, cotton, lettuce, potato and tomato, have been used to produce transgenic plants. Tobacco and other species, such as petunias, often serve as experimental models in which the methods have been developed and the genes first introduced and expressed.

DNA uptake can be accomplished by DNA alone or in the presence of PEG, which is a fusion agent, with plant protoplasts or by any variations of such methods known to those of skill in the art (see, e.g., U.S. Pat. No. 4,684,611 to Schilperoot et al.). Electroporation, which involves high-voltage electrical pulses to a solution containing a mixture of protoplasts and foreign DNA to create reversible pores, has been used, for example, to successfully introduce foreign genes into rice and *Brassica napus*. Microinjection of DNA into plant cells, including cultured cells and cells in intact plant organs and embryoids in tissue culture and microprojectile bombardment (acceleration of small high density particles, which contain the DNA, to high velocity with a particle gun apparatus, which forces the particles to penetrate plant cell walls and membranes) have also been used. All plant cells into which DNA can be introduced and that can be regenerated from the transformed cells can be used to produce transformed whole plants which contain the transferred artificial chromosome. The particular protocol and means for introduction of the DNA into the plant host may need to be adapted or refined to suit the particular plant species or cultivar.

c. Insect Cells

Insects are useful hosts for introduction of artificial chromosomes for numerous reasons, including, but not limited to: (a) amplification of genes encoding useful proteins can be accomplished in the artificial chromosome to obtain higher protein yields in insect cells; (b) insect cells support required post-translational modifications, such as glycosylation and phosphorylation, that can be required for protein biological functioning; (c) insect cells do not support mammalian viruses, and, thus, eliminate the problem of cross-contamination of products with such infectious agents; (d) this technology circumvents traditional recombinant baculovirus systems for production of nutritional, industrial or medicinal proteins in insect cell systems; (e) the low temperature optimum for insect cell growth (28° C.) permits reduced energy cost of production; (f) serum-free growth medium for insect cells permits lower production costs; (g) artificial chromosome-containing cells can be stored indefinitely at low temperature; and (h) insect larvae will be biological factories for production of nutritional, medicinal or industrial proteins by microinjection of fertilized insect eggs (see, e.g., Joy et al. (1991) *Current Science* 66:145-150, which provides a method for microinjecting heterologous DNA into *Bombyx mori* eggs).

Either MACs or insect-specific artificial chromosomes (BUGACs) will be used to introduce genes into insects. As described in the Examples, it appears that MACs will function in insects to direct expression of heterologous DNA contained thereon. For example, as described in the Examples, a MAC containing the *B. mori* actin gene promoter fused to the lacZ gene has been generated by transfection of EC3/7C5 cells with a plasmid containing the fusion gene. Subsequent fusion of the *B. mori* cells with the transfected EC3/7C5 cells that survived selection yielded a MAC-containing insect-mouse hybrid cell line in which β-galactosidase expression was detectable.

Insect host cells include, but are not limited to, hosts such as *Spodoptera frugiperda* (caterpillar), *Aedes aegypti* (mosquito), *Aedes albopictus* (mosquito), *Drosophila melanogaster* (fruitfly), *Bombyx mori* (silkworm), *Manduca sexta* (tomato horn worm) and *Trichoplusia ni* (cabbage looper). Efforts have been directed toward propagation of insect cells in culture. Such efforts have focused on the fall armyworm, *Spodoptera frugiperda*. Cell lines have been developed also from other insects such as the cabbage looper, *Trichoplusia ni* and the silkworm, *Bombyx mori*. It has also been suggested that analogous cell lines can be created using the tomato hornworm, *Manduca sexta*. To introduce DNA into an insect, it should be introduced into the larvae, and allowed to proliferate, and then the hemolymph recovered from the larvae so that the proteins can be isolated therefrom.

The preferred method herein for introduction of artificial chromosomes into insect cells is microinjection (see, e.g., Tamura et al. (1991) *Bio Ind.* 8:26-31; Nikolaev et al. (1989) *Mol. Biol.* (Moscow) 23:1177-87; and methods exemplified and discussed herein).

E. Applications for and Uses of Artificial Chromosomes

Artificial chromosomes provide convenient and useful vectors, and in some instances (e.g., in the case of very large heterologous genes) the only vectors, for introduction of heterologous genes into hosts. Virtually any gene of interest is amenable to introduction into a host via artificial chromosomes. Such genes include, but are not limited to, genes that encode receptors, cytokines, enzymes, proteases, hormones, growth factors, antibodies, tumor suppressor genes, therapeutic products and multigene pathways.

The artificial chromosomes provided herein will be used in methods of protein and gene product production, particularly using insects as host cells for production of such products, and in cellular (e.g., mammalian cell) production systems in which the artificial chromomsomes (particularly MACs) provide a reliable, stable and efficient means for optimizing the biomanufacturing of important compounds for medicine and industry. They are also intended for use in methods of gene therapy, and for production of transgenic plants and animals (discussed above, below and in the EXAMPLES).

1. Gene Therapy

Any nucleic acid encoding a therapeutic gene product or product of a multigene pathway may be introduced into a host animal, such as a human, or into a target cell line for introduction into an animal, for therapeutic purposes. Such therapeutic purposes include, genetic therapy to cure or to provide gene products that are missing or defective, to deliver agents, such as anti-tumor agents, to targeted cells or to an animal, and to provide gene products that will confer resistance or reduce susceptibility to a pathogen or ameliorate symptoms of a disease or disorder. The following are some exemplary genes and gene products. Such exemplification is not intended to be limiting.

a. Anti-HIV Ribozymes

As exemplified below, DNA encoding anti-HIV ribozymes can be introduced and expressed in cells using MACs, including the euchromatin-based minichromosomes and the SATACs. These MACs can be used to make a transgenic mouse that expresses a ribozyme and, thus, serves as a model for testing the activity of such ribozymes or from which ribozyme-producing cell lines can be made. Also, introduction of a MAC that encodes an anti-HIV ribozyme into human cells will serve as treatment for HIV infection. Such systems further demonstrate the viability of using any disease-specific ribozyme to treat or ameliorate a particular disease.

b. Tumor Suppressor Genes

Tumor suppressor genes are genes that, in their wild-type alleles, express proteins that suppress abnormal cellular proliferation. When the gene coding for a tumor suppressor protein is mutated or deleted, the resulting mutant protein or the complete lack of tumor suppressor protein expression may result in a failure to correctly regulate cellular proliferation. Consequently, abnormal cellular proliferation may take place, particularly if there is already existing damage to the cellular regulatory mechanism. A number of well-studied human tumors and tumor cell lines have been shown to have missing or nonfunctional tumor suppressor genes.

Examples of tumor suppression genes include, but are not limited to, the retinoblastoma susceptibility gene or RB gene, the p53 gene, the gene that is deleted in colon carcinoma (i.e., the DCC gene) and the neurofibromatosis type 1 (NF-1) tumor suppressor gene (see, e.g., U.S. Pat. No. 5,496,731; Weinberg et al. (1991) *Science* 254:1138-1146). Loss of function or inactivation of tumor suppressor genes may play a central role in the initiation and/or progression of a significant number of human cancers.

The p53 Gene

Somatic cell mutations of the p53 gene are said to be the most frequent of the gene mutations associated with human cancer (see, e.g., Weinberg et al. (1991) *Science* 254:1138-1146). The normal or wild-type p53 gene is a negative regulator of cell growth, which, when damaged, favors cell transformation. The p53 expression product is found in the nucleus, where it may act in parallel or cooperatively with other gene products. Tumor cell lines in which p53 has been deleted have been successfully treated with wild-type p53 vector to reduce tumorigenicity (see, Baker et al. (1990) *Science* 249:912-915).

DNA encoding the p53 gene and plasmids containing this DNA are well known (see, e.g., U.S. Pat. No. 5,260,191; see, also Chen et al. (1990) *Science* 250:1576; Farrel et al. (1991) *EMBO J.* 10:2879-2887; plasmids containing the gene are available from the ATCC, and the sequence is in the GenBank Database, accession nos. X54156, X60020, M14695, M16494, K03199).

c. The CFTR Gene

Cystic fibrosis (CF) is an autosomal recessive disease that affects epithelia of the airways, sweat glands, pancreas, and other organs. It is a lethal genetic disease associated with a defect in chloride ion transport, and is caused by mutations in the gene coding for the cystic fibrosis transmembrane conductance regulator (CFTR), a 1480 amino acid protein that has been associated with the expression of chloride conductance in a variety of eukaryotic cell types. Defects in CFTR destroy or reduce the ability of epithelial cells in the airways, sweat glands, pancreas and other tissues to transport chloride ions in response to cAMP mediated agonists and impair activation of apical membrane channels by cAMP dependent protein kinase A (PKA). Given the high incidence and devastating nature of this disease, development of effective CF treatments is imperative.

The CFTR gene (~250 kb) can be transferred into a MAC for use, for example, in gene therapy as follows. A CF-YAC (see Green et al. *Science* 250:94-98) may be modified to include a selectable marker, such as a gene encoding a protein that confers resistance to puromycin or hygromycin, and λ-DNA for use in site-specific integration into a neo-minichromosome or a SATAC. Such a modified CF-YAC can be introduced into MAC-containing cells, such as EC3/7C5 or 19C5xHa4 cells, by fusion with yeast protoplasts harboring the modified CF-YAC or microinjection of yeast nuclei harboring the modified CF-YAC into the cells. Stable transformants are then selected on the basis of antibiotic resistance. These transformants will carry the modified CF-YAC within the MAC contained in the cells.

2. Animals, Birds, Fish and Plants that are Genetically Altered to Possess Desired Traits Such as Resistance to Disease Artificial chromosomes are ideally suited for preparing animals, including vertebrates and invertebrates, including birds and fish as well as mammals, that possess certain desired traits, such as, for example, disease resistance, resistance to harsh environmental conditions, altered growth patterns, and enhanced physical characteristics.

One example of the use of artificial chromosomes in generating disease-resistant organisms involves the preparation of multivalent vaccines. Such vaccines include genes encoding multiple antigens that can be carried in a MAC, or species-specific artificial chromosome, and either delivered to a host to induce immunity, or incorporated into embryos to produce transgenic (non-human) animals and plants that are immune or less susceptible to certain diseases.

Disease-resistant animals and plants may also be prepared in which resistance or decreased susceptibility to disease is conferred by introduction into the host organism or embryo of artificial chromosomes containing DNA encoding gene products (e.g., ribozymes and proteins that are toxic to certain pathogens) that destroy or attenuate pathogens or limit access of pathogens to the host.

Animals and plants possessing desired traits that might, for example, enhance utility, processibility and commercial value of the organisms in areas such as the agricultural and ornamental plant industries may also be generated using artificial chromosomes in the same manner as described above for production of disease-resistant animals and plants. In such instances, the artificial chromosomes that are introduced into the organism or embryo contain DNA encoding gene products that serve to confer the desired trait in the organism.

Birds, particularly fowl such as chickens, fish and crustaceans will serve as model hosts for production of genetically altered organisms using artificial chromosomes.

3. Use of MACs and Other Artificial Chromosomes for Preparation and Screening of Libraries Since large fragments of DNA can be incorporated into each artificial chromosome, the chromosomes are well-suited for use as cloning vehicles that can accommodate entire genomes in the preparation of genomic DNA libraries, which then can be readily screened. For example, MACs may be used to prepare a genomic DNA library useful in the identification and isolation of functional centromeric DNA from different species of organisms. In such applications, the MAC used to prepare a genomic DNA library from a particular organism is one that is not functional in cells of that organism. That is, the MAC does not stably replicate, segregate or provide for expression of genes contained within it in cells of the organism. Preferably, the MACs contain an indicator gene (e.g., the lacZ gene encoding β-galactosidase or genes encoding products that confer resistance to antibiotics such as neomycin, puromycin, hygromycin) linked to a promoter that is capable of promoting transcription of the indicator gene in cells of the organism. Fragments of genomic DNA from the organism are incorporated into the MACs, and the MACs are transferred to cells from the organism. Cells that contain MACs that have incorporated functional centromeres contained within the genomic DNA fragments are identified by detection of expression of the marker gene.

4. Use of MACs and Other Artificial Chromosomes for Stable, High-Level Protein Production Cells containing the MACs and/or other artificial chromosomes provided herein are advantageously used for production of proteins, particularly several proteins from one cell line, such as multiple proteins involved in a biochemical pathway or multivalent vaccines. The genes encoding the proteins are introduced into the artificial chromosomes which are then introduced into cells. Alternatively, the heterologous gene(s) of interest are transferred into a production cell line that already contains artificial chromosomes in a manner that targets the gene(s) to the artificial chromosomes. The cells are cultured under conditions whereby the heterologous proteins are expressed. Because the proteins will be expressed at high levels in a stable permanent extra-genomic chromosomal system, selective conditions are not required.

Any transfectable cells capable of serving as recombinant hosts adaptable to continuous propagation in a cell culture system (see, e.g., McLean (1993) *Trends In Biotech.* 11:232-238) are suitable for use in an artificial chromosome-based protein production system. Exemplary host cell lines include, but are not limited to, the following: Chinese hamster ovary (CHO) cells (see, e.g., Zang et al. (1995) *Biotechnology* 13:389-392), HEK 293, $Ltk^-$, COS-7, DG44, and BHK cells. CHO cells are particularly preferred host cells. Selection of host cell lines for use in artificial chromosome-based protein production systems is within the skill of the art, but often will depend on a variety of factors, including the properties of the heterologous protein to be produced, potential toxicity of the protein in the host cell, any requirements for post-translational modification (e.g., glycosylation, amination, phosphorylation) of the protein, transcription factors available in the cells, the type of promoter element(s) being used to drive expression of the heterologous gene, whether production will be completely intracellular or the heterologous protein will preferably be secreted from the cell, and the types of processing enzymes in the cell.

The artificial chromosome-based system for heterologous protein production has many advantageous features. For example, as described above, because the heterologous DNA is located in an independent, extra-genomic artificial chromosome (as opposed to randomly inserted in an unknown area of the host cell genome or located as extrachromosomal element(s) providing only transient expression) it is stably maintained in an active transcription unit and is not subject to ejection via recombination or elimination during cell division. Accordingly, it is unnecessary to include a selection gene in the host cells and thus growth under selective conditions is also unnecessary. Furthermore, because the artificial chromosomes are capable of incorporating large segments of DNA, multiple copies of the heterologous gene and linked promoter element(s) can be retained in the chromosomes, thereby providing for high-level expression of the foreign protein(s). Alternatively, multiple copies of the gene can be linked to a single promoter element and several different genes may be linked in a fused polygene complex to a single promoter for expression of, for example, all the key proteins constituting a complete metabolic pathway (see, e.g., Beck von Bodman et al. (1995) *Biotechnology* 13:587-591). Alternatively, multiple copies of a single gene can be operatively linked to a single promoter, or each or one or several copies may be linked to different promoters or multiple copies of the same promoter. Additionally, because artificial chromosomes have an almost unlimited capacity for integration and expression of foreign genes, they can be used not only for the expression of genes encoding end-products of interest, but also for the expression of genes associated with optimal maintenance and metabolic management of the host cell, e.g., genes encoding growth factors, as well as genes that may facilitate rapid synthesis of correct form of the desired heterologous protein product, e.g., genes encoding processing enzymes and transcription factors.

The MACS are suitable for expression of any proteins or peptides, including proteins and peptides that require in vivo posttranslational modification for their biological activity. Such proteins include, but are not limited to antibody fragments, full-length antibodies, and multimeric antibodies, tumor suppressor proteins, naturally occurring or artificial antibodies and enzymes, heat shock proteins, and others.

Thus, such cell-based "protein factories" employing MACs can generated using MACs constructed with multiple copies (theoretically an unlimited number or at least up to a number such that the resulting MAC is about up to the size of a genomic chromosome (i.e., endogenous)) of protein-encoding genes with appropriate promoters, or multiple genes driven by a single promoter, i.e., a fused gene complex (such as a complete metabolic pathway in plant expression system; see, e.g., Beck von Bodman (1995) *Biotechnology* 13:587-591). Once such MAC is constructed, it can be transferred to a suitable cell culture system, such as a CHO cell line in protein-free culture medium (see, e.g., (1995) *Biotechnology* 13:389-39) or other immortalized cell lines (see, e.g., (1993) *TIBTECH* 11:232-238) where continuous production can be established.

The ability of MACs to provide for high-level expression of heterologous proteins in host cells is demonstrated, for example, by analysis of the H1D3 and G3D5 cell lines described herein and deposited with the ECACC. Northern blot analysis of mRNA obtained from these cells reveals that expression of the hygromycin-resistance and β-galactosidase genes in the cells correlates with the amplicon number of the megachromosome(s) contained therein.

F. Methods for the Synthesis of DNA Sequences Containing Repeated DNA Units

Generally, assembly of tandemly repeated DNA poses difficulties such as unambiguous annealing of the complementary oligos. For example, separately annealed products may ligate in an inverted orientation. Additionally, tandem or inverted repeats are particularly susceptible to recombination and deletion events that may disrupt the sequence. Selection of appropriate host organisms (e.g., $rec^-$ strains) for use in the cloning steps of the synthesis of sequences of tandemly repeated DNA units may aid in reduction and elimination of such events.

Methods are provided herein for the synthesis of extended DNA sequences containing repeated DNA units. These methods are particularly applicable to the synthesis of arrays of tandemly repeated DNA units, which are generally difficult or not possible to construct utilizing other known gene assembly strategies. A specific use of these methods is in the synthesis of sequences of any length containing simple (e.g., ranging from 2-6 nucleotides) tandem repeats (such as telomeres and satellite DNA repeats and trinucleotide repeats of possible clinical significance) as well as complex repeated DNA sequences. An particular example of the synthesis of a telomere sequence containing over 150 successive repeated hexamers utilizing these methods is provided herein.

The methods provided herein for synthesis of arrays of tandem DNA repeats are based in a series of extension steps in which successive doublings of a sequence of repeats results in an exponential expansion of the array of tandem repeats. These methods provide several advantages over previously known methods of gene assembly. For instance, the starting oligonucleotides are used only once. The intermediates in, as well as the final product of, the construction of the DNA arrays described herein may be obtained in cloned form in a microbial organism (e.g., *E. coli* and yeast). Of particular significance, with regard to these methods is the fact that sequence length increases exponentially, as opposed to linearly, in each extension step of the procedure even though only two oligonucleotides are required in the methods. The construction process does not depend on the compatibility of restriction enzyme recognition sequences and the sequence of the repeated DNA because restriction sites are used only temporarily during the assembly procedure. No adaptor is necessary, though a region of similar function is located between two of the restriction sites employed in the process. The only limitation with respect to restriction site use is that the two sites employed in the method must not be present elsewhere in the vector utilized in any cloning steps. These procedures can also be used to construct complex repeats with perfectly identical repeat units, such as the variable number tandem repeat (VNTR) 3' of the human apolipoprotein B100 gene (a repeat unit of 30 bp, 100% AT) or alphoid satellite DNA.

The method of synthesizing DNA sequences containing tandem repeats may generally be described as follows.

1. Starting Materials

Two oligonucleotides are utilized as starting materials. Oligonucleotide 1 is of length k of repeated sequence (the flanks of which are not relevant) and contains a relatively short stretch (60-90 nucleotides) of the repeated sequence, flanked with appropriately chosen restriction sites:

```
5'-S1>>>>>>>>>>>>>>>>>>>>>>>>>>>S2  -3'
```

wherein S1 is restriction site 1 cleaved by E1 (preferably an enzyme producing a 3'-overhang (e.g., PacI, PstI, SphI, NsiI, etc.) or blunt-end), S2 is a second restriction site cleaved by E2 (preferably an enzyme producing a 3'-overhang or one that cleaves outside the recognition sequence, such as TspRI), >represents a simple repeat unit, and '_' denotes a short (8-10) nucleotide flanking sequence complementary to oligonucleotide 2:

```
3'-    S3-5'
```

wherein S3 is a third restriction site for enzyme E3 and which is present in the vector to be used during the construction.

Because there is a large variety of restriction enzymes that recognize many different DNA sequences as cleavage sites, it should always be possible to select sites and enzymes (preferably those that yield a 3'-protruding end) suitable for these methods in connection with the synthesis of any one particular repeat array. In most cases, only 1 (or perhaps 2) nucleotide(s) of a restriction site is required to be present in the repeat sequence, and the remaining nucleotides of the restriction site can be removed, for example:

PacI: TTAAT/TAA-- (Klenow/dNTP) TAA--
PstI: CTGCA/G-- (Klenow/dNTP) G--
NsiI: ATGCA/T-- (Klenow/dNTP) T--
KpnI: GGTAC/C-- (Klenow/dNTP) C--

Though there is no known restriction enzyme leaving a single A behind, this problem can be solved with enzymes leaving behind none at all, for example:

TaiI: ACGT/(Klenow/dNTP)--
NlaIII: CATG/(Klenow/dNTP)--

Additionally, if mung bean nuclease is used instead of Klenow, then the following:

XbaI: T/CTAGA Mung bean nuclease A--

Furthermore, there are a number of restriction enzymes that cut outside of the recognition sequence, and in this case, there is no limitation at all:

TspRI NNCAGTGNN/-- (Klenow/dNTP)--
BsmI GAATG CN/-- (Klenow/dNTP)--
CTTAC/GN-- (Klenow/dNTP)--

2. Step 1—Annealing

Oligonucleotides 1 and 2 are annealed at a temperature selected depending on the length of overlap (typically in the range of 30-65° C.).

3. Step 2—Generating a Double-Stranded Molecule

The annealed oligonucleotides are filled-in with Klenow polymerase in the presence of dNTP to produce a double-stranded (ds) sequence:

```
5'-S1>>>>>>>>>>>>>>>>>>>>>>>>>>>S2   S3-3'

3'-S1<<<<<<<<<<<<<<<<<<<<<<<<<<<S2   S3-5'
```

4. Step 3—Incorporation of Double-Stranded DNA into a Vector

The double-stranded DNA is cleaved with restriction enzymes E1 and E3 and subsequently ligated into a vector (e.g., pUC 19 or a yeast vector) that has been cleaved with the same enzymes E1 and E3. The ligation product is used to transform competent host cells compatible with the vector being used (e.g., when pUC19 is used, bacterial cells such as *E. coli* DH5α are suitable hosts) which are then plated onto selection plates. Recombinants can be identified either by color (e.g., by X-gal staining for β-galactosidase expression) or by colony hybridization using $^{32}$P-labeled oligonucleotide 2 (detection by hybridization to oligonucleotide 2 is preferred because its sequence is removed in each of the subsequent extension steps and thus is present only in recombinants that contain DNA that has undergone successful extension of the repeated sequence).

5. Step 4—Isolation of Insert from the Plasmid

An aliquot of the recombinant plasmid containing k nucleotides of the repeat sequence is digested with restriction enzymes E1 and E3, and the insert is isolated on a gel (native polyacrylamide while the insert is short, but agarose can be used for isolation of longer inserts in subsequent steps). A second aliquot of the recombinant plasmid is cut with enzymes E2 (treated with Klenow and dNTP to remove the 3'-overhang) and E3, and the large fragment (plasmid DNA plus the insert) is isolated.

6. Step 5—Extension of the DNA Sequence of k Repeats

The two DNAs (the S1-S3 insert fragment and the vector plus insert) are ligated, plated to selective plates, and screened for extended recombinants as in Step 3. Now the length of the repeat sequence between restriction sites is twice that of the repeat sequence in the previous step, i.e., 2×k.

7. Step 6—Extension of the DNA Sequence of 2×k Repeats

Steps 4 and 5 are repeated as many times as needed to achieve the desired repeat sequence size. In each extension cycle, the repeat sequence size doubles, i.e., if m is the number of extension cycles, the size of the repeat sequence will be $k\times2^m$ nucleotides.

The following examples are included for illustrative purposes only and are not intended to limit the scope of the invention.

Example 1

General Materials and Methods

The following materials and methods are exemplary of methods that are used in the following Examples and that can be used to prepare cell lines containing artificial chromosomes. Other suitable materials and methods known to those of skill in the art may used. Modifications of these materials and methods known to those of skill in the art may also be employed.

A. Culture of Cell Lines, Cell Fusion, and Transfection of Cells

1. Chinese hamster K-20 cells and mouse A9 fibroblast cells were cultured in F-12 medium. EC3/7 (see, U.S. Pat. No. 5,288,625, and deposited at the European Collection of Animal cell Culture (ECACC) under accession no. 90051001; see, also Hadlaczky et al. (1991) *Proc. Natl. Acad. Sci. U.S.A.* 88:8106-8110 and U.S. application Ser. No. 08/375,271) and EC3/7C5 (see, U.S. Pat. No. 5,288,625 and Praznovszky et al. (1991) *Proc. Natl. Acad. Sci. U.S.A.* 88:11042-11046) mouse cell lines, and the KE1-2/4 hybrid cell line were maintained in F-12 medium containing 400 μg/ml G418 (SIGMA, St. Louis, Mo.).

2. TF1004G19 and TF1004G-19C5 mouse cells, described below, and the 19C5xHa4 hybrid, described below, and its sublines were cultured in F-12 medium containing up to 400 μg/ml Hygromycin B (Calbiochem). LP11 cells were maintained in F-12 medium containing 3-15 μg/ml Puromycin (SIGMA, St. Louis, Mo.).

3. Cotransfection of EC3/7C5 cells with plasmids (pH132, pCH110 available from Pharmacia, see, also Hall et al. (1983) *J. Mol. Appl. Gen.* 2:101-109) and with λ DNA was conducted using the calcium phosphate DNA precipitation method (see, e.g., Chen et al. (1987) *Mol. Cell. Biol.* 7:2745-2752), using 2-5 μg plasmid DNA and 20 μg λ phage DNA per $5\times10^6$ recipient cells.

4. Cell Fusion

Mouse and hamster cells were fused using polyethylene glycol (Davidson et al. (1976) *Som. Cell Genet.* 2:165-176). Hybrid cells were selected in HAT medium containing 400 μg/ml Hygromycin B.

Approximately $2\times10^7$ recipient and $2\times10^6$ donor cells were fused using polyethylene glycol (Davidson et al. (1976) *Som. Cell Genet.* 2:165-176). Hybrids were selected and maintained in F-12/HAT medium (Szybalsky et al. (1962) *Natl. Cancer Inst. Monogr.* 7:75-89) containing 10% FCS and 400 μg/ml G418. The presence of "parental" chromosomes in the hybrid cell lines was verified by in situ hybridization with species-specific probes using biotin-labeled human and hamster genomic DNA, and a mouse long interspersed repetitive DNA (pMCPE1.51).

5. Microcell Fusion

Microcell-mediated transfer of artificial chromosomes from EC3/7C5 cells to recipient cells was done according to Saxon et al. ((1985) *Mol. Cell. Biol.* 1:140-146) with the modifications of Goodfellow et al. ((1989) Techniques for mammalian genome transfer. In *Genome Analysis a Practical Approach*. K. E. Davies, ed., IRL Press, Oxford, Washington D.C. pp. 1-17) and Yamada et al. ((1990) *Oncogene* 5:1141-1147). Briefly, $5\times10^6$ EC3/7C5 cells in a T25 flask were treated first with 0.05 μg/ml colcemid for 48 hr and then with 10 μg/ml cytochalasin B for 30 min. The T25 flasks were centrifuged on edge and the pelleted microcells were suspended in serum free DME medium. The microcells were filtered through first a 5 micron and then a 3 micron polycarbonate filter, treated with 50 μg/ml of phytohemagglutin, and used for polyethylene glycol mediated fusion with recipient cells. Selection of cells containing the MMCneo was started 48 hours after fusion in medium containing 400-800 μg/ml G418.

Microcells were also prepared from 1B3 and GHB42 donor cells as follows in order to be fused with E2D6K cells (a CHO K-20 cell line carrying the puromycin N-acetyltransferase gene, i.e., the puromycin resistance gene, under the control of the SV40 early promoter). The donor cells were seeded to achieve 60-75% confluency within 24-36 hours. After that time, the cells were arrested in mitosis by exposure to colchicine (10 μg/ml) for 12 or 24 hours to induce micronucleation. To promote micronucleation of GHB42 cells, the cells were exposed to hypotonic treatment (10 min at 37° C.). After colchicine treatment, or after colchicine and hypotonic treatment, the cells were grown in colchicine-free medium.

The donor cells were trypsinized and centrifuged and the pellets were suspended in a 1:1 Percoll medium and incubated for 30-40 min at 37° C. After the incubation, $1\text{-}3\times10^7$ cells (60-70% micronucleation index) were loaded onto each Percoll gradient (each fusion was distributed on 1-2 gradients). The gradients were centrifuged at 19,000 rpm for 80 min in a Sorvall SS-34 rotor at 34-37° C. After centrifugation, two visible bands of cells were removed, centrifuged at 2000 rpm, 10 min at 4° C., resuspended and filtered through 8 μm pore size nucleopore filters.

The microcells prepared from the 1B3 and GHB42 cells were fused with E2D6K. The E2D6K cells were generated by $CaPO_4$ transfection of CHO K-20 cells with pCHTV2. Plasmid pCHTV2 contains the puromycin-resistance gene linked to the SV40 promoter and polyadenylation signal, the *Saccharomyces cerevisiae* URA3 gene, 2.4- and 3.2-kb fragments of a Chinese hamster chromosome 2-specific satellite DNA (HC-2 satellite; see Fatyol et al. (1994) *Nuc. Acids Res.* 22:3728-3736), two copies of the diphtheria toxin-A chain gene (one linked to the herpes simplex virus thymidine kinase (HSV-TK) gene promoter and SV40 polyadenylation signal and the other linked to the HSV-TK promoter without a polyadenylation signal), the ampicillin-resistance gene and the ColE1 origin of replication. Following transfection, puromycin-resistant colonies were isolated. The presence of the pCHTV2 plasmid in the E2D6K cell line was confirmed by nucleic acid amplification of DNA isolated from the cells.

The purified microcells were centrifuged as described above and resuspended in 2 ml of phytohemagglutinin-P (PHA-P, 100 μg/ml). The microcell suspension was then added to a 60-70% confluent recipient culture of E2D6K cells. The preparation was incubated at room temperature for 30-40 min to agglutinate the microcells. After the PHA-P was removed, the cells were incubated with 1 ml of 50% polyethyleneglycol (PEG) for one min. The PEG was removed and the culture was washed three times with F-12 medium without serum. The cells were incubated in non-selective medium for 48-60 hours. After this time, the cell culture was trypsinized and plated in F-12 medium containing 400 μg/ml hygromycin B and 10 g/ml puromycin to select against the parental cell lines.

Hybrid clones were isolated from the cells that had been cultured in selective medium. These clones were then analyzed for expression of β-galactosidase by the X-gal staining method. Four of five hybrid clones analyzed that had been generated by fusion of GHB42 microcells with E2D6K cells yielded positive staining results indicating expression of β-galactosidase from the lacZ gene contained in the megachromosome contributed by the GHB42 cells. Similarly, a hybrid clone that had been generated by fusion of 1B3 microcells with E2D6K cells yielded positive staining results indicating expression of β-galactosidase from the lacZ gene contained in the megachromosome contributed by the 1B3 cells. In situ hybridization analysis of the hybrid clones is also performed to analyze the mouse chromosome content of the mouse-hamster hybrid cells.

B. Chromosome Banding

Trypsin G-banding of chromosomes was performed using the method of Wang & Fedoroff ((1972) *Nature* 235:52-54), and the detection of constitutive heterochromatin with the BSG. C-banding method was done according to Sumner ((1972) *Exp. Cell Res.* 75:304-306). For the detection of chromosome replication by bromodeoxyuridine (BrdU) incorporation, the Fluorescein Plus Giemsa (FPG) staining method of Perry & Wolff ((1974) *Nature* 251:156-158) was used.

C. Immunolabelling of Chromosomes and In Situ Hybridization

Indirect immunofluorescence labelling with human anti-centromere serum LU851 (Hadlaczky et al. (1986) *Exp. Cell Res.* 167:1-15), and indirect immunofluorescence and in situ hybridization on the same preparation were performed as described previously (see, Hadlaczky et al. (1991) *Proc. Natl. Acad. Sci. U.S.A.* 88:8106-8110, see, also U.S. application Ser. No. 08/375,271). Immunolabelling with fluorescein-conjugated anti-BrdU monoclonal antibody (Boehringer) was performed according to the procedure recommended by the manufacturer, except that for treatment of mouse A9 chromosomes, 2 M hydrochloric acid was used at 37° C. for 25 min, and for chromosomes of hybrid cells, 1 M hydrochloric acid was used at 37° C. for 30 min.

D. Scanning Electron Microscopy

Preparation of mitotic chromosomes for scanning electron microscopy using osmium impregnation was performed as described previously (Sumner (1991) *Chromosoma* 100:410-418). The chromosomes were observed with a Hitachi S-800 field emission scanning electron microscope operated with an accelerating voltage of 25 kV.

E. DNA Manipulations, Plasmids and Probes

1. General Methods

All general DNA manipulations were performed by standard procedures (see, e.g., Sambrook et al. (1989) *Molecular cloning: A Laboratory Manual* Cold Spring Harbor Laboratory Press, Cold Spring Harbor, N.Y.). The mouse major satellite probe was provided by Dr. J. B. Rattner (University of Calgary, Alberta, Canada). Cloned mouse satellite DNA probes (see Wong et al. (1988) *Nucl. Acids Res.* 16:11645-11661), including the mouse major satellite probe, were gifts from Dr. J. B. Rattner, University of Calgary. Hamster chromosome painting was done with total hamster genomic DNA, and a cloned repetitive sequence specific to the centromeric region of chromosome 2 (Fátyol et al. (1994) *Nucl. Acids Res.* 22:3728-3736) was also used. Mouse chromosome painting was done with a cloned long interspersed repetitive sequence (PMCP1.51) specific for the mouse euchromatin.

For cotransfection and for in situ hybridization, the pCH110 β-galactosidase construct (Pharmacia or Invitrogen), and λcl 857 Sam7 phage DNA (New England Biolabs) were used.

2. Construction of Plasmid pPuroTel

Plasmid pPuroTel, which carries a Puromycin-resistance gene and a cloned 2.5 kb human telomeric sequence (see SEQ ID No. 3), was constructed from the pBabe-puro retroviral vector (Morgenstern et al. (1990) *Nucl. Acids Res.* 18:3587-3596; provided by Dr. L. Szekely (Microbiology and Tumorbiology Center, Karolinska Institutet, Stockholm); see, also Tonghua et al. (1995) *Chin. Med. J.* (Beijing, Engl. Ed.) 108:653-659; Couto et al. (1994) *Infect. Immun.* 62:2375-2378; Dunckley et al. (1992) *FEBS Lett.* 296:128-34; French et al. (1995) *Anal. Biochem.* 228:354-355; Liu et al. (1995) *Blood* 85:1095-1103; International PCT application Nos. WO 9520044; WO 9500178, and WO 9419456).

F. Deposited Cell Lines

Cell lines KE1-2/4, EC3/7C5, TF1004G19C5, 19C5xHa4, G3D5 and H1D3 have been deposited in accord with the Budapest Treaty at the European Collection of Animal Cell Culture (ECACC) under Accession Nos. 96040924, 96040925, 96040926, 96040927, 96040928 and 96040929, respectively. The cell lines were deposited on Apr. 9, 1996, at the European Collection of Animal Cell Cultures (ECACC) Vaccine Research and Production Laboratory, Public Health Laboratory Service, Centre for Applied Microbiology and Research, Porton Down, Salisbury, Wiltshire SP4 0JG, United Kingdom. The deposits were made in the name of Gyula Hadlaczky of H. 6723, SZEGED, SZAMOS U.1.A. IX. 36. HUNGARY, who has authorized reference to the deposited cell lines in this application.

Example 2

Preparation of EC3/7, EC3/7C5 and Related Cell Lines

The EC3/7 cell line is an LMTK$^-$ mouse cell line that contains the neo-centromere. The EC3/7C5 cell line is a single-cell subclone of EC3/7 that contains the neo-minichromosome.

A. EC3/7 Cell Line

As described in U.S. Pat. No. 5,288,625 (see, also Praznovszky et al. (1991) *Proc. Natl. Acad. Sci. U.S.A.* 88:11042-11046 and Hadlaczky et al. (1991) *Proc. Natl. Acad. Sci. U.S.A.* 88:8106-8110) de novo centromere formation occurs in a transformed mouse LMTK$^-$ fibroblast cell line (EC3/7) after cointegration of λ constructs (λCM8 and λgtWESneo) carrying human and bacterial DNA.

By cotransfection of a 14 kb human DNA fragment cloned in λ (λCM8) and a dominant marker gene (λgtWESneo), a selectable centromere linked to a dominant marker gene (neo-centromere) was formed in mouse LMTK$^-$ cell line EC3/7 (Hadlaczky et al. (1991) *Proc. Natl. Acad. Sci. U.S.A.* 88:8106-8110, see FIG. 1). Integration of the heterologous DNA (the λ DNA and marker gene-encoding DNA) occurred into the short arm of an acrocentric chromosome (chromosome 7 (see, FIG. 1B)), where an amplification process resulted in the formation of the new centromere (neo-centromere (see FIG. 1C)). On the dicentric chromosome (FIG. 1C), the newly formed centromere region contains all the heterologous DNA (human, λ, and bacterial) introduced into the cell and an active centromere.

Having two functionally active centromeres on the same chromosome causes regular breakages between the centromeres (see, FIG. 1E). The distance between the two centromeres on the dicentric chromosome is estimated to be ~10-15 Mb, and the breakage that separates the minichromosome occurred between the two centromeres. Such specific chromosome breakages result in the appearance (in approximately 10% of the cells) of a chromosome fragment that carries the neo-centromere (FIG. 1F). This chromosome fragment is principally composed of human, λ, plasmid, and neomycin-resistance gene DNA, but it also has some mouse chromosomal DNA. Cytological evidence suggests that during the stabilization of the MMCneo, there was an inverted duplication of the chromosome fragment bearing the neo-centromere. The size of minichromosomes in cell lines containing the MMCneo is approximately 20-30 Mb; this finding indicates a two-fold increase in size.

From the EC3/7 cell line, which contains the dicentric chromosome (FIG. 1E), two sublines (EC3/7C5 and EC3/7C6) were selected by repeated single-cell cloning. In these cell lines, the neo-centromere was found exclusively on a small chromosome (neo-minichromosome), while the formerly dicentric chromosome carried detectable amounts of the exogenously-derived DNA sequences but not an active neo-centromere (FIGS. 1F and 1G).

The minichromosomes of cell lines EC3/7C5 and EC3/7C6 are similar. No differences are detected in their architectures at either the cytological or molecular level. The minichromosomes were indistinguishable by conventional restriction endonuclease mapping or by long-range mapping using pulsed field electrophoresis and Southern hybridization. The cytoskeleton of cells of the EC3/7C6 line showed an increased sensitivity to colchicine, so the EC3/7C5 line was used for further detailed analysis.

B. Preparation of the EC3/7C5 and EC3/7C6 Cell Lines

The EC3/7C5 cells, which contain the neo-minichromosome, were produced by subcloning the EC3/7 cell line in high concentrations of G418 (40-fold the lethal dose) for 350 generations. Two single cell-derived stable cell lines (EC3/7C5 and EC3/7C6) were established. These cell lines carry the neo-centromere on minichromosomes and also contain the remaining fragment of the dicentric chromosome. Indirect immunofluorescence with anti-centromere antibodies and subsequent in situ hybridization experiments demonstrated that the minichromosomes derived from the dicentric chromosome. In EC3/7C5 and EC3/7C6 cell lines (140 and 128 metaphases, respectively) no intact dicentric chromosomes were found, and minichromosomes were detected in 97.2% and 98.1% of the cells, respectively. The minichromosomes have been maintained for over 150 cell generations. They do contain the remaining portion of the formerly dicentric chromosome.

Multiple copies of telomeric DNA sequences were detected in the marker centromeric region of the remaining portion of the formerly dicentric chromosome by in situ hybridization. This indicates that mouse telomeric sequences were coamplified with the foreign DNA sequences. These stable minichromosome-carrying cell lines provide direct evidence that the extra centromere is functioning and is capable of maintaining the minichromosomes (see, U.S. Pat. No. 5,288,625).

The chromosome breakage in the EC3/7 cells, which separates the neo-centromere from the mouse chromosome, occurred in the G-band positive "foreign" DNA region. This is supported by the observation of traces of λ and human DNA sequences at the broken end of the formerly dicentric chromosome. Comparing the G-band pattern of the chromosome fragment carrying the neo-centromere with that of the stable neo-minichromosome, reveals that the neo-minichromosome is an inverted duplicate of the chromosome fragment that bears the neo-centromere. This is also evidenced by the observation that although the neo-minichromosome carries only one functional centromere, both ends of the minichromosome are heterochromatic, and mouse satellite DNA sequences were found in these heterochromatic regions by in situ hybridization.

These two cell lines, EC3/7C5 and EC3/7C6, thus carry a selectable mammalian minichromosome (MMCneo) with a centromere linked to a dominant marker gene (Hadlaczky et al. (1991) *Proc. Natl. Acad. Sci. U.S.A.* 88:8106-8110). MMCneo is intended to be used as a vector for minichromosome-mediated gene transfer and has been used as model of a minichromosome-based vector system.

Long range mapping studies of the MMCneo indicated that human DNA and the neomycin-resistance gene constructs integrated into the mouse chromosome separately, followed by the amplification of the chromosome region that contains the exogenous DNA. The MMCneo contains about 30-50 copies of the λCM8 and λgtWESneo DNA in the form of approximately 160 kb repeated blocks, which together cover at least a 3.5 Mb region. In addition to these, there are mouse telomeric sequences (Praznovszky et al. (1991) *Proc. Natl. Acad. Sci. U.S.A.* 88:11042-11046) and any DNA of mouse origin necessary for the correct higher-ordered structural organization of chromatids.

Using a chromosome painting probe mCPE1.51 (mouse long interspersed repeated DNA), which recognizes exclusively euchromatic mouse DNA, detectable amounts of interspersed repeat sequences were found on the MMCneo by in situ hybridization. The neo-centromere is associated with a small but detectable amount of satellite DNA. The chromosome breakage that separates the neo-centromere from the mouse chromosome occurs in the "foreign" DNA region. This is demonstrated by the presence of λ and human DNA at the broken end of the formerly dicentric chromosome. At both ends of the MMCneo, however, there are traces of mouse major satellite DNA as evidenced by in situ hybridization. This observation suggests that the doubling in size of the chromosome fragment carrying the neo-centromere during the stabilization of the MMCneo is a result of an inverted duplication. Although mouse telomere sequences, which coamplified with the exogenous DNA sequences during the neo-centromere formation, may provide sufficient telomeres for the MMCneo, the duplication could have supplied the functional telomeres for the minichromosome.

The nucleotide sequence of portions of the neo-minichromosomes was determined as follows. Total DNA was isolated from EC3/7C5 cells according to standard procedures. The DNA was subjected to nucleic acid amplification using the Expand Long Template PCR system (Boehringer Mannheim) according to the manufacturer's procedures. The amplification procedure required only a single 33-mer oligonucleotide primer corresponding to sequence in a region of the phage λ right arm, which is contained in the neo-minichromosome. The sequence of this oligonucleotide is set forth as the first 33 nucleotides of SEQ ID No. 13. Because the neo-minichromosome contains a series of inverted repeats of this sequence, the single oligonucleotide was used as a forward and reverse primer resulting in amplification of DNA positioned between sets of inverted repeats of the phage λ DNA. Three products were obtained from the single amplification reaction, which suggests that the sequence of the DNA located between different sets of inverted repeats may differ. In a repeating nucleic acid unit within an artificial chromosome, minor differences may be present and may occur during culturing of cells containing the artificial chromosome. For example, base pair changes may occur as well as integration of mobile genetic elements and deletions of repeated sequences.

Each of the three products was subjected to DNA sequence analysis. The sequences of the three products are set forth in SEQ ID Nos. 13, 14, and 15, respectively. To be certain that the sequenced products were amplified from the neo-minichromosome, control amplifications were conducted using the same primers on DNA isolated from negative control cell lines (mouse Ltk$^-$ cells) lacking minichromosomes and the formerly dicentric chromosome, and positive control cell lines (the mouse-hamster hybrid cell line GB43 generated by treating 19C5xHa4 cells (see FIG. 4) with BrdU followed by growth in G418-containing selective medium and retreatment with BrdU) containing the neo-minichromosome only. Only the positive control cell line yielded the three amplification products; no amplification product was detected in the negative control reaction. The results obtained in the positive control amplification also demonstrate that the neo-minichromosome DNA, and not the fragment of the formerly dicentric mouse chromosome, was amplified.

The sequences of the three amplification products were compared to those contained in the Genbank/EMBL database. SEQ ID Nos. 13 and 14 showed high (~96%) homology to portions of DNA from intracisternal A-particles from mouse. SEQ ID No. 15 showed no significant homology with sequences available in the database. All three of these sequences may be used for generating gene targeting vectors as homologous DNAs to the neo-minichromosome.

C. Isolation and Partial Purification of Minichromosomes

Mitotic chromosomes of EC3/7C5 cells were isolated as described by Hadlaczky et al. ((1981) *Chromosoma* 81:537-555), using a glycine-hexylene glycol buffer system (Hadlaczky et al. (1982) *Chromosoma* 86:643-659). Chromosome suspensions were centrifuged at 1,200×g for 30 minutes. The supernatant containing minichromosomes was centrifuged at 5,000×g for 30 minutes and the pellet was resuspended in the appropriate buffer. Partially purified minichromosomes were stored in 50% glycerol at −20° C.

D. Stability of the MMCneo Maintenance and Neo Expression

EC3/7C5 cells grown in non-selective medium for 284 days and then transferred to selective medium containing 400 μg/ml G418 showed a 96% plating efficiency (colony formation) compared to control cells cultured permanently in the presence of G418. Cytogenetic analysis indicated that the MMCneo is stably maintained at one copy per cell under selective and non-selective culture conditions. Only two metaphases with two MMCneo were found in 2,270 metaphases analyzed.

Southern hybridization analysis showed no detectable changes in DNA restriction patterns, and similar hybridization intensities were observed with a neo probe when DNA from cells grown under selective or non-selective culture conditions were compared.

Northern analysis of RNA transcripts from the neo gene isolated from cells grown under selective and non-selective conditions showed only minor and not significant differences. Expression of the neo gene persisted in EC3/7C5 cells maintained in F-12 medium free of G418 for 290 days under non-selective culture conditions. The long-term expression of the neo gene(s) from the minichromosome may be influenced by the nuclear location of the MMCneo. In situ hybridization experiments revealed a preferential peripheral location of the MMCneo in the interphase nucleus. In more than 60% of the 2,500 nuclei analyses, the minichromosome was observed at the perimeter of the nucleus near the nuclear envelope.

Example 3

Minichromosome Transfer and Production of the λ-Neo-Chromosome

A. Minichromosome Transfer

The neo-minichromosome (referred to as MMCneo, FIG. 2C) has been used for gene transfer by fusion of minichromosome-containing cells (EC3/7C5 or EC3/7C6) with different mammalian cells, including hamster and human. Thirty-seven stable hybrid cell lines have been produced. All established hybrid cell lines proved to be true hybrids as evidenced by in situ hybridization using biotinylated human, and hamster genomic, or pMCPE1.51 mouse long interspersed repeated DNA probes for "chromosome painting". The MMCneo has also been successfully transferred into mouse A9, L929 and pluripotent F9 teratocarcinoma cells by fusion of microcells derived from EC3/7C5 cells. Transfer was confirmed by PCR, Southern blotting and in situ hybridization with minichromosome-specific probes. The cytogenetic analysis confirmed that, as expected for microcell fusion, a few cells (1-5%) received (or retained) the MMCneo.

These results demonstrate that the MMCneo is tolerated by a wide range of cells. The prokaryotic genes and the extra dosage for the human and λ sequences carried on the minichromosome seem to be not disadvantageous for tissue culture cells.

The MMCneo is the smallest chromosome of the EC3/7C5 genome and is estimated to be approximately 20-30 Mb, which is significantly smaller than the majority of the host cell (mouse) chromosomes. By virtue of the smaller size, minichromosomes can be partially purified from a suspension of isolated chromosomes by a simple differential centrifugation. In this way, minichromosome suspensions of 15-20% purity have been prepared. These enriched minichromosome preparations can be used to introduce, such as by microinjection or lipofection, the minichromosome into selected target cells. Target cells include therapeutic cells that can be use in methods of gene therapy, and also embryonic cells for the preparation of transgenic (non-human) animals.

The MMCneo is capable of autonomous replication, is stably maintained in cells, and permits persistent expression of the neo gene(s), even after long-term culturing under non-selective conditions. It is a non-integrative vector that appears to occupy a territory near the nuclear envelope. Its peripheral localization in the nucleus may have an important role in maintaining the functional integrity and stability of the MMCneo. Functional compartmentalization of the host nucleus may have an effect on the function of foreign sequences. In addition, MMCneo contains megabases of λ DNA sequences that should serve as a target site for homologous recombination and thus integration of desired gene(s) into the MMCneo. It can be transferred by cell and microcell fusion, microinjection, electroporation, lipid-mediated carrier systems or chromosome uptake. The neo-centromere of the MMCneo is capable of maintaining and supporting the normal segregation of a larger 150-200 Mb λneo-chromosome. This result demonstrates that the MMCneo chromosome should be useful for carrying large fragments of heterologous DNA.

B. Production of the λNeo-Chromosome

In the hybrid cell line KE1-2/4 made by fusion of EC3/7 and Chinese hamster ovary cells (FIG. 2), the separation of the neo-centromere from the dicentric chromosome was associated with a further amplification process. This amplification resulted in the formation of a stable chromosome of average size (i.e., the λneo-chromosome; see, Praznovszky et al. (1991) *Proc. Natl. Acad. Sci. U.S.A.* 88:11042-11046). The λneo-chromosome carries a terminally located functional centromere and is composed of seven large amplicons containing multiple copies of λ, human, bacterial, and mouse DNA sequences (see FIG. 2). The amplicons are separated by mouse major satellite DNA (Praznovszky et al. (1991) *Proc. Natl. Acad. Sci. U.S.A.* 88:11042-11046) which forms narrow bands of constitutive heterochromatin between the amplicons.

Example 4

Formation of the "Sausage Chromosome" (SC)

The findings set forth in the above EXAMPLES demonstrate that the centromeric region of the mouse chromosome 7 has the capacity for large-scale amplification (other results indicate that this capacity is not unique to chromosome 7). This conclusion is further supported by results from cotransfection experiments, in which a second dominant selectable marker gene and a non-selected marker gene were introduced into EC3/7C5 cells carrying the formerly dicentric chromosome 7 and the neo-minichromosome. The EC3/7C5 cell line was transformed with λ phage DNA, a hygromycin-resistance gene construct (pH132), and a β-galactosidase gene construct (pCH110). Stable transformants were selected in the presence of high concentrations (400 μg/ml) Hygromycin B, and analyzed by Southern hybridization. Established transformant cell lines showing multiple copies of integrated exogenous DNA were studied by in situ hybridization to localize the integration site(s), and by LacZ staining to detect β-galactosidase expression.

A. Materials and Methods

1. Construction of pH132

The pH132 plasmid carries the hygromycin B resistance gene and the anti-HIV-1 gag ribozyme (see, SEQ ID NO. 6 for DNA sequence that corresponds to the sequence of the ribozyme) under control of the β-actin promoter. This plasmid was constructed from pHyg plasmid (Sugden et al. (1985) *Mol. Cell. Biol.* 5:410-413; a gift from Dr. A. D. Riggs, Beckman Research Institute, Duarte; see, also, e.g., U.S. Pat. No. 4,997,764), and from pPC-RAG12 plasmid (see, Chang et al. (1990) *Clin Biotech* 2:23-31; provided by Dr. J. J. Rossi, Beckman Research Institute, Duarte; see, also U.S. Pat. Nos. 5,272,262, 5,149,796 and 5,144,019, which describes the anti-HIV gag ribozyme and construction of a mammalian expression vector containing the ribozyme insert linked to the β-actin promoter and SV40 late gene transcriptional termination and polyA signals). Construction of pPC-RAG12 involved insertion of the ribozyme insert flanked by BamHI linkers was into BamHI-digested pHβ-Apr-1gpt (see, Gunning et al. (1987) *Proc. Natl. Acad. Sci. U.S.A.* 84:4831-4835, see, also U.S. Pat. No. 5,144,019).

Plasmid pH132 was constructed as follows. First, pPC-RAG12 (described by Chang et al. (1990) *Clin. Biotech.* 2:23-31) was digested with BamHI to excise a fragment containing an anti-HIV ribozyme gene (referred to as ribozyme D by Chang et al. ((1990) *Clin. Biotech.* 2:23-31); see also U.S. Pat. No. 5,144,019 to Rossi et al., particularly FIG. 4 of the patent) flanked by the human β-actin promoter at the 5' end of the gene and the SV40 late transcriptional termination and polyadenylation signals at the 3' end of the gene. As described by Chang et al. ((1990) *Clin. Biotech.* 2:23-31), ribozyme D is targeted for cleavage of the translational initiation region of the HIV gag gene. This fragment of pPC-RAG12 was subcloned into pBluescript-KS(+) (Stratagene, La Jolla, Calif.) to produce plasmid 132. Plasmid 132 was then digested with XhoI and EcoRI to yield a fragment containing the ribozyme D gene flanked by the β-actin promoter at the 5' end and the SV40 termination and polyadenylation signals at the 3' end of the gene. This fragment was ligated to the largest fragment generated by digestion of pHyg (Sugden et al. (1985) *Mol. Cell. Biol.* 5:410-413) with EcoRI and SalI to yield pH132. Thus, pH132 is an ~9.3 kb plasmid containing the following elements: the β-actin promoter linked to an anti-HIV ribozyme gene followed by the SV40 termination and polyadenylation signals, the thymidine kinase gene promoter linked to the hygromycin-resistance gene followed by the thymidine kinase gene polyadenylation signal, and the *E. coli* ColE1 origin of replication and the ampicillin-resistance gene.

The plasmid pHyg (see, e.g., U.S. Pat. Nos. 4,997,764, 4,686,186 and 5,162,215), which confers resistance to hygromycin B using transcriptional controls from the HSV-1 tk gene, was originally constructed from pKan2 (Yates et al. (1984) *Proc. Natl. Acad. Sci. U.S.A.* 81:3806-3810) and pLG89 (see, Gritz et al. (1983) *Gene* 25:179-188). Briefly pKan2 was digested with SmaI and BglII to remove the sequences derived from transposon Tn5. The hygromycin-resistance hph gene was inserted into the digested pKan2 using blunt-end ligation at the SnaI site and "sticky-end" ligation (using 1 Weiss unit of T4 DNA ligase (BRL) in 20 microliter volume) at the BglII site. The SmaI and BglII sites of pKan2 were lost during ligation.

The resulting plasmid pH132, produced from introduction of the anti-HIV ribozyme construct with promoter and polyA site into pHyg, includes the anti-HIV ribozyme under control of the β-actin promoter as well as the hygromycin-resistance gene under control of the TK promoter.

2. Chromosome Banding

Trypsin G-banding of chromosomes was performed as described in EXAMPLE 1.

3. Cell Cultures

TF1004G19 and TF1004G-19C5 mouse cells and the 19C5xHa4 hybrid, described below, and its sublines were cultured in F-12 medium containing 400 μg/ml Hygromycin B (Calbiochem).

B. Cotransfection of EC3/7C5 to Produce TF1004G19

Cotransfection of EC3/7C5 cells with plasmids (pH132, pCH110 available from Pharmacia, see, also Hall et al. (1983) *J. Mol. Appl. Gen.* 2:101-109) and with λ DNA (λcl 857 Sam 7(New England Biolabs)) was conducted using the calcium phosphate DNA precipitation method (see, e.g., Chen et al. (1987) *Mol. Cell. Biol.* 7:2745-2752), using 2-5 μg plasmid DNA and 20 μg k phage DNA per $5\times10^6$ recipient cells.

C. Cell Lines Containing the Sausage Chromosome

Analysis of one of the transformants, designated TF1004G19, revealed that it has a high copy number of integrated pH132 and pCH110 sequences, and a high level of β-galactosidase expression. G-banding and in situ hybridization with a human probe (CM8; see, e.g., U.S. application Ser. No. 08/375,271) revealed unexpectedly that integration had occurred in the formerly dicentric chromosome 7 of the EC3/7C5 cell line. Furthermore, this chromosome carried a newly formed heterochromatic chromosome arm. The size of this heterochromatic arm varied between ~150 and ~800 Mb in individual metaphases.

By single cell cloning from the TF1004G19 cell line, a subclone TF1004G-19C5 (FIG. 2D), which carries a stable chromosome 7 with a ~100-150 Mb heterochromatic arm (the sausage chromosome) was obtained. This cell line has been deposited in the ECACC under Accession No. 96040926. This chromosome arm is composed of four to five satellite segments rich in satellite DNA, and evenly spaced integrated heterologous "foreign" DNA sequences. At the end of the compact heterochromatic arm of the sausage chromosome, a less condensed euchromatic terminal segment is regularly observed. This subclone was used for further analyses.

D. Demonstration that the Sausage Chromosome is Derived from the Formerly Dicentric Chromosome In situ hybridization with k phage and pH132 DNA on the TF1004G-19C5 cell line showed positive hybridization only on the minichromosome and on the heterochromatic arm of the "sausage" chromosome (FIG. 2D). It appears that the "sausage" chromosome (herein also referred to as the SC) developed from the formerly dicentric chromosome (FD) of the EC3/7C5 cell line.

To establish this, the integration sites of pCH110 and pH132 plasmids were determined. This was accomplished by in situ hybridization on these cells with biotin-labeled subfragments of the hygromycin-resistance gene and the β-galactosidase gene. Both experiments resulted in narrow hybridizing bands on the heterochromatic arm of the sausage chromosome. The same hybridization pattern was detected on the sausage chromosome using a mixture of biotin-labeled λ probe and pH132 plasmid, proving the cointegration of λ phages, pH132 and pCH110 plasmids.

To examine this further, the cells were cultured in the presence of the DNA-binding dye Hoechst 33258. Culturing of mouse cells in the presence of this dye results in under-condensation of the pericentric heterochromatin of metaphase chromosomes, thereby permitting better observation of the hybridization pattern. Using this technique, the heterochromatic arm of the sausage chromosome of TF1004G-19C5 cells showed regular under-condensation revealing the details of the structure of the "sausage" chromosome by in situ hybridization. Results of in situ hybridization on Hoechst-treated TF1004G-19C5 cells with biotin-labeled subfragments of hygromycin-resistance and β-galactosidase genes shows that these genes are localized only in the heterochromatic arm of the sausage chromosome. In addition, an equal banding hybridization pattern was observed. This pattern of repeating units (amplicons) clearly indicates that the sausage chromosome was formed by an amplification process and that the λ phage, pH132 and pCH110 plasmid DNA sequences border the amplicons.

In another series of experiments using fluorescence in situ hybridization (FISH) carried out with mouse major satellite DNA, the main component of the mouse pericentric heterochromatin, the results confirmed that the amplicons of the sausage chromosome are primarily composed of satellite DNA.

E. The Sausage Chromosome has One Centromere

To determine whether mouse centromeric sequences had participated in the amplification process forming the "sausage" chromosome and whether or not the amplicons carry inactive centromeres, in situ hybridization was carried out with mouse minor satellite DNA. Mouse minor satellite DNA is localized specifically near the centromeres of all mouse chromosomes. Positive hybridization was detected in all mouse centromeres including the sausage chromosome, which, however, only showed a positive signal at the beginning of the heterochromatic arm.

Indirect immunofluorescence with a human anti-centromere antibody (LU 851) which recognizes only functional centromeres (see, e.g., Hadlaczky et al. (1989) *Chromosoma* 97:282-288) proved that the sausage chromosome has only one active centromere. The centromere comes from the formerly dicentric part of the chromosome and co-localizes with the in situ hybridization signal of the mouse minor DNA probe.

F. The Selected and Non-Selected Heterologous DNA in the Heterochromatin of the Sausage Chromosome is Expressed 1. High Levels of the Heterologous Genes are Expressed The TF1004G-19C5 cell line thus carries multiple copies of hygromycin-resistance and β-galactosidase genes localized only in the heterochromatic arm of the sausage chromosome. The TF1004G-19C5 cells can grow very well in the presence of 200 μg/ml or even 400 μg/ml hygromycin B. (The level of expression was determined by Northern hybridization with a subfragment of the hygromycin-resistance gene and single copy gene.)

The expression of the non-selected β-galactosidase gene in the TF1004G-19C5 transformant was detected with LacZ staining of the cells. By this method one hundred percent of the cells stained dark blue, showing that there is a high level of β-galactosidase expression in all of TF1004G-19C5 cells.

2. The Heterologous Genes that are Expressed are in the Heterochromatin of the Sausage Chromosome To demonstrate that the genes localized in the constitutive heterochromatin of the sausage chromosome provide the hygromycin resistance and the LacZ staining capability of TF1004G-19C5 transformants (i.e., β-gal expression), PEG-induced cell fusion between TF1004G-19C5 mouse cells and Chinese hamster ovary cells was performed. The hybrids were selected and maintained in HAT medium containing G418 (400 μg/ml) and hygromycin (200 μg/ml). Two hybrid clones designated 19C5xHa3 and 19C5xHa4, which have been deposited in the ECACC under Accession No. 96040927, were selected. Both carry the sausage chromosome and the minichromosome.

Twenty-seven single cell derived colonies of the 19C5xHa4 hybrid were maintained and analyzed as individual subclones. In situ hybridization with hamster and mouse chromosome painting probes and hamster chromosome 2-specific probes verified that the 19C5xHa4 clone contains the complete Chinese hamster genome and a partial mouse genome. All 19C5xHa4 subclones retained the hamster genome, but different subclones showed different numbers of mouse chromosomes indicating the preferential elimination of mouse chromosomes.

To promote further elimination of mouse chromosomes, hybrid cells were repeatedly treated with BrdU. The BrdU treatments, which destabilize the genome, result in significant loss of mouse chromosomes. The BrdU-treated 19C5xHa4 hybrid cells were divided to three groups. One group of the hybrid cells (GH) was maintained in the presence of hygromycin (200 μg/ml) and G418 (400 μg/ml), and the other two groups of the cells were cultured under G418 (G) or hygromycin (H) selection conditions to promote the elimination of the sausage chromosome or minichromosome.

One month later, single cell derived subclones were established from these three subcultures of the 19C5xHa4 hybrid line. The subclones were monitored by in situ hybridization with biotin-labeled λ phage and hamster chromosome painting probes. Four individual clones (G2B5, G3C5, G4D6, G2B4) selected in the presence of G418 that had lost the sausage chromosome but retained the minichromosome were found. Under hygromycin selection only one subclone (H1D3) lost the minichromosome. In this clone the megachromosome (see Example 5) was present.

Since hygromycin-resistance and β-galactosidase genes were thought to be expressed from the sausage chromosome, the expression of these genes was analyzed in the four subclones that had lost the sausage chromosome. In the presence of 200 μg/ml hygromycin, one hundred percent of the cells of four individual subclones died. In order to detect the β-galactosidase expression hybrid, subclones were analyzed by LacZ staining. One hundred percent of the cells of the four subclones that lost the sausage chromosome also lost the LacZ staining capability. All of the other hybrid subclones that had not lost the sausage chromosome under the non-selective culture conditions showed positive LacZ staining.

These findings demonstrate that the expression of hygromycin-resistance and β-galactosidase genes is linked to the presence of the sausage chromosome. Results of in situ hybridizations show that the heterologous DNA is expressed from the constitutive heterochromatin of the sausage chromosome.

In situ hybridization studies of three other hybrid subclones (G2C6, G2D1, and G4D5) did not detect the presence of the sausage chromosome. By the LacZ staining method, some stained cells were detected in these hybrid lines, and when these subclones were transferred to hygromycin selection some colonies survived. Cytological analysis and in situ hybridization of these hygromycin-resistant colonies revealed the presence of the sausage chromosome, suggesting that only the cells of G2C6, G2D1 and G4D5 hybrids that had not lost the sausage chromosome were able to preserve the hygromycin resistance and β-galactosidase expression. These results confirmed that the expression of these genes is linked to the presence of the sausage chromosome. The level of β-galactosidase expression was determined by the immunoblot technique using a monoclonal antibody.

Hygromycin resistance and β-galactosidase expression of the cells which contained the sausage chromosome were provided by the genes localized in the mouse pericentric heterochromatin. This was demonstrated by performing Southern DNA hybridizations on the hybrid cells that lack the sausage chromosome using PCR-amplified subfragments of hygromycin-resistance and β-galactosidase genes as probes. None of the subclones showed hybridization with these probes; however, all of the analyzed clones contained the minichromosome. Other hybrid clones that contain the sausage chromosome showed intense hybridization with these DNA probes. These results lead to the conclusion that hygromycin resistance and β-galactosidase expression of the cells that contain the sausage chromosome were provided by the genes localized in the mouse pericentric heterochromatin.

Example 5

The Gigachromosome

As described in Example 4, the sausage chromosome was transferred into Chinese hamster cells by cell fusion. Using Hygromycin B/HAT and G418 selection, two hybrid clones 19C5xHa3 and 19C5xHa4 were produced that carry the sausage chromosome. In situ hybridization, using hamster and mouse chromosome-painting probes and a hamster chromosome 2-specific probe, verified that clone 19C5xHa4 contains a complete Chinese hamster genome as well as partial mouse genomes. Twenty-seven separate colonies of 19C5xHa4 cells were maintained and analyzed as individual subclones. Twenty-six out of 27 subclones contained a morphologically unchanged sausage chromosome.

In one subclone of the 19C5xHa3 cell line, 19C5xHa47 (see FIG. 2E), the heterochromatic arm of the sausage chromosome became unstable and showed continuous intrachromosomal growth. In extreme cases, the amplified chromosome arm exceeded 1000 Mb in size (gigachromosome).

Example 6

The Stable Megachromosome

A. Generation of Cell Lines Containing the Megachromosome

All 19C5xHa4 subclones retained a complete hamster genome, but different subclones showed different numbers of mouse chromosomes, indicating the preferential elimination of mouse chromosomes. As described in Example 4, to promote further elimination of mouse chromosomes, hybrid cells were treated with BrdU, cultured under G418 (G) or hygromycin (H) selection conditions followed by repeated treatment with $10^{-4}$ M BrdU for 16 hours and single cell subclones were established. The BrdU treatments appeared to destabilize the genome, resulting in a change in the sausage chromosome as well. A gradual increase in a cell population in which a further amplification had occurred was observed. In addition to the ~100-150 Mb heterochromatic arm of the sausage chromosome, an extra centromere and a ~150-250 Mb heterochromatic chromosome arm were formed, which differed from those of mouse chromosome 7. By the acquisition of another euchromatic terminal segment, a new submetacentric chromosome (megachromosome) was formed. Seventy-nine individual subclones were established from these BrdU-treated cultures by single-cell cloning: 42 subclones carried the intact megachromosome, 5 subclones carried the sausage chromosome, and in 32 subclones fragments or translocated segments of the megachromosome were observed. Twenty-six subclones that carried the megachromosome were cultured under non-selective conditions over a two-month period. In 19 out of 26 subclones, the megachromosome was retained. Those subclones which lost the megachromosomes all became sensitive to Hygromycin B and had no β-galactosidase expression, indicating that both markers were linked to the megachromosome.

Two sublines (G3D5 and H1D3), which were chosen for further experiments, showed no changes in the morphology of the megachromosome during more than 100 generations under selective conditions. The G3D5 cells had been obtained by growth of 19C5xHa4 cells in G418-containing medium followed by repeated BrdU treatment, whereas H1D3 cells had been obtained by culturing 19C5xHa4 cells in hygromycin-containing medium followed by repeated BrdU treatment.

B. Structure of the Megachromosome

The following results demonstrate that, apart from the euchromatic terminal segments, the integrated foreign DNA (and as in the exemplified embodiments, rDNA sequence), the whole megachromosome is constitutive heterochromatin, containing a tandem array of at least 40 (~7.5 Mb) blocks of mouse major satellite DNA (see FIGS. 2 and 3). Four satellite DNA blocks are organized into a giant palindrome (amplicon) carrying integrated exogenous DNA sequences at each end. The long and short arms of the submetacentric megachromosome contains 6 and 4 amplicons, respectively. It is of course understood that the specific organization and size of each component can vary among species, and also the chromosome in which the amplification event initiates.

1. The Megachromosome is Composed Primarily of Heterochromatin

Except for the terminal regions and the integrated foreign DNA, the megachromosome is composed primarily of heterochromatin. This was demonstrated by C-banding of the megachromosome, which resulted in positive staining characteristic of constitutive heterochromatin. Apart from the terminal regions and the integrated foreign DNA, the whole megachromosome appears to be heterochromatic. Mouse major satellite DNA is the main component of the pericentric, constitutive heterochromatin of mouse chromosomes and represents ~10% of the total DNA (Waring et al. (1966) *Science* 154:791-794). Using a mouse major satellite DNA probe for in situ hybridization, strong hybridization was observed throughout the megachromosome, except for its terminal regions. The hybridization showed a segmented pattern: four large blocks appeared on the short arm and usually 4-7 blocks were seen on the long arm. By comparing these segments with the pericentric regions of normal mouse chromosomes that carry ~15 Mb of major satellite DNA, the size of the blocks of major satellite DNA on the megachromosome was estimated to be ~30 Mb.

Using a mouse probe specific to euchromatin (pMCPE1.51; a mouse long interspersed repeated DNA probe), positive hybridization was detected only on the terminal segments of the megachromosome of the H1D3 hybrid subline. In the G3D5 hybrids, hybridization with a hamster-specific probe revealed that several megachromosomes contained terminal segments of hamster origin on the long arm. This observation indicated that the acquisition of the terminal segments on these chromosomes happened in the hybrid cells, and that the long arm of the megachromosome was the recently formed one arm. When a mouse minor satellite probe was used, specific to the centromeres of mouse chromosomes (Wong et al. (1988) *Nucl. Acids Res.* 16:11645-11661), a strong hybridization signal was detected only at the primary constriction of the megachromosome, which colocalized with the positive immunofluorescence signal produced with human anti-centromere serum (LU851).

In situ hybridization experiments with pH132, pCH110, and λ DNA probes revealed that all heterologous DNA was located in the gaps between the mouse major satellite DNA segments. Each segment of mouse major satellite DNA was bordered by a narrow band of integrated heterologous DNA, except at the second segment of the long arm where a double band of heterologous DNA existed, indicating that the major satellite DNA segment was missing or considerably reduced in size here. This chromosome region served as a useful cytological marker in identifying the long arm of the megachromosome. At a frequency of $10^{-4}$, "restoration" of these missing satellite DNA blocks was observed in one chromatid, when the formation of a whole segment on one chromatid occurred.

After Hoechst 33258 treatment (50 μg/ml for 16 hours), the megachromosome showed undercondensation throughout its length except for the terminal segments. This made it possible to study the architecture of the megachromosome at higher resolution. In situ hybridization with the mouse major satellite probe on undercondensed megachromosomes demonstrated that the ~30 Mb major satellite segments were composed of four blocks of ~7.5 Mb separated from each other by a narrow band of non-hybridizing sequences (FIG. 3). Similar segmentation can be observed in the large block of pericentric heterochromatin in metacentric mouse chromosomes from the LMTK$^-$ and A9 cell lines.

2. The Megachromosome is Composed of Segments Containing Two Tandem ~7.5 Mb Blocks Followed by Two Inverted Blocks Because of the asymmetry in thymidine content between the two strands of the DNA of the mouse major satellite, when mouse cells are grown in the presence of BrdU for a single S phase, the constitutive heterochromatin shows lateral asymmetry after FPG staining. Also, in the 19C5xHa4 hybrids, the thymidine-kinase (Tk) deficiency of the mouse fibroblast cells was complemented by the hamster Tk gene, permitting BrdU incorporation experiments.

A striking structural regularity in the megachromosome was detected using the FPG technique. In both chromatids, alternating dark and light staining that produced a checkered appearance of the megachromosome was observed. A similar picture was obtained by labelling with fluorescein-conjugated anti-BrdU antibody. Comparing these pictures to the segmented appearance of the megachromosome showed that one dark and one light FPG band corresponded to one ~30 Mb segment of the megachromosome. These results suggest that the two halves of the ~30 Mb segment have an inverted orientation. This was verified by combining in situ hybridization and immunolabelling of the incorporated BrdU with fluorescein-conjugated anti-BrdU antibody on the same chromosome. Since the ~30 Mb segments (or amplicons) of the megachromosome are composed of four blocks of mouse major satellite DNA, it can be concluded that two tandem ~7.5 Mb blocks are followed by two inverted blocks within one segment.

Large-scale mapping of megachromosome DNA by pulsed-field electrophoresis and Southern hybridization with "foreign" DNA probes revealed a simple pattern of restriction fragments. Using endonucleases with none, or only a single cleavage site in the integrated foreign DNA sequences, followed by hybridization with a hyg probe, 1-4 predominant fragments were detected. Since the megachromosome contains 10-12 amplicons with an estimated 3-8 copies of hyg sequences per amplicon (30-90 copies per megachromosome), the small number of hybridizing fragments indicates the homogeneity of DNA in the amplified segments.

3. Scanning Electron Microscopy of the Megachromosome Confirmed the Above Findings The homogeneous architecture of the heterochromatic arms of the megachromosome was confirmed by high resolution scanning electron microscopy. Extended arms of megachromosomes, and the pericentric heterochromatic region of mouse chromosomes, treated with Hoechst 33258, showed similar structure. The constitutive heterochromatic regions appeared more compact than the euchromatic segments. Apart from the terminal regions, both arms of the megachromosome were completely extended, and showed faint grooves, which should correspond to the border of the satellite DNA blocks in the non-amplified chromosomes and in the megachromosome. Without Hoechst treatment, the grooves seemed to correspond to the amplicon borders on the megachromosome arms. In addition, centromeres showed a more compact, finely fibrous appearance than the surrounding heterochromatin.

4. The Megachromosome of 1B3 Cells Contains rRNA Gene Sequence

The sequence of the megachromosome in the region of the sites of integration of the heterologous DNA was investigated by isolation of these regions through using cloning methods and sequence analysis of the resulting clones. The results of this analysis revealed that the heterologous DNA was located near mouse ribosomal RNA gene (i.e., rDNA) sequences contained in the megachromosome.

a. Cloning of Regions of the Megachromosomes in which Heterologous DNA had Integrated Megachromosomes were isolated from 1B3 cells (which were generated by repeated BrdU treatment and single cell cloning of H1xHE41 cells (see FIG. 4) and which contain a truncated megachromosome) using fluorescence-activated cell sorting methods as described herein (see Example 10). Following separation of the SATACs (megachromosomes) from the endogenous chromosomes, the isolated megachromosomes were stored in GH buffer (100 mM glycine, 1% hexylene glycol, pH 8.4-8.6 adjusted with saturated calcium hydroxide solution; see Example 10) and centrifuged into an agarose bed in 0.5 M EDTA.

Large-scale mapping of the megachromosome around the area of the site of integration of the heterologous DNA revealed that it is enriched in sequence containing rare-cutting enzyme sites, such as the recognition site for NotI. Additionally, mouse major satellite DNA (which makes up the majority of the megachromosome) does not contain NotI recognition sites. Therefore, to facilitate isolation of regions of the megachromosome associated with the site of integration of the heterologous DNA, the isolated megachromosomes were cleaved with NotI, a rare cutting restriction endonuclease with an 8-bp GC recognition site. Fragments of the megachromosome were inserted into plasmid pWE15 (Stratagene, La Jolla, Calif.) as follows. Half of a 100-μl low melting point agarose block (mega-plug) containing the isolated SATACs was digested with NotI overnight at 37° C. Plasmid pWE15 was similarly digested with NotI overnight. The mega-plug was then melted and mixed with the digested plasmid, ligation buffer and T4 ligase. Ligation was conducted at 16° C. overnight. Bacterial DH5α cells were transformed with the ligation product and transformed cells were plated onto LB/Amp plates. Fifteen to twenty colonies were grown on each plate for a total of 189 colonies. Plasmid DNA was isolated from colonies that survived growth on LB/Amp medium and was analyzed by Southern blot hybridization for the presence of DNA that hybridized to a pUC19 probe. This screening methodology assured that all clones, even clones lacking an insert but yet containing the pWE15 plasmid, would be detected. Any clones containing insert DNA would be expected to contain non-satellite, GC-rich megachromosome DNA sequences located at the site of integration of the heterologous DNA. All colonies were positive for hybridizing DNA.

Liquid cultures of all 189 transformants were used to generate cosmid minipreps for analysis of restriction sites within the insert DNA. Six of the original 189 cosmid clones contained an insert. These clones were designated as follows: 28 (~9-kb insert), 30 (~9-kb insert), 60 (~4-kb insert), 113 (~9-kb insert), 157 (~9-kb insert) and 161 (~9-kb insert). Restriction enzyme analysis indicated that three of the clones (113, 157 and 161) contained the same insert.

b. In Situ Hybridization Experiments Using Isolated Segments of the Megachromosome as Probes Insert DNA from clones 30, 113, 157 and 161 was purified, labeled and used as probes in in situ hybridization studies of several cell lines. Counterstaining of the cells with propidium iodide facilitated identification of the cytological sites of the hybridization signals. The locations of the signals detected within the cells are summarized in the following table:

| CELL TYPE | PROBE | LOCATION OF SIGNAL |
|---|---|---|
| Human Lymphocyte (male) | No. 161 | 4-5 pairs of acrocentric chromosomes at centromeric regions. |
| Mouse Spleen | No. 161 | Acrocentric ends of 4 pairs of chromosomes. |
| EC3/7C5 Cells | No. 161 | Minichromosome and the end of the formerly dicentric chromosome. Pericentric heterochromatin of one of the metacentric mouse chromosomes. Centromeric region of some of the other mouse chromosomes. |
| K20 Chinese Hamster Cells | No. 30 | Ends of at least 6 pairs of chromosomes. An interstitial signal on a short chromosome. |
| HB31 Cells (mouse-hamster hybrid cells derived from H1D3 cells by repeated BrdU treatment and single cell cloning which carries the megachromosome) | No. 30 | Acrocentric ends of at least 12 pairs of chromosomes. Centromeres of certain chromosomes and the megachromosome. Borders of the amplicons of the megachromosome. |
| Mouse Spleen Cells | No. 30 | Similar to signal observed for probe no. 161. Centromeres of 5 pairs of chromosomes. Weak cross-hybridization to pericentric heterochromatin. |
| HB31 Cells | No. 113 | Similar to signal observed for probe no. 30. |
| Mouse Spleen Cells | No. 113 | Centromeric region of 5 pairs of chromosomes. |
| K20 Cells | No. 113 | At least 6 pairs of chromosomes. Weak signal at some telomeres and several interspersed signals. |
| Human Lymphocyte Cells (male) | No. 157 | Similar to signal observed for probe no. 161. |

c. Southern Blot Hybridization Using Isolated Segments of the Megachromosome as Probes DNA was isolated from mouse spleen tissue, mouse LMTK$^{-}$ cells, K20 Chinese hamster ovary cells, EJ30 human fibroblast cells and H1D3 cells. The isolated DNA and lambda phage DNA, was subjected to Southern blot hybridization using inserts isolated from megachromosome clone nos. 30, 113, 157 and 161 as probes. Plasmid pWE15 was used as a negative control probe. Each of the four megachromosome clone inserts hybridized in a multi-copy manner (as demonstrated by the intensity of hybridization and the number of hybridizing bands) to all of the DNA samples, except the lambda phage DNA. Plasmid pWE15 hybridized to lambda DNA only.

d. Sequence Analysis of Megachromosome Clone No. 161

Megachromosome clone no. 161 appeared to show the strongest hybridization in the in situ and Southern hybridization experiments and was chosen for analysis of the insert sequence. The sequence analysis was approached by first subcloning the insert of cosmid clone no. 161 to obtain five subclones as follows.

To obtain the end fragments of the insert of clone no. 161, the clone was digested with NotI and BamHI and ligated with NotI/BamHI-digested pBluescript KS (Stratagene, La Jolla, Calif.). Two fragments of the insert of clone no. 161 were obtained: a 0.2-kb and a 0.7-kb insert fragment. To subclone the internal fragment of the insert of clone no. 161, the same digest was ligated with BamHI-digested pUC19. Three fragments of the insert of clone no. 161 were obtained: a 0.6-kb, a 1.8-kb and a 4.8-kb insert fragment.

The ends of all the subcloned insert fragments were first sequenced manually. However, due to their extremely high GC content, autoradiographs were difficult to interpret and sequencing was repeated using an ABI sequencer and the dye-terminator cycle protocol. A comparison of the sequence data to sequences in the GENBANK database revealed that the insert of clone no. 161 corresponds to an internal section of the mouse ribosomal RNA gene (rDNA) repeat unit between positions 7551-15670 as set forth in GENBANK accession no. X82564, which is provided as SEQ ID NO. 16 herein. The sequence data obtained for the insert of clone no. 161 is set forth in SEQ ID NOS. 18-24. Specifically, the individual subclones corresponded to the following positions in GENBANK accession no. X82564 (i.e., SEQ ID NO. 16) and in SEQ ID NOs. 18-24:

| Subclone | Start in X82564 | End in X82564 | Site | SEQ ID No. |
|---|---|---|---|---|
| 161k1 | 7579 | 7755 | NotI, BamHI | 18 |
| 161m5 | 7756 | 8494 | BamHI | 19 |
| 161m7 | 8495 | 10231 | BamHI | 20 (shows only sequence corresponding to nt. 8495-8950), 21 (shows only sequence corresponding to nt. 9851-10231) |
| 161m12 | 10232 | 15000 | BamHI | 22 (shows only sequence corresponding to nt. 10232-10600), 23 (shows only sequence corresponding to nt. 14267-15000), |
| 161k2 | 15001 | 15676 | NotI, BamHI | 24 |

The sequence set forth in SEQ ID NOs. 18-24 diverges in some positions from the sequence presented in positions 7551-15670 of GENBANK accession no. X82564. Such divergence may be attributable to random mutations between repeat units of rDNA. The results of the sequence analysis of clone no. 161, which reveal that it corresponds to rDNA, correlate with the appearance of the in situ hybridization signal it generated in human lymphocytes and mouse spleen cells. The hybridization signal was clearly observed on acrocentric chromosomes in these cells, and such types of chromosomes are known to include rDNA adjacent to the pericentric satellite DNA on the short arm of the chromosome. Furthermore, rRNA genes are highly conserved in mammals as supported by the cross-species hybridization of clone no. 161 to human chromosomal DNA.

To isolate amplification-replication control regions such as those found in rDNA, it may be possible to subject DNA isolated from megachromosome-containing cells, such as H1D3 cells, to nucleic acid amplification using, e.g., the polymerase chain reaction (PCR) with the following primers: amplification control element forward primer (1-30)

(SEQ ID NO. 25)
5'-GAGGAATTCCCCTATCCCTAATCCAGATTGGTG-3' amplification control element reverse primer (2142-2112)

(SEQ ID NO. 26)
5'-AAACTGCAGGCCGAGCCACCTCTCTTCTGTGTTTG-3' origin of replication region forward primer (2116-2141)

(SEQ ID NO. 27)
5'-AGGAATTCACAGAAGAGAGGTGGCTCGGCCTGC-3' origin of replication region reverse primer (5546-5521)

(SEQ ID NO. 28)
5'-AGCCTGCAGGAAGTCATACCTGGGGAGGTGGCCC-3'

C. Summary of the Formation of the Megachromosome

FIG. 2 schematically sets forth events leading to the formation of a stable megachromosome beginning with the generation of a dicentric chromosome in a mouse LMTK$^-$ cell line: (A) A single E-type amplification in the centromeric region of the mouse chromosome 7 following transfection of LMTK$^-$ cells with λCM8 and λgtWESneo generates the neo-centromere linked to the integrated foreign DNA, and forms a dicentric chromosome. Multiple E-type amplification forms the λneo-chromosome, which was derived from chromosome 7 and stabilized in a mouse-hamster hybrid cell line; (B) Specific breakage between the centromeres of a dicentric chromosome 7 generates a chromosome fragment with the neo-centromere, and a chromosome 7 with traces of foreign DNA at the end; (C) Inverted duplication of the fragment bearing the neo-centromere results in the formation of a stable neo-minichromosome; (D) Integration of exogenous DNA into the foreign DNA region of the formerly dicentric chromosome 7 initiates H-type amplification, and the formation of a heterochromatic arm. By capturing a euchromatic terminal segment, this new chromosome arm is stabilized in the form of the "sausage" chromosome; (E) BrdU treatment and/or drug selection appears to induce further H-type amplification, which results in the formation of an unstable gigachromosome: (F) Repeated BrdU treatments and/or drug selection induce further H-type amplification including a centromere duplication, which leads to the formation of another heterochromatic chromosome arm. It is split off from the chromosome 7 by chromosome breakage and acquires a terminal segment to form the stable megachromosome.

D. Expression of β-Galactosidase and Hygromycin Transferase Genes in Cell Lines Carrying the Megachromosome or Derivatives Thereof.

The level of heterologous gene (i.e., β-galactosidase and hygromycin transferase genes) expression in cell lines containing the megachromosome or a derivative thereof was quantitatively measured. The relationship between the copy-number of the heterologous genes and the level of protein expressed therefrom was also determined.

1. Materials and Methods a. Cell Lines

Heterologous gene expression levels of H1D3 cells, carrying a 250-400 Mb megachromosome as described above, and mM2C1 cells, carrying a 50-60 Mb micro-megachromosome, were quantitatively evaluated. mM2C1 cells were generated by repeated BrdU treatment and single cell cloning of the H1xHe41 cell line (mouse-hamster-human hybrid cell line carrying the megachromosome and a single human chromosome with CD4 and neo$^r$ genes; see FIG. 4). The cell lines were grown under standard conditions in F12 medium under selective (120 μg/ml hygromycin) or non-selective conditions.

b. Preparation of Cell Extract for β-Galactosidase Assays

Monolayers of mM2C1 or H1D3 cell cultures were washed three times with phosphate-buffered saline (PBS). Cells were scraped by rubber policemen and suspended and washed again in PBS. Washed cells were resuspended into 0.25 M Tris-HCl, pH 7.8, and disrupted by three cycles of freezing in liquid nitrogen and thawing at 37° C. The extract was clarified by centrifugation at 12,000 rpm for 5 min. at 4° C.

c. β-Galactosidase Assay

The β-galactosidase assay mixture contained 1 mM $MgCl_2$, 45 mM β-mercaptoethanol, 0.8 mg/ml o-nitrophenyl-β-D-galactopyranoside and 66 mM sodium phosphate, pH 7.5. After incubating the reaction mixture with the cell extract at 37° C. for increasing time, the reaction was terminated by the addition of three volumes of 1M $Na_2CO_3$, and the optical density was measured at 420 nm. Assay mixture incubated without cell extract was used as a control. The linear range of the reaction was determined to be between 0.1-0.8 $OD_{420}$. One unit of β-galactosidase activity is defined as the amount of enzyme that will hydrolyse 3 nmoles of o-nitrophenyl-β-D-galactopyranoside in 1 minute at 37° C.

d. Preparation of Cell Extract for Hygromycin Phosphotransferase Assay

Cells were washed as described above and resuspended into 20 mM Hepes buffer, pH 7.3, 100 mM potassium acetate, 5 mM Mg acetate and 2 mM dithiothreitol). Cells were disrupted at 0° C. by six 10 sec bursts in an MSE ultrasonic disintegrator using a microtip probe. Cells were allowed to cool for 1 min after each ultrasonic burst. The extracts were clarified by centrifuging for 1 min at 2000 rpm in a microcentrifuge.

e. Hygromycin Phosphotransferase Assay

Enzyme activity was measured by means of the phosphocellulose paper binding assay as described by Haas and Dowding ((1975). *Meth. Enzymol.* 43:611-628). The cell extract was supplemented with 0.1 M ammonium chloride and 1 mM adenosine-γ-$^{32}$P-triphosphate (specific activity: 300 Ci/mmol). The reaction was initiated by the addition of 0.1 mg/ml hygromycin and incubated for increasing time at 37° C. The reaction was terminated by heating the samples for 5 min at 75° C. in a water bath, and after removing the precipitated proteins by centrifugation for 5 min in a microcentrifuge, an aliquot of the supernatant was spotted on a piece of Whatman P-81 phosphocellulose paper (2 $cm^2$). After 30 sec at room temperature the papers are placed into 500 ml of hot (75° C.) distilled water for 3 min. While the radioactive ATP remains in solution under these conditions, hygromycin phosphate binds strongly and quantitatively to phosphocellulose. The papers are rinsed 3 times in 500 ml of distilled water and the bound radioactivity was measured in toluene scintillation cocktail in a Beckman liquid scintillation counter. Reaction mixture incubated without added hygromycin served as a control.

f. Determination of the Copy-Number of the Heterologous Genes

DNA was prepared from the H1D3 and mM2C1 cells using standard purification protocols involving SDS lysis of the cells followed by Proteinase K treatment and phenol/chloroform extractions. The isolated DNA was digested with an appropriate restriction endonuclease, fractionated on agarose gels, blotted to nylon filters and hybridized with a radioactive probe derived either from the β-galactosidase or the hygromycin phosphotransferase genes. The level of hybridization was quantified in a Molecular Dynamics PhosphorImage Analyzer. To control the total amount of DNA loaded from the different cells lines, the filters were reprobed with a single copy gene, and the hybridization of β-galactosidase and hygromycin phosphotransferase genes was normalized to the single copy gene hybridization.

g. Determination of Protein Concentration

The total protein content of the cell extracts was measured by the Bradford colorimetric assay using bovine serum albumin as standard.

2. Characterization of the β-Galactosidase and Hygromycin Phsophotransferase Activity Expressed in H1D3 and mM2C1 Cells In order to establish quantitative conditions, the most important kinetic parameters of β-galactosidase and hygromycin phosphotransferase activity have been studied. The β-galactosidase activity measured with a colorimetric assay was linear between the 0.1-0.8 $OD_{420}$ range both for the nM2C1 and H1D3 cell lines. The β-galactosidase activity was also proportional in both cell lines with the amount of protein added to the reaction mixture within 5-100 μg total protein concentration range. The hygromycin phosphotransferase activity of nM2C1 and H1D3 cell lines was also proportional with the reaction time or the total amount of added cell extract under the conditions described for the β-galactosidase.

a. Comparison of β-Galactosidase Activity of mM2C1 and H1D3 Cell Lines

Cell extracts prepared from logarithmically growing mM2C1 and H1D3 cell lines were tested for β-galactosidase activity, and the specific activities were compared in 10 independent experiments. The β-galactosidase activity of H1D3 cell extracts was 440±25 U/mg total protein. Under identical conditions the β-galactosidase activity of the mM2C1 cell extracts was 4.8 times lower: 92±13 U/mg total protein.

β-galactosidase activities of highly subconfluent, subconfluent and nearly confluent cultures of H1D3 and mM2C1 cell lines were also compared. In these experiments different numbers of logarithmic H1D3 and mM2C1 cells were seeded in constant volume of culture medium and grown for 3 days under standard conditions. No significant difference was found in the β-galactosidase specific activities of cell cultures grown at different cell densities, and the ratio of H1D3/mM2C1 β-galactosidase specific activities was also similar for all three cell densities. In confluent, stationary cell cultures of H1D3 or mM2C1 cells, however, the expression of β-galactosidase significantly decreased due likely to cessation of cell division as a result of contact inhibition.

b. Comparison of Hygromycin Phosphotransferase Activity of H1D3 and mM2C1 Cell Lines The bacterial hygromycin phosphotransferase is present in a membrane-bound form in H1D3 or mM2C1 cell lines. This follows from the observation that the hygromycin phosphotransferase activity can be completely removed by high speed centrifugation of these cell extracts, and the enzyme activity can be recovered by resuspending the high speed pellet.

The ratio of the enzyme's specific activity in H1D3 and mM2C1 cell lines was similar to that of β-galactosidase activity, i.e., H1D3 cells have 4.1 times higher specific activity compared with mM2C1 cells.

c. Hygromycin Phosphotransferase Activity in H1D3 and mM2C1 Cells Grown Under Non-Selective Conditions The level of expression of the hygromycin phosphotransferase gene was measured on the basis of quantitation of the specific enzyme activities in H1D3 and mM2C1 cell lines grown under non-selective conditions for 30 generations. The absence of hygromycin in the medium did not influence the expression of the hygromycin phosphotransferase gene.

3. Quantitation of the Number of β-Galactosidase and Hygromycin Phosphotransferase Gene Copies in H1D3 and mM2C1 Cell Lines As described above, the β-galactosidase and hygromycin phosphotransferase genes are located only within the megachromosome, or micro-megachromosome in H1D3 and mM2C1 cells. Quantitative analysis of genomic Southern blots of DNA isolated from H1D3 and mM2C1 cell lines with the PhosphorImage Analyzer revealed that the copy number of α-galactosidase genes integrated into the megachromosome is approximately 10 times higher in H1D3 cells than in mM2C1 cells. The copy-number of hygromycin phosphotransferase genes is approximately 7 times higher in H1D3 cells than in mM2C1 cells.

4. Summary and Conclusions of Results of Quantitation of Heterologous Gene Expression in Cells Containing Megachromosomes or Derivatives Thereof Quantitative determination of β-galactosidase activity of higher eukaryotic cells (e.g., H1D3 cells) carrying the bacterial β-galactosidase gene in heterochromatic megachromosomes confirmed the observed high-level expression of the integrated bacterial gene detected by cytological staining methods. It has generally been established in reports of studies of the expression of foreign genes in transgenic animals that, although transgene expression shows correct tissue and developmental specificity, the level of expression is typically low and shows extensive position-dependent variability (i.e., the level of transgene expression depends on the site of chromosomal integration). It is has been assumed that the low-level transgene expression may be due to the absence of special DNA sequences which can insulate the transgene from the inhibitory effect of the surrounding chromatin and promote the formation of active chromatin structure required for efficient gene expression. Several cis-activating DNA sequence elements have been identified that abolish this position-dependent variability, and can ensure high-level expression of the transgene locus activating region (LAR) sequences in higher eukaryotes and specific chromatin structure (scs) elements in lower eukaryotes (see, et al. Eissenberg and Elgin (1991) *Trends in Genet.* 7:335-340). If these cis-acting DNA sequences are absent, the level of transgene expression is low and copy-number independent.

Although the bacterial β-galactosidase reporter gene contained in the heterochromatic megachromosomes of H1D3 and mM2C1 cells is driven by a potent eukaryotic promoter-enhancer element, no specific cis-acting DNA sequence element was designed and incorporated into the bacterial DNA construct which could function as a boundary element. Thus, the high-level β-galactosidase expression measured in these cells is of significance, particularly because the β-galactosidase gene in the megachromosome is located in a long, compact heterochromatic environment, which is known to be able to block gene expression. The megachromosome appears to contain DNA sequence element(s) in association with the bacterial DNA sequences that function to override the inhibitory effect of heterochromatin on gene expression.

The specificity of the heterologous gene expression in the megachromosome is further supported by the observation that the level of β-galactosidase expression is copy-number dependent. In the H1D3 cell line, which carries a full-size megachromosome, the specific activity of β-galactosidase is about 5-fold higher than in mM2C1 cells, which carry only a smaller, truncated version of the megachromosome. A comparison of the number of β-galactosidase gene copies in H1D3 and mM2C1 cell lines by quantitative hybridization techniques confirmed that the expression of β-galactosidase is copy-number dependent. The number of integrated β-galactosidase gene copies is approximately 10-fold higher in the H1D3 cells than in mM2C1 cells. Thus, the cell line containing the greater number of copies of the β-galactosidase gene also yields higher levels of β-galactosidase activity, which supports the copy-number dependency of expression. The copy number dependency of the β-galactosidase and hygromycin phosphotransferase enzyme levels in cell lines carrying different derivatives of the megachromosome indicates that neither the chromatin organization surrounding the site of integration of the bacterial genes, nor the heterochromatic environment of the megachromosome suppresses the expression of the genes.

The relative amount of β-galactosidase protein expressed in H1D3 cells can be estimated based on the $V_{max}$ of this enzyme (500 for homogeneous, crystallized bacterial β-galactosidase (Naider et al. (1972) *Biochemistry* 11:3202-3210)) and the specific activity of H1D3 cell protein. A $V_{max}$ of 500 means that the homogeneous β-galactosidase protein hydrolyzes 500 μmoles of substrate per minute per mg of enzyme protein at 37° C. One mg of total H1D3 cell protein extract can hydrolyze 1.4 μmoles of substrate per minute at 37° C., which means that 0.28% of the protein present in the H1D3 cell extract is β-galactosidase. The hygromycin phosphotransferase is present in a membrane-bound form in H1D3 and mM2C1 cells. The tendency of the enzyme to integrate into membranes in higher eukaryotic cells may be related to its periplasmic localization in prokaryotic cells. The bacterial hygromycin phosphotransferase has not been purified to homogeneity; thus, its $V_{max}$ has not been determined. Therefore, no estimate can be made on the total amount of hygromycin phosphotransferase protein expressed in these cell lines. The 4-fold higher specific activity of hygromycin phosphotransferase in H1D3 cells as compared to mM2C1 cells, however, indicates that its expression is also copy number dependent.

The constant and high level expression of the β-galactosidase gene in H1D3 and mM2C1 cells, particularly in the absence of any selective pressure for the expression of this gene, clearly indicates the stability of the expression of genes carried in the heterochromatic megachromosomes. This conclusion is further supported by the observation that the level of hygromycin phosphotransferase expression did not change when H1D3 and mM2C1 cells were grown under non-selective conditions. The consistent high-level, stable, and copy-number dependent expression of bacterial marker genes clearly indicates that the megachromosome is an ideal vector system for expression of foreign genes.

Example 7

Summary of Some of the Cell Lines with SATACS and Minichromosomes that Have Been Constructed 1. EC3/7-Derived Cell Lines The $LMTK^-$-derived cell line, which is a mouse fibroblast cell line, was transfected with λCM8 and λgtWESneo DNA (see, EXAMPLE 2) to produce transformed cell lines. Among these, was EC3/7, deposited at the European Collection of Animal cell Culture (ECACC) under Accession No. 90051001 (see, U.S. Pat. No. 5,288,625; see, also Hadlaczky et al. (1991) *Proc. Natl. Acad. Sci. U.S.A.* 88:8106-8110 and U.S. application Ser. No. 08/375,271). This cell line contains the dicentric chromosome with the neo-centromere. Recloning and selection produced cell lines such as EC3/7C5, which are cell lines with the stable neo-minichromosome and the formerly dicentric chromosome (see, FIG. 2C).

2. KE1-2/4 Cells

Fusion of EC3/7 with CHO-K20 cells and selection with G418/HAT produced hybrid cell lines, among these was KE1-2/4, which has been deposited with the ECACC under Accession No. 96040924. KE1-2/4 is a stable cell line that contains the λneo-chromosome (see, FIG. 2; see, also U.S. Pat. No. 5,288,625), produced by E-type amplifications. KE1-2/4 has been transfected with vectors containing λ DNA, selectable markers, such as the puromycin-resistance gene, and genes of interest, such as p53 and the anti-HIV ribozyme gene. These vectors target the gene of interest into the λneo-chromosome by virtue of homologous recombination with the heterologous DNA in the chromosome.

3. C5 pMCT53 Cells

The EC3/7C5 cell line has been co-transfected with pH132, pCH110 and λ DNA (see, EXAMPLE 2) as well as other constructs. Various clones and subclones have been selected. For example transformation with a construct that includes p53 encoding DNA, produced cells designated C5 pMCT53.

4. TF1004G24 Cells

As discussed above, cotransfection of EC3/7C5 cells with plasmids (pH132, pCH110 available from Pharmacia, see, also Hall et al. (1983) *J. Mol. Appl. Gen.* 2:101-109) and with λ DNA (λcl 857 Sam 7 (New England Biolabs)) produced transformed cells. Among these is TF1004G24, which contains the DNA encoding the anti-HIV ribozyme in the neo-minichromosome. Recloning of TF1004G24 produced numerous cell lines. Among these is the NHHL24 cell line. This cell line also has the anti-HIV ribozyme in the neo-minichromosome and expresses high levels of β-gal. It has been fused with CHO-K20 cells to produce various hybrids.

5. TF1004G19-Derived Cells

Recloning and selection of the TF1004G transformants produced the cell line TF1004G19, discussed above in EXAMPLE 4, which contains the unstable sausage chromosome and the neo-minichromosome. Single cell cloning produced the TF1004G-19C5 (see FIG. 4) cell line, which has a stable sausage chromosome and the neo-minichromosome. TF1004G-19C5 has been fused with CHO cells and the hybrids grown under selective conditions to produce the 19C5xHa4 and 19C5xHa3 cell lines (see, EXAMPLE 4) and others. Recloning of the 19C5xHa3 cell line yielded a cell line containing a gigachromosome, i.e., cell line 19C5xHa47, see FIG. 2E. BrdU treatment of 19C5xHa4 cells and growth under selective conditions (neomycin (G) and/or hygromycin (H)) has produced hybrid cell lines such as the G3D5 and G4D6 cell lines and others. G3D5 has the neo-minichromosome and the megachromosome. G4D6 has only the neo-minichromosome.

Recloning of 19C5xHa4 cells in H medium produced numerous clones. Among these is H1D3 (see FIG. 4), which has the stable megachromosome. Repeated BrdU treatment and recloning of H1D3 cells has produced the HB31 cell line, which has been used for transformations with the pTEMPUD, pTEMPU, pTEMPU3, and pCEPUR-132 vectors (see, Examples 12 and 14, below).

H1D3 has been fused with a $CD4^+$ Hela cell line that carries DNA encoding CD4 and neomycin resistance on a plasmid (see, e.g., U.S. Pat. Nos. 5,413,914, 5,409,810, 5,266,600, 5,223,263, 5,215,914 and 5,144,019, which describe these Hela cells). Selection with GH has produced hybrids, including H1xHE41 (see FIG. 4), which carries the megachromosome and also a single human chromosome that includes the CD4neo construct. Repeated BrdU treatment and single cell cloning has produced cell lines with the megachromosome (cell line 1B3, see FIG. 4). About 25% of the 1B3 cells have a truncated megachromosome (~90-120 Mb). Another of these subclones, designated 2C5, was cultured on hygromycin-containing medium and megachromosome-free cell lines were obtained and grown in G418-containing medium. Recloning of these cells yielded cell lines such as IB4 and others that have a dwarf megachromosome (~150-200 Mb), and cell lines, such as I1C3 and mM2C1, which have a micro-megachromosome (~50-90 Mb). The micro-megachromosome of cell line mM2C1 has no telomeres; however, if desired, synthetic telomeres, such as those described and generated herein, may be added to the mM2C1 cell micro-megachromosomes. Cell lines containing smaller truncated megachromosomes, such as the mM2C1 cell line containing the micro-megachromosome, can be used to generate even smaller megachromosomes, e.g., 10-30 Mb in size. This may be accomplished, for example, by breakage and fragmentation of the micro-megachromosome in these cells through exposing the cells to X-ray irradiation, BrdU or telomere-directed in vivo chromosome fragmentation.

Example 8

Replication of the Megachromosome

The homogeneous architecture of the megachromosomes provides a unique opportunity to perform a detailed analysis of the replication of the constitutive heterochromatin.

A. Materials and Methods

1. Culture of Cell Lines

H1D3 mouse-hamster hybrid cells carrying the megachromosome (see, EXAMPLE 4) were cultured in F-12 medium containing 10% fetal calf serum (FCS) and 400 μg/ml Hygromycin B (Calbiochem). G3D5 hybrid cells (see, Example 4) were maintained in F-12 medium containing 10% FCS, 400 μg/ml Hygromycin B (Calbiochem), and 400 μg/ml G418 (SIGMA). Mouse A9 fibroblast cells were cultured in F-12 medium supplemented with 10% FCS.

2. BrdU Labelling

In typical experiments, 20-24 parallel semi-confluent cell cultures were set up in 10 cm Petri dishes. Bromodeoxyuridine (BrdU) (Fluka) was dissolved in distilled water alkalized with a drop of NaOH, to make a $10^{-2}$ M stock solution. Aliquots of 10-50 μl of this BrdU stock solution were added to each 10 ml culture, to give a final BrdU concentration of 10-50 μM. The cells were cultured in the presence of BrdU for 30 min, and then washed with warm complete medium, and incubated without BrdU until required. At this point, 5 μg/ml colchicine was added to a sample culture every 1 or 2 h. After 1-2 h colchicine treatment, mitotic cells were collected by "shake-off" and regular chromosome preparations were made for immunolabelling.

3. Immunolabelling of Chromosomes and In Situ Hybridization

Immunolabelling with fluorescein-conjugated anti-BrdU monoclonal antibody (Boehringer) was done according to the manufacturer's recommendations, except that for mouse A9 chromosomes, 2 M hydrochloric acid was used at 37° C. for 25 min, while for chromosomes of hybrid cells, 1 M hydrochloric acid was used at 37° C. for 30 min. In situ hybridization with biotin-labelled probes, and indirect immunofluorescence and in situ hybridization on the same preparation, were performed as described previously (Hadlaczky et al. (1991) *Proc. Natl. Acad. Sci. U.S.A.* 88:8106-8110, see, also U.S. Pat. No. 5,288,625).

4. Microscopy

All observations and microphotography were made by using a Vanox AHBS (Olympus) microscope. Fujicolor 400 Super G or Fujicolor 1600 Super HG high-speed color negatives were used for photographs.

B. Results

The replication of the megachromosome was analyzed by BrdU pulse labelling followed by immunolabelling. The basic parameters for DNA labelling in vivo were first established. Using a 30-min pulse of 50 μM BrdU in parallel cultures, samples were taken and fixed at 5 min intervals from the beginning of the pulse, and every 15 min up to 1 h after the removal of BrdU. Incorporated BrdU was detected by immunolabelling with fluorescein-conjugated anti-BrdU monoclonal antibody. At the first time point (5 min) 38% of the nuclei were labelled, and a gradual increase in the number of labelled nuclei was observed during incubation in the presence of BrdU, culminating in 46% in the 30-min sample, at the time of the removal of BrdU. At further time points (60, 75, and 90 min) no significant changes were observed, and the fraction of labelled nuclei remained constant (44.5-46%).

These results indicate that (i) the incorporation of the BrdU is a rapid process, (ii) the 30 min pulse-time is sufficient for reliable labelling of S-phase nuclei, and (iii) the BrdU can be effectively removed from the cultures by washing.

The length of the cell cycle of the H1D3 and G3D5 cells was estimated by measuring the time between the appearance of the earliest BrdU signals on the extreme late replicating chromosome segments and the appearance of the same pattern only on one of the chromatids of the chromosomes after one completed cell cycle. The length of G2 period was determined by the time of the first detectable BrdU signal on prophase chromosomes and by the labelled mitoses method (Qastler et al. (1959) *Exp. Cell Res.* 17:420-438). The length of the S-phase was determined in three ways: (i) on the basis of the length of cell cycle and the fraction of nuclei labelled during the 30-120 min pulse; (ii) by measuring the time between the very end of the replication of the extreme late replicating chromosomes and the detection of the first signal on the chromosomes at the beginning of S phase; (iii) by the labelled mitoses method. In repeated experiments, the duration of the cell cycle was found to be 22-26 h, the S phase 10-14 h, and the G2 phase 3.5-4.5 h.

Analyses of the replication of the megachromosome were made in parallel cultures by collecting mitotic cells at two hour intervals following two hours of colchicine treatment. In a repeat experiment, the same analysis was performed using one hour sample intervals and one hour colchicine treatment. Although the two procedures gave comparable results, the two hour sample intervals were viewed as more appropriate since approximately 30% of the cells were found to have a considerably shorter or longer cell cycle than the average. The characteristic replication patterns of the individual chromosomes, especially some of the late replicating hamster chromosomes, served as useful internal markers for the different stages of S-phase. To minimize the error caused by the different lengths of cell cycles in the different experiments, samples were taken and analyzed throughout the whole cell cycle until the appearance of the first signals on one chromatid at the beginning of the second S-phase.

The sequence of replication in the megachromosome is as follows. At the very beginning of the S-phase, the replication of the megachromosome starts at the ends of the chromosomes. The first initiation of replication in an interstitial position can usually be detected at the centromeric region. Soon after, but still in the first quarter of the S-phase, when the terminal region of the short arm has almost completed its replication, discrete initiation signals appear along the chromosome arms. In the second quarter of the S-phase, as replication proceeds, the BrdU-labelled zones gradually widen, and the checkered pattern of the megachromosome becomes clear (see, e.g., FIG. 2F). At the same time, pericentric regions of mouse chromosomes also show intense incorporation of BrdU. The replication of the megachromosome peaks at the end of the second quarter and in the third quarter of the S-phase. At the end of the third quarter, and at the very beginning of the last quarter of the S-phase, the megachromosome and the pericentric heterochromatin of the mouse chromosomes complete their replication. By the end of S-phase, only the very late replicating segments of mouse and hamster chromosomes are still incorporating BrdU.

The replication of the whole genome occurs in distinct phases. The signal of incorporated BrdU increased continuously until the end of the first half of the S-phase, but at the beginning of the third quarter of the S-phase chromosome segments other than the heterochromatic regions hardly incorporated BrdU. In the last quarter of the S-phase, the BrdU signals increased again when the extreme late replicating segments showed very intense incorporation.

Similar analyses of the replication in mouse A9 cells were performed as controls. To increase the resolution of the immunolabelling pattern, pericentric regions of A9 chromosomes were decondensed by treatment with Hoechst 33258. Because of the intense replication of the surrounding euchromatic sequences, precise localization of the initial BrdU signal in the heterochromatin was normally difficult, even on undercondensed mouse chromosomes. On those chromosomes where the initiation signal(s) were localized unambiguously, the replication of the pericentric heterochromatin of A9 chromosomes was similar to that of the megachromosome. Chromosomes of A9 cells also exhibited replication patterns and sequences similar to those of the mouse chromosomes in the hybrid cells. These results indicate that the replicators of the megachromosome and mouse chromosomes retained their original timing and specificity in the hybrid cells.

By comparing the pattern of the initiation sites obtained after BrdU incorporation with the location of the integration sites of the "foreign" DNA in a detailed analysis of the first quarter of the S-phase, an attempt was made to identify origins of replication (initiation sites) in relation to the amplicon structure of the megachromosome. The double band of integrated DNA on the long arm of the megachromosome served as a cytological marker. The results showed a colocalization of the BrdU and in situ hybridization signals found at the cytological level, indicating that the "foreign" DNA sequences are in close proximity to the origins of replication, presumably integrated into the non-satellite sequences between the replicator and the satellite sequences (see, FIG. 3). As described in Example 6.B.4, the rDNA sequences detected in the megachromosome are also localized at the amplicon borders at the site of integration of the "foreign" DNA sequences, suggesting that the origins of replication responsible for initiation of replication of the megachromosome involve rDNA sequences. In the pericentric region of several other chromosomes, dot-like BrdU signals can also be observed that are comparable to the initiation signals on the megachromosome. These signals may represent similar initiation sites in the heterochromatic regions of normal chromosomes.

At a frequency of $10^{-4}$, "uncontrolled" amplification of the integrated DNA sequences was observed in the megachromosome. Consistent with the assumption (above) that "foreign" sequences are in proximity of the replicators, this spatially restricted amplification is likely to be a consequence of uncontrolled repeated firings of the replication origin(s) without completing the replication of the whole segment.

C. Discussion

It has generally been thought that the constitutive heterochromatin of the pericentric regions of chromosomes is late replicating (see, e.g., Miller (1976) *Chromosoma* 55:165-170). On the contrary, these experiments evidence that the replication of the heterochromatic blocks starts at a discrete initiation site in the first half of the S-phase and continues through approximately three-quarters of S-phase. This difference can be explained in the following ways: (i) in normal chromosomes, actively replicating euchromatic sequences that surround the satellite DNA obscure the initiation signals, and thus the precise localization of initiation sites is obscured; (ii) replication of the heterochromatin can only be detected unambiguously in a period during the second half of the S-phase, when the bulk of the heterochromatin replicates and most other chromosomal regions have already completed their replication, or have not yet started it. Thus, low resolution cytological techniques, such as analysis of incorporation of radioactively labelled precursors by autoradiography, only detect prominent replication signals in the heterochromatin in the second half of S-phase, when adjacent euchromatic segments are no longer replicating.

In the megachromosome, the primary initiation sites of replication colocalize with the sites where the "foreign" DNA sequences and rDNA sequences are integrated at the amplicon borders. Similar initiation signals were observed at the same time in the pericentric heterochromatin of some of the mouse chromosomes that do not have "foreign" DNA, indicating that the replication initiation sites at the borders of amplicons may reside in the non-satellite flanking sequences of the satellite DNA blocks. The presence of a primary initiation site at each satellite DNA doublet implies that this large chromosome segment is a single huge unit of replication (megareplicon) delimited by the primary initiation site and the termination point at each end of the unit. Several lines of evidence indicate that, within this higher-order replication unit, "secondary" origins and replicons contribute to the complete replication of the megareplicon:

1. The total replication time of the heterochromatic regions of the megachromosome was ~9-11 h. At the rate of movement of replication forks, 0.5-5 kb per minute, that is typical of eukaryotic chromosomes (Kornberg et al. (1992) *DNA Replication.* 2nd. ed., New York: W.H. Freeman and Co, p. 474), replication of a ~15 Mb replicon would require 50-500 h. Alternatively, if only a single replication origin was used, the average replication speed would have to be 25 kb per minute to complete replication within 10 h. By comparing the intensity of the BrdU signals on the euchromatic and the heterochromatic chromosome segments, no evidence for a 5to 50-fold difference in their replication speed was found.

2. Using short BrdU pulse labelling, a single origin of replication would produce a replication band that moves along the replicon, reflecting the movement of the replication fork. In contrast, a widening of the replication zone that finally gave rise to the checkered pattern of the megachromosome was observed, and within the replication period, the most intensive BrdU incorporation occurred in the second half of the S-phase. This suggests that once the megareplicator has been activated, it permits the activation and firing of "secondary" origins, and that the replication of the bulk of the satellite DNA takes place from these "secondary" origins during the second half of the S-phase. This is supported by the observation that in certain stages of the replication of the megachromosome, the whole amplicon can apparently be labelled by a short BrdU pulse.

Megareplicators and secondary replication origins seem to be under strict temporal and spatial control. The first initiation within the megachromosomes usually occurred at the centromere, and shortly afterward all the megareplicators become active. The last segment of the megachromosome to complete replication was usually the second segment of the long arm. Results of control experiments with mouse A9 chromosomes indicate that replication of the heterochromatin of mouse chromosomes corresponds to the replication of the megachromosome amplicons. Therefore, the pre-existing temporal control of replication in the heterochromatic blocks is preserved in the megachromosome. Positive (Hassan et al. (1994) *J. Cell. Sci.* 107:425-434) and negative (Haase et al. (1994) *Mol. Cell. Biol.* 14:2516-2524) correlations between transcriptional activity and initiation of replication have been proposed. In the megachromosome, transcription of the integrated genes seems to have no effect on the original timing of the replication origins. The concerted, precise timing of the megareplicator initiations in the different amplicons suggests the presence of specific, cis-acting sequences, origins of replication.

Considering that pericentric heterochromatin of mouse chromosomes contains thousands of short, simple repeats spanning 7-15 Mb, and the centromere itself may also contain hundreds of kilobases, the existence of a higher-order unit of replication seems probable. The observed uncontrolled intrachromosomal amplification restricted to a replication initiation region of the megachromosome is highly suggestive of a rolling-circle type amplification, and provides additional evidence for the presence of a replication origin in this region.

The finding that a specific replication initiation site occurs at the boundaries of amplicons suggests that replication might play a role in the amplification process. These results suggest that each amplicon of the megachromosome can be regarded as a huge megareplicon defined by a primary initiation site (megareplicator) containing "secondary" origins of replication. Fusion of replication bubbles from different origins of bi-directional replication (DePamphilis (1993) *Ann. Rev. Biochem.* 62:29-63) within the megareplicon could form a giant replication bubble, which would correspond to the whole megareplicon. In the light of this, the formation of megabase-size amplicons can be accommodated by a replication-directed amplification mechanism. In H and E-type amplifications, intrachromosomal multiplication of the amplicons was observed (see, above EXAMPLES), which is consistent with the unequal sister chromatid exchange model. Induced or spontaneous unscheduled replication of a megareplicon in the constitutive heterochromatin may also form new amplicon(s) leading to the expansion of the amplification or to the heterochromatic polymorphism of "normal" chromosomes. The "restoration" of the missing segment on the long arm of the megachromosome may well be the result of the re-replication of one amplicon limited to one strand.

Taken together, without being bound by any theory, a replication-directed mechanism is a plausible explanation for the initiation of large-scale amplifications in the centromeric regions of mouse chromosomes, as well as for the de novo chromosome formations. If specific (amplificator, i.e., sequences controlling amplification) sequences play a role in promoting the amplification process, sequences at the primary replication initiation site (megareplicator) of the megareplicon are possible candidates.

The presence of rRNA gene sequence at the amplicon borders near the foreign DNA in the megachromosome suggests that this sequence contributes to the primary replication initiation site and participates in large-scale amplification of the pericentric heterochromatin in de novo formation of SATACs. Ribosomal RNA genes have an intrinsic amplification mechanism that provides for multiple copies of tandem genes. Thus, for purposes herein, in the construction of SATACs in cells, rDNA will serve as a region for targeted integration, and as components of SATACs constructed in vitro.

Example 9

Generation of Chromosomes with Amplified Regions Derived from Mouse Chromosome 1

To show that the events described in EXAMPLES 2-7 are not unique to mouse chromosome 7 and to show that the EC7/3 cell line is not required for formation of the artificial chromosomes, the experiments have been repeated using different initial cell lines and DNA fragments. Any cell or cell line should be amenable to use or can readily be determined that it is not.

A. Materials

The LP11 cell line was produced by the "scrape-loading" transfection method (Fechheimer et al. (1987) *Proc. Natl. Acad. Sci. U.S.A.* 84:8463-8467) using 25 μg plasmid DNA for $5\times10^6$ recipient cells. LP11 cells were maintained in F-12 medium containing 3-15 μg/ml Puromycin (SIGMA).

B. Amplification in LP11 Cells

The large-scale amplification described in the above Examples is not restricted to the transformed EC3/7 cell line or to the chromosome 7 of mouse. In an independent transformation experiment, $LMTK^-$ cells were transfected using the calcium phosphate precipitation procedure with a selectable puromycin-resistance gene-containing construct designated pPuroTel (see Example 1.E.2. for a description of this plasmid), to establish cell line LP11. Cell line LP11 carries chromosome(s) with amplified chromosome segments of different lengths (~150-600 Mb). Cytological analysis of the LP11 cells indicated that the amplification occurred in the pericentric region of the long arm of a submetacentric chromosome formed by Robertsonian translocation. This chromosome arm was identified by G-banding as chromosome 1. C-banding and in situ hybridization with mouse major satellite DNA probe showed that an E-type amplification had occurred: the newly formed region was composed of an array of euchromatic chromosome segments containing different amounts of heterochromatin. The size and C-band pattern of the amplified segments were heterogeneous. In several cells, the number of these amplified units exceeded 50; single-cell subclones of LP11 cell lines, however, carry stable marker chromosomes with 10-15 segments and constant C-band patterns.

Sublines of the thymidine kinase-deficient LP11 cells (e.g., LP11-15P 1C5/7 cell line) established by single-cell cloning of LP11 cells were transfected with a thymidine kinase gene construct. Stable $TK^+$ transfectants were established.

Example 10

Isolation of SATACS and Other Chromosomes with Atypical Base Content and/or Size I. Isolation of Artificial Chromosomes from Endogenous Chromosomes Artificial chromosomes, such as SATACs, may be sorted from endogenous chromosomes using any suitable procedures, and typically involve isolating metaphase chromosomes, distinguishing the artificial chromosomes from the endogenous chromosomes, and separating the artificial chromosomes from endogenous chromosomes. Such procedures will generally include the following basic steps: (1) culture of a sufficient number of cells (typically about $2\times10^7$ mitotic cells) to yield, preferably on the order of $1\times10^6$ artificial chromosomes, (2) arrest of the cell cycle of the cells in a stage of mitosis, preferably metaphase, using a mitotic arrest agent such as colchicine, (3) treatment of the cells, particularly by swelling of the cells in hypotonic buffer, to increase susceptibility of the cells to disruption, (4) by application of physical force to disrupt the cells in the presence of isolation buffers for stabilization of the released chromosomes, (5) dispersal of chromosomes in the presence of isolation buffers for stabilization of free chromosomes, (6) separation of artificial from endogenous chromosomes and (7) storage (and shipping if desired) of the isolated artificial chromosomes in appropriate buffers. Modifications and variations of the general procedure for isolation of artificial chromosomes, for example to accommodate different cell types with differing growth characteristics and requirements and to optimize the duration of mitotic block with arresting agents to obtain the desired balance of chromosome yield and level of debris, may be empirically determined.

Steps 1-5 relate to isolation of metaphase chromosomes. The separation of artificial from endogenous chromosomes (step 6) may be accomplished in a variety of ways. For example, the chromosomes may be stained with DNA-specific dyes such as Hoeschst 33258 and chromomycin $A_3$ and sorted into artificial and endogenous chromosomes on the basis of dye content by employing fluorescence-activated cell sorting (FACS). To facilitate larger scale isolation of the artificial chromosomes, different separation techniques may be employed such as swinging bucket centrifugation (to effect separation based on chromosome size and density) (see, e.g., Mendelsohn et al. (1968) *J. Mol. Biol.* 32:101-108), zonal rotor centrifugation (to effect separation on the basis of chromosome size and density) (see, e.g., Burki et al. (1973) *Prep. Biochem.* 3:157-182; Stubblefield et al. (1978) *Biochem. Biophys. Res. Commun.* 83:1404-1414, velocity sedimentation (to effect separation on the basis of chromosome size and shape) (see e.g., Collard et al. (1984) *Cytometry* 5:9-19). Immuno-affinity purification may also be employed in larger scale artificial chromosome isolation procedures. In this process, large populations of artificial chromosome-containing cells (asynchronous or mitotically enriched) are harvested en masse and the mitotic chromosomes (which can be released from the cells using standard procedures such as by incubation of the cells in hypotonic buffer and/or detergent treatment of the cells in conjunction with physical disruption of the treated cells) are enriched by binding to antibodies that are bound to solid state matrices (e.g. column resins or magnetic beads). Antibodies suitable for use in this procedure bind to condensed centromeric proteins or condensed and DNA-bound histone proteins. For example, autoantibody LU851 (see Hadlaczky et al. (1989) *Chromosoma* 97:282-288), which recognizes mammalian centromeres may be used for large-scale isolation of chromosomes prior to subsequent separation of artificial from endogenous chromosomes using methods such as FACS. The bound chromosomes would be washed and eventually eluted for sorting. Immunoaffinity purification may also be used directly to separate artificial chromosomes from endogenous chromosomes. For example, SATACs may be generated in or transferred to (e.g., by microinjection or microcell fusion as described herein) a cell line that has chromosomes that contain relatively small amounts of heterochromatin, such as hamster cells (e.g., V79 cells or CHO-K1 cells). The SATACs, which are predominantly heterochromatin, are then separated from the endogenous chromosomes by utilizing anti-heterochromatin binding protein (*Drosophila* HP-1) antibody conjugated to a solid matrix. Such matrix preferentially binds SATACs relative to hamster chromosomes. Unbound hamster chromosomes are washed away from the matrix and the SATACs are eluted by standard techniques.

A. Cell Lines and Cell Culturing Procedures

In one isolation procedure, 1B3 mouse-hamster-human hybrid cells (see, FIG. 4) carrying the megachromosome or the truncated megachromosome were grown in F-12 medium supplemented with 10% fetal calf serum, 150 μg/ml hygromycin B and 400 μg/ml G418. GHB42 (a cell line recloned from G3D5 cells) mouse-hamster hybrid cells carrying the megachromosome and the minichromosome were also cultured in F-12 medium containing 10% fetal calf serum, 150 μg/ml hygromycin B and 400 μg/ml G418. The doubling time of both cell lines was about 24-40 hours, typically about 32 hours.

Typically, cell monolayers are passaged when they reach about 60-80% confluence and are split every 48-72 hours. Cells that reach greater than 80% confluence senesce in culture and are not preferred for chromosome harvesting. Cells may be plated in 100-200 100-mm dishes at about 50-70% confluency 12-30 hours before mitotic arrest (see, below).

Other cell lines that may be used as hosts for artificial chromosomes and from which the artificial chromosomes may be isolated include, but are not limited to, PtK1 (NBL-3) marsupial kidney cells (ATCC accession no. CCL35), CHO-K1 Chinese hamster ovary cells (ATCC accession no. CCL61), V79-4 Chinese hamster lung cells (ATCC accession no. CCL93), Indian muntjac skin cells (ATCC accession no. CCL157), LMTK(−) thymidine kinase deficient murine L cells (ATCC accession no. CCL1.3), Sf9 fall armyworm (*Spodoptera frugiperda*) ovary cells (ATCC accession no. CRL 1711) and any generated heterokaryon (hybrid) cell lines, such as, for example, the hamster-murine hybrid cells described herein, that may be used to construct MACs, particularly SATACs.

Cell lines may be selected, for example, to enhance efficiency of artificial chromosome production and isolation as may be desired in large-scale production processes. For instance, one consideration in selecting host cells may be the artificial chromosome-to-total chromosome ratio of the cells. To facilitate separation of artificial chromosomes from endogenous chromosomes, a higher artificial chromosome-to-total chromosome ratio might be desirable. For example, for H1D3 cells (a murine/hamster heterokaryon; see FIG. 4), this ratio is 1:50, i.e., one artificial chromosome (the megachromosome) to 50 total chromosomes. In contrast, Indian muntjac skin cells (ATCC accession no. CCL157) contain a smaller total number of chromosomes (a diploid number of chromosomes of 7), as do kangaroo rat cells (a diploid number of chromosomes of 12) which would provide for a higher artificial chromosome-to-total chromosome ratio upon introduction of, or generation of, artificial chromosomes in the cells.

Another consideration in selecting host cells for production and isolation of artificial chromosomes may be size of the endogenous chromosomes as compared to that of the artificial chromosomes. Size differences of the chromosomes may be exploited to facilitate separation of artificial chromosomes from endogenous chromosomes. For example, because Indian muntjac skin cell chromosomes are considerably larger than minichromosomes and truncated megachromosomes, separation of the artificial chromosome from the muntjac chromosomes may possibly be accomplished using univariate (one dye, either Hoechst 33258 or Chromomycin A3) FACS separation procedures.

Another consideration in selecting host cells for production and isolation of artificial chromosomes may be the doubling time of the cells. For example, the amount of time required to generate a sufficient number of artificial chromosome-containing cells for use in procedures to isolate artificial chromosomes may be of significance for large-scale production. Thus, host cells with shorter doubling times may be desirable. For instance, the doubling time of V79 hamster lung cells is about 9-10 hours in comparison to the approximately 32-hour doubling time of H1D3 cells.

Accordingly, several considerations may go into the selection of host cells for the production and isolation of artificial chromosomes. It may be that the host cell selected as the most desirable for de novo formation of artificial chromosomes is not optimized for large-scale production of the artificial chromosomes generated in the cell line. In such cases, it may be possible, once the artificial chromosome has been generated in the initial host cell line, to transfer it to a production cell line more well suited to efficient, high-level production and isolation of the artificial chromosome. Such transfer may be accomplished through several methods, for example through microcell fusion, as described herein, or microinjection into the production cell line of artificial chromosomes purified from the generating cell line using procedures such as described herein. Production cell lines preferably contain two or more copies of the artificial chromosome per cell.

B. Chromosome Isolation

In general, cells are typically cultured for two generations at exponential growth prior to mitotic arrest. To accumulate mitotic 1B3 and GHB42 cells in one particular isolation procedure, 5 μg/ml colchicine was added for 12 hours to the cultures. The mitotic index obtained was 60-80%. The mitotic cells were harvested by selective detachment by gentle pipetting of the medium on the monolayer cells. It is also possible to utilize mechanical shake-off as a means of releasing the rounded-up (mitotic) cells from the plate. The cells were sedimented by centrifugation at 200×g for 10 minutes.

Cells (grown on plastic or in suspension) may be arrested in different stages of the cell cycle with chemical agents other than colchicine, such as hydroxyurea, vinblastine, colcemid or aphidicolin. Chemical agents that arrest the cells in stages other than mitosis, such as hydroxyurea and aphidicolin, are used to synchronize the cycles of all cells in the population and then are removed from the cell medium to allow the cells to proceed, more or less simultaneously, to mitosis at which time they may be harvested to disperse the chromosomes. Mitotic cells could be enriched for a mechanical shake-off (adherent cells). The cell cycles of cells within a population of MAC-containing cells may also be synchronized by nutrient, growth factor or hormone deprivation which leads to an accumulation of cells in the $G_1$ or $G_0$ stage; readdition of nutrients or growth factors then allows the quiescent cells to re-enter the cell cycle in synchrony for about one generation. Cell lines that are known to respond to hormone deprivation in this manner, and which are suitable as hosts for artificial chromosomes, include the Nb2 rat lymphoma cell line which is absolutely dependent on prolactin for stimulation of proliferation (see Gout et al. (1980) *Cancer Res.* 40:2433-2436). Culturing the cells in prolactin-deficient medium for 18-24 hours leads to arrest of proliferation, with cells accumulating early in the $G_1$ phase of the cell cycle. Upon addition of prolactin, all the cells progress through the cell cycle until M phase at which point greater than 90% of the cells would be in mitosis (addition of colchicine could increase the amount of the mitotic cells to greater than 95%). The time between reestablishing proliferation by prolactin addition and harvesting mitotic cells for chromosome separation may be empirically determined.

Alternatively, adherent cells, such as V79 cells, may be grown in roller bottles and mitotic cells released from the plastic surface by rotating the roller bottles at 200 rpm or greater (Shwarchuk et al. (1993) *Int. J. Radiat. Biol.* 64:601-612). At any given time, approximately 1% of the cells in an exponentially growing asynchronous population is in M-phase. Even without the addition of colchicine, $2\times10^7$ mitotic cells have been harvested from four 1750-$cm^2$ roller bottles after a 5-min spin at 200 rpm. Addition of colchicine for 2 hours may increase the yield to $6\times10^8$ mitotic cells.

Several procedures may be used to isolate metaphase chromosomes from these cells, including, but not limited to, one based on a polyamine buffer system (Cram et al. (1990) *Methods in Cell Biology* 33:377-382), one on a modified hexylene glycol buffer system (Hadlaczky et al. (1982) *Chromosoma* 86:643-65), one on a magnesium sulfate buffer system (Van den Engh et al. (1988) *Cytometry* 9:266-270 and Van den Engh et al. (1984) *Cytometry* 5:108), one on an acetic acid fixation buffer system (Stoehr et al. (1982) *Histochemistry* 74:57-61), and one on a technique utilizing hypotonic KCl and propidium iodide (Cram et al. (1994) XVII meeting of the International Society for Analytical Cytology, October 16-21, Tutorial IV *Chromosome Analysis and Sorting with Commerical Flow Cytometers*; Cram et al. (1990) *Methods in Cell Biology* 33:376).

1. Polyamine Procedure

In the polyamine procedure that was used in isolating artificial chromosomes from either 1B3 or GHB42 cells, about $10^7$ mitotic cells were incubated in 10 ml hypotonic buffer (75 mM KCl, 0.2 mM spermine, 0.5 mM spermidine) for 10 minutes at room temperature to swell the cells. The cells are swollen in hypotonic buffer to loosen the metaphase chromosomes but not to the point of cell lysis. The cells were then centrifuged at 100×g for 8 minutes, typically at room temperature. The cell pellet was drained carefully and about $10^7$ cells were resuspended in 1 ml polyamine buffer (15 mM Tris-HCl, 20 mM NaCl, 80 mM KCl, 2 mM EDTA, 0.5 mM EGTA, 14 mM β-mercaptoethanol, 0.1% digitonin, 0.2 mM Spermine, 0.5 mM spermidine) for physical dispersal of the metaphase chromosomes. Chromosomes were then released by gently drawing the cell suspension up and expelling it through a 22 G needle attached to a 3 ml plastic syringe. The chromosome concentration was about 1-$3\times10^8$ chromosomes/ml.

The polyamine buffer isolation protocol is well suited for obtaining high molecular weight chromosomal DNA (Sillar and Young (1981) *J. Histochem. Cytochem.* 29:74-78; Van-Dilla et al. (1986) *Biotechnology* 4:537-552; Bartholdi et al. (1988) In "Molecular Genetics of Mammalian Cells" (M. Goettsman, ed.), *Methods in Enzymology* 151:252-267. Academic Press, Orlando). The chromosome stabilizing buffer uses the polyamines spermine and spermidine to stabilize chromosome structure (Blumenthal et al. (1979) *J. Cell Biol.*

81:255-259; Lalande et al. (1985) *Cancer Genet. Cytogenet.* 23:151-157) and heavy metals chelators to reduce nuclease activity.

The polyamine buffer protocol has wide applicability, however, as with other protocols, the following variables must be optimized for each cell type: blocking time, cell concentration, type of hypotonic swelling buffer, swelling time, volume of hypotonic buffer, and vortexing time. Chromosomes prepared using this protocol are typically highly condensed.

There are several hypotonic buffers that may be used to swell the cells, for example buffers such as the following: 75 mM KCl; 75 mM KCl, 0.2 mM spermine, 0.5 mM spermidine; Ohnuki's buffer of 16.2 mM sodium nitrate, 6.5 mM sodium acetate, 32.4 mM KCl (Ohnuki (1965) *Nature* 208: 916-917 and Ohnuki (1968) *Chromosoma* 25:402-428); and a variation of Ohnuki's buffer that additionally contains 0.2 mM spermine and 0.5 mM spermidine. The amount and hypotonicity of added buffer vary depending on cell type and cell concentration. Amounts may range from 2.5-5.5 ml per $10^7$ cells or more. Swelling times may vary from 10-90 minutes depending on cell type and which swelling buffer is used. The composition of the polyamine isolation buffer may also be varied. For example, one modified buffer contains 15 mM Tris-HCl, pH 7.2, 70 mM NaCl, 80 mM KCl, 2 mM EDTA, 0.5 mM EGTA, 14 mM beta-mercaptoethanol, 0.25% Triton-X, 0.2 mM spermine and 0.5 mM spermidine.

Chromosomal dispersal may also be accomplished by a variety of physical means. For example, cell suspension may be gently drawn up and expelled in a 3-ml syringe fitted with a 22-gauge needle (Cram et al. (1990) *Methods in Cell Biology* 33:377-382), cell suspension may be agitated on a bench-top vortex (Cram et al. (1990) *Methods in Cell Biology* 33:377-382), cell suspension may be disrupted with a homogenizer (Sillar and Young (1981) *J. Histochem. Cytochem.* 29:74-78; Carrano et al. (1979) *Proc. Natl. Acad. Sci. U.S.A.* 76:1382-1384) and cell suspension may be disrupted with a bench-top ultrasonic bath (Stoehr et al. (1982) *Histochemistry* 74:57-61).

2. Hexylene Glycol Buffer System

In the hexylene glycol buffer procedure that was used in isolating artificial chromosomes from either 1B3 or GHB42 cells, about $8\times10^6$ mitotic cells were resuspended in 10 ml glycine-hexylene glycol buffer (100 mM glycine, 1% hexylene glycol, pH 8.4-8.6 adjusted with saturated Ca-hydroxide solution) and incubated for 10 minutes at 37° C., followed by centrifugation for 10 minutes to pellet the nuclei. The supernatant was centrifuged again at 200×g for 20 minutes to pellet the chromosomes. Chromosomes were resuspended in isolation buffer ($1\text{-}3\times10^8$ chromosomes/ml).

The hexylene glycol buffer composition may also be modified. For example, one modified buffer contains 25 mM Tris-HCl, pH 7.2, 750 mM hexylene glycol, 0.5 mM $CaCl_2$, 1.0 mM $MgCl_2$ (Carrano et al. (1979) *Proc. Natl. Acad. Sci. U.S.A.* 76:1382-1384).

3. Magnesium-Sulfate Buffer System

This buffer system may be used with any of the methods of cell swelling and chromosomal dispersal, such as described above in connection with the polyamine and hexylene glycol buffer systems. In this procedure, mitotic cells are resuspended in the following buffer: 4.8 mM HEPES, pH 8.0, 9.8 mM $MgSO_4$, 48 mM KCl, 2.9 mM dithiothreitol (Van den Engh et al. (1985) *Cytometry* 6:92 and Van den Engh et al. (1984) *Cytometry* 5:108).

4. Acetic Acid Fixation Buffer System

This buffer system may be used with any of the methods of cell swelling and chromosomal dispersal, such as described above in connection with the polyamine and hexylene glycol buffer systems. In this procedure, mitotic cells are resuspended in the following buffer: 25 mM Tris-HCl, pH 3.2, 750 mM 1,6-hexanediol, 0.5 mM $CaCl_2$, 1.0% acetic acid (Stoehr et al. (1982) *Histochemistry* 74:57-61).

5. KCl-Propidium Iodide Buffer System

This buffer system may be used with any of the methods of cell swelling and chromosomal dispersal, such as described above in connection with the polyamine and hexylene glycol buffer systems. In this procedure, mitotic cells are resuspended in the following buffer: 25 mM KCl, 50 μg/ml propidium iodide, 0.33% Triton X-100, 333 μg/ml RNase (Cram et al. (1990) *Methods in Cell Biology* 33:376).

The fluorescent dye propidium iodide is used and also serves as a chromosome stabilizing agent. Swelling of the cells in the hypotonic medium (which may also contain propidium iodide) may be monitored by placing a small drop of the suspension on a microscope slide and observing the cells by phase/fluorescent microscopy. The cells should exclude the propidium iodide while swelling, but some may lyse prematurely and show chromosome fluorescence. After the cells have been centrifuged and resuspended in the KCl-propidium iodide buffer system, they will be lysed due to the presence of the detergent in the buffer. The chromosomes may then be dispersed and then incubated at 37° C. for up to 30 minutes to permit the RNase to act. The chromosome preparation is then analyzed by flow cytometry. The propidium iodide fluorescence can be excited at the 488 m wavelength of an argon laser and detected through an OG 570 optical filter by a single photomultiplier tube. The single pulse may be integrated and acquired in an univariate histogram. The flow cytometer may be aligned to a CV of 2% or less using small (1.5 μm diameter) microspheres. The chromosome preparation is filtered through 60 μm nylon mesh before analysis.

C. Staining of Chromosomes with DNA-Specific Dyes

Subsequent to isolation, the chromosome preparation was stained with Hoechst 33258 at 6 μg/ml and chromomycin A3 at 200 μg/ml. Fifteen minutes prior to analysis, 25 mM Na-sulphite and 10 mM Na-citrate were added to the chromosome suspension.

D. Flow Sorting of Chromosomes

Chromosomes obtained from 1B3 and GHB42 cells and maintained were suspended in a polyamine-based sheath buffer (0.5 mM EGTA, 2.0 mM EDTA, 80 mM KCl, 70 mM NaCl, 15 mM Tris-HCl, pH 7.2, 0.2 mM spermine and 0.5 mM spermidine) (Sillar and Young (1981) *J. Histochem. Cytochem.* 29:74-78). The chromosomes were then passed through a dual-laser cell sorter (FACStar Plus or FAXStar Vantage Becton Dickinson Immunocytometry System; other dual-laser sorters may also be used, such as those manufactured by Coulter Electronics (Elite ESP) and Cytomation (MoFlo)) in which two lasers were set to excite the dyes separately, allowing a bivariate analysis of the chromosome by size and base-pair composition. Because of the difference between the base composition of the SATACs and the other chromosomes and the resulting difference in interaction with the dyes, as well as size differences, the SATACs were separated from the other chromosomes.

E. Storage of the Sorted Artificial Chromosomes

Sorted chromosomes may be pelleted by centrifugation and resuspended in a variety of buffers, and stored at 4° C. For example, the isolated artificial chromosomes may be stored in GH buffer (100 mM glycine, 1% hexylene glycol pH 8.4-8.6 adjusted with saturated Ca-hydroxide solution) (see, e.g., Hadlaczky et al. (1982) *Chromosoma* 86:643-659) for one day and embedded by centrifugation into agarose. The sorted chromosomes were centrifuged into an agarose bed and the plugs are stored in 500 mM EDTA at 4° C. Additional storage buffers include CMB-I/polyamine buffer (17.5 mM Tris-HCl, pH 7.4, 1.1 mM EDTA, 50 mM epsilon-amino caproic acid, 5 mM benzamide-HCl, 0.40 mM spermine, 1.0 mM spermidine, 0.25 mM EGTA, 40 mM KCl, 35 mM NaCl) and CMB-II/polyamine buffer (100 mM glycine, pH 7.5, 78 mM hexylene glycol, 0.1 mM EDTA, 50 mM epsilon-amino caproic acid, 5 mM benzamide-HCl, 0.40 mM spermine, 1.0 mM spermidine, 0.25 mM EGTA, 40 mM KCl, 35 mM NaCl).

When microinjection is the intended use, the sorted chromosomes are stored in 30% glycerol at −20° C. Sorted chromosomes may also be stored without glycerol for short periods of time (3-6 days) in storage buffers at 4° C. Exemplary buffers for microinjection include CBM-I (10 mM Tris-HCl, pH 7.5, 0.1 mM EDTA, 50 mM epsilon-amino caproic acid, 5 mM benzamide-HCl, 0.30 mM spermine, 0.75 mM spermidine), CBM-II (100 mM glycine, pH 7.5, 78 mM hexylene glycol, 0.1 mM EDTA, 50 mM epsilon-amino caproic acid, 5 mM benzamide-HCl, 0.30 mM spermine, 0.75 mM spermidine).

For long-term storage of sorted chromosomes, the above buffers are preferably supplemented with 50% glycerol and stored at −20° C.

F. Quality Control

1. Analysis of the Purity

The purity of the sorted chromosomes was checked by fluorescence in situ hybridization (FISH) with a biotin-labeled mouse satellite DNA probe (see, Hadlaczky et al. (1991) *Proc. Natl. Acad. Sci. U.S.A.* 88:8106-8110). Purity of the isolated chromosomes was about 97-99%.

2. Characteristics of the Sorted Chromosomes

Pulsed field gel electrophoresis and Southern hybridization were carried out to determine the size distribution of the DNA content of the sorted artificial chromosomes.

G. Functioning of the Purified Artificial Chromosomes

To check whether their activity is preserved, the purified artificial chromosomes may be microinjected (using methods such as those described in Example 13) into primary cells, somatic cells and stem cells which are then analyzed for expression of the heterologous genes carried by the artificial chromosomes, e.g., such as analysis for growth on selective medium and assays of β-galactosidase activity.

II. Sorting of Mammalian Artificial Chromosome-Containing Microcells

A. Micronucleation

Cells were grown to 80-90% confluency in 4 T150 flasks. Colcemid was added to a final concentration of 0.06 μg/ml, and then incubated with the cells at 37° C. for 24 hours.

B. Enucleation

Ten μg/ml cytochalasin B was added and the resulting microcells were centrifuged at 15,000 rpm for 70 minutes at 28-33° C.

C. Purification of Microcells by Filtration

The microcells were purified using Swinnex filter units and Nucleopore filters (5 μm and 3 μm).

D. Staining and Sorting Microcells

As above, the cells were stained with Hoechst and chromomycin A3 dyes. The microcells were sorted by cell sorter to isolate the microcells that contain the mammalian artificial chromosomes.

E. Fusion

The microcells that contain the artificial chromosome are fused, for example, as described in Example 1.A.5., to selected primary cells, somatic cells, embryonic stem cells to generate transgenic (non-human) animals and for gene therapy purposes, and to other cells to deliver the chromosomes to the cells.

Example 11

Introduction of Mammalian Artificial Chromosomes into Insect Cells

Insect cells are useful hosts for MACs, particularly for use in the production of gene products, for a number of reasons, including:

1. A mammalian artificial chromosome provides an extra-genomic specific integration site for introduction of genes encoding proteins of interest (reduced chance of mutation in production system).

2. The large size of an artificial chromosome permits megabase size DNA integration so that genes encoding an entire pathway leading to a protein or nonprotein of therapeutic value, such as an alkaloid (digitalis, morphine, TAXOL) can be accommodated by the artificial chromosome.

3. Amplification of genes encoding useful proteins can be accomplished in the artificial mammalian chromosome to obtain higher protein yields in insect cells.

4. Insect cells support required post-translational modifications (glycosylation, phosphorylation) essential for protein biological function.

5. Insect cells do not support mammalian viruses—eliminates cross-contamination of product with human infectious agents.

6. The ability to introduce chromosomes circumvents traditional recombinant baculovirus systems for production of nutritional, industrial or medicinal proteins in insect cell systems.

7. The low temperature optimum for insect cell growth (28° C.) permits reduced energy cost of production.

8. Serum free growth medium for insect cells will result in lower production costs.

9. Artificial chromosome-containing cells can be stored indefinitely at low temperature.

10. Insect larvae will serve as biological factories for the production of nutritional, medicinal or industrial proteins by microinjection of fertilized insect eggs.

A. Demonstration that Insect Cells Recognize Mammalian Promoters

Gene constructs containing a mammalian promoter, such as the CMV promoter, linked to a detectable marker gene (*Renilla* luciferase gene (see, e.g., U.S. Pat. No. 5,292,658 for a description of DNA encoding the *Renilla* luciferase, and plasmid pTZrLuc-1, which can provide the starting material for construction of such vectors, see also SEQ ID No. 10) and also including the simian virus 40 (SV40) promoter operably linked to the β-galactosidase gene were introduced into the cells of two species *Trichoplusia ni* (cabbage looper) and *Bombyx mori* (silk worm).

After transferring the constructs into the insect cell lines either by electroporation or by microinjection, expression of the marker genes was detected in luciferase assays (see e.g., Example 12.C.3) and in β-galactosidase assays (such as lacZ staining assays) after a 24-h incubation. In each case a positive result was obtained in the samples containing the genes which was absent in samples in which the genes were omitted. In addition, a *B. mori* β-actin promoter-*Renilla* luciferase gene fusion was introduced into the *T. ni* and *B. mori* cells which yielded light emission after transfection. Thus, certain mammalian promoters function to direct expression of these marker genes in insect cells. Therefore, MACs are candidates for expression of heterologous genes in insect cells.

B. Construction of Vectors for Use in Insect Cells and Fusion with Mammalian cells 1. Transform LMTK$^-$ cells with expression vector with:

a. *B. mori* β-actin promoter—Hyg$^r$ selectable marker gene for insect cells, and b. SV40 or CMV promoters controlling a puromycin$^r$ selectable marker gene for mammalian cells.

2. Detect expression of the mammalian promoter in LMTK cells (puromycin$^r$ LMTK cells)

3. Use puromycin$^r$ cells in fusion experiments with *Bombyx* and *Trichoplusia* cells, select Hyg$^r$ cells.

C. Insertion of the MACs into Insect Cells

These experiments are designed to detect expression of a detectable marker gene (such as the β-galactosidase gene expressed under the control of a mammalian promoter, such as pSV40) located on a MAC that has been introduced into an insect cell. Data indicate that β-gal was expressed.

Insect cells are fused with mammalian cells containing mammalian artificial chromosomes, e.g., the minichromosome (EC3/7C5) or the mini and the megachromosome (such as GHB42, which is a cell line recloned from G3D5) or a cell line that carries only the megachromosome (such as H1D3 or a redone therefrom). Fusion is carried out as follows:

1. mammalian+insect cells (50/50%) in log phase growth are mixed;

2. calcium/PEG cell fusion: (10 min-0.5 h);

3. heterokaryons (+72 h) are selected.

The following selection conditions to select for insect cells that contain a MAC can be used: (+=positive selection; −=negative selection):

1. growth at 28° C. (+insect cells, −mammalian cells);

2. Graces insect cell medium (SIGMA) (−mammalian cells);

3. no exogenous $CO_2$ (−mammalian cells); and/or 4. antibiotic selection (Hyg or G418) (+transformed insect cells).

Immediately following the fusion protocol, many heterokaryons (fusion events) are observed between the mammalian and each species of insect cells (up to 90% heterokaryons). After growth (2+ weeks) on insect medium containing G418 and/or hygromycin at selection levels used for selection of transformed mammalian cells, individual colonies are detected growing on the fusion plates. By virtue of selection for the antibiotic resistance conferred by the MAC and selection for insect cells, these colonies should contain MACs.

The *B. mori* β-actin gene promoter has been shown to direct expression of the β-galactosidase gene in *B. mori* cells and mammalian cells (e.g., EC3/7C5 cells). The *B. mori* β-actin gene promoter is, thus, particularly useful for inclusion in MACs generated in mammalian cells that will subsequently be transferred into insect cells because the presence of any marker gene linked to the promoter can be determined in the mammalian and resulting insect cell lines.

Example 12

Preparation of Chromosome Fragmentation Vectors and other Vectors for Targeted Integration of DNA into MACs Fragmentation of the megachromosome should ultimately result in smaller stable chromosomes that contain about 15 Mb to 50 Mb that will be easily manipulated for use as vectors. Vectors to effect such fragmentation should also aid in determination and identification of the elements required for preparation of an in vitro-produced artificial chromosome.

Reduction in the size of the megachromosome can be achieved in a number of different ways including: stress treatment, such as by starvation, or cold or heat treatment; treatment with agents that destabilize the genome or nick DNA, such as BrdU, coumarin, EMS and others; treatment with ionizing radiation (see, e.g., Brown (1992) *Curr. Opin. Genes Dev.* 2:479-486); and telomere-directed in vivo chromosome fragmentation (see, e.g., Farr et al. (1995) *EMBO J.* 14:5444-5454).

Figure 5:
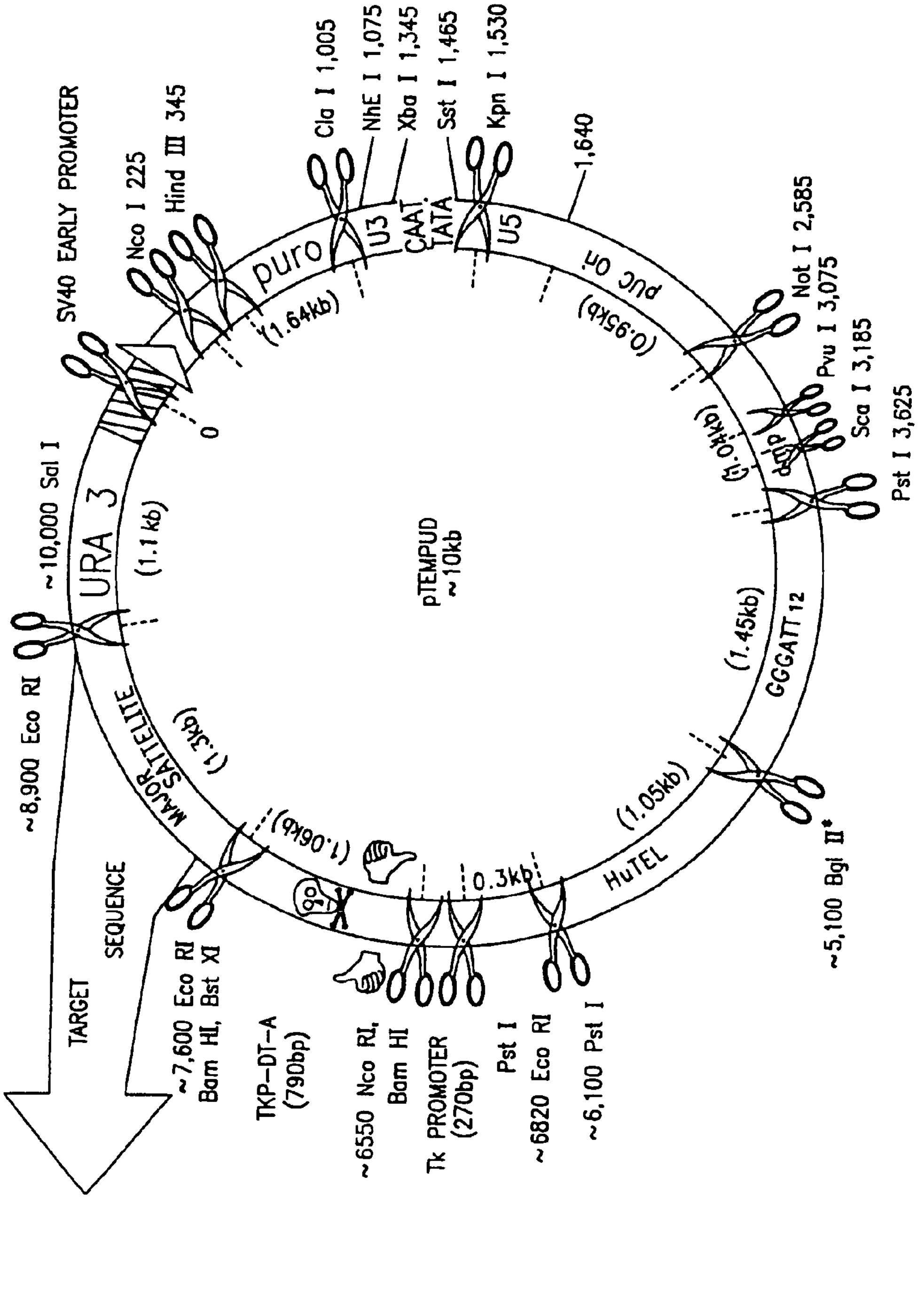
FIG. 5 is a diagram of the plasmid pTEMPUD.

A. Preparation of Vectors for Fragmentation of the Artificial Chromosome and Also for Targeted Integration of Selected Gene Products 1. Construction of pTEMPUD Plasmid pTEMPUD (see FIG. 5) is a mouse homologous recombination "killer" vector for in vivo chromosome fragmentation, and also for inducing large-scale amplification via site-specific integration. With reference to FIG. 5, the ~3,625-bp SalI-PstI fragment was derived from the pBabe-puro retroviral vector (see, Morgenstern et al. (1990) *Nucleic Acids Res.* 18:3587-3596). This fragment contains DNA encoding ampicillin resistance, the pUC origin of replication, and the puromycin N-acetyl transferase gene under control of the SV40 early promoter. The URA3 gene portion comes from the pYAC5 cloning vector (SIGMA). URA3 was cut out of pYAC5 with SalI-XhoI digestion, cloned into pNEB193 (New England Biolabs), which was then cut with EcoRI-SalI and ligated to the SalI site of pBabepuro to produce pPU.

A 1293-bp fragment (see SEQ ID No. 1) encoding the mouse major satellite, was isolated as an EcoRI fragment from a DNA library produced from mouse LMTK$^-$ fibroblast cells and inserted into the EcoRI site of pPU to produce pMPU.

The TK promoter-driven diphtheria toxin gene (DT-A) was derived from pMC1DT-A (see, Maxwell et al. (1986) *Cancer Res.* 46:4660-4666) by BglII-XhoI digestion and cloned into the pMC1neo poly A expression vector (STRATAGENE, La Jolla, Calif.) by replacing the neomycin-resistance gene coding sequence. The TK promoter, DT-A gene and poly A sequence were removed from this vector, cohesive ends were filled with Klenow and the resulting fragment blunt end-ligated and ligated into the SnaBI (TACGTA) of pMPU to produce pMPUD.

The Hutel 2.5-kb fragment (see SEQ ID No. 3) was inserted at the PstI site (see the 6100 PstI-3625 PstI fragment on pTEMPUD) of pMPUD to produce pTEMPUD. This fragment includes a human telomere. It includes a unique BglII site (see nucleotides 1042-1047 of SEQ ID No.3), which will be used as a site for introduction of a synthetic telomere that includes multiple repeats (80) of TTAGGG with BamHI and BglII ends for insertion into the BglII site which will then remain unique, since the BamHI overhang is compatible with the BglII site. Ligation of a BamHI fragment to a BglII destroys the BglII site, so that only a single BglII site will remain. Selection for the unique BglII site insures that the synthetic telomere will be inserted in the correct orientation. The unique BglII site is the site at which the vector is linearized.

To generate a synthetic telomere made up of multiple repeats of the sequence TTAGGG, attempts were made to clone or amplify ligation products of 30-mer oligonucleotides containing repeats of the sequence. Two 30-mer oligonucleotides, one containing four repeats of TTAGGG bounded on each end of the complete run of repeats by half of a repeat and the other containing five repeats of the complement AATCCC, were annealed. The resulting double-stranded molecule with 3-bp protruding ends, each representing half of a repeat, was expected to ligate with itself to yield concatamers of n×30 bp. However, this approach was unsuccessful, likely due to formation of quadruplex DNA from the G-rich strand. Similar difficulty has been encountered in attempts to generate long repeats of the pentameric human satellite II and III units. Thus, it appears that, in general, any oligomer sequence containing periodically spaced consecutive series of guanine nucleotides is likely to form undesired quadruplex formation that hinders construction of long double-stranded DNAs containing the sequence.

Therefore, in another attempt to construct a synthetic telomere for insertion into the BglII site of pTEMPUD, the starting material was based on the complementary C-rich repeat sequence (i.e., AATCCC) which would not be susceptible to quadruplex structure formation. Two plasmids, designated pTEL280110 and pTel280111, were constructed as follows to serve as the starting materials.

First, a long oligonucleotide containing 9 repeats of the sequence AATCCC (i.e., the complement of telomere sequence TTAGGG) in reverse order bounded on each end of the complete run of repeats by half of a repeat (therefore, in essence, containing 10 repeats), and recognition sites for PstI and PacI restriction enzymes was synthesized using standard methods. The oligonucleotide sequence is as follows:

(SEQ ID NO. 29)
5'-AAACTGCAGGTTAATTAACCCTAACCCTAACCCTAACCCTAACCCTA
ACCCTAACCCTAACCCTAACCCTAACCCGGGAT-3'

A partially complementary short oligonucleotide of sequence

3'-TTGGGCCCTAGGCTTAAGG-5' (SEQ ID NO. 30)

was also synthesized. The oligonucleotides were gel-purified, annealed, repaired with Klenow polymerase and digested with EcoRI and PstI. The resulting EcoRI/PstI fragment was ligated with EcoRI/PstI-digested pUC19. The resulting plasmid was used to transform *E. coli* DH5α competent cells and plasmid DNA (pTel102) from one of the transformants surviving selection on LB/ampicillin was digested with PacI, rendered blunt-ended by Klenow and dNTPs and digested with HindIII. The resulting 2.7-kb fragment was gel-purified.

Simultaneously, the same plasmid was amplified by the polymerase chain reaction using extended and more distal 26-mer M13 sequencing primers. The amplification product was digested with SmaI and HindIII, the double-stranded 84-bp fragment containing the 60-bp telomeric repeat (plus 24 bp of linker sequence) was isolated on a 6% native polyacrylamide gel, and ligated with the double-digested pTel102 to yield a 120-bp telomeric sequence. This plasmid was used to transform DH5α cells. Plasmid DNA from two of the resulting recombinants that survived selection on ampicillin (100 μg/ml) was sequenced on an ABI DNA sequencer using the dye-termination method. One of the plasmids, designated pTel29, contained a sequence of 20 repeats of the sequence TTAGGG (i.e., 19 successive repeats of TTAGGG bounded on each end of the complete run of repeats with half of a repeat). The other plasmid, designated pTel28, had undergone a deletion of 2 bp (TA) at the junction where the two sequences, each containing, in essence, 10 repeats of the TTAGGG sequence, that had been ligated to yield the plasmid. This resulted in a GGGTGGG motif at the junction in pTel28. This mutation provides a useful tag in telomere-directed chromosome fragmentation experiments. Therefore, the pTel29 insert was amplified by PCR using pUC/M13 sequencing primers based on sequence somewhat longer and farther from the polylinker than usual as follows:

5'-GCCAGGGTTTTCCCAGTCACGACGT-3' (SEQ ID NO. 31)

or in some experiments

5'-GCTGCAAGGCGATTAAGTTGGGTAAC-3' (SEQ ID NO. 32)

as the m13 forward primer, and

5'-TATGTTGTGTGGAATTGTGAGCGGAT-3' (SEQ ID NO. 33)

as the m13 reverse primer.

The amplification product was digested with SmaI and HindIII. The resulting 144-bp fragment was gel-purified on a 6% native polyacrylamide gel and ligated with pTel28 that had been digested with PacI, blunt-ended with Klenow and dNTP and then digested with HindIII to remove linker. The ligation yielded a plasmid designated pTel2801 containing a telomeric sequence of 40 repeats of the sequence TTAGGG in which one of the repeats (i.e., the 30th repeat) lacked two nucleotides (TA), due to the deletion that had occurred in pTel28, to yield a repeat as follows: TGGG.

In the next extension step, pTel2801 was digested with SmaI and HindIII and the 264-bp insert fragment was gel-purified and ligated with pTel2801 which had been digested with PacI, blunt-ended and digested with HindIII. The resulting plasmid was transformed into DH5α cells and plasmid DNA from 12 of the resulting transformants that survived selection on ampicillin was examined by restriction enzyme analysis for the presence of a 0.5-kb EcoRI/PstI insert fragment. Eleven of the recombinants contained the expected 0.5-kb insert. The inserts of two of the recombinants were sequenced and found to be as expected. These plasmids were designated pTel280110 and pTel280111. These plasmids, which are identical, both contain 80 repeats of the sequence TTAGGG, in which two of the repeats (i.e., the 30th and 70th repeats) lacked two nucleotides (TA), due to the deletion that had occurred in pTel28, to yield a repeat as follows: TGGG. Thus, in each of the cloning steps (except the first), the length of the synthetic telomere doubled; that is, it was increasing in size exponentially. Its length was $60\times2^n$ bp, wherein n is the number of extension cloning steps undertaken. Therefore, in principle (assuming *E. coli*, or any other microbial host, e.g., yeast, tolerates long tandem repetitive DNA), it is possible to assemble any desirable size of safe telomeric repeats.

In a further extension step, pTel280110 was digested with PacI, blunt-ended with Klenow polymerase in the presence of dNTP, then digested with HindIII. The resulting 0.5-kb fragment was gel purified. Plasmid pTel280111 was cleaved with SmaI and HindIII and the 3.2-kb fragment was gel-purified and ligated to the 0.5-kb fragment from pTel280110. The resulting plasmid was used to transform DH5α cells. Plasmid DNA was purified from transformants surviving ampicillin selection. Nine of the selected recombinants were examined by restriction enzyme analysis for the presence of a 1.0-kb EcoRI/PstI fragment. Four of the recombinants (designated pTlk2, pTlk6, pTlk7 and pTlk8) were thus found to contain the desired 960 bp telomere DNA insert sequence that included 160 repeats of the sequence TTAGGG in which four of the repeats lacked two nucleotides (TA), due to the deletion that had occurred in pTel28, to yield a repeat as follows: TGGG. Partial DNA sequence analysis of the EcoRI/PstI fragment of two of these plasmids (i.e., pTlk2 and pTlk6), in which approximately 300 bp from both ends of the fragment were elucidated, confirmed that the sequence was composed of successive repeats of the TTAGGG sequence.

In order to add PmeI and BglII sites to the synthetic telomere sequence, pTlk2 was digested with PacI and PstI and the 3.7-kb fragment (i.e., 2.7-kb pUC19 and 1.0-kb repeat sequence) was gel-purified and ligated at the PstI cohesive end with the following oligonucleotide 5'-GGGTTTAAA-CAGATCTCTGCA-3' (SEQ ID NO. 34). The ligation product was subsequently repaired with Klenow polymerase and dNTP, ligated to itself and transformed into *E. coli* strain DH5α. A total of 14 recombinants surviving selection on ampicillin were obtained. Plasmid DNA from each recombinant was able to be cleaved with BglII indicating that this added unique restriction site had been retained by each recombinant. Four of the 14 recombinants contained the complete 1-kb synthetic telomere insert, whereas the insert of the remaining 10 recombinants had undergone deletions of various lengths. The four plasmids in which the 1-kb synthetic telomere sequence remained intact were designated pTlkV2, pTlkV5, pTlkV8 an pTlkV12. Each of these plasmids could also be digested with PmeI; in addition the presence of both the BglII and PmeI sites was verified by sequence analysis. Any of these four plasmids can be digested with BamHI and BglII to release a fragment containing the 1-kb synthetic telomere sequence which is then ligated with BglII-digested pTEMPUD.

2. Use of pTEMPUD for In Vivo Chromosome Fragmentation

Linearization of pTEMPUD by BglII results in a linear molecule with a human telomere at one end. Integration of this linear fragment into the chromosome, such as the megachromosome in hybrid cells or any mouse chromosome which contains repeats of the mouse major satellite sequence results in integration of the selectable marker puromycin-resistance gene and cleavage of the plasmid by virtue of the telomeric end. The DT gene prevents that entire linear fragment from integrating by random events, since upon integration and expression it is toxic. Thus random integration will be toxic, so site-directed integration into the targeted DNA will be selected. Such integration will produce fragmented chromosomes.

The fragmented truncated chromosome with the new telomere will survive, and the other fragment without the centromere will be lost. Repeated in vivo fragmentations will ultimately result in selection of the smallest functioning artificial chromosome possible. Thus, this vector can be used to produce minichromosomes from mouse chromosomes, or to fragment the megachromosome. In principle, this vector can be used to target any selected DNA sequence in any chromosome to achieve fragmentation.

3. Construction of pTERPUD

A fragmentation/targeting vector analogous to pTEMPUD for in vivo chromosome fragmentation, and also for inducing large-scale amplification via site-specific integration but which is based on mouse rDNA sequence instead of mouse major satellite DNA has been designated pTERPUD. In this vector, the mouse major satellite DNA sequence of pTEMPUD has been replaced with a 4770-bp BamHI fragment of megachromosome clone 161 which contains sequence corresponding to nucleotides 10,232-15,000 in SEQ ID NO. 16.

4. pHASPUD and pTEMPhu3

Vectors that specifically target human chromosomes can be constructed from pTEMPUD. These vectors can be used to fragment specific human chromosomes, depending upon the selected satellite sequence, to produce human minichromosomes, and also to isolate human centromeres.

a. pHASPUD

To render pTEMPUD suitable for fragmenting human chromosomes, the mouse major satellite sequence is replaced with human satellite sequences. Unlike mouse chromosomes, each human chromosome has a unique satellite sequence. For example, the mouse major satellite has been replaced with a human hexameric α-satellite (or alphoid satellite) DNA sequence. This sequence is an 813-bp fragment (nucleotide 232-1044 of SEQ ID No. 2) from clone pS12, deposited in the EMBL database under Accession number X60716, isolated from a human colon carcinoma cell line Colo320 (deposited under Accession No. ATCC CCL 220.1). The 813-bp alphoid fragment can be obtained from the pS12 clone by nucleic acid amplification using synthetic primers, each of which contains an EcoRI site, as follows:

```
                                         (SEQ ID No. 4)
GGGGAATTCAT TGGGATGTTT CAGTTGA    forward primer

                                         (SEQ ID No. 5)
CGAAAGTCCCC CCTAGGAGAT CTTAAGGA   reverse primer.
```

Digestion of the amplified product with EcoRI results in a fragment with EcoRI ends that includes the human α-satellite sequence. This sequence is inserted into pTEMPUD in place of the EcoRI fragment that contains the mouse major satellite to yield pHASPUD.

Vector pHASPUD was linearized with BglII and used to transform EJ30 (human fibroblast) cells by scrape loading. Twenty-seven puromycin-resistant transformant strains were obtained.

b. pTEMPhu3

In pTEMPhu3, the mouse major satellite sequence is replaced by the 3 kb human chromosome 3-specific α-satellite from D3Z1 (deposited under ATCC Accession No. 85434; see, also Yrokov (1989) *Cytogenet. Cell Genet.* 51:1114).

5. Use of the pTEMPHU3 to Induce Amplification on Human Chromosome #3

Each human chromosome contains unique chromosome-specific alphoid sequence. Thus, pTEMPHU3, which is targeted to the chromosome 3-specific α-satellite, can be introduced into human cells under selective conditions, whereby large-scale amplification of the chromosome 3 centromeric region and production of a de novo chromosome ensues. Such induced large-scale amplification provides a means for inducing de novo chromosome formation and also for in vivo cloning of defined human chromosome fragments up to megabase size.

For example, the break-point in human chromosome 3 is on the short arm near the centromere. This region is involved in renal cell carcinoma formation. By targeting pTEMPhu3 to this region, the induced large-scale amplification may contain this region, which can then be cloned using the bacterial and yeast markers in the pTEMPhu3 vector.

The pTEMPhu3 cloning vector allows not only selection for homologous recombinants, but also direct cloning of the integration site in YACS. This vector can also be used to target human chromosome 3, preferably with a deleted short arm, in a mouse-human monochromosomal microcell hybrid line. Homologous recombinants can be screened by nucleic acid amplification (PCR), and amplification can be screened by DNA hybridization, Southern hybridization, and in situ hybridization. The amplified region can be cloned into a YAC. This vector and these methods also permit a functional analysis of cloned chromosome regions by reintroducing the cloned amplified region into mammalian cells.

B. Preparation of Libraries in YAC Vectors for Cloning of Centromeres and Identification of Functional Chromosomal Units Another method that may be used to obtain smaller-sized functional mammalian artificial chromosome units and to clone centromeric DNA involves screening of mammalian DNA YAC vector-based libraries and functional analysis of potential positive clones in a transgenic mouse model system. A mammalian DNA library is prepared in a YAC vector, such as YRT2 (see Schedl et al. (1993) *Nuc. Acids Res.* 21:4783-4787), which contains the murine tyrosinase gene. The library is screened for hybridization to mammalian telomere and centromere sequence probes. Positive clones are isolated and microinjected into pronuclei of fertilized oocytes of NMRI/Han mice following standard techniques. The embryos are then transferred into NMRI/Han foster mothers. Expression of the tyrosinase gene in transgenic offspring confers an identifiable phenotype (pigmentation). The clones that give rise to tyrosinase-expressing transgenic mice are thus confirmed as containing functional mammalian artificial chromosome units.

Alternatively, fragments of SATACs may be introduced into the YAC vectors and then introduced into pronuclei of fertilized oocytes of NMRI/Han mice following standard techniques as above. The clones that give rise to tyrosinase-expressing transgenic mice are thus confirmed as containing functional mammalian artificial chromosome units, particularly centromeres.

C. Incorporation of Heterologous Genes into Mammalian Artificial Chromosomes through the Use of Homology Targeting Vectors As described above, the use of mammalian artificial chromosomes for expression of heterologous genes obviates certain negative effects that may result from random integration of heterologous plasmid DNA into the recipient cell genome.

An essential feature of the mammalian artificial chromosome that makes it a useful tool in avoiding the negative effects of random integration is its presence as an extra-genomic gene source in recipient cells. Accordingly, methods of specific, targeted incorporation of heterologous genes exclusively into the mammalian artificial chromosome, without extraneous random integration into the genome of recipient cells, are desired for heterologous gene expression from a mammalian artificial chromosome.

One means of achieving site-specific integration of heterologous genes into artificial chromosomes is through the use of homology targeting vectors. The heterologous gene of interest in subcloned into a targeting vector which contains nucleic acid sequences that are homologous to nucleotides present in the artificial chromosome. The vector is then introduced into cells containing the artificial chromosome for specific site-directed integration into the artificial chromosome through a recombination event at sites of homology between the vector and the chromosome. The homology targeting vectors may also contain selectable markers for ease of identifying cells that have incorporated the vector into the artificial chromosome as well as lethal selection genes that are expressed only upon extraneous integration of the vector into the recipient cell genome. Two exemplary homology targeting vectors, λCF-7 and pλCF-7-DTA, are described below.

1. Construction of Vector λCF-7

Vector λCF-7 contains the cystic fibrosis transmembrane conductance regulator (CFTR) gene as an exemplary therapeutic molecule-encoding nucleic acid that may be incorporated into mammalian artificial chromosomes for use in gene therapy applications. This vector, which also contains the puromycin-resistance gene as a selectable marker, as well as the *Saccharomyces cerevisiae* ura3 gene (orotidine-5'-phosphate decarboxylase), was constructed in a series of steps as follows.

a. Construction of pURA

Plasmid pURA was prepared by ligating a 2.6-kb SalI/XhoI fragment from the yeast artificial chromosome vector pYAC5 (Sigma; see also Burke et al. (1987) *Science* 236:806-812 for a description of YAC vectors as well as GenBank Accession no. U01086 for the complete sequence of pYAC5) containing the *S. cerevisiae* ura3 gene with a 3.3-kb SalI/SmaI fragment of pHyg (see, e.g., U.S. Pat. Nos. 4,997,764, 4,686,186 and 5,162,215. and the description above). Prior to ligation the XhoI end was treated with Klenow polymerase for blunt end ligation to the SmaI end of the 3.3 kb fragment of pHyyg. Thus, pURA contains the *S. cerevisiae* ura3 gene, and the *E. coli* ColE1 origin of replication and the ampicillin-resistance gene. The uraE gene is included to provide a means to recover the integrated construct from a mammalian cell as a YAC clone.

b. Construction of pUP2

Plasmid pURA was digested with SalI and ligated to a 1.5-kb SalI fragment of pCEPUR. Plasmid pCEPUR is produced by ligating the 1.1 kb SalI-NhaI fragment of pBabe-puro (Morgenstern et al. (1990) *Nucl. Acids Res.* 18:3587-3596; provided by Dr. L. Székely (Microbiology and Tumorbiology Center, Karolinska Institutet, Stockholm); see, also Tonghua et al. (1995) *Chin. Med. J.* (Beijing, Engl. Ed.) 108:653-659; Couto et al. (1994) *Infect. Immun.* 62:2375-2378; Dunckley et al. (1992) *FEBS Lett.* 296:128-34; French et al. (1995) *Anal. Biochem.* 228:354-355; Liu et al. (1995) *Blood* 85:1095-1103; International PCT application Nos. WO 9520044; WO 9500178, and WO 9419456) to the NheI-NruI fragment of pCEP4 (Invitrogen).

The resulting plasmid, pUP2, contains the all the elements of pURA plus the puromycin-resistance gene linked to the SV40 promoter and polyadenylation signal from pCEPUR.

c. Construction of pUP-CFTR

The intermediate plasmid pUP-CFTR was generated in order to combine the elements of pUP2 into a plasmid along with the CFTR gene. First, a 4.5-kb SalI fragment of pCMV-CFTR that contains the CFTR-encoding DNA (see, also, Riordan et al. (1989) *Science* 245:1066-1073, U.S. Pat. No. 5,240,846, and Genbank Accession no. M28668 for the sequence of the CFTR gene) containing the CFTR gene only was ligated to XhoI-digested pCEP4 (Invitrogen and also described herein) in order to insert the CFTR gene in the multiple cloning site of the Epstein Barr virus-based (EBV) vector pCEP4 (Invitrogen, San Diego, Calif.; see also Yates et al. (1985) *Nature* 313:812-815; see, also U.S. Pat. No. 5,468,615) between the CMV promoter and SV40 polyadenylation signal. The resulting plasmid was designated pCEP-CFTR. Plasmid pCEP-CFTR was then digested with SalI and the 5.8-kb fragment containing the CFTR gene flanked by the CMV promoter and SV40 polyadenylation signal was ligated to SalI-digested pUP2 to generate pUP-CFTR. Thus, pUP-CFTR contains all elements of pUP2 plus the CFTR gene linked to the CMV promoter and SV40 polyadenylation signal.

d. Construction of λCF-7

Plasmid pUP-CFTR was then linearized by partial digestion with EcoRI and the 13 kb fragment containing the CFTR gene was ligated with EcoRI-digested Charon 4Aλ (see Blattner et al. (1977) *Science* 196:161; Williams and Blattner (1979) *J. Virol.* 29:555 and Sambrook et al. (1989) *Molecular Cloning, A Laboratory Manual*, Second Ed., Cold Spring Harbor Laboratory Press, Volume 1, Section 2.18, for descriptions of Charon 4Aλ). The resulting vector, λCF8, contains the Charon 4λ bacteriophage left arm, the CFTR gene linked to the CMV promoter and SV40 polyadenylation signal, the ura3 gene, the puromycin-resistance gene linked to the SV40 promoter and polyadenylation signal, the thymidine kinase promoter (TK), the ColE1 origin of replication, the ampicillin resistance gene and the Charon 4Aλ bacteriophage right arm. The λCF8 construct was then digested with XhoI and the resulting 27.1 kb was ligated to the 0.4 kb XhoI/EcoRI fragment of pJBP86 (described below), containing the SV40 polyA signal and the EcoRI-digested Charon 4A λ right arm. The resulting vector λCF-7 contains the Charon 4A λ left arm, the CFTR encoding DNA linked to the CMV promoter and SV40 polyA signal, the ura3 gene, the puromycin resistance gene linked to the SV40 promoter and polyA signal and the Charon 4A λ right arm. The λ DNA fragments provide encode sequences homologous to nucleotides present in the exemplary artificial chromosomes.

The vector is then introduced into cells containing the artificial chromosomes exemplified herein. Accordingly, when the linear λCF-7 vector is introduced into megachromosome-carrying fusion cell lines, such as described herein, it will be specifically integrated into the megachromosome through recombination between the homologous bacteriophage λ sequences of the vector and the artificial chromosome.

2. Construction of Vector λCF-7-DTA

Vector λCF-7-DTA also contains all the elements contained in λCF-7, but additionally contains a lethal selection marker, the diphtheria toxin-A (DT-A) gene as well as the ampicillin-resistance gene and an origin of replication. This vector was constructed in a series of steps as follows.

a. Construction of pJBP86

Plasmid pJBP86 was used in the construction of λCF-7, above. A 1.5-kb SalI fragment of pCEPUR containing the puromycin-resistance gene linked to the SV40 promoter and polyadenylation signal was ligated to HindIII-digested pJB8 (see, e.g., Ish-Horowitz et al. (1981) *Nucleic Acids Res.* 9:2989-2998; available from ATCC as Accession No. 37074; commercially available from Amersham, Arlington Heights, Ill.). Prior to ligation the SalI ends of the 1.5 kb fragment of pCEPUR and the HindIII linearized pJB8 ends were treated with Klenow polymerase. The resulting vector pJBP86 contains the puromycin resistance gene linked to the SV40 promoter and polyA signal, the 1.8 kb COS region of Charon 4 μm, the ColE1 origin of replication and the ampicillin resistance gene.

b. Construction of pMEP-DTA

A 1.1-kb XhoI/SalI fragment of pMC1-DT-A (see, e.g., Maxwell et al. (1986) *Cancer Res.* 46:4660-4666) containing the diphtheria toxin-A gene was ligated to XhoI-digested pMEP4 (Invitrogen, San Diego, Calif.) to generate pMEP-DTA. To produce pMC1-DT-A, the coding region of the DTA gene was isolated as a 800 bp PstIHindIII fragment from p2249-1 and inserted into pMC1neopolyA (pMC1 available from Stratagene) in place of the neo gene and under the control of the TK promoter. The resulting construct pMC1DT-A was digested with HindIII, the ends filled by Klenow and SalI linkers were ligated to produce a 1061 bp TK-DTA gene cassette with an XhoI end (5') and a SalI end containing the 270 bp TK promoter and the ~790 bp DT-A fragment. This fragment was ligated into XhoI-digested pMEP4.

Plasmid pMEP-DTA thus contains the DT-A gene linked to the TK promoter and SV40, ColE1 origin of replication and the ampicillin-resistance gene.

c. Construction of pJB83-DTA9

Plasmid pJB8 was digested with HindIII and ClaI and ligated with an oligonucleotide (see SEQ ID NOs. 7 and 8 for the sense and antisense strands of the oligonucleotide, respectively) to generate pJB83. The oligonucleotide that was ligated to ClaI/HindIII-digested pJB8 contained the recognition sites of SwaI PacI and SrfI restriction endonucleases. These sites will permit ready linearization of the pλCF-7-DTA construct.

Next, a 1.4-kb XhoI/SalI fragment of pMEP-DTA, containing the DT-A gene was ligated to SalI-digested pJB83 to generate pJB83-DTA9.

d. Construction of λCF-7-DTA

The 12-bp overhangs of λCF-7 were removed by Mung bean nuclease and subsequent T4 polymerase treatments. The resulting 41.1-kb linear λCF-7 vector was then ligated to pFB83-DTA9 which had been digested with ClaI and treated with T4 polymerase. The resulting vector, λCF-7-DTA, contains all the elements of λCF-7 as well as the DT-A gene linked to the TK promoter and the SV40 polyadenylation signal, the 1.8 kB Charon 4A λ COS region, the ampicillin-resistance gene (from pJB83-DTA9) and the Col E1 origin of replication (from pJB83-DT9A).

D. Targeting Vectors Using Luciferase Markers: Plasmid pMCT-RUC

Plasmid pMCT-RUC (14 kbp) was constructed for site-specific targeting of the *Renilla* luciferase (see, e.g., U.S. Pat. Nos. 5,292,658 and 5,418,155 for a description of DNA encoding *Renilla* luciferase, and plasmid pTZrLuc-1, which can provide the starting material for construction of such vectors) gene to a mammalian artificial chromosome. The relevant features of this plasmid are the *Renilla* luciferase gene under transcriptional control of the human cytomegalovirus immediate-early gene enhancer/promoter; the hygromycin-resistance gene a, positive selectable marker, under the transcriptional control of the thymidine kinase promoter. In particular, this plasmid contains plasmid pAG60 (see, e.g., U.S. Pat. Nos. 5,118,620, 5,021,344, 5,063,162 and 4,946, 952; see, also Colbert-Garapin et al. (1981) *J. Mol. Biol.* 150:1-14), which includes DNA (i.e., the neomycin-resistance gene) homologous to the minichromosome, as well as the *Renilla* and hygromycin-resistance genes, the HSV-tk gene under control of the tk promoter as a negative selectable marker for homologous recombination, and a unique HpaI site for linearizing the plasmid.

This construct was introduced, via calcium phosphate transfection, into EC3/7C5 cells (see, Lorenz et al. (1996) *J. Biolum. Chemilum.* 11:31-37). The EC3/7C5 cells were maintained as a monolayer (see, Gluzman (1981) *Cell* 23:175-183). Cells at 50% confluency in 100 mm Petri dishes were used for calcium phosphate transfection (see, Harper et al. (1981) *Chromosoma* 83:431-439) using 10 μg of linearized pMCT-RUC per plate. Colonies originating from single transfected cells were isolated and maintained in F-12 medium containing hygromycin (300 μg/mL) and 10% fetal bovine serum. Cells were grown in 100 mm Petri dishes prior to the *Renilla* luciferase assay.

The *Renilla* luciferase assay was performed (see, e.g., Matthews et al. (1977) *Biochemistry* 16:85-91). Hygromycin-resistant cell lines obtained after transfection of EC3/7C5 cells with linearized plasmid pMCT-RUC ("B" cell lines) were grown to 100% confluency for measurements of light emission in vivo and in vitro. Light emission was measured in vivo after about 30 generations as follows: growth medium was removed and replaced by 1 mL RPMI 1640 containing coelenterazine (1 mmol/L final concentration). Light emission from cells was then visualized by placing the Petri dishes in a low light video image analyzer (Hamamatsu Argus-100). An image was formed after 5 min. of photon accumulation using 100% sensitivity of the photon counting tube. For measuring light emission in vitro, cells were trypsinized and harvested from one Petri dish, pelleted, resuspended in 1 mL assay buffer (0.5 mol/L NaCl, 1 mmol/L EDTA, 0.1 mol/L potassium phosphate, pH 7.4) and sonicated on ice for 10 s. Lysates were than assayed in a Turner TD-20e luminometer for 10 s after rapid injection of 0.5 mL of 1 mmol/L coelenterazine, and the average value of light emission was recorded as LU (1 LU=$1.6\times10^6$ hu/s for this instrument).

Independent cell lines of EC3/7C5 cells transfected with linearized plasmid pMCT-RUC showed different levels of *Renilla* luciferase activity. Similar differences in light emission were observed when measurements were performed on lysates of the same cell lines. This variation in light emission was probably due to a position effect resulting from the random integration of plasmid pMCT-RUC into the mouse genome, since enrichment for site targeting of the luciferase gene was not performed in this experiment.

To obtain transfectant populations enriched in cells in which the luciferase gene had integrated into the minichromosome, transfected cells were grown in the presence of ganciclovir. This negative selection medium selects against cells in which the added pMCT-RUC plasmid integrated into the host EC3/7C5 genome. This selection thereby enriches the surviving transfectant population with cells containing pMCT-RUC in the minichromosome. The cells surviving this selection were evaluated in luciferase assays which revealed a more uniform level of luciferase expression. Additionally, the results of in situ hybridization assays indicated that the *Renilla* luciferase gene was contained in the minichromosome in these cells, which further indicates successful targeting of pMCT-RUC into the minichromosome.

Plasmid pNEM-1, a variant of pMCT-RUC which also contains λ DNA to provide an extended region of homology to the minichromosome (see, other targeting vectors, below), was also used to transfect EC3/7C5 cells. Site-directed targeting of the *Renilla* luciferase gene and the hygromycin-resistance gene in pNEM-1 to the minichromosome in the recipient EC3/7C5 cells was achieved. This was verified by DNA amplification analysis and by in situ hybridization. Additionally, luciferase gene expression was confirmed in luciferase assays of the transfectants.

E. Protein Secretion Targeting Vectors

Isolation of heterologous proteins produced intracellularly in mammalian cell expression systems requires cell disruption under potentially harsh conditions and purification of the recombinant protein from cellular contaminants. The process of protein isolation may be greatly facilitated by secretion of the recombinantly produced protein into the extracellular medium where there are fewer contaminants to remove during purification. Therefore, secretion targeting vectors have been constructed for use with the mammalian artificial chromosome system.

A useful model vector for demonstrating production and secretion of heterologous protein in mammalian cells contains DNA encoding a readily detectable reporter protein fused to an efficient secretion signal that directs transport of the protein to the cell membrane and secretion of the protein from the cell. Vectors pLNCX-ILRUC and pLNCX-ILRUCλ, described below, are examples of such vectors. These vectors contain DNA encoding an interleukin-2 (IL2) signal peptide-*Renilla reniformis* luciferase fusion protein. The IL-2 signal peptide (encoded by the sequence set forth in SEQ ID No. 9) directs secretion of the luciferase protein, to which it is linked, from mammalian cells. Upon secretion from the host mammalian cell, the IL-2 signal peptide is cleaved from the fusion protein to deliver mature, active, luciferase protein to the extracellular medium. Successful production and secretion of this heterologous protein can be readily detected by performing luciferase assays which measure the light emitted upon exposure of the medium to the bioluminescent luciferin substrate of the luciferase enzyme. Thus, this feature will be useful when artificial chromosomes are used for gene therapy. The presence of a functional artificial chromosome carrying an IL-Ruc fusion with the accompanying therapeutic genes will be readily monitored. Body fluids or tissues can be sampled and tested for luciferase expression by adding luciferin and appropriate cofactors and observing the bioluminescence.

1. Construction of Protein Secretion Vector pLNCX-IL-RUC

Vector pLNCX-ILRUC contains a human IL-2 signal peptide-*R. reniformis* fusion gene linked to the human cytomegalovirus (CMV) immediate early promoter for constitutive expression of the gene in mammalian cells. The construct was prepared as follows.

a. Preparation of the IL-2 Signal Sequence-Encoding DNA

A 69-bp DNA fragment containing DNA encoding the human IL-2 signal peptide was obtained through nucleic acid amplification, using appropriate primers for IL-2, of an HEK 293 cell line (see, e.g., U.S. Pat. No. 4,518,584 for an IL-2 encoding DNA; see, also SEQ ID No. 9; the IL-2 gene and corresponding amino acid sequence is also provided in the Genbank Sequence Database as accession nos. K02056 and J00264). The signal peptide includes the first 20 amino acids shown in the translations provided in both of these Genbank entries and in SEQ ID NO. 9. The corresponding nucleotide sequence encoding the first 20 amino acids is also provided in these entries (see, e.g., nucleotides 293-352 of accession no. K02056 and nucleotides 478-537 of accession no. J00264), as well as in SEQ ID NO. 9. The amplification primers included an EcoRI site (GAATTC) for subcloning of the DNA fragment after ligation into pGEMT (Promega). The forward primer is set forth in SEQ ID No. 11 and the sequence of the reverse primer is set forth in SEQ ID No. 12.

```
                                        (SEQ ID No. 11)
TTTGAATTCATGTACAGGATGCAACTCCTG             forward

                                        (SEQ ID No. 12)
TTTGAATTCAGTAGGTGCACTGTTTGTGAC             reverse
```

b. Preparation of the *R. reniformis* Luciferase-Encoding DNA

The initial source of the *R. reniformis* luciferase gene was plasmid pLXSN-RUC. Vector pLXSN (see, e.g., U.S. Pat. Nos. 5,324,655, 5,470,730, 5,468,634, 5,358,866 and Miller et al. (1989) *Biotechniques* 7:980) is a retroviral vector capable of expressing heterologous DNA under the transcriptional control of the retroviral LTR; it also contains the neomycin-resistance gene operatively linked for expression to the SV40 early region promoter. The *R. reniformis* luciferase gene was obtained from plasmid pTZrLuc-1 (see, e.g., U.S. Pat. No. 5,292,658; see also the Genbank Sequence Database accession no. M63501; and see also Lorenz et al. (1991) *Proc. Natl. Acad. Sci. U.S.A.* 88:4438-4442) and is shown as SEQ ID NO. 10. The 0.97 kb EcoRI/SmaI fragment of pTZrLuc-1 contains the coding region of the *Renilla* luciferase-encoding DNA. Vector pLXSN was digested with and ligated with the luciferase gene contained on a pLXSN-RUC, which contains the luciferase gene located operably linked to the viral LTR and upstream of the SV40 promoter, which directs expression of the neomycin-resistance gene.

c. Fusion of DNA Encoding the IL-2 Signal Peptide and the *R. reniformis* Luciferase Gene to Yield pLXSN-ILRUC The pGEMT vector containing the IL-2 signal peptide-encoding DNA described in 1.a. above was digested with EcoRI, and the resulting fragment encoding the signal peptide was ligated to EcoRI-digested pLXSN-RUC. The resulting plasmid, called pLXSN-ILRUC, contains the IL-2 signal peptide-encoding DNA located immediately upstream of the *R. reniformis* gene in pLXSN-RUC. Plasmid pLXSN-ILRUC was then used as a template for nucleic acid amplification of the fusion gene in order to add a SmaI site at the 3' end of the fusion gene. The amplification product was subcloned into linearized (EcoRI/SmaI-digested) pGEMT (Promega) to generate ILRUC-pGEMT.

d. Introduction of the Fusion Gene into a Vector Containing Control Elements for Expression in Mammalian Cells Plasmid ILRUC-pGEMT was digested with KspI and SmaI to release a fragment containing the IL-2 signal peptide-luciferase fusion gene which was ligated to HpaI-digested pLNCX. Vector pLNCX (see, e.g., U.S. Pat. Nos. 5,324,655 and 5,457,182; see, also Miller and Rosman (1989) *Biotechniques* 7:980-990) is a retroviral vector for expressing heterologous DNA under the control of the CMV promoter; it also contains the neomycin-resistance gene under the transcriptional control of a viral promoter. The vector resulting from the ligation reaction was designated pLNCX-ILRUC. Vector pLNCX-ILRUC contains the IL-2 signal peptide-luciferase fusion gene located immediately downstream of the CMV promoter and upstream of the viral 3' LTR and polyadenylation signal in pLNCX. This arrangement provides for expression of the fusion gene under the control of the CMV promoter. Placement of the heterologous protein-encoding DNA (i.e., the luciferase gene) in operative linkage with the IL-2 signal peptide-encoding DNA provides for expression of the fusion in mammalian cells transfected with the vector such that the heterologous protein is secreted from the host cell into the extracellular medium.

2. Construction of Protein Secretion Targeting Vector pLNCX-ILRUCλ

Vector pLNCX-ILRUC may be modified so that it can be used to introduce the IL-2 signal peptide-luciferase fusion gene into a mammalian artificial chromosome in a host cell. To facilitate specific incorporation of the pLNCX-ILRUC expression vector into a mammalian artificial chromosome, nucleic acid sequences that are homologous to nucleotides present in the artificial chromosome are added to the vector to permit site directed recombination.

Exemplary artificial chromosomes described herein contain λphage DNA. Therefore, protein secretion targeting vector pLNCX-ILRUCλ was prepared by addition of λ phage DNA (from Charon 4A arms) to produce the secretion vector pLNCX-ILRUC.

3. Expression and Secretion of *R. reniformis* Luciferase from Mammalian Cells a. Expression of *R. reniformis* Luciferase Using pLNCX-ILRUC Mammalian cells (LMTK$^-$ from the ATCC) were transiently transfected with vector pLNCX-ILRUC (~10 g) by electroporation (BIORAD, performed according to the manufacturer's instructions). Stable transfectants produced by growth in G418 for neo selection have also been prepared.

Transfectants were grown and then analyzed for expression of luciferase. To determine whether active luciferase was secreted from the transfected cells, culture media were assayed for luciferase by addition of coelenterazine (see, e.g., Matthews et al. (1977) *Biochemistry* 16:85-91).

The results of these assays establish that vector pLNCX-ILRUC is capable of providing constitutive expression of heterologous DNA in mammalian host cells. Furthermore, the results demonstrate that the human IL-2 signal peptide is capable of directing secretion of proteins fused to the C-terminus of the peptide. Additionally, these data demonstrate that the *R. reniformis* luciferase protein is a highly effective reporter molecule, which is stable in a mammalian cell environment, and forms the basis of a sensitive, facile assay for gene expression.

b. *Renilla reniformis* Luciferase Appears to be Secreted from LMTK$^-$ cells.

(i) *Renilla* Luciferase Assay of Cell Pellets

The following cells were tested:

cells with no vector: LMTK$^-$ cells without vector as a negative control;

cells transfected with pLNCX only;

cells transfected with RUC-pLNCX (*Renilla* luciferase gene in pLNCX vector);

cells transfected with pLNCX-ILRUC (vector containing the IL-2 leader sequence+*Renilla* luciferase fusion gene in pLNCX vector).

Forty-eight hours after electroporation, the cells and culture medium were collected. The cell pellet from 4 plates of cells was resuspended in 1 ml assay buffer and was lysed by sonication. Two hundred μl of the resuspended cell pellet was used for each assay for luciferase activity (see, e.g., Matthews et al. (1977) *Biochemistry* 16:85-91). The assay was repeated three times and the average bioluminescence measurement was obtained.

The results showed that there was relatively low background bioluminescence in the cells transformed with pLNCX or the negative control cells; there was a low level observed in the cell pellet from cells containing the vector with the IL-2 leader sequence-luciferase gene fusion and more than 5000 RLU in the sample from cells containing RUC-pLNCX.

(ii) *Renilla* Luciferase Assay of Cell Medium

Forty milliliters of medium from 4 plates of cells were harvested and spun down. Two hundred microliters of medium was used for each luciferase activity assay. The assay was repeated several times and the average bioluminescence measurement was obtained. These results showed that a relatively high level of bioluminescence was detected in the cell medium from cells transformed with PLNCX-ILRUC; about 10-fold lower levels (slightly above the background levels in medium from cells with no vector or transfected with pLNCX only) was detected in the cells transfected with RUC-pLNCX.

(iii) Conclusions

The results of these experiments demonstrated that *Renilla* luciferase appears to be secreted from LMTK$^-$ cells under the direction of the IL-2 signal peptide. The medium from cells transfected with *Renilla* luciferase-encoding DNA linked to the DNA encoding the IL-2 secretion signal had substantially higher levels of *Renilla* luciferase activity than controls or cells containing luciferase-encoding DNA without the signal peptide-encoding DNA. Also, the differences between the controls and cells containing luciferase encoding-DNA demonstrate that the luciferase activity is specifically from luciferase, not from a non-specific reaction. In addition, the results from the medium of RUC-pLNCX transfected cells, which is similar to background, show that the luciferase activity in the medium does not come from cell lysis, but from secreted luciferase.

c. Expression of *R. reniformis* Luciferase Using pLNCX-ILRUCλ

To express the IL-2 signal peptide-*R. reniformis* fusion gene from an mammalian artificial chromosome, vector pLNCX-ILRUCλ is targeted for site-specific integration into a mammalian artificial chromosome through homologous recombination of the λ DNA sequences contained in the chromosome and the vector. This is accomplished by introduction of pLNCX-ILRUCλ into either a fusion cell line harboring mammalian artificial chromosomes or mammalian host cells that contain mammalian artificial chromosomes. If the vector is introduced into a fusion cell line harboring the artificial chromosomes, for example through microinjection of the vector or transfection of the fusion cell line with the vector, the cells are then grown under selective conditions. The artificial chromosomes, which have incorporated vector pLNCX-ILRUCλ, are isolated from the surviving cells, using purification procedures as described above, and then injected into the mammalian host cells.

Alternatively, the mammalian host cells may first be injected with mammalian artificial chromosomes which have been isolated from a fusion cell line. The host cells are then transfected with vector pLNCX-ILRUCλ and grown.

The recombinant host cells are then assayed for luciferase expression as described above.

F. Other Targeting Vectors

These vectors, which are based on vector pMCT-RUC, rely on positive and negative selection to insure insertion and selection for the double recombinants. A single crossover results in incorporation of the DT-A, which kills the cell, double crossover recombinations delete the DT-1 gene.

1. Plasmid pNEM1 contains:

DT-A: Diphtheria toxin gene (negative selectable marker)
Hyg: Hygromycin gene (positive selectable marker)
ruc: *Renilla* luciferase gene (non-selectable marker)
1: LTR-MMTV promoter
2: TK promoter
3: CMV promoter
MMR: Homology region (plasmid pAG60)

2. plasmid pNEM-2 and -3 are similar to pNEM 1 except for different negative selectable markers:

pNEM-1: diphtheria toxin gene as "—" selectable marker
pNEM-2: hygromycin antisense gene as "—" selectable marker
pNEM-3: thymidine kinase HSV-1 gene as "—" selectable marker 3. Plasmid—λDNA based homology:

pNEMλ-1: base vector
pNEMλ-2: base vector containing p5=gene
1: LTR MMTV promoter
2: SV40 promoter
3: CMV promoter
4: μTIIA promoter (metallothionein gene promoter)—homology region (plasmid pAG60) λL.A. and λR.A. homology regions for λ left and right arms (λgt-WES).

Example 13

Microinjection of Mammalian Cells with Plasmid DNA

These procedures will be used to microinject MACs into eukaryotic cells, including mammalian and insect cells.

The microinjection technique is based on the use of small glass capillaries as a delivery system into cells and has been used for introduction of DNA fragments into nuclei (see, e.g., Chalfie et al. (1994) *Science* 263:802-804). It allows the transfer of almost any type of molecules, e.g., hormones, proteins, DNA and RNA, into either the cytoplasm or nuclei of recipient cells This technique has no cell type restriction and is more efficient than other methods, including $Ca2^+$-mediated gene transfer and liposome-mediated gene transfer. About 20-30% of the injected cells become successfully transformed.

Microinjection is performed under a phase-contrast microscope. A glass microcapillary, prefilled with the DNA sample, is directed into a cell to be injected with the aid of a micromanipulator. An appropriate sample volume (1-10 pl) is transferred into the cell by gentle air pressure exerted by a transjector connected to the capillary. Recipient cells are grown on glass slides imprinted with numbered squares for convenient localization of the injected cells.

a. Materials and Equipment

Nunclon tissue culture dishes 35×10 mm, mouse cell line EC3/7C5 Plasmid DNA pCH110 (Pharmacia), Purified Green Florescent Protein (GFP) (GFPs from *Aequorea* and *Renilla* have been purified and also DNA encoding GFPs has been cloned; see, e.g., Prasher et al. (1992) *Gene* 111:229-233; International PCT Application No. WO 95/07463, which is based on U.S. application Ser. No. 08/119,678 and U.S. application Ser. No. 08/192,274), ZEISS Axiovert 100 microscope, Eppendorf transjector 5246, Eppendorf micromanipulator 5171, Eppendorf Cellocate coverslips, Eppendorf microloaders, Eppendorf femtotips and other standard equipment.

b. Protocol for Injecting (1) Fibroblast cells are grown in 35 mm tissue culture dishes (37° C., 5% $CO_2$) until the cell density reaches 80% confluency. The dishes are removed from the incubator and medium is added to about a 5 mm depth.

(2) The dish is placed onto the dish holder and the cells observed with 10× objective; the focus is desirably above the cell surface.

(3) Plasmid or chromosomal DNA solution (1 ng/μl) and GFP protein solution are further purified by centrifuging the DNA sample at a force sufficient to remove any particular debris (typically about 10,000 rpm for 10 minutes in a microcentrifuge).

(4) Two 2 μl of the DNA solution (1 ng/μl) is loaded into a microcapillary with an Eppendorf microloader. During loading, the loader is inserted to the tip end of the microcapillary. GFP (1 mg/ml) is loaded with the same procedure.

(5) The protecting sheath is removed from the microcapillary and the microcapillary is fixed onto the capillary holder connected with the micromanipulator.

(6) The capillary tip is lowered to the surface of the medium and is focused on the cells gradually until the tip of the capillary reaches the surface of a cell. The capillary is lowered further so that the it is inserted into the cell. Various parameters, such as the level of the capillary, the time and pressure, are determined for the particular equipment. For example, using the fibroblast cell line C5 and the above-noted equipment, the best conditions are: injection time 0.4 second, pressure 80 psi. DNA can then be automatically injected into the nuclei of the cells.

(7) After injection, the cells are returned to the incubator, and incubated for about 18-24 hours.

(8) After incubation the number of transformants can be determined by a suitable method, which depends upon the selection marker. For example, if green fluorescent protein is used, the assay can be performed using UV light source and fluorescent filter set at 0-24 hours after injection. If β-gal-containing DNA, such as DNA-derived from pHC110, has been injected, then the transformants can be assayed for β-gal.

(c) Detection of β-Galactosidase in Cells Injected with Plasmid DNA

The medium is removed from the culture plate and the cells are fixed by addition of 5 ml of fixation Solution I: (1% glutaraldehyde; 0.1 M sodium phosphate buffer, pH 7.0; 1 mM $MgCl_2$), and incubated for 15 minutes at 37° C. Fixation Solution I is replaced with 5 ml of X-gal Solution II: (0.2% X-gal, 10 mM sodium phosphate buffer (pH 7.0), 150 mM NaCl, 1 mM $MgCl_2$, 3.3 mM $K_4Fe(CN)_6H_2O$, 3.3 mM $K_3Fe(CN)_6$), and the plates are incubated for 30-60 minutes at 37° C. The X-gal solution is removed and 2 ml of 70% glycerol is added to each dish. Blue stained cells are identified under a light microscope.

This method will be used to introduce a MAC, particularly the MAC with the anti-HIV megachromosome, to produce a mouse model for anti-HIV activity.

Example 14

Transgenic (Non-Human) Animals

Transgenic (non-human) animals can be generated that express heterologous genes which confer desired traits, e.g., disease resistance, in the animals. A transgenic mouse is prepared to serve as a model of a disease-resistant animal. Genes that encode vaccines or that encode therapeutic molecules can be introduced into embryos or ES cells to produce animals that express the gene product and thereby are resistant to or less susceptible to a particular disorder.

The mammalian artificial megachromosome and others of the artificial chromosomes, particularly the SATACs, can be used to generate transgenic (non-human) animals, including mammals and birds, that stably express genes conferring desired traits, such as genes conferring resistance to pathogenic viruses. The artificial chromosomes can also be used to produce transgenic (non-human) animals, such as pigs, that can produce immunologically humanized organs for xenotransplantation.

For example, transgenic mice containing a transgene encoding an anti-HIV ribozyme provide a useful model for the development of stable transgenic (non-human) animals using these methods. The artificial chromosomes can be used to produce transgenic (non-human) animals, particularly, cows, goats, mice, oxen, camels, pigs and sheep, that produce the proteins of interest in their milk; and to produce transgenic chickens and other egg-producing fowl, that produce therapeutic proteins or other proteins of interest in their eggs. For example, use of mammary gland-specific promoters for expression of heterologous DNA in milk is known (see, e.g. U.S. Pat. No. 4,873,316). In particular, a milk-specific promoter or a promoter, preferably linked to a milk-specific signal peptide, specifically activated in mammary tissue is operatively linked to the DNA of interest, thereby providing expression of that DNA sequence in milk.

1. Development of Control Transgenic Mice Expressing Anti-HIV Ribozyme

Control transgenic mice are generated in order to compare stability and amounts of transgene expression in mice developed using transgene DNA carried on a vector (control mice) with expression in mice developed using transgenes carried in an artificial megachromosome.

a. Development of Control Transgenic Mice Expressing β-Galactosidase

One set of control transgenic mice was generated by microinjection of mouse embryos with the β-galactosidase gene alone. The microinjection procedure used to introduce the plasmid DNA into the mouse embryos is as described in Example 13, but modified for use with embryos (see, e.g., e.g., Hogan et al. (1994) *Manipulating the Mouse Embryo: A Laboratory Manual*, Cold Spring Harbor Laboratory Press, Cold Spring Harbor, N.Y., see, especially pages 255-264 and Appendix 3). Fertilized mouse embryos (Strain CB6 obtained from Charles River Co.) were injected with 1 ng of plasmid pCH110 (Pharmacia) which had been linearized by digestion with BamHI. This plasmid contains the β-galactosidase gene linked to the SV40 late promoter. The β-galactosidase gene product provides a readily detectable marker for successful transgene expression. Furthermore, these control mice provide confirmation of the microinjection procedure used to introduce the plasmid into the embryos. Additionally, because the megachromosome that is transferred to the mouse embryos in the model system (see below) also contains the β-galactosidase gene, the control transgenic mice that have been generated by injection of pCH110 into embryos serve as an analogous system for comparison of heterologous gene expression from a plasmid versus from a gene carried on an artificial chromosome.

After injection, the embryos are cultured in modified HTF medium under 5% $CO_2$ at 37° C. for one day until they divide to form two cells. The two-cell embryos are then implanted into surrogate mother female mice (for procedures see, *Manipulating the Mouse Embryo: A Laboratory Manual* (1994) Hogan et al., eds., Cold Spring Harbor Laboratory Press, Cold Spring Harbor, N.Y., pp. 127 et seq.).

b. Development of Control Transgenic Mice Expressing Anti-HIV Ribozyme

One set of anti-HIV ribozyme gene-containing control transgenic mice was generated by microinjection of mouse embryos with plasmid pCEPUR-132 which contains three different genes: (1) DNA encoding an anti-HIV ribozyme, (2) the puromycin-resistance gene and (3) the hygromycin-resistance gene. Plasmid pCEPUR-132 was constructed by ligating portions of plasmid pCEP-132 containing the anti-HIV ribozyme gene (referred to as ribozyme D by Chang et al. ((1990) *Clin. Biotech.* 2:23-31); see also U.S. Pat. No. 5,144,019 to Rossi et al., particularly FIG. 4 of the patent) and the hygromycin-resistance gene with a portion of plasmid pCEPUR containing the puromycin-resistance gene.

Plasmid pCEP-132 was constructed as follows. Vector pCEP4 (Invitrogen, San Diego, Calif.; see also Yates et al. (1985) *Nature* 313:812-815) was digested with XhoI which cleaves in the multiple cloning site region of the vector. This ~10.4-kb vector contains the hygromycin-resistance gene linked to the thymidine kinase gene promoter and polyadenylation signal, as well as the ampicillin-resistance gene and ColE1 origin of replication and EBNA-1 (Epstein-Barr virus nuclear antigen) genes and OriP. The multiple cloning site is flanked by the cytomegalovirus promoter and SV40 polyadenylation signal.

XhoI-digested pCEP4 was ligated with a fragment obtained by digestion of plasmid 132 (see Example 4 for a description of this plasmid) with XhoI and SalI. This XhoI/SalI fragment contains the anti-HIV ribozyme gene linked at the 3' end to the SV40 polyadenylation signal. The plasmid resulting from this ligation was designated pCEP-132. Thus, in effect, pCEP-132 comprises pCEP4 with the anti-HIV ribozyme gene and SV40 polyadenylation signal inserted in the multiple cloning site for CMV promoter-driven expression of the anti-HIV ribozyme gene.

To generate pCEPUR-132, pCEP-132 was ligated with a fragment of pCEPUR. pCEPUR was prepared by ligating a 7.7-kb fragment generated upon NheI/NruI digestion of pCEP4 with a 1.1-kb NheI/SnaBI fragment of pBabe (see Morgenstern and Land (1990) *Nucleic Acids Res.* 18:3587-3596 for a description of pBabe) that contains the puromycin-resistance gene linked at the 5' end to the SV40 promoter. Thus, pCEPUR is made up of the ampicillin-resistance and EBNA1 genes, as well as the ColE1 and OriP elements from pCEP4 and the puromycin-resistance gene from pBabe. The puromycin-resistance gene in pCEPUR is flanked by the SV40 promoter (from pBabe) at the 5' end and the SV40 polyadenylation signal (from pCEP4) at the 3' end.

Plasmid pCEPUR was digested with XhoI and SalI and the fragment containing the puromycin-resistance gene linked at the 5' end to the SV40 promoter was ligated with XhoI-digested pCEP-132 to yield the ~12.1-kb plasmid designated pCEPUR-132. Thus, pCEPUR-132, in effect, comprises pCEP-132 with puromycin-resistance gene and SV40 promoter inserted at the XhoI site. The main elements of pCEPUR-132 are the hygromycin-resistance gene linked to the thymidine kinase promoter and polyadenylation signal, the anti-HIV ribozyme gene linked to the CMV promoter and SV40 polyadenylation signal, and the puromycin-resistance gene linked to the SV40 promoter and polyadenylation signal. The plasmid also contains the ampicillin-resistance and EBNA1 genes and the ColE1 origin of replication and OriP.

Zygotes were prepared from (C57BL/6JxCBA/J) F1 female mice (see, e.g., *Manipulating the Mouse Embryo: A Laboratory Manual* (1994) Hogan et al., eds., Cold Spring Harbor Laboratory Press, Cold Spring Harbor, N.Y., p. 429), which had been previously mated with a (C57BL/6JxCBA/J) F1 male. The male pronuclei of these F2 zygotes were injected (see, *Manipulating the Mouse Embryo: A Laboratory Manual* (1994) Hogan et al., eds., Cold Spring Harbor Laboratory Press, Cold Spring Harbor, N.Y.) with pCEPUR-132 (~3 μg/ml), which had been linearized by digestion with NruI. The injected eggs were then implanted in surrogate mother female mice for development into transgenic offspring.

These primary carrier offspring were analyzed (as described below) for the presence of the transgene in DNA isolated from tail cells. Seven carrier mice that contained transgenes in their tail cells (but that may not carry the transgene in all their cells, i.e., they may be chimeric) were allowed to mate to produce non-chimeric or germ-line heterozygotes. The heterozygotes were, in turn, crossed to generate homozygote transgenic offspring.

2. Development of Model Transgenic Mice Using Mammalian Artificial Chromosomes

Fertilized mouse embryos are microinjected (as described above) with megachromosomes (1-10 pL containing 0-1 chromosomes/pL) isolated from fusion cell line G3D5 or H1D3 (described above). The megachromosomes are isolated as described herein. Megachromosomes isolated from either cell line carry the anti-HIV ribozyme (ribozyme D) gene as well as the hygromycin-resistance and β-galactosidase genes. The injected embryos are then developed into transgenic mice as described above.

Alternatively, the megachromosome-containing cell line G3D5* or H1D3* is fused with mouse embryonic stem cells (see, e.g., U.S. Pat. No. 5,453,357, commerically available; see *Manipulating the Mouse Embryo: A Laboratory Manual* (1994) Hogan et al., eds., Cold Spring Harbor Laboratory Press, Cold Spring Harbor, N.Y., pages 253-289) following standard procedures see also, e.g., *Guide to Techniques in Mouse Development* in *Methods in Enzymology* Vol. 25, Wassarman and De Pamphilis, eds. (1993), pages 803-932). (It is also possible to deliver isolated megachromosomes into embryonic stem cells using the Microcell procedure (such as that described above).) The stem cells are cultured in the presence of a fibroblast (e.g., STO fibroblasts that are resistant to hygromycin and puromycin). Cells of the resultant fusion cell line, which contains megachromosomes carrying the transgenes (i.e., anti-HIV ribozyme, hygromycin-resistance and β-galactosidase genes), are then transplanted into mouse blastocysts, which are in turn implanted into a surrogate mother female mouse where development into a transgenic mouse will occur.

Mice generated by this method are chimeric; the transgenes will be expressed in only certain areas of the mouse, e.g., the head, and thus may not be expressed in all cells.

3. Analysis of Transgenic Mice for Transgene Expression

Beginning when the transgenic mice, generated as described above, are three-to-four weeks old, they can be analyzed for stable expression of the transgenes that were transferred into the embryos (or fertilized eggs) from which they develop. The transgenic mice may be analyzed in several ways as follows.

a. Analysis of Cells Obtained from the Transgenic Mice

Cell samples (e.g., spleen, liver and kidney cells, lymphocytes, tail cells) are obtained from the transgenic mice. Any cells may be tested for transgene expression. If, however, the mice are chimeras generated by microinjection of fertilized eggs or by fusion of embryonic stem cells with megachromosome-containing cells, only cells from areas of the mouse that carry the transgene are expected to express the transgene. If the cells survive growth on hygromycin (or hygromycin and puromycin or neomycin, if the cells are obtained from mice generated by transfer of both antibiotic-resistance genes), this is one indication that they are stably expressing the transgenes. RNA isolated from the cells according to standard methods may also be analyzed by northern blot procedures to determine if the cells express transcripts that hybridize to nucleic acid probes based on the antibiotic-resistance genes. Additionally, cells obtained from the transgenic mice may also be analyzed for β-galactosidase expression using standard assays for this marker enzyme (for example, by direct staining of the product of a reaction involving β-galactosidase and the X-gal substrate, see, e.g., Jones (1986) *EMBO* 5:3133-3142, or by measurement of β-galactosidase activity, see, e.g., Miller (1972) in *Experiments in Molecular Genetics* pp. 352-355, Cold Spring Harbor Press). Analysis of β-galactosidase expression is particularly used to evaluate transgene expression in cells obtained from control transgenic mice in which the only transgene transferred into the embryo was the β-galactosidase gene.

Stable expression of the anti-HIV ribozyme gene in cells obtained from the transgenic mice may be evaluated in several ways. First, DNA isolated from the cells according to standard procedures may be subjected to nucleic acid amplification using primers corresponding to the ribozyme gene sequence. If the gene is contained within the cells, an amplified product of pre-determined size is detected upon hybridization of the reaction mixture to a nucleic acid probe based on the ribozyme gene sequence. Furthermore, DNA isolated from the cells may be analyzed using Southern blot methods for hybridization to such a nucleic acid probe. Second, RNA isolated from the cells may be subjected to northern blot hybridization to determine if the cells express RNA that hybridizes to nucleic acid probes based on the ribozyme gene. Third, the cells may be analyzed for the presence of anti-HIV ribozyme activity as described, for example, in Chang et al. (1990) *Clin. Biotech.* 2:23-31. In this analysis, RNA isolated from the cells is mixed with radioactively labeled HIV gag target RNA which can be obtained by in vitro transcription of gag gene template under reaction conditions favorable to in vitro cleavage of the gag target, such as those described in Chang et al. (1990) *Clin. Biotech.* 2:23-31. After the reaction has been stopped, the mixture is analyzed by gel electrophoresis to determine if cleavage products smaller in size than the whole template are detected; presence of such cleavage fragments is indicative of the presence of stably expressed ribozyme.

b. Analysis of Whole Transgenic Mice

Whole transgenic mice that have been generated by transfer of the anti-HIV ribozyme gene (as well as selection and marker genes) into embryos or fertilized eggs can additionally be analyzed for transgene expression by challenging the mice with infection with HIV. It is possible for mice to be infected with HIV upon intraperitoneal injection with high-producing HIV-infected U937 cells (see, e.g., Locardi et al. (1992) *J. Virol.* 66:1649-1654). Successful infection may be confirmed by analysis of DNA isolated from cells, such as peripheral blood mononuclear cells, obtained from transgenic mice that have been injected with HIV-infected human cells.

The DNA of infected transgenic mice cells will contain HIV-specific gag and env sequences, as demonstrated by, for example, nucleic acid amplification using HIV-specific primers. If the cells also stably express the anti-HIV ribozyme, then analysis of RNA extracts of the cells should reveal the smaller gag fragments arising by cleavage of the gag transcript by the ribozyme.

Additionally, the transgenic mice carrying the anti-HIV ribozyme gene can be crossed with transgenic mice expressing human CD4 (i.e., the cellular receptor for HIV) (see Gillespie et al. (1993) *Mol. Cell. Biol.* 13:2952-2958; Hanna et al. (1994) *Mol. Cell. Biol.* 14:1084-1094; and Yeung et al. (1994) *J. Exp. Med.* 180:1911-1920, for a description of transgenic mice expressing human CD4). The offspring of these crossed transgenic mice expressing both the CD4 and anti-HIV ribozyme transgenes should be more resistant to infection (as a result of a reduction in the levels of active HIV in the cells) than mice expressing CD4 alone (without expressing anti-HIV ribozyme).

4. Development of Transgenic Chickens Using Artificial Chromosomes

The development of transgenic chickens has many applications in the improvement of domestic poultry, an agricultural species of commercial significance, such as disease resistance genes and genes encoding therapeutic proteins. It appears that efforts in the area of chicken transgenesis have been hampered due to difficulty in achieving stable expression of transgenes in chicken cells using conventional methods of gene transfer via random introduction into recipient cells. Artificial chromosomes are, therefore, particularly useful in the development of transgenic chickens because they provide for stable maintenance of transgenes in host cells.

a. Preparation of Artificial Chromosomes for Introduction of Transgenes into Recipient Chicken Cells (i) Mammalian Artificial Chromosomes Mammalian artificial chromosomes, such as the SATACs and minichromosomes described herein, can be modified to incorporate detectable reporter genes and/or transgenes of interest for use in developing transgenic chickens. Alternatively, chicken-specific artificial chromosomes can be constructed using the methods herein. In particular, chicken artificial chromosomes (CACs) can be prepared using the methods herein for preparing MACs; or, as described above, the chicken libraries can be introduced into MACs provided herein and the resulting MACs introduced into chicken cells and those that are functional in chicken cells selected.

As described in Examples 4 and 7, and elsewhere herein, artificial chromosome-containing mouse LMTK$^-$-derived cell lines, or minichromosome-containing cell lines, as well as hybrids thereof, can be transfected with selected DNA to generate MACs (or CACs) that have integrated the foreign DNA for functional expression of heterologous genes contained within the DNA.

To generate MACs or CACs containing transgenes to be expressed in chicken cells, the MAC-containing cell lines may be transfected with DNA that includes λ DNA and transgenes of interest operably linked to a promoter that is capable of driving expression of genes in chicken cells. Alternatively, the minichromosomes or MACs (or CACs), produced as described above, can be isolated and introduced into cells, followed by targeted integration of selected DNA. Vectors for targeted integration are provided herein or can be constructed as described herein.

Promoters of interest include constitutive, inducible and tissue (or cell)-specific promoters known to those of skill in the art to promote expression of genes in chicken cells. For example, expression of the lacZ gene in chicken blastodermal cells and primary chicken fibroblasts has been demonstrated using a mouse heat-shock protein 68 (hsp 68) promoter (phspPTlacZpA; see Brazolot et al. (1991) *Mol. Reprod. Devel.* 30:304-312), a $Zn^{2+}$-inducible chicken metallothionein (cMt) promoter (pCBcMtlacZ; see Brazolot et al. (1991) *Mol. Reprod. Devel.* 30:304-312), the constitutive Rous sarcoma virus and chicken β-actin promoters in tandem (pmiwZ; see Brazolot et al. (1991) *Mol. Reprod. Devel.* 30:304-312) and the constitutive cytomegalovirus (CMV) promoter. Of particular interest herein are egg-specific promoters that are derived from genes, such as ovalbumin and lysozyme, that are expressed in eggs.

The choice of promoter will depend on a variety of factors, including, for example, whether the transgene product is to be expressed throughout the transgenic chicken or restricted to certain locations, such as the egg. Cell-specific promoters functional in chickens include the steroid-responsive promoter of the egg ovalbumin protein-encoding gene (see Gaub et al. (1987) *EMBO J.* 6:2313-2320; Tora et al. (1988) *EMBO J.* 7:3771-3778; Park et al. (1995) *Biochem. Mol. Biol. Int. (Australia)* 36:811-816).

(ii) Chicken Artificial Chromosomes

Additionally, chicken artificial chromosomes may be generated using methods described herein. For example, chicken cells, such as primary chicken fibroblasts (see Brazolot et al. (1991) *Mol. Reprod. Devel.* 30:304-312), may be transfected with DNA that encodes a selectable marker (such as a protein that confers resistance to antibiotics) and that includes DNA (such as chicken satellite DNA) that targets the introduced DNA to the pericentric region of the endogenous chicken chromosomes. Transfectants that survive growth on selection medium are then analyzed, using methods described herein, for the presence of artificial chromosomes, including minichromosomes, and particularly SATACs. An artificial chromosome-containing transfectant cell line may then be transfected with DNA encoding the transgene of interest (fused to an appropriate promoter) along with DNA that targets the foreign DNA to the chicken artificial chromosome.

b. Introduction of Artificial Chromosomes Carrying Transgenes of Interest into Recipient Chicken Cells Cell lines containing artificial chromosomes that harbor transgene(s) of interest (i.e., donor cells) may be fused with recipient chicken cells in order to transfer the chromosomes into the recipient cells. Alternatively, the artificial chromosomes may be isolated from the donor cells, for example, using methods described herein (see, e.g., Example 10), and directly introduced into recipient cells.

Exemplary chicken recipient cell lines include, but are not limited to, stage X blastoderm cells (see, e.g., Brazolot et al. (1991) *Mol. Reprod. Dev.* 30:304-312; Etches et al. (1993)

*Poultry Sci.* 72:882-889; Petitte et al. (1990) *Development* 108:185-189) and chick zygotes (see, e.g., Love et al. (1994) *Biotechnology* 12:60-63).

For example, microcell fusion is one method for introduction of artificial chromosomes into avian cells (see, e.g., Dieken et al. ((1996) *Nature Genet.* 12:174-182 for methods of fusing microcells with DT40 chicken pre-B cells). In this method, microcells are prepared (for example, using procedures described in Example 1.A.5) from the artificial chromosome-containing cell lines and fused with chicken recipient cells.

Isolated artificial chromosomes may be directly introduced into chicken recipient cell lines through, for example, lipid-mediated carrier systems, such as lipofection procedures (see, e.g., Brazolot et al. (1991) *Mol. Reprod. Dev.* 30:304-312) or direct microinjection. Microinjection is generally preferred for introduction of the artificial chromosomes into chicken zygotes (see, e.g., Love et al. (1994) *Biotechnology* 12:60-63).

c. Development of Transgenic Chickens

Transgenic chickens may be developed by injecting recipient Stage X blastoderm cells (which have received the artificial chromosomes) into embryos at a similar stage of development (see, e.g., Etches et al. (1993) *Poultry Sci.* 72:882-889; Petitte et al. (1990) *Development* 108:185-189; and Carsience et al. (1993) *Development* 117: 669-675). The recipient chicken embryos within the shell are candled and allowed to hatch to yield a germline chimeric chicken that will express the transgene(s) in some of its cells.

Alternatively, the artificial chromosomes may be introduced into chick zygotes, for example through direct microinjection (see, e.g., Love et al. (1994) *Biotechnology* 12:60-63), which thereby are incorporated into at least a portion of the cells in the chicken. Inclusion of a tissue-specific promoter, such an egg-specific promoter, will ensure appropriate expression of operatively-linked heterologous DNA.

The DNA of interest may also be introduced into a minichromosome, by methods provided herein. The minichromosome may either be one provided herein, or one generated in chicken cells using the methods herein. The heterologous DNA will be introduced using a targeting vector, such as those provided herein, or constructed as provided herein.

Since modifications will be apparent to those of skill in this art, it is intended that this invention be limited only by the scope of the appended claims.

The invention claimed is:

1. A method for amplifying nucleic acid in a plant cell, comprising:

introducing a DNA fragment into a plant cell, wherein the DNA fragment comprises a selectable marker that confers resistance under selective conditions, and comprises rDNA;

growing the cell under selective conditions to produce cells that have incorporated the DNA fragment or a portion thereof that comprises the selectable marker into the pericentric heterochromatin of a chromosome, wherein incorporation results in amplification of the region containing pericentric heterochromatin; and identifying from among the resulting cells those that include a chromosome or fragment thereof with a portion that has undergone amplification, wherein the portion of the chromosome that has undergone amplification comprises pericentric heterochromatin and the DNA fragment or portion thereof that comprises the selectable marker.

2. The method of claim 1, wherein the plant is tobacco, rice, maize, rye, soybean, *Brassica napus*, cotton, lettuce, potato, tomato or *arabidopsis*.

3. The method of claim 1, wherein the cell is a protoplast.

4. The method of claim 1, wherein the portion that has undergone amplification comprises centromeric nucleic acid.

5. The method of claim 1, wherein the DNA fragment that is introduced comprises heterologous nucleic acid in addition to a selectable marker.

6. The method of claim 5, wherein the portion that has undergone amplification comprises the heterologous nucleic acid.

7. The method of claim 1, wherein the amplification results in a de novo centromere, and the method further comprises growing the cell under conditions whereby a cell with a sausage chromosome or heterochromatic arm is produced.

8. The method of claim 1, wherein the plant cell is a tobacco, rice, maize, rye, soybean, *Brassica napus*, cotton, lettuce, potato, tomato or *arabidopsis* cell.

9. The method of claim 1, wherein the plant cell is a monocot or dicot cell.

10. The method of claim 1, wherein the plant cell is a plant protoplast.

11. The method of claim 1, further comprising isolating the identified cell.

* * * * *

UNITED STATES PATENT AND TRADEMARK OFFICE

CERTIFICATE OF CORRECTION

PATENT NO. : 8,389,802 B2
APPLICATION NO. : 11/284877
DATED : March 5, 2013
INVENTOR(S) : Hadlaczky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 281 days.

Signed and Sealed this
Eleventh Day of November, 2014

Michelle K. Lee
*Deputy Director of the United States Patent and Trademark Office*

SEQUENCE LISTING (1) GENERAL INFORMATION:

(iii) NUMBER OF SEQUENCES: 34

(2) INFORMATION FOR SEQ ID NO: 1:

(i) SEQUENCE CHARACTERISTICS:
(A) LENGTH: 1293 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 1:

```
GAATTCATCA TTTTTCANGT CCTCAAGTGG ATGTTTCTCA TTTNCCATGA TTTTAAGTTT     60

TCTCGCCATA TTCCTGGTCC TACAGTGTGC ATTTCTCCAT TTTNCACGTT TTNCAGTGAT    120

TTCGTCATTT TCAAGTCCTC AAGTGGATGT TTCTCATTTN CCATGAATTT CAGTTTTCTN    180

GCCATATTCC ACGTCCTACA GNGGACATTT CTAAATTTNC CACCTTTTTC AGTTTTCCTC    240

GCCATATTTC ACGTCCTAAA ATGTGTATTT CTCGTTTNCC GTGATTTTCA GTTTTCTCGC    300

CAGATTCCAG GTCCTATAAT GTGCATTTCT CATTTNNCAC GTTTTTCAGT GATTTCGTCA    360

TTTTTTCAAG TCGGCAAGTG GATGTTTCTC ATTTNCCATG ATTTNCAGTT TTCTTGNAAT    420

ATTCCATGTC CTACAATGAT CATTTTTAAT TTTCCACCTT TTCATTTTTC CACGCCATAT    480

TTCATGTCCT AAAGTGTATA TTTCTCCTTT TCCGCGATTT TCAGTTTTCT CGCCATATTC    540

CAGGTCCTAC AGTGTGCATT CCTCATTTTT CACCTTTTTC ACTGATTTCG TCATTTTTCA    600

AGTCGTCAAC TGGATCTTTC TAATTTTCCA TGATTTTCAG TTATCTTGTC ATATTCCATG    660
```

```
TCCTACAGTG GACATTTCTA AATTTTCCAA CTTTTTCAAT TTTTCTCGAC ATATTTGACG    720

TGCTAAAGTG TGTATTTCTT ATTTTCCGTG ATTTTCAGTT TTCTCGCCAT ATTCCAGGTC    780

CTAATAGTGT GCATTTCTCA TTTTTCACGT TTTTCAGTGA TTTCGTCATT TTTTCCAGTT    840

GTCAAGGGGA TGTTTCTCAT TTTCCATGAG TGTCAGTTTT CTTGCTATAT TCCATGTCCT    900

ACAGTGACAT TTCTAAATAT TATACCTTTT TCAGTTTTTC TCACCATATT TCACGTCCTA    960

AAGTATATAT TTCTCATTTT CCCTGATTTT CAGTTTCCTT GCCATATTCC AGGTCCTACA   1020

GTGTGCATTT CTCATTTTTC ACGTTTTTCA GTAATTTCTT CATTTTTTAA GCCCTCAAAT   1080

GGATGTTTCT CATTTTCCAT GATTTTCAGT TTTCTTGCCA TATACCATGT CCTACAGTGG   1140

ACATTTCTAA ATTATCCACC TTTTTCAGTT TTTCATCGGC ACATTTCACG TCCTAAAGTG   1200

TGTATTTCTA ATTTTCAGTG ATTTTCAGTT TTCTCGCCAT ATTCCAGGAC CTACAGTGTG   1260

CATTTCTCAT TTTTCACGTT TTTCAGTGAA TTC                                1293
```

(2) INFORMATION FOR SEQ ID NO: 2:

(i) SEQUENCE CHARACTERISTICS:
(A) LENGTH: 1044 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 2:

```
AGGCCTATGG TGAAAAAGGA AATATCTTCC CCTGAAAACT AGACAGAAGG ATTCTCAGAA     60

TCTTATTTGT GATGTGCGCC CCTCAACTAA CAGTGTTGAA GCTTTCTTTT GATAGAGCAG    120

TTTTGAAACA CTCTTTTTGT AAAATCTGCA AGAGGATATT TGGATAGCTT TGAGGATTTC    180

CGTTGGAAAC GGGATTGTCT TCATATAAAC CCTAGACAGA AGCATTCTCA GAAGCTTCAT    240

TGGGATGTTT CAGTTGAAGT CACAGTGTTG AACAGTCCCC TTTCATAGAG CAGGTTTGAA    300

ACACTCTTTT TTGTAGTATC TGGAAGTGGA CATTTGGAGC GATCTCAGGA CTGCGGTGAA    360

AAAGGAAATA TCTTCCAATA AAAGCTAGAT AGAGGCAATG TCAGAAACCT TTTTCATGAT    420

GTATCTACTC AGCTAACAGA GTTGAACCTT CCTTTGAGAG AGCAGTTTTG AAACACTCTT    480

TTTGTGGAAT CTGCAAGTGG ATATTTGTCT AGCTTTGAGG ATTTCGTTGG GAAACGGGAT    540

TACATATAAA AAGCAGACAG CAGCATTCCC AGAAACTTCT TTGTGATGTT TGCATTCAAG    600

TCACAGAGTT GAACATTCCC TTTCATAGAG CAGGTTTGAA ACACACTTTT TGATGTATCT    660

GGATGTGGAC ATTTGCAGCG CTTTCAGGCC TAAGGTGAAA AGGAAATATC TTCCCCTGAA    720

AACTAGACAG AAGCATTCTC AGAAACTTAT TTGTGATGTG CGCCCTCAAC TAACAGTGTT    780

GAAGCTTTCT TTTGATAGAG GCAGTTTTGA AACACTCTTT TGTGGAATCT GCAAGTGGAT    840

ATTTGTCTAG CTTTGAGGAT TTCTTTGGAA ACGGGATTAC ATATAAAAAG CAGACAGCAG    900

CATTCCCAGA ATCTTGTTTG TGATGTTTGC ATTCAAGTCA CAGAGTTGAA CATTCCCTTT    960

CAGAGAGCAG GTTTGAACAC TCTTTTTATA GTATCTGGAT GTGGACATTT GGAGCGCTTT   1020
```

-continued

CAGGGGGGAT CCTCTAGAAT TCCT 1044

(2) INFORMATION FOR SEQ ID NO: 3:

(i) SEQUENCE CHARACTERISTICS:
(A) LENGTH: 2492 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 3:

CTGCAGCTGG GGGTCTCCAA TCAGGCAGGG GCCCCTTACT ACTCAGATGG GGTGGCCGAG 60

TAGGGGAAGG GGGTGCAGGC TGCATGAGTG GACACAGCTG TAGGACTACC TGGGGGCTGT 120

GGATCTATGG GGGTGGGGAG AAGCCCAGTG ACAGTGCCTA GAAGAGACAA GGTGGCCTGA 180

GAGGGTCTGA GGAACATAGA GCTGGCCATG TTGGGGCCAG GTCTCAAGCA GGAAGTGAGG 240

AATGGGACAG GCTTGAGGAT ACTCTACTCA GTAGCCAGGA TAGCAAGGAG GGCTTGGGGT 300

TGCTATCCTG GGGTTCAACC CCCCAGGTTG AAGGCCCTGG GGGAGATGGT CCCAGGACAT 360

ATTACAATGG ACACAGGAGG TTGGGACACC TGGAGTCACC AAACAAAACC ATGCCAAGAG 420

AGACCATGAG TAGGGGTGTC CAGTCCAGCC CTCTGACTGA GCTGCATTGT TCAAATCCAA 480

AGGGCCCCTG CTGCCACCTA GTGGCTGATG GCATCCACAT GACCCTGGGC CACACGCGTT 540

TAGGGTCTCT GTGAAGACCA AGATCCTTGT TACATTGAAC GACTCCTAAA TGAGCAGAGA 600

TTTCCACCTA TTCGAAACAA TCACATAAAA TCCATCCTGG AAAAAGCCTG GGGGATGGCA 660

CTAAGGCTAG GGATAGGGTG GGATGAAGAT TATAGTTACA GTAAGGGGTT TAGGGTTAGG 720

GATCAACGTT GGTTAGGAGT TAGGGATACA GTAGGGTACC GGTAGGGTTA GGGGTTAGGG 780

TTAGGGGTTA GGGTTAGGGT TAGGGTTAGG GTTAGGGTTA GGGGTTAGGG GTTAGGGTTA 840

GGGTTAGGTT TTGGGGTGGC GTATTTTGGT CTTATACGCT GTGTTCCACT GGCAATGAAA 900

AGAGTTCTTG TTTTTCCTTC AGCAATTTGT CATTTTTAAA AGAGTTTAGC AATTCTAACA 960

GATATAGACC AGCTGTGCTA TCTCATTGTG GTTTTCAATT GTAACCACAT TGTGGTTTCA 1020

ATGTGTTTAC TTGCCATCTG TAGATCTTCT TTGCGTGAGG TGTCTGTTCA GATGTGTGTG 1080

CATTTCTTGN NTTTNGGCTG TTTAACTTAT TGTTTAGTTT TAATAATTTT TTATATATTT 1140

GAAGACAAAT CTTTCTCAGA TGTGTATTTG CAAATATTTC TTCAATATGA GGCTTGCTTT 1200

TGTCTCTAAC AAGGTCTCTT CAGAGATAAC TTAAATATAA GAAATCCACA CTGTCACTTC 1260

TTTTGTGTAT ATCTACCTTT TGTGTCATTT GTTAAAATTC ATTACCAAAC CCAAAGGCAG 1320

ATAGCTTTTC TTCTATTGTT TCTTCTAGAA ATTTGTATAG TTTTGCATTT TTAGTGTAAG 1380

GATGATTTTG AGTGATTATT TGTGTAAGTT GTAAAGTTTT CGTCTATATC CATATCATTT 1440

CTTATGGTTT CCAATTAATC GTTCCCTCAC TATTTTTGGG AAAGACACAG GATAGTGGGC 1500

TTTGTTAGAG TAGATAGGTA GCTAGACATG AACAGGAGGG GGCCTCCTGG AAAAGGGAAA 1560

GTCTGGGAAG GCTCACCTGG AGGACCACCA AAAATTCACA TATTAGTAGC ATCTCTAGTG 1620

CTGGAGTGGA TGGGCACTTG TCAATTGTGG GTAGGAGGGA AAAGAGGTCC TATGCAGAAA 1680

-continued

GAAACTCCCT AGAACTCCTC TGAAGATGCC CCAATCATTC ACTCTGCAAT AAAAATGTCA 1740

GAATATTGCT AGCTACATGC TGATAAGGNN AAAGGGGACA TTCTTAAGTG AAACCTGGCA 1800

CCATAAGTAC AGATTAGGGC AGAGAAGGAC ATTCAAAAGA GGCAGGCGCA GTAGGTACAA 1860

ACGTGATCGC TGTCAGTGTG CCTGGGATGG CGGGAAGGAG GCTGGTGCCA GAGTGGATTC 1920

GTATTGATCA CCACACATAT ACCTCAACCA ACAGTGAGGA GGTCCCACAA GCCTAAGTGG 1980

GGCAAGTTGG GGAGCTAAGG CAGTAGCAGG AAAACCAGAC AAAGAAAACA GGTGGAGACT 2040

TGAGACAGAG GCAGGAATGT GAAGAAATCC AAAATAAAAT TCCCTGCACA GGACTCTTAG 2100

GCTGTTTAAT GCATCGCTCA GTCCCACTCC TCCCTATTTT TCTACAATAA ACTCTTTACA 2160

CTGTGTTTCT TTTCAATGAA GTTATCTGCC ATCTTTGTAT TGCCTCTTGG TGAAAATGTT 2220

TCTTCCAAGT TAAACAAGAA CTGGGACATC AGCTCTCCCC AGTAATAGCT CCGTTTCAGT 2280

TTGAATTTAC AGAACTGATG GGCTTAATAA CTGGCGCTCT GACTTTAGTG GTGCAGGAGG 2340

CCGTCACACC GGGACCAAGA GTGCCCTGCC TAGTCCCCAT CTGCCCGCAG GTGGCGGCTG 2400

CCTCGACACT GACAGCAATA GGGTCCGGCA GTGTCCCCAG CTGCCAGCAG GGGGCGTACG 2460

ACGACTACAC TGTGAGCAAG AGGGCCCTGC AG 2492

(2) INFORMATION FOR SEQ ID NO: 4:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 4:

GGGGAATTCA TTGGGATGTT TCAGTTGA 28

(2) INFORMATION FOR SEQ ID NO: 5:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 5:

CGAAAGTCCC CCCTAGGAGA TCTTAAGGA 29

(2) INFORMATION FOR SEQ ID NO: 6:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 6:

CCGCTTAATA CTCTGATGAG TCCGTGAGGA CGAAACGCTC TCGCACC 47

(2) INFORMATION FOR SEQ ID NO: 7:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 7:

CGATTTAAAT TAATTAAGCC CGGGC 25

(2) INFORMATION FOR SEQ ID NO: 8:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 8:

TAAATTTAAT TAATTCGGGC CCGTCGA 27

(2) INFORMATION FOR SEQ ID NO: 9:

(i) SEQUENCE CHARACTERISTICS:
(A) LENGTH: 69 base pairs
(B) TYPE: nucleic acid (C) STRANDEDNESS: single
(D) TOPOLOGY: linear (ii) MOLECULE TYPE: Genomic DNA (xi) SEQUENCE DESCRIPTION: SEQ ID NO: 9:

```
ATG TAC AGG ATG CAA CTC CTG TCT TGC ATT GCA CTA AGT CTT GCA CTT       48
Met Tyr Arg Met Gln Leu Leu Ser Cys Ile Ala Leu Ser Leu Ala Leu

GTC ACA AAC AGT GCA CCT ACT                                           69
Val Thr Asn Ser Ala Pro Thr
```

(2) INFORMATION FOR SEQ ID NO: 10:

(i) SEQUENCE CHARACTERISTICS:
(A) LENGTH: 945 base pairs
(B) TYPE: nucleic acid
(C) STRANDEDNESS: single
(D) TOPOLOGY: linear (ii) MOLECULE TYPE: cDNA (vi) ORIGINAL SOURCE:

(ix) FEATURE:
(A) NAME/KEY: Coding Sequence
(B) LOCATION: 1...942
(D) OTHER INFORMATION: Renilla Reinformis Luciferase (x) PUBLICATION INFORMATION:
(H) DOCUMENT NUMBER: 5,418,155

(xi) SEQUENCE DESCRIPTION: SEQ ID NO: 10:

```
AGC TTA AAG ATG ACT TCG AAA GTT TAT GAT CCA GAA CAA AGG AAA CGG       48
Ser Leu Lys Met Thr Ser Lys Val Tyr Asp Pro Glu Gln Arg Lys Arg
 1               5                  10                  15

ATG ATA ACT GGT CCG CAG TGG TGG GCC AGA TGT AAA CAA ATG AAT GTT       96
Met Ile Thr Gly Pro Gln Trp Trp Ala Arg Cys Lys Gln Met Asn Val
            20                  25                  30

CTT GAT TCA TTT ATT AAT TAT TAT GAT TCA GAA AAA CAT GCA GAA AAT      144
Leu Asp Ser Phe Ile Asn Tyr Tyr Asp Ser Glu Lys His Ala Glu Asn
        35                  40                  45

GCT GTT ATT TTT TTA CAT GGT AAC GCG GCC TCT TCT TAT TTA TGG CGA      192
Ala Val Ile Phe Leu His Gly Asn Ala Ala Ser Ser Tyr Leu Trp Arg
    50                  55                  60

CAT GTT GTG CCA CAT ATT GAG CCA GTA GCG CGG TGT ATT ATA CCA GAT      240
His Val Val Pro His Ile Glu Pro Val Ala Arg Cys Ile Ile Pro Asp
65                  70                  75                  80

CTT ATT GGT ATG GGC AAA TCA GGC AAA TCT GGT AAT GGT TCT TAT AGG      288
Leu Ile Gly Met Gly Lys Ser Gly Lys Ser Gly Asn Gly Ser Tyr Arg
                85                  90                  95

TTA CTT GAT CAT TAC AAA TAT CTT ACT GCA TGG TTG AAC TTC TTA ATT      336
Leu Leu Asp His Tyr Lys Tyr Leu Thr Ala Trp Leu Asn Phe Leu Ile
            100                 105                 110

TAC CAA AGA AGA TCA TTT TTT GTC GGC CAT GAT TGG GGT GCT TGT TTG      384
Tyr Gln Arg Arg Ser Phe Phe Val Gly His Asp Trp Gly Ala Cys Leu
        115                 120                 125

GCA TTT CAT TAT AGC TAT GAG CAT CAA GAT AAG ATC AAA GCA ATA GTT      432
Ala Phe His Tyr Ser Tyr Glu His Gln Asp Lys Ile Lys Ala Ile Val
    130                 135                 140

CAC GCT GAA AGT GTA GTA GAT GTG ATT GAA TCA TGG GAT GAA TGG CCT      480
His Ala Glu Ser Val Val Asp Val Ile Glu Ser Trp Asp Glu Trp Pro
145                 150                 155                 160

GAT ATT GAA GAA GAT ATT GCG TTG ATC AAA TCT GAA GAA GGA GAA AAA      528
Asp Ile Glu Glu Asp Ile Ala Leu Ile Lys Ser Glu Glu Gly Glu Lys
                165                 170                 175
```

```
ATG GTT TTG GAG AAT AAC TTC TTC GTG GAA ACC ATG TTG CCA TCA AAA      576
Met Val Leu Glu Asn Asn Phe Phe Val Glu Thr Met Leu Pro Ser Lys
            180                 185                 190

ATC ATG AGA AAG TTA GAA CCA GAA GAA TTT GCA GCA TAT CTT GAA CCA      624
Ile Met Arg Lys Leu Glu Pro Glu Glu Phe Ala Ala Tyr Leu Glu Pro
        195                 200                 205

TTC AAA GAG AAA GGT GAA GTT CGT CGT CCA ACA TTA TCA TGG CCT CGT      672
Phe Lys Glu Lys Gly Glu Val Arg Arg Pro Thr Leu Ser Trp Pro Arg
    210                 215                 220

GAA ATC CCG TTA GTA AAA GGT GGT AAA CCT GAC GTT GTA CAA ATT GTT      720
Glu Ile Pro Leu Val Lys Gly Gly Lys Pro Asp Val Val Gln Ile Val
225                 230                 235                 240

AGG AAT TAT AAT GCT TAT CTA CGT GCA AGT GAT GAT TTA CCA AAA ATG      768
Arg Asn Tyr Asn Ala Tyr Leu Arg Ala Ser Asp Asp Leu Pro Lys Met
                245                 250                 255

TTT ATT GAA TCG GAT CCA GGA TTC TTT TCC AAT GCT ATT GTT GAA GGC      816
Phe Ile Glu Ser Asp Pro Gly Phe Phe Ser Asn Ala Ile Val Glu Gly
            260                 265                 270

GCC AAG AAG TTT CCT AAT ACT GAA TTT GTC AAA GTA AAA GGT CTT CAT      864
Ala Lys Lys Phe Pro Asn Thr Glu Phe Val Lys Val Lys Gly Leu His
        275                 280                 285

TTT TCG CAA GAA GAT GCA CCT GAT GAA ATG GGA AAA TAT ATC AAA TCG      912
Phe Ser Gln Glu Asp Ala Pro Asp Glu Met Gly Lys Tyr Ile Lys Ser
    290                 295                 300

TTC GTT GAG CGA GTT CTC AAA AAT GAA CAA TAA                          945
Phe Val Glu Arg Val Leu Lys Asn Glu Gln
305                 310
```

(2) INFORMATION FOR SEQ ID NO: 11:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 11:

```
TTTGAATTC A TGTACAGGAT GCAACTCCTG                                     30
```

(2) INFORMATION FOR SEQ ID NO: 12:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:

(xi) SEQUENCE DESCRIPTION: SEQ ID NO: 12:

TTTGAATTCA GTAGGTGCAC TGTTTGTCAC 30

(2) INFORMATION FOR SEQ ID NO: 13:

(i) SEQUENCE CHARACTERISTICS:
(A) LENGTH: 1434 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 13:

CCTCCACGCA CGTTGTGATA TGTAGATGAT AATCATTATC AGAGCAGCGT TGGGGGATAA 60

TGTCGACATT TCCACTCCCA ATGACGGTGA TGTATAATGC TCAAGTATTC TCCTGCTTTT 120

TTACCACTAA CTAGGAACTG GGTTTGGCCT TAATTCAGAC AGCCTTGGCT CTGTCTGGAC 180

AGGTCCAGAC GACTGACACC ATTAACACTT TGTCAGCCTC AGTGACTACA GTCATAGATG 240

AACAGGCCTC AGCTAATGTC AAGATACAGA GAGGTCTCAT GCTGGTTAAT CAACTCATAG 300

ATCTTGTCCA GATACAACTA GATGTATTAT GACAAATAAC TCAGCAGGGA TGTGAACAAA 360

AGTTTCCGGG ATTGTGTGTT ATTTCCATTC AGTATGTTAA ATTTACTAGG ACAGCTAATT 420

TGTCAAAAAG TCTTTTTCAG TATATGTTAC AGAATTGGAT GGCTGAATTT GAACAGATCC 480

TTCGGGAATT GAGACTTCAG GTCAACTCCA CGCGCTTGGA CCTGTCGCTG ACCAAAGGAT 540

TACCCAATTG GATCTCCTCA GCATTTTCTT TCTTTAAAAA ATGGGTGGGA TTAATATTAT 600

TTGGAGATAC ACTTTGCTGT GGATTAGTGT TGCTTCTTTG ATTGGTCTGT AAGCTTAAGG 660

CCCAAACTAG GAGAGACAAG GTGGTTATTG CCCAGGCGCT TGCAGGACTA GAACATGGAG 720

CTTCCCCTGA TATATGGTTA TCTATGCTTA GGCAATAGGT CGCTGGCCAC TCAGCTCTTA 780

TATCCCACGA GGCTAGTCTC ATTGTACGGG ATAGAGTGAG TGTGCTTCAG CAGCCCGAGA 840

GAGTTGCAAG GCTAAGCACT GCAATGGAAA GGCTCTGCGG CATATATGTG CCTATTCTAG 900

GGGGACATGT CATCTTTCAT GAAGGTTCAG TGTCCTAGTT CCCTTCCCCC AGGCAAAACG 960

ACACGGGAGC AGGTCAGGGT TGCTCTGGGT AAAAGCCTGT GAGCCTGGGA GCTAATCCTG 1020

TACATGGCTC CTTTACCTAC ACACTGGGGA TTTGACCTCT ATCTCCACTC TCATTAATAT 1080

GGGTGGCCTA TTTGCTCTTA TTAAAAGGAA AGGGGGAGAT GTTGGGAGCC GCGCCCACAT 1140

TCGCCGTTAC AAGATGGCGC TGACAGCTGT GTTCTAAGTG GTAAACAAAT AATCTGCGCA 1200

TGTGCCGAGG GTGGTTCTTC ACTCCATGTG CTCTGCCTTC CCCGTGACGT CAACTCGGCC 1260

GATGGGCTGC AGCCAATCAG GGAGTGACAC GTCCTAGGCG AAGGAGAATT CTCCTTAATA 1320

GGGACGGGGT TTCGTTCTCT CTCTCTCTCT TGCTTCTCTC TCTTGCTTTT TCGCTCTCTT 1380

GCTTCCCGTA AAGTGATAAT GATTATCATC TACATATCAC AACGTGCGTG GAGG 1434

(2) INFORMATION FOR SEQ ID NO: 14:

(i) SEQUENCE CHARACTERISTICS:
(A) LENGTH: 1400 base pairs

-continued (B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 14:

CCTCCACGCA CGTTGTGATA TGTAGATGAT AATCATTATC AGAGCAGCGT TGGGGGATAA 60

TGTCGACATT TCCACTCCCA ATGACGGTGA TGTATAATGC TCAAGTATTC TCCTGCTTTT 120

TTACCACTAA CTAGGAACTG GGTTTGGCCT TAATTCAGAC AGCCTTGGCT CTGTCTGGAC 180

AGGTCCAGAT ACAACTAGAT GTATTATGAC AAATAACTCA GCAGGGATGT GAACAAAAGT 240

TTCCGGGATT GCGTGTTATT TCCATCCAGT ATGTTAAATT TACTAGGGCA GCTAATTTGT 300

CAAAAAGTCT TTTCCAGTAT ATGTTACAGA ATTGGATGGC TGAATTTGAA CAGATCCTTC 360

GGGAATTGAG ACTTCAGGTC AACTCCACGC GCTTGGACCT GTCCCTGACC AAAGGATTAC 420

CCAATTGGAT CTCCTCAGCA TTTTCTTTCT TTAAAAAATG GGTGGGATTA ATATTATTTG 480

GAGATACACT TTGCTGTGGA TTAGTGTTGC TTCTTTGATT GGTCTGTAAG CTTAAGGCCC 540

AAACTAGGAG AGACAAGGTG GTTATTGCCC AGGCGCTTGC AGGACTAGAA CATGGAGCTT 600

CCCCTGATAT ATCTATGCTT AGGCAATAGG TCGCTGGCCA CTCAGCTCTT ATATCCCATG 660

AGGCTAGTCT CATTGCACGG GATAGAGTGA GTGTGCTTCA GCAGCCCGAG AGAGTTGCAC 720

GGCTAAGCAC TGCAATGGAA AGGCTCTGCG GCATATATGA GCCTATTCTA GGGAGACATG 780

TCATCTTTCA AGAAGGTTGA GTGTCCAAGT GTCCTTCCTC CAGGCAAAAC GACACGGGAG 840

CAGGTCAGGG TTGCTCTGGG TAAAAGCCTG TGAGCCTAAG AGCTAATCCT GTACATGGCT 900

CCTTTACCTA CACACTGGGG ATTTGACCTC TATCTCCACT CTCATTAATA TGGGTGGCCT 960

ATTTGCTCTT ATTAAAAGGA AAGGGGGAGA TGTTGGGAGC CGCGCCCACA TTCGCCGTTA 1020

CAAGATGGCG CTGACAGCTG TGTTCTAAGT GGTAAACAAA TAATCTGCGC ATGCGCCGAG 1080

GGTGGTTCTT CACTCCATGT GCTCTGCCTT CCCCGTGACG TCAACTCGGC CGATGGGCTG 1140

CAGTCAATCA GGGAGTGACA CGTCCTAGGC GAAGGAAAAT TCTCCTTAAT AGGGACGGGG 1200

TTTCGTTTTC TCTCTCTCTT GCTTCGCTCT CTCTTGCTTC TTGCTCTCTT TTCCTGAAGA 1260

TGTAAGAATA AAGCTTTGCC GCAGAAGATT CTGGTCTGTG GTGTTCTTCC TGGCCGGTCG 1320

TGAGAACGCG TCTAATAACA ATTGGTGCCG AAACCCGGGT GATAATGATT ATCATCTACA 1380

TATCACAACG TGCGTGGAGG 1400

(2) INFORMATION FOR SEQ ID NO: 15:

(i) SEQUENCE CHARACTERISTICS:
(A) LENGTH: 1369 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

-continued (vi) ORIGINAL SOURCE:

(xi) SEQUENCE DESCRIPTION: SEQ ID NO: 15:

CCTCCACGCA CGTTGTGATA TGTAGATGAT AATCATTATC ACTTTACGGG TCCTTTCACT 60

ACAACTGCCA CGAGGCCCCG TGCTCTGGTA ATAGATCTTT GCTGAAAAGG CACACACATG 120

ACACATTACT CAAGGTGGGC TCATCTGAGC TGCAGATTCA GCTTAATATG AATCTTGCCA 180

ATTGTGTGAA ATCATAAATC TTCAAAGTGA CACTCATTGC CAGACACAGG TGCCCACCTT 240

TGGCATAATA AACAAACACA AATTATCTAT TATATAAAGG GTGTTAGAAG ATGCTTTAGA 300

ATACAAATAA ATCATGGTAG ATAACAGTAA GTTGAGAGCT TAAATTTAAT AAAGTGATAT 360

ACCTAATAAA AATTAAATTA AGAAGGTGTG AATATACTAC AGTAGGTAAA TTATTTCATT 420

AATTTATTTT CTTTCTTAAT CCTTTATAAT GTTTTCTGCT ATTGTCAATT GCACATCCAT 480

ATGTTCAATT CTTCACTGTA ATGAAGAAAT GTAGTAAATA TACTTTCCGA ACAAGTTGTA 540

TCAAATATGT TACACTTGAT TCCGTGTGTT ACTTATCATT TTATTATTAT ATTGATTGCA 600

TTCCTTCGTT ACTTGATATT ATTACAAGGT ACATATTTAT TCTCTCAGAT CTTCATTATA 660

CTCTAACCAT TTTATAACAT ACTTTATTTA TTCATTTCTT ATGTGTGCTG TGAGGCACAA 720

ATGCCAGAGA GAACTTGAGC AGATAAGAGG ACAAATTGCA AGAGTCAGTT ACCTCCTGCT 780

GTTCCTTGGA AACTCAGGAT CAAATTCAGG TTGTCAGGCT TGGCAGCATG CACTTTTTAC 840

CAGTGCCTCC ATCTTGCTAG CCCTGAACAT CAAGCTTTGC AGACAGACAG GCTACACTAA 900

GTGAACTGGT CATTCACAGC ATGCATGGTG ATTTATTGTT ACTTTCTATT CCATGCCTTT 960

ACTATTTCTA CTAGGTGCTA GCTAGTACTG TATTTCGAGA TAGAAGTTAC TGAAAGAAAA 1020

TTACATTGTT TTCTATAGAT CCTTGATACT CTTTCAGCAG ATATAGAGTT TTAATCAGGT 1080

CCTAGACCCT TTCTTCACTC TTATTAAATA CTAAGTACAA ATTAAGTTTA TCCAAAACAG 1140

TACGGATGTT GATTTTGTGC AGTTCTACTA TGATAATAGT CTAGCTTCAT AAATCTGACA 1200

CACTTATTGG GAATGTTTTT GTTAATAAAA GATTCAGGTG TTACTCTAGG TCAAGAGAAT 1260

ATTAAACATC AGTCCCAAAT TACAAACTTC AATAAAAGAT TTGACTCTCC AGTGGTGGCA 1320

ATATAAAGTG ATAATGATTA TCATCTACAT ATCACAACGT GCGTGGAGG 1369

(2) INFORMATION FOR SEQ ID NO: 16:

(i) SEQUENCE CHARACTERISTICS:
(A) LENGTH: 22118 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 16:

GAATTCCCCT ATCCCTAATC CAGATTGGTG GAATAACTTG GTATAGATGT TTGTGCATTA 60

AAAACCCTGT AGGATCTTCA CTCTAGGTCA CTGTTCAGCA CTGGAACCTG AATTGTGGCC 120

CTGAGTGATA GGTCCTGGGA CATATGCAGT TCTGCACAGA CAGACAGACA GACAGACAGA 180

CAGACAGACA GACAGACGTT ACAAACAAAC ACGTTGAGCC GTGTGCCAAC ACACACACAA 240

-continued

```
ACACCACTCT GGCCATAATT ATTGAGGACG TTGATTTATT ATTCTGTGTT TGTGAGTCTG    300
TCTGTCTGTC TGTCTGTCTG TCTGTCTGTC TATCAAACCA AAAGAAACCA AACAATTATG    360
CCTGCCTGCC TGCCTGCCTG CCTACACAGA GAAATGATTT CTTCAATCAA TCTAAAACGA    420
CCTCCTAAGT TTGCCTTTTT TCTCTTTCTT TATCTTTTTC TTTTTTCTTT TCTTCTTCCT    480
TCCTTCCTTC CTTCCTTCCT TCCTTCCTTT CTTTCTTTCT TTCTTTCTTT CTTACTTTCT    540
TTCTTTCCTT CTTACATTTA TTCTTTTCAT ACATAGTTTC TTAGTGTAAG CATCCCTGAC    600
TGTCTTGAAG ACACTTTGTA GGCCTCAATC CTGTAAGAGC CTTCCTCTGC TTTTCAAATG    660
CTGGCATGAA TGTTGTACCT CACTATGACC AGCTTAGTCT TCAAGTCTGA GTTACTGGAA    720
AGGAGTTCCA AGAAGACTGG TTATATTTTT CATTTATTAT TGCATTTTAA TTAAAATTTA    780
ATTTCACCAA AAGAATTTAG ACTGACCAAT TCAGAGTCTG CCGTTTAAAA GCATAAGGAA    840
AAAGTAGGAG AAAAACGTGA GGCTGTCTGT GGATGGTCGA GGCTGCTTTA GGGAGCCTCG    900
TCACCATTCT GCACTTGCAA ACCGGGCCAC TAGAACCCGG TGAAGGGAGA AACCAAAGCG    960
ACCTGGAAAC AATAGGTCAC ATGAAGGCCA GCCACCTCCA TCTTGTTGTG CGGGAGTTCA   1020
GTTAGCAGAC AAGATGGCTG CCATGCACAT GTTGTCTTTC AGCTTGGTGA GGTCAAAGTA   1080
CAACCGAGTC ACAGAACAAG GAAGTATACA CAGTGAGTTC CAGGTCAGCC AGAGTTTACA   1140
CAGAGAAACC ACATCTTGAA AAAAACAAAA AAATAAATTA AATAAATATA ATTTAAAAAT   1200
TTAAAAATAG CCGGGAGTGA TGGCGCATGT CTTTAATCCC AGCTCTCTTC AGGCAGAGAT   1260
GGGAGGATTT CTGAGTTTGA GGCCAGCCTG GTCTGCAAAG TGAGTTCCAG GACAGTCAGG   1320
GCTATACAGA GAAACCCTGT CTTGAAAACT AAACTAAATT AAACTAAACT AAACTAAAAA   1380
AATATAAAAT AAAAATTTTA AAGAATTTTA AAAAACTACA GAAATCAAAC ATAAGCCCAC   1440
GAGATGGCAA GTAACTGCAA TCATAGCAGA AATATTATAC ACACACACAC ACACAGACTC   1500
TGTCATAAAA TCCAATGTGC CTTCATGATG ATCAAATTTC GATAGTCAGT AATACTAGAA   1560
GAATCATATG TCTGAAAATA AAAGCCAGAA CCTTTTCTGC TTTTGTTTTC TTTTGCCCCA   1620
AGATAGGGTT TCTCTCAGTG TATCCCTGGC ATCCCTGCCT GGAACTTCCT TTGTAGGTTT   1680
GGTAGCCTCA AACTCAGAGA GGTCCTCTCT GCCTGCCTGC CTGCCTGCCT GCCTGCCTGC   1740
CTGCCTGCCT GCCTGCCTCA CTTCTTCTGC CACCCACACA ACCGAGTCGA ACCTAGGATC   1800
TTTATTTCTT TCTCTTTCTC TCTTCTTTCT TTCTTTCTTT CTTTCTTTCT TTCTTTCTTT   1860
CTTTCTTTCT TTCTTATTCA ATTAGTTTTC AATGTAAGTG TGTGTTTGTG CTCTATCTGC   1920
TGCCTATAGG CCTGCTTGCC AGGAGAGGGC AACAGAACCT AGGAGAAACC ACCATGCAGC   1980
TCCTGAGAAT AAGTGAAAAA ACAACAAAAA AAGGAAATTC TAATCACATA GAATGTAGAT   2040
ATATGCCGAG GCTGTCAGAG TGCTTTTTAA GGCTTAGTGT AAGTAATGAA AATTGTTGTG   2100
TGTCTTTTAT CCAAACACAG AAGAGAGGTG GCTCGGCCTG CATGTCTGTT GTCTGCATGT   2160
AGACCAGGCT GGCCTTGAAC ACATTAATCT GTCTGCCTCT GCTTCCCTAA TGCTGCGATT   2220
AAAGGCATGT GCCACCACTG CCCGGACTGA TTTCTTCTTT TTTTTTTTTT TGGAAAATAC   2280
CTTTCTTTCT TTTTCTCTCT CTCTTTCTTC CTTCCTTCCT TTCTTTCTAT TCTTTTTTTC   2340
TTTCTTTTTT CTTTTTTTTT TTTTTTTTAA AATTTGCCTA AGGTTAAAGG TGTGCTCCAC   2400
AATTGCCTCA GCTCTGCTCT AATTCTCTTT AAAAAAAAAC AAACAAAAAA AAAACCAAAA   2460
CAGTATGTAT GTATGTATAT TTAGAAGAAA TACTAATCCA TTAATAACTC TTTTTTCCTA   2520
AAATTCATGT CATTCTTGTT CCACAAAGTG AGTTCCAGGA CTTACCAGAG AAACCCTGTG   2580
TTCAAATTTC TGTGTTCAAG GTCACCCTGG CTTACAAAGT GAGTTCCAAG TCCGATAGGG   2640
```

-continued

CTACACAGAA AAACCATATC TCAGAAAAAA AAAAAGTTCC AAACACACAC ACACACACAC 2700

ACACACACAC ACACACACAC ACACACACAC ACACACACAG CGCGCCGCGG CGATGAGGGG 2760

AAGTCGTGCC TAAAATAAAT ATTTTTCTGG CCAAAGTGAA AGCAAATCAC TATGAAGAGG 2820

TACTCCTAGA AAAAATAAAT ACAAACGGGC TTTTTAATCA TTCCAGCACT GTTTTAATTT 2880

AACTCTGAAT TTAGTCTTGG AAAAGGGGGC GGGTGTGGGT GAGTGAGGGC GAGCGAGCAG 2940

ACGGGCGGGC GGGCGGGTGA GTGGCCGGCG GCGGTGGCAG CGAGCACCAG AAAACAACAA 3000

ACCCCAAGCG GTAGAGTGTT TTAAAAATGA GACCTAAATG TGGTGGAACG GAGGTCGCCG 3060

CCACCCTCCT CTTCCACTGC TTAGATGCTC CCTTCCCCTT ACTGTGCTCC CTTCCCCTAA 3120

CTGTGCCTAA CTGTGCCTGT TCCCTCACCC CGCTGATTCG CCAGCGACGT ACTTTGACTT 3180

CAAGAACGAT TTTGCCTGTT TTCACCGCTC CCTGTCATAC TTTCGTTTTT GGGTGCCCGA 3240

GTCTAGCCCG TTCGCTATGT TCGGGCGGGA CGATGGGGAC CGTTTGTGCC ACTCGGGAGA 3300

AGTGGTGGGT GGGTACGCTG CTCCGTCGTG CGTGCGTGAG TGCCGGAACC TGAGCTCGGG 3360

AGACCCTCCG GAGAGACAGA ATGAGTGAGT GAATGTGGCG GCGCGTGACG GATCTGTATT 3420

GGTTTGTATG GTTGATCGAG ACCATTGTCG GGCGACACCT AGTGGTGACA AGTTTCGGGA 3480

ACGCTCCAGG CCTCTCAGGT TGGTGACACA GGAGAGGGAA GTGCCTGTGG TGAGGCGACC 3540

AGGGTGACAG GAGGCCGGGC AAGCAGGCGG GAGCGTCTCG GAGATGGTGT CGTGTTTAAG 3600

GACGGTCTCT AACAAGGAGG TCGTACAGGG AGATGGCCAA AGCAGACCGA GTTGCTGTAC 3660

GCCCTTTTGG GAAAAATGCT AGGGTTGGTG GCAACGTTAC TAGGTCGACC AGAAGGCTTA 3720

AGTCCTACCC CCCCCCCCCT TTTTTTTTTT TTTCCTCCAG AAGCCCTCTC TTGTCCCCGT 3780

CACCGGGGGC ACCGTACATC TGAGGCCGAG AGGACGCGAT GGGCCCGGCT TCCAAGCCGG 3840

TGTGGCTCGG CCAGCTGGCG CTTCGGGTCT TTTTTTTTTT TTTTTTTTTT TTTTCCTCCA 3900

GAAGCCTTGT CTGTCGCTGT CACCGGGGGC GCTGTACTTC TGAGGCCGAG AGGACGCGAT 3960

GGGCCCCGGC TTCCAAGCCG GTGTGGCTCG GCCAGCTGGA GCTTCGGGTC TTTTTTTTTT 4020

TTTTTTTTTT TTTTTTTCTC CAGAAGCCTT GTCTGTCGCT GTCACCGGGG GCGCTGTACT 4080

TCTGAGGCCG AGAGGACGCG ATGGGTCGGC TTCCAAGCCG ATGTGGCGGG GCCAGCTGGA 4140

GCTTCGGGTT TTTTTTTTTC CTCCAGAAGC CCTCTCTTGT CCCCGTCACC GGGGGCGCTG 4200

TACTTCTGAG GCCGAGAGGA CGTGATGGGC CCGGGTTCCA GGCGGATGTC GCCCGGTCAG 4260

CTGGAGCTTT GGATCTTTTT TTTTTTTTTT CCTCCAGAAG CCCTCTCTTG TCCCCGTCAC 4320

CGGGGGCACC TTACATCTGA GGGCGAGAGG ACGTGATGGG TCCGGCTTCC AAGCCGATGT 4380

GGCGGGGCCA GCTGGAGCTT CGGGTTTTTT TTTTTTCCTC CAGAAGCCCT CTCTTGTCCC 4440

CGTCACCGGG GGCGCTGTAC TTCTGAGGCC GAGAGGACGT GATGGGCCCG GGTTCCAGGC 4500

GGATGTCGCC CGGTCAGCTG GAGCTTTGGA TCATTTTTTT TTTTCCCTCC AGAAGCCCTC 4560

TCTTGTCCCC GTCACCGGGG GCACCGTACA TCTGAGGCCG AGAGGACACG ATGGGCCTGT 4620

CTTCCAAGCC GATGTGGCCC GGCCAGCTGG AGCTTCGGGT CTTTTTTTTT TTTTTTCCTC 4680

CAGAAGCCTT GTCTGTCGCT GTCACCCGGG GCGCTGTACT TCTGAGGCCG AGAGGACGCG 4740

ATGGGCCCGG CTTCCAAGCC GGTGTGGCTC GGCCAGCTGG AGCTTCGGGT CTTTTTTTTT 4800

TTTTTTTTTT TTCCTCCAGA AACCTTGTCT GTCGCTGTCA CCCGGGGCGC TTGTACTTCT 4860

GATGCCGAGA GGACGCGATG GGCCCGTCTT CCAGGCCGAT GTGGCCCGGT CAGCTGGAGC 4920

TTTGGATCTT TTTTTTTTTT TTTTCCTCCA GAAGCCCTCT CTTGTCCCCG TCACCGGGGG 4980

CACCTTACAT CTGAGGCCTA GAGGACACGA TGGGCCCGGG TTCCAGGCCG ATGTGGCCCG 5040

-continued

```
GTCAGCTGGA GCTTTGGATC TTTTTTTTTT TTTTCTTCCA GAAGCCCTCT TGTCCCCGTC   5100
ACCGGTGGCA CTGTACATCT GAGGCGGAGA GGACATTATG GGCCCGGCTT CCAATCCGAT   5160
GTGGCCCGGT CAGCTGGAGC TTTGGATCTT ATTTTTTTTT TAATTTTTTC TTCCAGAAGC   5220
CCTCTTGTCC CTGTCACCGG TGGCACGGTA CATCTGAGGC CGAGAGGACA TTATGGGCCC   5280
GGCTTCCAGG CCGATGTGGC CCGGTCAGCT GGAGCTTTGG ATCTTTTTTT TTTTTTTTCT   5340
TTTTTCCTCC AGAAGCCCTC TCTGTCCCTG TCACCGGGGG CCCTGTACGT CTGAGGCCGA   5400
GGGAAAGCTA TGGGCGCGGT TTTCTTTCAT TGACCTGTCG GTCTTATCAG TTCTCCGGGT   5460
TGTCAGGGTC GACCAGTTGT TCCTTTGAGG TCCGGTTCTT TTCGTTATGG GGTCATTTTT   5520
GGGCCACCTC CCCAGGTATG ACTTCCAGGC GTCGTTGCTC GCCTGTCACT TTCCTCCCTG   5580
TCTCTTTTAT GCTTGTGATC TTTTCTATCT GTTCCTATTG GACCTGGAGA TAGGTACTGA   5640
CACGCTGTCC TTTCCCTATT AACACTAAAG GACACTATAA AGAGACCCTT TCGATTTAAG   5700
GCTGTTTTGC TTGTCCAGCC TATTCTTTTT ACTGGCTTGG GTCTGTCGCG GTGCCTGAAG   5760
CTGTCCCCGA GCCACGCTTC CTGCTTTCCC GGGCTTGCTG CTTGCGTGTG CTTGCTGTGG   5820
GCAGCTTGTG ACAACTGGGC GCTGTGACTT TGCTGCGTGT CAGACGTTTT TCCCGATTTC   5880
CCCGAGGTGT CGTTGTCACA CCTGTCCCGG TTGGAATGGT GGAGCCAGCT GTGGTTGAGG   5940
GCCACCTTAT TTCGGCTCAC TTTTTTTTTT TTTTTTTCTC TTGGAGTCCC GAACCTCCGC   6000
TCTTTTCTCT TCCCGGTCTT TCTTCCACAT GCCTCCCGAG TGCATTTCTT TTTGTTTTTT   6060
TTCTTTTTTT TTTTTTTTTT TTGGGGAGGT GGAGAGTCCC GAGTACTTCA CTCCTGTCTG   6120
TGGTGTCCAA GTGTTCATGC CACGTGCCTC CCGAGTGCAC TTTTTTTTGT GGCAGTCGCT   6180
CGTTGTGTTC TCTTGTTCTG TGTCTGCCCG TATCAGTAAC TGTCTTGCCC CGCGTGTAAG   6240
ACATTCCTAT CTCGCTTGTT TCTCCCGATT GCGCGTCGTT GCTCACTCTT AGATCGATGT   6300
GGTGCTCCGG AGTTCTCTTC GGGCCAGGGC CAAGCCGCGC CAGGCGAGGG ACGGACATTC   6360
ATGGCGAATG GCGGCCGCTC TTCTCGTTCT GCCAGCGGGC CCTCGTCTCT CCACCCCATC   6420
CGTCTGCCGG TGGTGTGTGG AAGGCAGGGG TGCGGCTCTC CGGCCCGACG CTGCCCCGCG   6480
CGCACTTTTC TCAGTGGTTC GCGTGGTCCT TGTGGATGTG TGAGGCGCCC GGTTGTGCCC   6540
TCACGTGTTT CACTTTGGTC GTGTCTCGCT TGACCATGTT CCCAGAGTCG GTGGATGTGG   6600
CCGGTGGCGT TGCATACCCT TCCCGTCTGG TGTGTGCACG CGCTGTTTCT TGTAAGCGTC   6660
GAGGTGCTCC TGGAGCGTTC CAGGTTTGTC TCCTAGGTGC CTGCTTCTGA GCTGGTGGTG   6720
GCGCTCCCCA TTCCCTGGTG TGCCTCCGGT GCTCCGTCTG GCTGTGTGCC TTCCCGTTTG   6780
TGTCTGAGAA GCCCGTGAGA GGGGGGTCGA GGAGAGAAGG AGGGGCAAGA CCCCCCTTCT   6840
TCGTCGGGTG AGGCGCCCAC CCCGCGACTA GTACGCCTGT GCGTAGGGCT GGTGCTGAGC   6900
GGTCGCGGCT GGGGTTGGAA AGTTTCTCGA GAGACTCATT GCTTTCCCGT GGGGAGCTTT   6960
GAGAGGCCTG GCTTTCGGGG GGGACCGGTT GCAGGGTCTC CCCTGTCCGC GGATGCTCAG   7020
AATGCCCTTG GAAGAGAACC TTCCTGTTGC CGCAGACCCC CCCGCGCGGT CGCCCGCGTG   7080
TTGGTCTTCT GGTTTCCCTG TGTGCTCGTC GCATGCATCC TCTCTCGGTG GCCGGGGCTC   7140
GTCGGGGTTT TGGGTCCGTC CCGCCCTCAG TGAGAAAGTT TCCTTCTCTA GCTATCTTCC   7200
GGAAAGGGTG CGGGCTTCTT ACGGTCTCGA GGGGTCTCTC CCGAATGGTC CCCTGGAGGG   7260
CTCGCCCCCT GACCGCCTCC CGCGCGCGCA GCGTTTGCTC TCTCGTCTAC CGCGGCCCGC   7320
GGCCTCCCCG CTCCGAGTTC GGGGAGGGAT CACGCGGGGC AGAGCCTGTC TGTCGTCCTG   7380
CCGTTGCTGC GGAGCATGTG GCTCGGCTTG TGTGGTTGGT GGCTGGGGAG AGGGCTCCGT   7440
```

GCACACCCCC GCGTGCGCGT ACTTTCCTCC CCTCCTGAGG GCCGCCGTGC GGACGGGGTG 7500

TGGGTAGGCG ACGGTGGGCT CCCGGGTCCC CACCCGTCTT CCCGTGCCTC ACCCGTGCCT 7560

TCCGTCGCGT GCGTCCCTCT CGCTCGCGTC CACGACTTTG GCCGCTCCCG CGACGGCGGC 7620

CTGCGCCGCG CGTGGTGCGT GCTGTGTGCT TCTCGGGCTG TGTGGTTGTG TCGCCTCGCC 7680

CCCCCCTTCC CGCGGCAGCG TTCCCACGGC TGGCGAAATC GCGGGAGTCC TCCTTCCCCT 7740

CCTCGGGGTC GAGAGGGTCC GTGTCTGGCG TTGATTGATC TCGCTCTCGG GGACGGGACC 7800

GTTCTGTGGG AGAACGGCTG TTGGCCGCGT CCGGCGCGAC GTCGGACGTG GGGACCCACT 7860

GCCGCTCGGG GGTCTTCGTC GGTAGGCATC GGTGTGTCGG CATCGGTCTC TCTCTCGTGT 7920

CGGTGTCGCC TCCTCGGGCT CCCGGGGGGC CGTCGTGTTT CGGGTCGGCT CGGCGCTGCA 7980

GGTGTGGTGG GACTGCTCAG GGGAGTGGTG CAGTGTGATT CCCGCCGGTT TTGCCTCGCG 8040

TGCCCTGACC GGTCCGACGC CCGAGCGGTC TCTCGGTCCC TTGTGAGGAC CCCCTTCCGG 8100

GAGGGGCCCG TTTCGGCCGC CCTTGCCGTC GTCGCCGGCC CTCGTTCTGC TGTGTCGTTC 8160

CCCCCTCCCC GCTCGCCGCA GCCGGTCTTT TTTCCTCTCT CCCCCCCTCT CCTCTGACTG 8220

ACCCGTGGCC GTGCTGTCGG ACCCCCCGCA TGGGGGCGGC CGGGCACGTA CGCGTCCGGG 8280

CGGTCACCGG GGTCTTGGGG GGGGGCCGAG GGGTAAGAAA GTCGGCTCGG CGGGCGGGAG 8340

GAGCTGTGGT TTGGAGGGCG TCCCGGCCCC GCGGCCGTGG CGGTGTCTTG CGCGGTCTTG 8400

GAGAGGGCTG CGTGCGAGGG GAAAAGGTTG CCCCGCGAGG GCAAAGGGAA AGAGGCTAGC 8460

AGTGGTCATT GTCCCGACGG TGTGGTGGTC TGTTGGCCGA GGTGCGTCTG GGGGGCTCGT 8520

CCGGCCCTGT CGTCCGTCGG GAAGGCGCGT GTTGGGGCCT GCCGGAGTGC CGAGGTGGGT 8580

ACCCTGGCGG TGGGATTAAC CCCGCGCGCG TGTCCCGGTG TGGCGGTGGG GGCTCCGGTC 8640

GATGTCTACC TCCCTCTCCC CGAGGTCTCA GGCCTTCTCC GCGCGGGCTC TCGGCCCTCC 8700

CCTCGTTCCT CCCTCTCGCG GGGTTCAAGT CGCTCGTCGA CCTCCCCTCC TCCGTCCTTC 8760

CATCTCTCGC GCAATGGCGC CGCCCGAGTT CACGGTGGGT TCGTCCTCCG CCTCCGCTTC 8820

TCGCCGGGGG CTGGCCGCTG TCCGGTCTCT CCTGCCCGAC CCCCGTTGGC GTGGTCTTCT 8880

CTCGCCGGCT TCGCGGACTC CTGGCTTCGC CCGGAGGGTC AGGGGGCTTC CCGGTTCCCC 8940

GACGTTGCGC CTCGCTGCTG TGTGCTTGGG GGGGGCCCGC TGCGGCCTCC GCCCGCCCGT 9000

GAGCCCCTGC CGCACCCGCC GGTGTGCGGT TTCGCGCCGC GGTCAGTTGG GCCCTGGCGT 9060

TGTGTCGCGT CGGGAGCGTG TCCGCCTCGC GGCGGCTAGA CGCGGGTGTC GCCGGGCTCC 9120

GACGGGTGGC CTATCCAGGG CTCGCCCCCG CCGACCCCCG CCTGCCCGTC CCGGTGGTGG 9180

TCGTTGGTGT GGGGAGTGAA TGGTGCTACC GGTCATTCCC TCCCGCGTGG TTTGACTGTC 9240

TCGCCGGTGT CGCGCTTCTC TTTCCGCCAA CCCCCACGCC AACCCACCAC CCTGCTCTCC 9300

CGGCCCGGTG CGGTCGACGT TCCGGCTCTC CCGATGCCGA GGGGTTCGGG ATTTGTGCCG 9360

GGGACGGAGG GGAGAGCGGG TAAGAGAGGT GTCGGAGAGC TGTCCCGGGG CGACGCTCGG 9420

GTTGGCTTTG CCGCGTGCGT GTGCTCGCGG ACGGGTTTTG TCGGACCCCG ACGGGGTCGG 9480

TCCGGCCGCA TGCACTCTCC CGTTCCGCGC GAGCGCCCGC CCGGCTCACC CCCGGTTTGT 9540

CCTCCCGCGA GGCTCTCCGC CGCCGCCGCC TCCTCCTCCT CTCTCGCGCT CTCTGTCCCG 9600

CCTGGTCCTG TCCCACCCCC GACGCTCCGC TCGCGCTTCC TTACCTGGTT GATCCTGCCA 9660

GGTAGCATAT GCTTGTCTCA AAGATTAAGC CATGCATGTC TAAGTACGCA CGGCCGGTAC 9720

AGTGAAACTG CGAATGGCTC ATTAAATCAG TTATGGTTCC TTTGGTCGCT CGCTCCTCTC 9780

CTACTTGGAT AACTGTGGTA ATTCTAGAGC TAATACATGC CGACGGGCGC TGACCCCCCT 9840

-continued

```
TCCCGGGGGG GGATGCGTGC ATTTATCAGA TCAAAACCAA CCCGGTGAGC TCCCTCCCGG   9900
CTCCGGCCGG GGGTCGGGCG CCGGCGGCTT GGTGACTCTA GATAACCTCG GGCCGATCGC   9960
ACGCCCCCCG TGGCGGCGAC GACCCATTCG AACGTCTGCC CTATCAACTT TCGATGGTAG  10020
TCGCCGTGCC TACCATGGTG ACCACGGGTG ACGGGGAATC AGGGTTCGAT TCCGGAGAGG  10080
GAGCCTGAGA AACGGCTACC ACATCCAAGG AAGGCAGCAG GCGCGCAAAT TACCCACTCC  10140
CGACCCGGGG AGGTAGTGAC GAAAAATAAC AATACAGGAC TCTTTCGAGG CCCTGTAATT  10200
GGAATGAGTC CACTTTAAAT CCTTTAACGA GGATCCATTG GAGGGCAAGT CTGGTGCCAG  10260
CAGCCGCGGT AATTCCAGCT CCAATAGCGT ATATTAAAGT TGCTGCAGTT AAAAAGCTCG  10320
TAGTTGGATC TTGGGAGCGG GCGGGCGGTC CGCCGCGAGG CGAGTCACCG CCCGTCCCCG  10380
CCCCTTGCCT CTCGGCGCCC CCTCGATGCT CTTAGCTGAG TGTCCCGCGG GGCCCGAAGC  10440
GTTTACTTTG AAAAAATTAG AGTGTTCAAA GCAGGCCCGA GCCGCCTGGA TACCGCAGCT  10500
AGGAATAATG GAATAGGACC GCGGTTCTAT TTTGTTGGTT TTCGGAACTG AGGCCATGAT  10560
TAAGAGGGAC GGCCGGGGGC ATTCGTATTG CGCCGCTAGA GGTGAAATTC TTGGACCGGC  10620
GCAAGACGGA CCAGAGCGAA AGCATTTGCC AAGAATGTTT TCATTAATCA AGAACGAAAG  10680
TCGGAGGTTC GAAGACGATC AGATACCGTC GTAGTTCCGA CCATAAACGA TGCCGACTGG  10740
CGATGCGGCG GCGTTATTCC CATGACCCGC CGGGCAGCTT CCGGGAAACC AAAGTCTTTG  10800
GGTTCCGGGG GGAGTATGGT TGCAAAGCTG AAACTTAAAG GAATTGACGG AAGGGCACCA  10860
CCAGGAGTGG GCCTGCGGCT TAATTTGACT CAACACGGGA AACCTCACCC GGCCCGGACA  10920
CGGACAGGAT TGACAGATTG ATAGCTCTTT CTCGATTCCG TGGGTGGTGG TGCATGGCCG  10980
TTCTTAGTTG GTGGAGCGAT TTGTCTGGTT AATTCCGATA ACGAACGAGA CTCTGGCATG  11040
CTAACTAGTT ACGCGACCCC CGAGCGGTCG GCGTCCCCCA ACTTCTTAGA GGGACAAGTG  11100
GCGTTCAGCC ACCCGAGATT GAGCAATAAC AGGTCTGTGA TGCCCTTAGA TGTCCGGGGC  11160
TGCACGCGCG CTACACTGAC TGGCTCAGCG TGTGCCTACC CTGCGCCGGC AGGCGCGGGT  11220
AACCCGTTGA ACCCCATTCG TGATGGGGAT CGGGGATTGC AATTATTCCC CATGAACGAG  11280
GAATTCCCAG TAAGTGCGGG TCATAAGCTT GCGTTGATTA AGTCCCTGCC CTTTGTACAC  11340
ACCGCCCGTC GCTACTACCG ATTGGATGGT TTAGTGAGGC CCTCGGATCG GCCCCGCCGG  11400
GGTCGGCCCA CGGCCCTGGC GGAGCGCTGA GAAGACGGTC GAACTTGACT ATCTAGAGGA  11460
AGTAAAAGTC GTAACAAGGT TTCCGTAGGT GAACCTGCGG AAGGATCATT AAACGGGAGA  11520
CTGTGGAGGA GCGGCGGCGT GGCCCGCTCT CCCCGTCTTG TGTGTGTCCT CGCCGGGAGG  11580
CGCGTGCGTC CCGGGTCCCG TCGCCCGCGT GTGGAGCGAG GTGTCTGGAG TGAGGTGAGA  11640
GAAGGGGTGG GTGGGGTCGG TCTGGGTCCG TCTGGGACCG CCTCCGATTT CCCCTCCCCC  11700
TCCCCTCTCC CTCGTCCGGC TCTGACCTCG CCACCCTACC GCGGCGGCGG CTGCTCGCGG  11760
GCGTCTTGCC TCTTTCCCGT CCGGCTCTTC CGTGTCTACG AGGGGCGGTA CGTCGTTACG  11820
GGTTTTTGAC CCGTCCCGGG GGCGTTCGGT CGTCGGGGCG CGCGCTTTGC TCTCCCGGCA  11880
CCCATCCCCG CCGCGGCTCT GGCTTTTCTA CGTTGGCTGG GGCGGTTGTC GCGTGTGGGG  11940
GGATGTGAGT GTCGCGTGTG GGCTCGCCCG TCCCGATGCC ACGCTTTTCT GGCCTCGCGT  12000
GTCCTCCCCG CTCCTGTCCC GGGTACCTAG CTGTCGCGTT CCGGCGCGGA GGTTTAAGGA  12060
CCCCGGGGGG GTCGCCCTGC CGCCCCCAGG GTCGGGGGGC GGTGGGGCCC GTAGGGAAGT  12120
CGGTCGTTCG GGCGGCTCTC CCTCAGACTC CATGACCCTC CTCCCCCCGC TGCCGCCGTT  12180
CCCGAGGCGG CGGTCGTGTG GGGGGGTGGA TGTCTGGAGC CCCCTCGGGC GCCGTGGGGG  12240
```

-continued

CCCGACCCGC GCCGCCGGCT TGCCCGATTT CCGCGGGTCG GTCCTGTCGG TGCCGGTCGT 12300

GGGTTCCCGT GTCGTTCCCG TGTTTTTCCG CTCCCGACCC TTTTTTTTTC CTCCCCCCCA 12360

CACGTGTCTC GTTTCGTTCC TGCTGGCCGG CCTGAGGCTA CCCCTCGGTC CATCTGTTCT 12420

CCTCTCTCTC CGGGGAGAGG AGGGCGGTGG TCGTTGGGGG ACTGTGCCGT CGTCAGCACC 12480

CGTGAGTTCG CTCACACCCG AAATACCGAT ACGACTCTTA GCGGTGGATC ACTCGGCTCG 12540

TGCGTCGATG AAGAACGCAG CTAGCTGCGA GAATTAATGT GAATTGCAGG ACACATTGAT 12600

CATCGACACT TCGAACGCAC TTGCGGCCCC GGGTTCCTCC CGGGGCTACG CCTGTCTGAG 12660

CGTCGGTTGA CGATCAATCG CGTCACCCGC TGCGGTGGGT GCTGCGCGGC TGGGAGTTTG 12720

CTCGCAGGGC CAACCCCCCA ACCCGGGTCG GGCCCTCCGT CTCCCGAAGT TCAGACGTGT 12780

GGGCGGTTGT CGGTGTGGCG CGCGCGCCCG CGTCGCGGAG CCTGGTCTCC CCCGCGCATC 12840

CGCGCTCGCG GCTTCTTCCC GCTCCGCCGT TCCCGCCCTC GCCCGTGCAC CCCGGTCCTG 12900

GCCTCGCGTC GGCGCCTCCC GGACCGCTGC CTCACCAGTC TTTCTCGGTC CCGTGCCCCG 12960

TGGGAACCCA CCGCGCCCCC GTGGCGCCCG GGGGTGGGCG CGTCCGCATC TGCTCTGGTC 13020

GAGGTTGGCG GTTGAGGGTG TGCGTGCGCC GAGGTGGTGG TCGGTCCCCT GCGGCCGCGG 13080

GGTTGTCGGG GTGGCGGTCG ACGAGGGCCG GTCGGTCGCC TGCGGTGGTT GTCTGTGTGT 13140

GTTTGGGTCT TGCGCTGGGG GAGGCGGGGT CGACCGCTCG CGGGGTTGGC GCGGTCGCCC 13200

GGCGCCGCGC ACCCTCCGGC TTGTGTGGAG GGAGAGCGAG GGCGAGAACG GAGAGAGGTG 13260

GTATCCCCGG TGGCGTTGCG AGGGAGGGTT TGGCGTCCCG CGTCCGTCCG TCCCTCCCTC 13320

CCTCGGTGGG CGCCTTCGCG CCGCACGCGG CCGCTAGGGG CGGTCGGGGC CCGTGGCCCC 13380

CGTGGCTCTT CTTCGTCTCC GCTTCTCCTT CACCCGGGCG GTACCCGCTC CGGCGCCGGC 13440

CCGCGGGACG CCGCGGCGTC CGTGCGCCGA TGCGAGTCAC CCCCGGGTGT TGCGAGTTCG 13500

GGGAGGGAGA GGGCCTCGCT GACCCGTTGC GTCCCGGCTT CCCTGGGGGG GACCCGGCGT 13560

CTGTGGGCTG TGCGTCCCGG GGGTTGCGTG TGAGTAAGAT CCTCCACCCC CGCCGCCCTC 13620

CCCTCCCGCC GGCCTCTCGG GGACCCCCTG AGACGGTTCG CCGGCTCGTC CTCCCGTGCC 13680

GCCGGGTGCC GTCTCTTTCC CGCCCGCCTC CTCGCTCTCT TCTTCCCGCG GCTGGGCGCG 13740

TGTCCCCCCT TTCTGACCGC GACCTCAGAT CAGACGTGGC GACCCGCTGA ATTTAAGCAT 13800

ATTAGTCAGC GGAGGAAAAG AAACTAACCA GGATTCCCTC AGTAACGGCG AGTGAACAGG 13860

GAAGAGCCCA GCGCCGAATC CCCGCCGCGC GTCGCGGCGT GGGAAATGTG GCGTACGGAA 13920

GACCCACTCC CCGGCGCCGC TCGTGGGGGG CCCAAGTCCT TCTGATCGAG GCCCAGCCCG 13980

TGGACGGTGT GAGGCCGGTA GCGGCCCCGG CGCGCCGGGC TCGGGTCTTC CCGGAGTCGG 14040

GTTGCTTGGG AATGCAGCCC AAAGCGGGTG GTAAACTCCA TCTAAGGCTA AATACCGGCA 14100

CGAGACCGAT AGTCAACAAG TACCGTAAGG GAAAGTTGAA AAGAACTTTG AAGAGAGAGT 14160

TCAAGAGGGC GTGAAACCGT TAAGAGGTAA ACGGGTGGGG TCCGCGCAGT CCGCCCGGAG 14220

GATTCAACCC GGCGGCGCGC GTCCGGCCGT GCCCGGTGGT CCCGGCGGAT CTTTCCCGCT 14280

CCCCGTTCCT CCCGACCCCT CCACCCGCGC GTCGTTCCCC TCTTCCTCCC CGCGTCCGGC 14340

GCCTCCGGCG GCGGGCGCGG GGGGTGGTGT GGTGGTGGCG CGCGGGCGGG GCCGGGGGTG 14400

GGGTCGGCGG GGGACCGCCC CCGGCCGGCG ACCGGCCGCC GCCGGGCGCA CTTCCACCGT 14460

GGCGGTGCGC CGCGACCGGC TCCGGGACGG CCGGGAAGGC CCGGTGGGGA AGGTGGCTCG 14520

GGGGGGGCGG CGCGTCTCAG GGCGCGCCGA ACCACCTCAC CCCGAGTGTT ACAGCCCTCC 14580

GGCCGCGCTT TCGCCGAATC CCGGGGCCGA GGAAGCCAGA TACCCGTCGC CGCGCTCTCC 14640

-continued

```
CTCTCCCCCC GTCCGCCTCC CGGGCGGGCG TGGGGGTGGG GGCCGGGCCG CCCCTCCCAC  14700
GGCGCGACCG CTCTCCCACC CCCCTCCGTC GCCTCTCTCG GGGCCCGGTG GGGGGCGGGG  14760
CGGACTGTCC CCAGTGCGCC CCGGGCGTCG TCGCGCCGTC GGGTCCCGGG GGGACCGTCG  14820
GTCACGCGTC TCCCGACGAA GCCGAGCGCA CGGGGTCGGC GGCGATGTCG GCTACCCACC  14880
CGACCCGTCT TGAAACACGG ACCAAGGAGT CTAACGCGTG CGCGAGTCAG GGGCTCGTCC  14940
GAAAGCCGCC GTGGCGCAAT GAAGGTGAAG GGCCCCGCCC GGGGGCCCGA GGTGGGATCC  15000
CGAGGCCTCT CCAGTCCGCC GAGGGCGCAC CACCGGCCCG TCTCGCCCGC CGCGCCGGGG  15060
AGGTGGAGCA CGAGCGTACG CGTTAGGACC CGAAAGATGG TGAACTATGC TTGGGCAGGG  15120
CGAAGCCAGA GGAAACTCTG GTGGAGGTCC GTAGCGGTCC TGACGTGCAA ATCGGTCGTC  15180
CGACCTGGGT ATAGGGGCGA AAGACTAATC GAACCATCTA GTAGCTGGTT CCCTCCGAAG  15240
TTTCCCTCAG GATAGCTGGC GCTCTCGCTC CCGACGTACG CAGTTTTATC CGGTAAAGCG  15300
AATGATTAGA GGTCTTGGGG CCGAAACGAT CTCAACCTAT TCTCAAACTT TAAATGGGTA  15360
AGAAGCCCGG CTCGCTGGCG TGGAGCCGGG CGTGGAATGC GAGTGCCTAG TGGGCCACTT  15420
TTGGTAAGCA GAACTGGCGC TGCGGGATGA ACCGAACGCC GGGTTAAGGC GCCCGATGCC  15480
GACGCTCATC AGACCCCAGA AAAGGTGTTG GTTGATATAG ACAGCAGGAC GGTGGCCATG  15540
GAAGTCGGAA TCCGCTAAGG AGTGTGTAAC AACTCACCTG CCGAATCAAC TAGCCCTGAA  15600
AATGGATGGC GCTGGAGCGT CGGGCCCATA CCCGGCCGTC GCCGCAGTCG GAACGGAACG  15660
GGACGGGAGC GGCCGCGGGT GCGCGTCTCT CGGGGTCGGG GGTGCGTGGC GGGGGCCCGT  15720
CCCCCGCCTC CCCTCCGCGC GCCGGGTTCG CCCCCGCGGC GTCGGGCCCC GCGGAGCCTA  15780
CGCCGCGACG AGTAGGAGGG CCGCTGCGGT GAGCCTTGAA GCCTAGGGCG CGGGCCCGGG  15840
TGGAGCCGCC GCAGGTGCAG ATCTTGGTGG TAGTAGCAAA TATTCAAACG AGAACTTTGA  15900
AGGCCGAAGT GGAGAAGGGT TCCATGTGAA CAGCAGTTGA ACATGGGTCA GTCGGTCCTG  15960
AGAGATGGGC GAGTGCCGTT CCGAAGGGAC GGGCGATGGC CTCCGTTGCC CTCGGCCGAT  16020
CGAAAGGGAG TCGGGTTCAG ATCCCCGAAT CCGGAGTGGC GGAGATGGGC GCCGCGAGGC  16080
CAGTGCGGTA ACGCGACCGA TCCCGGAGAA GCCGGCGGGA GGCCTCGGGG AGAGTTCTCT  16140
TTTCTTTGTG AAGGGCAGGG CGCCCTGGAA TGGGTTCGCC CCGAGAGAGG GGCCCGTGCC  16200
TTGGAAAGCG TCGCGGTTCC GGCGGCGTCC GGTGAGCTCT CGCTGGCCCT TGAAAATCCG  16260
GGGGAGAGGG TGTAAATCTC GCGCCGGGCC GTACCCATAT CCGCAGCAGG TCTCCAAGGT  16320
GAACAGCCTC TGGCATGTTG GAACAATGTA GGTAAGGGAA GTCGGCAAGC CGGATCCGTA  16380
ACTTCGGGAT AAGGATTGGC TCTAAGGGCT GGGTCGGTCG GGCTGGGGCG CGAAGCGGGG  16440
CTGGGCGCGC GCCGCGGCTG GACGAGGCGC CGCCGCCCTC TCCCACGTCC GGGGAGACCC  16500
CCCGTCCTTT CCGCCCGGGC CCGCCCTCCC CTCTTCCCCG CGGGGCCCCG TCGTCCCCCG  16560
CGTCGTCGCC ACCTCTCTTC CCCCCTCCTT CTTCCCGTCG GGGGGCGGGT CGGGGGTCGG  16620
CGCGCGGCGC GGGCTCCGGG GCGGCGGGTC CAACCCCGCG GGGGTTCCGG AGCGGGAGGA  16680
ACCAGCGGTC CCCGGTGGGG CGGGGGGCCC GGACACTCGG GGGGCCGGCG GCGGCGGCGA  16740
CTCTGGACGC GAGCCGGGCC CTTCCCGTGG ATCGCCTCAG CTGCGGCGGG CGTCGCGGCC  16800
GCTCCCGGGG AGCCCGGCGG GTGCCGGCGC GGGTCCCCTC CCCGCGGGGC CTCGCTCCAC  16860
CCCCCCATCG CCTCTCCCGA GGTGCGTGGC GGGGGCGGGC GGGCGTGTCC CGCGCGTGTG  16920
GGGGGAACCT CCGCGTCGGT GTTCCCCCGC CGGGTCCGCC CCCCGGGCCG CGGTTTTCCG  16980
CGCGGCGCCC CCGCCTCGGC CGGCGCCTAG CAGCCGACTT AGAACTGGTG CGGACCAGGG  17040
```

-continued

GAATCCGACT GTTTAATTAA AACAAAGCAT CGCGAAGGCC CGCGGCGGGT GTTGACGCGA 17100

TGTGATTTCT GCCCAGTGCT CTGAATGTCA AAGTGAAGAA ATTCAATGAA GCGCGGGTAA 17160

ACGGCGGGAG TAACTATGAC TCTCTTAAGG TAGCCAAATG CCTCGTCATC TAATTAGTGA 17220

CGCGCATGAA TGGATGAACG AGATTCCCAC TGTCCCTACC TACTATCCAG CGAAACCACA 17280

GCCAAGGGAA CGGGCTTGGC GGAATCAGCG GGGAAAGAAG ACCCTGTTGA GCTTGACTCT 17340

AGTCTGGCAC GGTGAAGAGA CATGAGAGGT GTAGAATAAG TGGGAGGCCC CCGGCGCCCG 17400

GCCCCGTCCT CGCGTCGGGG TCGGGGCACG CCGGCCTCGC GGGCCGCCGG TGAAATACCA 17460

CTACTCTCAT CGTTTTTTCA CTGACCCGGT GAGGCGGGGG GGCGAGCCCC GAGGGGCTCT 17520

CGCTTCTGGC GCCAAGCGTC CGTCCCGCGC GTGCGGGCGG GCGCGACCCG CTCCGGGGAC 17580

AGTGCCAGGT GGGGAGTTTG ACTGGGGCGG TACACCTGTC AAACGGTAAC GCAGGTGTCC 17640

TAAGGCGAGC TCAGGGAGGA CAGAAACCTC CCGTGGAGCA GAAGGGCAAA AGCTCGCTTG 17700

ATCTTGATTT TCAGTACGAA TACAGACCGT GAAAGCGGGG CCTCACGATC CTTCTGACCT 17760

TTTGGGTTTT AAGCAGGAGG TGTCAGAAAA GTTACCACAG GGATAACTGG CTTGTGGCGG 17820

CCAAGCGTTC ATAGCGACGT CGCTTTTTGA TCCTTCGATG TCGGCTCTTC CTATCATTGT 17880

GAAGCAGAAT TCACCAAGCG TTGGATTGTT CACCCACTAA TAGGGAACGT GAGCTGGGTT 17940

TAGACCGTCG TGAGACAGGT TAGTTTTACC CTACTGATGA TGTGTTGTTG CCATGGTAAT 18000

CCTGCTCAGT ACGAGAGGAA CCGCAGGTTC AGACATTTGG TGTATGTGCT TGGCTGAGGA 18060

GCCAATGGGG CGAAGCTACC ATCTGTGGGA TTATGACTGA ACGCCTCTAA GTCAGAATCC 18120

GCCCAAGCGG AACGATACGG CAGCGCCGAA GGAGCCTCGG TTGGCCCCGG ATAGCCGGGT 18180

CCCCGTCCGT CCCGCTCGGC GGGGTCCCCG CGTCGCCCCG CGGCGGCGCG GGGTCTCCCC 18240

CCGCCGGGCG TCGGGACCGG GGTCCGGTGC GGAGAGCCGT TCGTCTTGGG AAACGGGGTG 18300

CGGCCGGAAA GGGGGCCGCC CTCTCGCCCG TCACGTTGAA CGCACGTTCG TGTGGAACCT 18360

GGCGCTAAAC CATTCGTAGA CGACCTGCTT CTGGGTCGGG GTTTCGTACG TAGCAGAGCA 18420

GCTCCCTCGC TGCGATCTAT TGAAAGTCAG CCCTCGACAC AAGGGTTTGT CTCTGCGGGC 18480

TTTCCCGTCG CACGCCCGCT CGCTCGCACG CGACCGTGTC GCCGCCCGGG CGTCACGGGG 18540

GCGGTCGCCT CGGCCCCCGC GCGGTTGCCC GAACGACCGT GTGGTGGTTG GGGGGGGGAT 18600

CGTCTTCTCC TCCGTCTCCC GAGGACGGTT CGTTTCTCTT TCCCCTTCCG TCGCTCTCCT 18660

TGGGTGTGGG AGCCTCGTGC CGTCGCGACC GCGGCCTGCC GTCGCCTGCC GCCGCAGCCC 18720

CTTGCCCTCC GGCCTTGGCC AAGCCGGAGG GCGGAGGAGG GGGATCGGCG GCGGCGGCGA 18780

CCGCGGCGCG GTGACGCACG GTGGGATCCC CATCCTCGGC GCGTCCGTCG GGGACGGCCG 18840

GTTGGAGGGG CGGGAGGGGT TTTTCCCGTG AACGCCGCGT TCGGCGCCAG GCCTCTGGCG 18900

GCCGGGGGGG CGCTCTCTCC GCCCGAGCAT CCCCACTCCC GCCCCTCCTC TTCGCGCGCC 18960

GCGGCGGCGA CGTGCGTACG AGGGGAGGAT GTCGCGGTGT GGAGGCGGAG AGGGTCCGGC 19020

GCGGCGCCTC TTCCATTTTT TCCCCCCCAA CTTCGGAGGT CGACCAGTAC TCCGGGCGAC 19080

ACTTTGTTTT TTTTTTTTCC CCCGATGCTG GAGGTCGACC AGATGTCCGA AAGTGTCCCC 19140

CCCCCCCCCC CCCCCCGGCG CGGAGCGGCG GGGCCACTCT GGACTCTTTT TTTTTTTTTT 19200

TTTTTTTTTT TTAAATTCCT GGAACCTTTA GGTCGACCAG TTGTCCGTCT TTTACTCCTT 19260

CATATAGGTC GACCAGTACT CCGGGTGGTA CTTTGTCTTT TTCTGAAAAT CCCAGAGGTC 19320

GACCAGATAT CCGAAAGTCC TCTCTTTCCC TTTACTCTTC CCCACAGCGA TTCTCTTTTT 19380

TTTTTTTTTT TTTGGTGTGC CTCTTTTTGA CTTATATACA TGTAAATAGT GTGTACGTTT 19440

-continued

```
ATATACTTAT AGGAGGAGGT CGACCAGTAC TCCGGGCGAC ACTTTGTTTT TTTTTTTTTT  19500
TCCACCGATG ATGGAGGTCG ACCAGATGTC CGAAAGTGTC CCGTCCCCCC CCTCCCCCCC  19560
CCGCGACGCG GCGGGCTCAC TCTGGACTCT TTTTTTTTTT TTTTTTTTTT TTTAAATTTC  19620
TGGAACCTTA AGGTCGACCA GTTGTCCGTC TTTCACTCAT TCATATAGGT CGACCGGTGG  19680
TACTTTGTCT TTTTCTGAAA ATCGCAGAGG TCGACCAGAT GTCAGAAAGT CTGGTGGTCG  19740
ATAAATTATC TGATCTAGAT TTGTTTTTCT GTTTTTCAGT TTTGTGTTGT TTTGTGTTGT  19800
TTTGTGTTGT TTTGTTTTGT TTTGTTTTGT TTTGTTTTGT TTTGTTTTGT TTTGTTTTGT  19860
TTTGTGTTGT GTTGTGTTGT GTTGTGTTGG GTTGGGTTGG GTTGGGTTGG GTTGGGTTGG  19920
GTTGGGTTGG GTTGGGTTGT GTTGTTTGGT TTTGTGTTGT TTGGTGTTGT TGGTTTTGTT  19980
TTGTTTGCTG TTGTTTTGTG TTTTGCGGGT CGAACAGTTG TCCCTAACCG AGTTTTTTTG  20040
TACACAAACA TGCACTTTTT TTAAAATAAA TTTTTAAAAT AAATGCGAAA ATCGACCAAT  20100
TATCCCTTTC CTTCTCTCTC TTTTTTAAAA ATTTTCTTTG TGTGTGTGTG TGTGTGTGTG  20160
TGTGTGTGTG TGCGTGTGTG TGTGTGTGTG CGTGCAGCGT GCGCGCGCTC GTTTTATAAA  20220
TACTTATAAT AATAGGTCGC CGGGTGGTGG TAGCTTCCCG GACTCCAGAG GCAGAGGCAG  20280
GCAGACTTCT GAGTTCGAGG CCAGCCTGGT CTACAGAGGA ACCCTGTCTC GAAAAATGAA  20340
AATAAATACA TACATACATA CATACATACA TACATACATA CATACATACA TACATATGAG  20400
GTTGACCAGT TGTCAATCCT TTAGAATTTT GTTTTTAATT AATGTGATAG AGAGATAGAT  20460
AATAGATAGA TGGATAGAGT GATACAAATA TAGGTTTTTT TTTCAGTAAA TATGAGGTTG  20520
ATTAACCACT TTTCCCTTTT TAGGTTTTTT TTTTTTTCCC CTGTCCATGT GGTTGCTGGG  20580
ATTTGAACTC AGGACCCTGG CAGGTCAACT GGAAAACGTG TTTTCTATAT ATATAAATAG  20640
TGGTCTGTCT GCTGTTTGTT TGTTTGCTTG CTTGCTTGCT TGCTTGCTTG CTTGCTTGCT  20700
TGCTTTTTTT TTTCTTCTGA GACAGTATTT CTCTGTGTAA CCTGGTGCCC TGAAACTCAC  20760
TCTGTAGACC AGCCTGGCCT CAATCGAACT CAGAAATCCT CCTGCCTCTT GTCTACCTCC  20820
CAATTTTGGA GTAAAGGTGT GCTACACCAC TGCCTGGCAT TATTATCATT ATCATTATTA  20880
ATTTTATTAT TAGACAGAAC GAAATCAACT AGTTGGTCCT GTTTCGTTAA TTCATTTGAA  20940
ATTAGTTGGA CCAATTAGTT GGCTGGTTTG GGAGGTTTCT TTTGTTTCCG ATTTGGGTGT  21000
TTGTGGGGCT GGGGATCAGG TATCTCAACG GAATGCATGA AGGTTAAGGT GAGATGGCTC  21060
GATTTTTGTA AAGATTACTT TTCTTAGTCT GAGGAAAAAA TAAAATAATA TTGGGCTACG  21120
TTTCATTGCT TCATTTCTAT TTCTCTTTCT TTCTTTCTTT CTTTCAGATA AGGAGGTCGG  21180
CCAGTTCCTC CTGCCTTCTG GAAGATGTAG GCATTGCATT GGGAAAAGCA TTGTTTGAGA  21240
GATGTGCTAG TGAACCAGAG AGTTTGGATG TCAAGCCGTA TAATGTTTAT TACAATATAG  21300
AAAAGTTCTA ACAAAGTGAT CTTTAACTTT TTTTTTTTTT TTTCTCCTTC TACTTCTACT  21360
TGTTCTCACT CTGCCACCAA CGCGCTTTGT ACATTGAATG TGAGCTTTGT TTTGCTTAAC  21420
AGACATATAT TTTTTCTTTT GGTTTTGCTT GACATGGTTT CCCTTTCTAT CCGTGCAGGG  21480
TTCCCAGACG GCCTTTTGAG AATAAAATGG GAGGCCAGAA CCAAAGTCTT TTGAATAAAG  21540
CACCACAACT CTAACCTGTT TGGCTGTTTT CCTTCCCAAG GCACAGATCT TTCCCAGCAT  21600
GGAAAAGCAT GTAGCAGTTG TAGGACACAC TAGACGAGAG CACCAGATCT CATTGTGGGT  21660
GGTTGTGAAC CACCCACCAT GTGGTTGCCT GGGATTTGAA CTCAGGATCT TCAGAAGACG  21720
AGTCAGGGCT CTAAACCGAT GAGCCATCTC TCCAGCCCTC CTACATTCCT TCTTAAGGCA  21780
TGAATGATCC CAGCATGGGA AGACAGTCTG CCCTCTTTGT GGTATATCAC CATATACTCA  21840
```

ATAAAATAAT GAAATGAATG AAGTCTCCAC GTATTTATTT CTTCGAGCTA TCTAAATTCT 21900

CTCACAGCAC CTCCCCCTCC CCCACACTGC CTTTCTCCCT ATGTTTGGGT GGGGCTGGGG 21960

GAGGGGTGGG GTGGGGGCAG GGATCTGCAT GTCTTCTTGC AGGTCTGTGA ACTATTTGCG 22020

ATGGCCTGGT TCTCTGAACT GTTGAGCCTT GTCTATCCAG AGGCTGACTG GCTAGTTTTC 22080

TACCTGAAGT CCCTGAGTGA TGATTTCCCT GTGAATTC 22118

(2) INFORMATION FOR SEQ ID NO: 17:

(i) SEQUENCE CHARACTERISTICS:
(A) LENGTH: 42999 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 17:

GCTGACACGC TGTCCTCTGG CGACCTGTCG TCGGAGAGGT TGGGCCTCCG GATGCGCGCG 60

GGGCTCTGGC CTCACGGTGA CCGGCTAGCC GGCCGCGCTC CTGCCTTGAG CCGCCTGCCG 120

CGGCCCGCGG GCCTGCTGTT CTCTCGCGCG TCCGAGCGTC CCGACTCCCG GTGCCGGCCC 180

GGGTCCGGGT CTCTGACCCA CCCGGGGGCG GCGGGGAAGG CGGCGAGGGC CACCGTGCCC 240

CGTGCGCTCT CCGCTGCGGG CGCCCGGGGC GCCGCACAAC CCCACCCGCT GGCTCCGTGC 300

CGTGCGTGTC AGGCGTTCTC GTCTCCGCGG GGTTGTCCGC CGCCCCTTCC CCGGAGTGGG 360

GGGTGGCCGG AGCCGATCGG CTCGCTGGCC GGCCGGCCTC CGCTCCCGGG GGGCTCTTCG 420

ATCGATGTGG TGACGTCGTG CTCTCCCGGG CCGGGTCCGA GCCGCGACGG GCGAGGGGCG 480

GACGTTCGTG GCGAACGGGA CCGTCCTTCT CGCTCCGCCC GCGCGGTCCC CTCGTCTGCT 540

CCTCTCCCCG CCCGCCGGCC GGCGTGTGGG AAGGCGTGGG GTGCGGACCC CGGCCCGACC 600

TCGCCGTCCC GCCCGCCGCC TTCGCTTCGC GGGTGCGGGC CGGCGGGGTC CTCTGACGCG 660

GCAGACAGCC CTGCCTGTCG CCTCCAGTGG TTGTCGACTT GCGGGCGGCC CCCCTCCGCG 720

GCGGTGGGGG TGCCGTCCCG CCGGCCCGTC GTGCTGCCCT CTCGGGGGGG GTTTGCGCGA 780

GCGTCGGCTC CGCCTGGGCC CTTGCGGTGC TCCTGGAGCG CTCCGGGTTG TCCCTCAGGT 840

GCCCGAGGCC GAACGGTGGT GTGTCGTTCC CGCCCCCGGC GCCCCCTCCT CCGGTCGCCG 900

CCGCGGTGTC CGCGCGTGGG TCCTGAGGGA GCTCGTCGGT GTGGGGTTCG AGGCGGTTTG 960

AGTGAGACGA GACGAGACGC GCCCCTCCCA CGCGGGGAAG GGCGCCCGCC TGCTCTCGGT 1020

GAGCGCACGT CCCGTGCTCC CCTCTGGCGG GTGCGCGCGG GCCGTGTGAG CGATCGCGGT 1080

GGGTTCGGGC CGGTGTGACG CGTGCGCCGG CCGGCCGCCG AGGGGCTGCC GTTCTGCCTC 1140

CGACCGGTCG TGTGTGGGTT GACTTCGGAG GCGCTCTGCC TCGGAAGGAA GGAGGTGGGT 1200

GGACGGGGGG GCCTGGTGGG GTTGCGCGCA CGCGCGCACC GGCCGGGCCC CCGCCCTGAA 1260

CGCGAACGCT CGAGGTGGCC GCGCGCAGGT GTTTCCTCGT ACCGCAGGGC CCCCTCCCTT 1320

CCCCAGGCGT CCCTCGGCGC CTCTGCGGGC CCGAGGAGGA GCGGCTGGCG GGTGGGGGGA 1380

GTGTGACCCA CCCTCGGTGA GAAAAGCCTT CTCTAGCGAT CTGAGAGGCG TGCCTTGGGG 1440

GTACCGGATC CCCCGGGCCG CCGCCTCTGT CTCTGCCTCC GTTATGGTAG CGCTGCCGTA 1500

-continued

```
GCGACCCGCT CGCAGAGGAC CCTCCTCCGC TTCCCCCTCG ACGGGGTTGG GGGGGAGAAG   1560
CGAGGGTTCC GCCGGCCACC GCGGTGGTGG CCGAGTGCGG CTCGTCGCCT ACTGTGGCCC   1620
GCGCCTCCCC CTTCCGAGTC GGGGGAGGAT CCCGCCGGGC CGGGCCCGGC GCTCCCACCC   1680
AGCGGGTTGG GACGCGGCGG CCGGCGGGCG GTGGGTGTGC GCGCCCGGCG CTCTGTCCGG   1740
CGCGTGACCC CCTCCGTCCG CGAGTCGGCT CTCCGCCCGC TCCCGTGCCG AGTCGTGACC   1800
GGTGCCGACG ACCGCGTTTG CGTGGCACGG GGTCGGGCCC GCCTGGCCCT GGGAAAGCGT   1860
CCCACGGTGG GGGCGCGCCG GTCTCCCGGA GCGGGACCGG GTCGGAGGAT GGACGAGAAT   1920
CACGAGCGAC GGTGGTGGTG GCGTGTCGGG TTCGTGGCTG CGGTCGCTCC GGGGCCCCCG   1980
GTGGCGGGGC CCCGGGGCTC GCGAGGCGGT TCTCGGTGGG GGCCGAGGGC CGTCCGGCGT   2040
CCCAGGCGGG GCGCCGCGGG ACCGCCCTCG TGTCTGTGGC GGTGGGATCC CGCGGCCGTG   2100
TTTTCCTGGT GGCCCGGCCG TGCCTGAGGT TTCTCCCCGA GCCGCCGCCT CTGCGGGCTC   2160
CCGGGTGCCC TTGCCCTCGC GGTCCCCGGC CCTCGCCCGT CTGTGCCCTC TTCCCCGCCC   2220
GCCGCCCGCC GATCCTCTTC TTCCCCCCGA GCGGCTCACC GGCTTCACGT CCGTTGGTGG   2280
CCCCGCCTGG GACCGAACCC GGCACCGCCT CGTGGGGCGC CGCCGCCGGC CACTGATCGG   2340
CCCGGCGTCC GCGTCCCCCG GCGCGCGCCT TGGGGACCGG GTCGGTGGCG CGCCGCGTGG   2400
GGCCCGGTGG GCTTCCCGGA GGGTTCCGGG GGTCGGCCTG CGGCGCGTGC GGGGGAGGAG   2460
ACGGTTCCGG GGGACCGGCC GCGGCTGCGG CGGCGGCGGT GGTGGGGGGA GCCGCGGGGA   2520
TCGCCGAGGG CCGGTCGGCC GCCCCGGGTG CCCCGCGGTG CCGCCGGCGG CGGTGAGGCC   2580
CCGCGCGTGT GTCCCGGCTG CGGTCGGCCG CGCTCGAGGG GTCCCCGTGG CGTCCCCTTC   2640
CCCGCCGGCC GCCTTTCTCG CGCCTTCCCC GTCGCCCCGG CCTCGCCCGT GGTCTCTCGT   2700
CTTCTCCCGG CCCGCTCTTC CGAACCGGGT CGGCGCGTCC CCCGGGTGCG CCTCGCTTCC   2760
CGGGCCTGCC GCGGCCCTTC CCCGAGGCGT CCGTCCCGGG CGTCGGCGTC GGGGAGAGCC   2820
CGTCCTCCCC GCGTGGCGTC GCCCCGTTCG GCGCGCGCGT GCGCCCGAGC GCGGCCCGGT   2880
GGTCCCTCCC GGACAGGCGT TCGTGCGACG TGTGGCGTGG GTCGACCTCC GCCTTGCCGG   2940
TCGCTCGCCC TCTCCCCGGG TCGGGGGGTG GGGCCCGGGC CGGGGCCTCG GCCCCGGTCG   3000
CTGCCTCCCG TCCCGGGCGG GGGCGGGCGC GCCGGCCGGC CTCGGTCGCC CTCCCTTGGC   3060
CGTCGTGTGG CGTGTGCCAC CCCTGCGCCG GCGCCCGCCG GCGGGGCTCG GAGCCGGGCT   3120
TCGGCCGGGC CCCGGGCCCT CGACCGGACC GGCTGCGCGG GCGCTGCGGC CGCACGGCGC   3180
GACTGTCCCC GGGCCGGGCA CCGCGGTCCG CCTCTCGCTC GCCGCCCGGA CGTCGGGGCC   3240
GCCCCGCGGG GCGGGCGGAG CGCCGTCCCC GCCTCGCCGC CGCCCGCGGG CGCCGGCCGC   3300
GCGCGCGCGC GCGTGGCCGC CGGTCCCTCC CGGCCGCCGG GCGCGGGTCG GGCCGTCCGC   3360
CTCCTCGCGG GCGGGCGCGA CGAAGAAGCG TCGCGGGTCT GTGGCGCGGG GCCCCCGGTG   3420
GTCGTGTCGC GTGGGGGGCG GGTGGTTGGG GCGTCCGGTT CGCCGCGCCC CGCCCCGGCC   3480
CCACCGGTCC CGGCCGCCGC CCCCGCGCCC GCTCGCTCCC TCCCGTCCGC CCGTCCGCGG   3540
CCCGTCCGTC CGTCCGTCCG TCGTCCTCCT CGCTTGCGGG GCGCCGGGCC CGTCCTCGCG   3600
AGGCCCCCCG GCCGGCCGTC CGGCCGCGTC GGGGGCTCGC CGCGCTCTAC CTTACCTACC   3660
TGGTTGATCC TGCCAGTAGC ATATGCTTGT CTCAAAGATT AAGCCATGCA TGTCTAAGTA   3720
CGCACGGCCG GTACAGTGAA ACTGCGAATG GCTCATTAAA TCAGTTATGG TTCCTTTGGT   3780
CGCTCGCTCC TCTCCTACTT GGATAACTGT GGTAATTCTA GAGCTAATAC ATGCCGACGG   3840
GCGCTGACCC CCTTCGCGGG GGGGATGCGT GCATTTATCA GATCAAAACC AACCCGGTCA   3900
```

-continued

```
GCCCCTCTCC GGCCCCGGCC GGGGGGCGGG CGCCGGCGGC TTTGGTGACT CTAGATAACC   3960
TCGGGCCGAT CGCACGCCCC CCGTGGCGGC GACGACCCAT TCGAACGTCT GCCCTATCAA   4020
CTTTCGATGG TAGTCGCCGT GCCTACCATG GTGACCACGG GTGACGGGGA ATCAGGGTTC   4080
GATTCCGGAG AGGGAGCCTG AGAAACGGCT ACCACATCCA AGGAAGGCAG CAGGCGCGCA   4140
AATTACCCAC TCCCGACCCG GGGAGGTAGT GACGAAAAAT AACAATACAG GACTCTTTCG   4200
AGGCCCTGTA ATTGGAATGA GTCCACTTTA AATCCTTTAA CGAGGATCCA TTGGAGGGCA   4260
AGTCTGGTGC CAGCAGCCGC GGTAATTCCA GCTCCAATAG CGTATATTAA AGTTGCTGCA   4320
GTTAAAAAGC TCGTAGTTGG ATCTTGGGAG CGGGCGGGCG GTCCGCCGCG AGGCGAGCCA   4380
CCGCCCGTCC CCGCCCCTTG CCTCTCGGCG CCCCCTCGAT GCTCTTAGCT GAGTGTCCCG   4440
CGGGGCCCGA AGCGTTTACT TTGAAAAAAT TAGAGTGTTC AAAGCAGGCC CGAGCCGCCT   4500
GGATACCGCA GCTAGGAATA ATGGAATAGG ACCGCGGTTC TATTTTGTTG GTTTTCGGAA   4560
CTGAGGCCAT GATTAAGAGG GACGGCCGGG GGCATTCGTA TTGCGCCGCT AGAGGTGAAA   4620
TTCTTGGACC GGCGCAAGAC GGACCAGAGC GAAAGCATTT GCCAAGAATG TTTTCATTAA   4680
TCAAGAACGA AAGTCGGAGG TTCGAAGACG ATCAGATACC GTCGTAGTTC CGACCATAAA   4740
CGATGCCGAC CGGCGATGCG GCGGCGTTAT TCCCATGACC CGCCGGGCAG CTTCCGGGAA   4800
ACCAAAGTCT TTGGGTTCCG GGGGGAGTAT GGTTGCAAAG CTGAAACTTA AAGGAATTGA   4860
CGGAAGGGCA CCACCAGGAG TGGAGCCTGC GGCTTAATTT GACTCAACAC GGGAAACCTC   4920
ACCCGGCCCG GACACGGACA GGATTGACAG ATTGATAGCT CTTTCTCGAT TCCGTGGGTG   4980
GTGGTGCATG GCCGTTCTTA GTTGGTGGAG CGATTTGTCT GGTTAATTCC GATAACGAAC   5040
GAGACTCTGG CATGCTAACT AGTTACGCGA CCCCCGAGCG GTCGGCGTCC CCCAACTTCT   5100
TAGAGGGACA AGTGGCGTTC AGCCACCCGA GATTGAGCAA TAACAGGTCT GTGATGCCCT   5160
TAGATGTCCG GGGCTGCACG CGCGCTACAC TGACTGGCTC AGCGTGTGCC TACCCTACGC   5220
CGGCAGGCGC GGGTAACCCG TTGAACCCCA TTCGTGATGG GGATCGGGGA TTGCAATTAT   5280
TCCCCATGAA CGAGGGAATT CCCGAGTAAG TGCGGGTCAT AAGCTTGCGT TGATTAAGTC   5340
CCTGCCCTTT GTACACACCG CCCGTCGCTA CTACCGATTG GATGGTTTAG TGAGGCCCTC   5400
GGATCGGCCC CGCCGGGGTC GGCCCACGGC CCTGGCGGAG CGCTGAGAAG ACGGTCGAAC   5460
TTGACTATCT AGAGGAAGTA AAAGTCGTAA CAAGGTTTCC GTAGGTGAAC CTGCGGAAGG   5520
ATCATTAACG GAGCCCGGAG GGCGAGGCCC GCGGCGGCGC CGCCGCCGCC GCGCGCTTCC   5580
CTCCGCACAC CCACCCCCCC ACCGCGACGC GGCGCGTGCG CGGGCGGGGC CCGCGTGCCC   5640
GTTCGTTCGC TCGCTCGTTC GTTCGCCGCC CGGCCCCGCC GCCGCGAGAG CCGAGAACTC   5700
GGGAGGGAGA CGGGGGGGAG AGAGAGAGAG AGAGAGAGAG AGAGAGAGAG AGAGAGAGAA   5760
AGAAGGGCGT GTCGTTGGTG TGCGCGTGTC GTGGGGCCGG CGGGCGGCGG GGAGCGGTCC   5820
CCGGCCGCGG CCCCGACGAC GTGGGTGTCG GCGGGCGCGG GGGCGGTTCT CGGCGGCGTC   5880
GCGGCGGGTC TGGGGGGGTC TCGGTGCCCT CCTCCCCGCC GGGGCCCGTC GTCCGGCCCC   5940
GCCGCGCCGG CTCCCCGTCT TCGGGGCCGG CCGGATTCCC GTCGCCTCCG CCGCGCCGCT   6000
CCGCGCCGCC GGGCACGGCC CCGCTCGCTC TCCCCGGCCT TCCCGCTAGG GCGTCTCGAG   6060
GGTCGGGGGC CGGACGCCGG TCCCCTCCCC CGCCTCCTCG TCCGCCCCCC CGCCGTCCAG   6120
GTACCTAGCG CGTTCCGGCG CGGAGGTTTA AAGACCCCTT GGGGGGATCG CCCGTCCGCC   6180
CGTGGGTCGG GGGCGGTGGT GGGCCCGCGG GGGAGTCCCG TCGGGAGGGG CCCGGCCCCT   6240
CCCGCGCCTC CACCGCGGAC TCCGCTCCCC GGCCGGGGCC GCGCCGCCGC CGCCGCCGCG   6300
```

-continued

GCGGCCGTCG GGTGGGGGCT TTACCCGGCG GCCGTCGCGC GCCTGCCGCG CGTGTGGCGT 6360

GCGCCCCGCG CCGTGGGGGC GGGAACCCCC GGGCGCCTGT GGGGTGGTGT CCGCGCTCGC 6420

CCCCGCGTGG GCGGCGCGCG CCTCCCCGTG GTGTGAAACC TTCCGACCCC TCTCCGGAGT 6480

CCGGTCCCGT TTGCTGTCTC GTCTGGCCGG CCTGAGGCAA CCCCCTCTCC TCTTGGGCGG 6540

GGGGGGCGGG GGGACGTGCC GCGCCAGGAA GGGCCTCCTC CCGGTGCGTC GTCGGGAGCG 6600

CCCTCGCCAA ATCGACCTCG TACGACTCTT AGCGGTGGAT CACTCGGCTC GTGCGTCGAT 6660

GAAGAACGCA GCTAGCTGCG AGAATTAATG TGAATTGCAG GACACATTGA TCATCGACAC 6720

TTCGAACGCA CTTGCGGCCC CGGGTTCCTC CCGGGGCTAC GCCTGTCTGA GCGTCGCTTG 6780

CCGATCAATC GCCCCGGGGG TGCCTCCGGG CTCCTCGGGG TGCGCGGCTG GGGGTTCCCT 6840

CGCAGGGCCC GCCGGGGGCC CTCCGTCCCC CTAAGCGCAG ACCCGGCGGC GTCCGCCCTC 6900

CTCTTGCCGC CGCGCCCGCC CCTTCCCCCT CCCCCCGCGG GCCCTGCGTG GTCACGCGTC 6960

GGGTGGCGGG GGGGAGAGGG GGGCGCGCCC GGCTGAGAGA GACGGGGAGG GCGGCGCCGC 7020

CGCCGGAAGA CGGAGAGGGA AAGAGAGAGC CGGCTCGGGC CGAGTTCCCG TGGCCGCCGC 7080

CTGCGGTCCG GGTTCCTCCC TCGGGGGGCT CCCTCGCGCC GCGCGCGGCT CGGGGTTCGG 7140

GGTTCGTCGG CCCCGGCCGG GTGGAAGGTC CCGTGCCCGT CGTCGTCGTC GTCGCGCGTC 7200

GTCGGCGGTG GGGGCGTGTT GCGTGCGGTG TGGTGGTGGG GGAGGAGGAA GGCGGGTCCG 7260

GAAGGGGAAG GGTGCCGGCG GGGAGAGAGG GTCGGGGGAG CGCGTCCCGG TCGCCGCGGT 7320

TCCGCCGCCC GCCCCCGGTG GCGGCCCGGC GTCCGGCCGA CCGGCCGCTC CCCGCGCCCC 7380

TCCTCCTCCC CGCCGCCCCT CCTCCGAGGC CCCGCCCGTC CTCCTCGCCC TCCCCGCGCG 7440

TACGCGCGCG CGCCCGCCCG CCCGGCTCGC CTCGCGGCGC GTCGGCCGGG GCCGGGAGCC 7500

CGCCCCGCCG CCCGCCCGTG GCCGCGGCGC CGGGGTTCGC GTGTCCCCGG CGGCGACCCG 7560

CGGGACGCCG CGGTGTCGTC CGCCGTCGCG CGCCCGCCTC CGGCTCGCGG CCGCGCCGCG 7620

CCGCGCCGGG GCCCCGTCCC GAGCTTCCGC GTCGGGGCGG CGCGGCTCCG CCGCCGCGTC 7680

CTCGGACCCG TCCCCCCGAC CTCCGCGGGG GAGACGCGCC GGGGCGTGCG GCGCCCGTCC 7740

CGCCCCCGGC CCGTGCCCCT CCCTCCGGTC GTCCCGCTCC GGCGGGGCGG CGCGGGGGCG 7800

CCGTCGGCCG CGCGCTCTCT CTCCCGTCGC CTCTCCCCCT CGCCGGGCCC GTCTCCCGAC 7860

GGAGCGTCGG GCGGGCGGTC GGGCCGGCGC GATTCCGTCC GTCCGTCCGC CGAGCGGCCC 7920

GTCCCCCTCC GAGACGCGAC CTCAGATCAG ACGTGGCGAC CCGCTGAATT TAAGCATATT 7980

AGTCAGCGGA GGAAAAGAAA CTAACCAGGA TTCCCTCAGT AACGGCGAGT GAACAGGGAA 8040

GAGCCCAGCG CCGAATCCCC GCCCCGCGGG GCGCGGGACA TGTGGCGTAC GGAAGACCCG 8100

CTCCCCGGCG CCGCTCGTGG GGGGCCCAAG TCCTTCTGAT CGAGGCCCAG CCCGTGGACG 8160

GTGTGAGGCC GGTAGCGGCC GGCGCGCGCC CGGGTCTTCC CGGAGTCGGG TTGCTTGGGA 8220

ATGCAGCCCA AAGCGGGTGG TAAACTCCAT CTAAGGCTAA ATACCGGCAC GAGACCGATA 8280

GTCAACAAGT ACCGTAAGGG AAAGTTGAAA AGAACTTTGA AGAGAGAGTT CAAGAGGGCG 8340

TGAAACCGTT AAGAGGTAAA CGGGTGGGGT CCGCGCAGTC CGCCCGGAGG ATTCAACCCG 8400

GCGGCGGGTC CGGCCGTGTC GGCGGCCCGG CGGATCTTTC CCGCCCCCCG TTCCTCCCGA 8460

CCCCTCCACC CGCCCTCCCT TCCCCCGCCG CCCCTCCTCC TCCTCCCCGG AGGGGGCGGG 8520

CTCCGGCGGG TGCGGGGGTG GGCGGGCGGG GCCGGGGGTG GGGTCGGCGG GGGACCGTCC 8580

CCCGACCGGC GACCGGCCGC CGCCGGGCGC ATTTCCACCG CGGCGGTGCG CCGCGACCGG 8640

CTCCGGGACG GCTGGGAAGG CCCGGCGGGG AAGGTGGCTC GGGGGGCCCC GTCCGTCCGT 8700

-continued

```
CCGTCCTCCT CCTCCCCCGT CTCCGCCCCC CGGCCCCGCG TCCTCCCTCG GGAGGGCGCG   8760
CGGGTCGGGG CGGCGGCGGC GGCGGCGGTG GCGGCGGCGG CGGGGGCGGC GGGACCGAAA   8820
CCCCCCCCGA GTGTTACAGC CCCCCCGGCA GCAGCACTCG CCGAATCCCG GGGCCGAGGG   8880
AGCGAGACCC GTCGCCGCGC TCTCCCCCCT CCCGGCGCCC ACCCCCGCGG GGAATCCCCC   8940
GCGAGGGGGG TCTCCCCCGC GGGGGCGCGC CGGCGTCTCC TCGTGGGGGG GCCGGGCCAC   9000
CCCTCCCACG GCGCGACCGC TCTCCCACCC CTCCTCCCCG CGCCCCCGCC CCGGCGACGG   9060
GGGGGGTGCC GCGCGCGGGT CGGGGGGCGG GGCGGACTGT CCCCAGTGCG CCCCGGGCGG   9120
GTCGCGCCGT CGGGCCCGGG GGAGGTTCTC TCGGGGCCAC GCGCGCGTCC CCCGAAGAGG   9180
GGGACGGCGG AGCGAGCGCA CGGGGTCGGC GGCGACGTCG GCTACCCACC CGACCCGTCT   9240
TGAAACACGG ACCAAGGAGT CTAACACGTG CGCGAGTCGG GGGCTCGCAC GAAAGCCGCC   9300
GTGGCGCAAT GAAGGTGAAG GCCGGCGCGC TCGCCGGCCG AGGTGGGATC CCGAGGCCTC   9360
TCCAGTCCGC CGAGGGCGCA CCACCGGCCC GTCTCGCCCG CCGCGCCGGG GAGGTGGAGC   9420
ACGAGCGCAC GTGTTAGGAC CCGAAAGATG GTGAACTATG CCTGGGCAGG GCGAAGCCAG   9480
AGGAAACTCT GGTGGAGGTC CGTAGCGGTC CTGACGTGCA AATCGGTCGT CCGACCTGGG   9540
TATAGGGGCG AAAGACTAAT CGAACCATCT AGTAGCTGGT TCCCTCCGAA GTTTCCCTCA   9600
GGATAGCTGG CGCTCTCGCA GACCCGACGC ACCCCCGCCA CGCAGTTTTA TCCGGTAAAG   9660
CGAATGATTA GAGGTCTTGG GGCCGAAACG ATCTCAACCT ATTCTCAAAC TTTAAATGGG   9720
TAAGAAGCCC GGCTCGCTGG CGTGGAGCCG GGCGTGGAAT GCGAGTGCCT AGTGGGCCAC   9780
TTTTGGTAAG CAGAACTGGC GCTGCGGGAT GAACCGAACG CCGGGTTAAG GCGCCCGATG   9840
CCGACGCTCA TCAGACCCCA GAAAAGGTGT TGGTTGATAT AGACAGCAGG ACGGTGGCCA   9900
TGGAAGTCGG AATCCGCTAA GGAGTGTGTA ACAACTCACC TGCCGAATCA ACTAGCCCTG   9960
AAAATGGATG GCGCTGGAGC GTCGGGCCCA TACCCGGCCG TCGCCGGCAG TCGAGAGTGG  10020
ACGGGAGCGG CGGGGGCGGC GCGCGCGCGC GCGCGTGTGG TGTGCGTCGG AGGGCGGCGG  10080
CGGCGGCGGC GGCGGGGGTG TGGGGTCCTT CCCCCGCCCC CCCCCCCACG CCTCCTCCCC  10140
TCCTCCCGCC CACGCCCCGC TCCCCGCCCC CGGAGCCCCG CGGACGCTAC GCCGCGACGA  10200
GTAGGAGGGC CGCTGCGGTG AGCCTTGAAG CCTAGGGCGC GGGCCCGGGT GGAGCCGCCG  10260
CAGGTGCAGA TCTTGGTGGT AGTAGCAAAT ATTCAAACGA GAACTTTGAA GGCCGAAGTG  10320
GAGAAGGGTT CCATGTGAAC AGCAGTTGAA CATGGGTCAG TCGGTCCTGA GAGATGGGCG  10380
AGCGCCGTTC CGAAGGGACG GGCGATGGCC TCCGTTGCCC TCGGCCGATC GAAAGGGAGT  10440
CGGGTTCAGA TCCCCGAATC CGGAGTGGCG GAGATGGGCG CCGCGAGGCG TCCAGTGCGG  10500
TAACGCGACC GATCCCGGAG AAGCCGGCGG GAGCCCCGGG GAGAGTTCTC TTTTCTTTGT  10560
GAAGGGCAGG GCGCCCTGGA ATGGGTTCGC CCCGAGAGAG GGGCCCGTGC CTTGGAAAGC  10620
GTCGCGGTTC CGGCGGCGTC CGGTGAGCTC TCGCTGGCCC TTGAAAATCC GGGGGAGAGG  10680
GTGTAAATCT CGCGCCGGGC CGTACCCATA TCCGCAGCAG GTCTCCAAGG TGAACAGCCT  10740
CTGGCATGTT GGAACAATGT AGGTAAGGGA AGTCGGCAAG CCGGATCCGT AACTTCGGGA  10800
TAAGGATTGG CTCTAAGGGC TGGGTCGGTC GGGCTGGGGC GCGAAGCGGG GCTGGGCGCG  10860
CGCCGCGGCT GGACGAGGCG CGCGCCCCCC CCACGCCCGG GGCACCCCCC TCGCGGCCCT  10920
CCCCCGCCCC ACCCGCGCGC GCCGCTCGCT CCCTCCCCAC CCCGCGCCCT CTCTCTCTCT  10980
CTCTCCCCCG CTCCCCGTCC TCCCCCCTCC CCGGGGGAGC GCCGCGTGGG GGCGCGGCGG  11040
GGGGAGAAGG GTCGGGGCGG CAGGGGCCGC GCGGCGGCCG CCGGGGCGGC CGGCGGGGGC  11100
```

```
AGGTCCCCGC GAGGGGGGCC CCGGGGACCC GGGGGGCCGG CGGCGGCGCG GACTCTGGAC  11160
GCGAGCCGGG CCCTTCCCGT GGATCGCCCC AGCTGCGGCG GGCGTCGCGG CCGCCCCCGG  11220
GGAGCCCGGC GGCGGCGCGG CGCGCCCCCC ACCCCCACCC CACGTCTCGG TCGCGCGCGC  11280
GTCCGCTGGG GGCGGGAGCG GTCGGGCGGC GGCGGTCGGC GGGCGGCGGG GCGGGGCGGT  11340
TCGTCCCCCC GCCCTACCCC CCCGGCCCCG TCCGCCCCCC GTTCCCCCCT CCTCCTCGGC  11400
GCGCGGCGGC GGCGGCGGCA GGCGGCGGAG GGGCCGCGGG CCGGTCCCCC CCGCCGGGTC  11460
CGCCCCCGGG GCCGCGGTTC CGCGCGCGCC TCGCCTCGGC CGGCGCCTAG CAGCCGACTT  11520
AGAACTGGTG CGGACCAGGG GAATCCGACT GTTTAATTAA AACAAAGCAT CGCGAAGGCC  11580
CGCGGCGGGT GTTGACGCGA TGTGATTTCT GCCCAGTGCT CTGAATGTCA AAGTGAAGAA  11640
ATTCAATGAA GCGCGGGTAA ACGGCGGGAG TAACTATGAC TCTCTTAAGG TAGCCAAATG  11700
CCTCGTCATC TAATTAGTGA CGCGCATGAA TGGATGAACG AGATTCCCAC TGTCCCTACC  11760
TACTATCCAG CGAAACCACA GCCAAGGGAA CGGGCTTGGC GGAATCAGCG GGGAAAGAAG  11820
ACCCTGTTGA GCTTGACTCT AGTCTGGCAC GGTGAAGAGA CATGAGAGGT GTAGAATAAG  11880
TGGGAGGCCC CCGGCGCCCC CCCGGTGTCC CCGCGAGGGG CCCGGGGCGG GGTCCGCGGC  11940
CCTGCGGGCC GCCGGTGAAA TACCACTACT CTGATCGTTT TTTCACTGAC CCGGTGAGGC  12000
GGGGGGGCGA GCCCGAGGGG CTCTCGCTTC TGGCGCCAAG CGCCCGCCCG GCCGGGCGCG  12060
ACCCGCTCCG GGGACAGTGC CAGGTGGGGA GTTTGACTGG GGCGGTACAC CTGTCAAACG  12120
GTAACGCAGG TGTCCTAAGG CGAGCTCAGG GAGGACAGAA ACCTCCCGTG GAGCAGAAGG  12180
GCAAAAGCTC GCTTGATCTT GATTTTCAGT ACGAATACAG ACCGTGAAAG CGGGGCCTCA  12240
CGATCCTTCT GACCTTTTGG GTTTTAAGCA GGAGGTGTCA GAAAAGTTAC CACAGGGATA  12300
ACTGGCTTGT GGCGGCCAAG CGTTCATAGC GACGTCGCTT TTTGATCCTT CGATGTCGGC  12360
TCTTCCTATC ATTGTGAAGC AGAATTCGCC AAGCGTTGGA TTGTTCACCC ACTAATAGGG  12420
AACGTGAGCT GGGTTTAGAC CGTCGTGAGA CAGGTTAGTT TTACCCTACT GATGATGTGT  12480
TGTTGCCATG GTAATCCTGC TCAGTACGAG AGGAACCGCA GGTTCAGACA TTTGGTGTAT  12540
GTGCTTGGCT GAGGAGCCAA TGGGGCGAAG CTACCATCTG TGGGATTATG ACTGAACGCC  12600
TCTAAGTCAG AATCCCGCCC AGGCGAACGA TACGGCAGCG CCGCGGAGCC TCGGTTGGCC  12660
TCGGATAGCC GGTCCCCCGC CTGTCCCCGC CGGCGGGCCG CCCCCCCCTC CACGCGCCCC  12720
GCCGCGGGAG GGCGCGTGCC CCGCCGCGCG CCGGGACCGG GGTCCGGTGC GGAGTGCCCT  12780
TCGTCCTGGG AAACGGGGCG CGGCCGGAAA GGCGGCCGCC CCCTCGCCCG TCACGCACCG  12840
CACGTTCGTG GGGAACCTGG CGCTAAACCA TTCGTAGACG ACCTGCTTCT GGGTCGGGGT  12900
TTCGTACGTA GCAGAGCAGC TCCCTCGCTG CGATCTATTG AAAGTCAGCC CTCGACACAA  12960
GGGTTTGTCC GCGCGCGCGT GCGTGCGGGG GGCCCGGCGG GCGTGCGCGT TCGGCGCCGT  13020
CCGTCCTTCC GTTCGTCTTC CTCCCTCCCG GCCTCTCCCG CCGACCGCGG CGTGGTGGTG  13080
GGGTGGGGGG GAGGGCGCGC GACCCCGGTC GGCCGCCCCG CTTCTTCGGT TCCCGCCTCC  13140
TCCCCGTTCA CGCCGGGGCG GCTCGTCCGC TCCGGGCCGG GACGGGGTCC GGGGAGCGTG  13200
GTTTGGGAGC CGCGGAGGCG CCGCGCCGAG CCGGGCCCCG TGGCCCGCCG GTCCCCGTCC  13260
CGGGGGTTGG CCGCGCGGCG CGGTGGGGGG CCACCCGGGG TCCCGGCCCT CGCGCGTCCT  13320
TCCTCCTCGC TCCTCCGCAC GGGTCGACCG ACGAACCGCG GGTGGCGGGC GGCGGGCGGC  13380
GAGCCCCACG GGCGTCCCCG CACCCGGCCG ACCTCCGCTC GCGACCTCTC CTCGGTCGGG  13440
CCTCCGGGGT CGACCGCCTG CGCCCGCGGG CGTGAGACTC AGCGGCGTCT CGCCGTGTCC  13500
```

-continued

```
CGGGTCGACC GCGGCCTTCT CCACCGAGCG GCGGTGTAGG AGTGCCCGTC GGGACGAACC  13560
GCAACCGGAG CGTCCCCGTC TCGGTCGGCA CCTCCGGGGT CGACCAGCTG CCGCCCGCGA  13620
GCTCCGGACT TAGCCGGCGT CTGCACGTGT CCCGGGTCGA CCAGCAGGCG GCCGCCGGAC  13680
GCAGCGGCGC ACGCACGCGA GGGCGTCGAT TCCCCTTCGC GCGCCCGCGC CTCCACCGGC  13740
CTCGGCCCGC GGTGGAGCTG GGACCACGCG GAACTCCCTC TCCCACATTT TTTTCAGCCC  13800
CACCGCGAGT TTGCGTCCGC GGGACCTTTA AGAGGGAGTC ACTGCTGCCG TCAGCCAGTA  13860
CTGCCTCCTC CTTTTTCGCT TTTAGGTTTT GCTTGCCTTT TTTTTTTTTT TTTTTTTTTT  13920
TTTTTTCTTT CTTTCTTTCT TTCTTTCTTT CTTTCTTTCT TTCTTTCTTT CGCTTGTCTT  13980
CTTCTTGTGT TCTCTTCTTG CTCTTCCTCT GTCTGTCTCT CTCTCTCTCT CTCTCTCTGT  14040
CTCTCGCTCT CGCCCTCTCT CTCTTCTCTC TCTCTCTCTC TCTCTCTCTG TCTCTCGCTC  14100
TCGCCCTCTC TCTCTCTCTT CTCTCTGTCT CTCTCTCTCT CTCTCTCTCT CTCTCTCTCT  14160
GTCGCTCTCG CCCTCTCGCT CTCTCTCTGT CTCTGTCTGT GTCTCTCTCT CTCCCTCCCT  14220
CCCTCCCTCC CTCCCTCCCT CCCTCCCCTT CCTTGGCGCC TTCTCGGCTC TTGAGACTTA  14280
GCCGCTGTCT CGCCGTACCC CGGGTCGACC GGCGGGCCTT CTCCACCGAG CGGCGTGCCA  14340
CAGTGCCCGT CGGGACGAGC CGGACCCGCC GCGTCCCCGT CTCGGTCGGC ACCTCCGGGG  14400
TCGACCAGCT GCCGCCCGCG AGCTCCGGAC TTAGCCGGCG TCTGCACGTG TCCCGGGTCG  14460
ACCAGCAGGC GGCCGCCGGA CGCAGCGGCG CACCGACGGA GGGCGCTGAT TCCCGTTCAC  14520
GCGCCCGCGC CTCCACCGGC CTCGGCCCGC CGTGGAGCTG GGACCACGCG GAACTCCCTC  14580
TCCTACATTT TTTTCAGCCC CACCGCGAGT TTGCGTCCGC GGGACCTTTA AGAGGGAGTC  14640
ACTGCTGCCG TCAGCCAGTA CTGCCTCCTC CTTTTTCGCT TTTAGGTTTT GCTTGCCTTT  14700
TTTTTTTTTT TTTTTTTTTT TTTTTTCTTT CTTTCTTTCT TTCTTTCTTT CTTTCTTTCT  14760
TTCTTTCTTT CTTTCGCTCT CGCTCTCTCG CTCTCTCCCT CGCTCGTTTC TTTCTTTCTC  14820
TTTCTCTCTC TCTCTCTCTC TCTCTCTCTC TCTGTCTCTC GCTCTCGCCC TCTCTCTCTC  14880
TTTCTCTCTC TCTCTGTCTC TCTCTCTCTC TCTCTCTCTC TCTCTCTCTC CCTCCCTCCC  14940
TCCCCCTCCC TCCCTCTCTC CCCTTCCTTG GCGCCTTCTC GGCTCTTGAG ACTTAGCCGC  15000
TGTCTCGCCG TGTCCCGGGT CGACCGGCGG GCCTTCTCCA CCGAGCGGCG TGCCACAGTG  15060
CCCGTCGGGA CGAGCCGGAC CCGCCGCGTC CCCGTCTCGG TCGGCACCTC CGGGGTCGAC  15120
CAGCTGCCGC CCGCGAGCTC CGGACTTAGC CGGCGTCTGC ACGTGTCCCG GGTCGACCAG  15180
CAGGCGGCCG CCGGACGCTG CGGCGCACCG ACGCGAGGGC GTCGATTCCG GTTCACGCGC  15240
CGGCGACCTC CACCGGCCTC GGCCCGCGGT GGAGCTGGGA CCACGCGGAA CTCCCTCTCC  15300
CACATTTTTT TCAGCCCCAC CGCGAGTTTG CGTCCGCGGG ACTTTTAAGA GGGAGTCACT  15360
GCTGCCGTCA GCCAGTAATG CTTCCTCCTT TTTTGCTTTT TGGTTTTGCC TTGCGTTTTC  15420
TTTCTTTCTT TCTTTCTTTC TTTCTTTCTT TCTTTCTTTC TCTCTCTCTC TCTCTCTCTC  15480
TCTCTGTCTC TCTCTCTCTG TCTCTCTCCC CTCCCTCCCT CCTTGGTGCC TTCTCGGCTC  15540
GCTGCTGCTG CTGCCTCTGC CTCCACGGTT CAAGCAAACA GCAAGTTTTC TATTTCGAGT  15600
AAAGACGTAA TTTCACCATT TTGGCCGGGC TGGTCTCGAA CTCCCGACCT AGTGATCCGC  15660
CCGCCTCGGC CTCCCAAAGA CTGCTGGGAG TACAGATGTG AGCCACCATG CCCGGCCGAT  15720
TCCTTCCTTT TTTCAATCTT ATTTTCTGAA CGCTGCCGTG TATGAACATA CATCTACACA  15780
CACACACACA CACACACACA CACACACACA CACACACACA CACACACCCC GTAGTGATAA  15840
AACTATGTAA ATGATATTTC CATAATTAAT ACGTTTATAT TATGTTACTT TTAATGGATG  15900
```

-continued

```
AATATGTATC GAAGCCCCAT TTCATTTACA TACACGTGTA TGTATATCCT TCCTCCCTTC  15960
CTTCATTCAT TATTTATTAA TAATTTTCGT TTATTTATTT TCTTTTCTTT TGGGGCCGGC  16020
CCGCCTGGTC TTCTGTCTCT GCGCTCTGGT GACCTCAGCC TCCCAAATAG CTGGGACTAC  16080
AGGGATCTCT TAAGCCCGGG AGGAGAGGTT AACGTGGGCT GTGATCGCAC ACTTCCACTC  16140
CAGCTTACGT GGGCTGCGGT GCGGTGGGGT GGGGTGGGGT GGGGTGGGGT GCAGAGAAAA  16200
CGATTGATTG CGATCTCAAT TGCCTTTTAG CTTCATTCAT ACCCTGTTAT TTGCTCGTTT  16260
ATTCTCATGG GTTCTTCTGT GTCATTGTCA CGTTCATCGT TTGCTTGCCT GCTTGCCTGT  16320
TTATTTCCTT CCTTCCTTCC TTCCTTCCTT CCTTCCTTCC TTCCTTCCTT CCCTCCCTTA  16380
CTGGCAGGGT CTTCCTCTGT CTCTGCCGCC CAGGATCACC CCAACCTCAA CGCTTTGGAC  16440
CGACCAAACG GTCGTTCTGC CTCTGATCCC TCCCATCCCC ATTACCTGAG ACTACAGGCG  16500
CGCACCACCA CACCGGCTGA CTTTTATGTT GTTTCTCATG TTTTCCGTAG GTAGGTATGT  16560
GTGTGTGTGT GTGTGTGTGT GTGTGTGTGT GTGTGTGTGT GTGTGTGTGT GTGTGTATCT  16620
ATGTATGTAC GTATGTATGT ATGTATGTGA GTGAGATGGG TTTCGGGGTT CTATCATGTT  16680
GCCCACGCTG GTCTCGAACT CCTGTCCTCA AGCAATCCGC CTGCCTGCCT CGGCCGCCCA  16740
CACTGCTGCT ATTACAGGCG TGAGACGCTG CGCCTGGCTC CTTCTACATT TGCCTGCCTG  16800
CCTGCCTGCC TGCCTGCCTA TCAATCGTCT TCTTTTTAGT ACGGATGTCG TCTCGCTTTA  16860
TTGTCCATGC TCTGGGCACA CGTGGTCTCT TTTCAAACTT CTATGATTAT TATTATTGTA  16920
GGCGTCATCT CACGTGTCGA GGTGATCTCG AACTTTTAGG CTCCAGAGAT CCTCCCGCAT  16980
CGGCCTCCCG GAGTGCTGTG ATGACACGCG TGGGCACGGT ACGCTCTGGT CGTGTTTGTC  17040
GTGGGTCGGT TCTTTCCGTT TTTAATACGG GGACTGCGAA CGAAGAAAAT TTTCAGACGC  17100
ATCTCACCGA TCCGCCTTTT CGTTCTTTCT TTTTATTCTC TTTAGACGGA GTTTCACTCT  17160
TGTCGCCCAG GGTGGAGTAC GATGGCGGCT CTCGGCTCAC CGCACCCTCC GCCTCCCAGG  17220
TTCAAGTGAT TCTCCTGCCT CAGCCTTCCC GAGTAGCTGG AATGACAGAG ATGAGCCATC  17280
GTGCCCGGCT AATTTTTCTA TTTTTAGTAC AGATGGGGTT TCTCCATCTT GGTCAGGCTG  17340
GTCTTCAACT TCCGACCGTT GGAGAATCTT AACTTTCTTG GTGGTGGTTG TTTTCCTTTT  17400
TCTTTTTTTT TCTTTTCTTT TCTTTCCTTC TCCTCCCCCC CCCACCCCCC TTGTCGTCGT  17460
CCTCCTCCTC CTCCTCCTCC TCCTCCTCCT CCTCCTCCTC CTCCTCCTCC TCTTTCATTT  17520
CTTTCAGCTG GGCTCTCCTA CTTGTGTTGC TCTGTTGCTC ACGCTGGTCT CAAACTCCTG  17580
GCCTTGACTC TTCTCCCGTC ACATCCGCCG TCTGGTTGTT GAAATGAGCA TCTCTCGTAA  17640
AATGGAAAAG ATGAAAGAAA TAAACACGAA GACGGAAAGC ACGGTGTGAA CGTTTCTCTT  17700
GCCGTCTCCC GGGGTGTACC TTGGACCCGG AAACACGGAG GGAGCTTGGC TGAGTGGGTT  17760
TTCGGTGCCG AAACCTCCCG AGGGCCTCCT TCCCTCTCCC CCTTGTCCCC GCTTCTCCGC  17820
CAGCCGAGGC TCCCACCGCC GCCCCTGGCA TTTTCCATAG GAGAGGTATG GGAGAGGACT  17880
GACACGCCTT CCAGATCTAT ATCCTGCCGG ACGTCTCTGG CTCGGCGTGC CCCACCGGCT  17940
ACCTGCCACC TTCCAGGGAG CTCTGAGGCG GATGCGACCC CCACCCCCCC GTCACGTCCC  18000
GCTACCCTCC CCCGGCTGGC CTTTGCCGGG CGACCCCAGG GGAACCGCGT TGATGCTGCT  18060
TCGGATCCTC CGGCGAAGAC TTCCACCGGA TGCCCCGGGT GGGCCGGTTG GGATCAGACT  18120
GGACCACCCC GGACCGTGCT GTTCTTGGGG GTGGGTTGAC GTACAGGGTG GACTGGCAGC  18180
CCCAGCATTG TAAAGGGTGC GTGGGTATGG AAATGTCACC TAGGATGCCC TCCTTCCCTT  18240
CGGTCTGCCT TCAGCTGCCT CAGGCGTGAA GACAACTTCC CATCGGAACC TCTTCTCTTC  18300
```

-continued

```
CCTTTCTCCA GCACACAGAT GAGACGCACG AGAGGGAGAA ACAGCTCAAT AGATACCGCT  18360
GACCTTCATT TGTGGAATCC TCAGTCATCG ACACACAAGA CAGGTGACTA GGCAGGGACA  18420
CAGATCAAAC ACTATTTCCG GGTCCTCGTG GTGGGATTGG TCTCTCTCTC TCTCTCTCTC  18480
TCTCTCTCTC TCTCTCTCTC TCTCGCACGC GCACGCGCGC ACACACACAC ACAATTTCCA  18540
TATCTAGTTC ACAGAGCACA CTCACTTCCC CTTTTCACAG TACGCAGGCT GAGTAAAACG  18600
CGCCCCACCC TCCACCCGTT GGCTGACGAA ACCCCTTCTC TACAATTGAT GAAAAAGATG  18660
ATCTGGGCCG GGCACGCTAG CTCACGCCTG TCACTCCGGC ACTTTGGGAG GCCGAGGCGG  18720
GTGGATCGCT TGGGGCCGGG AGTTCGAGAC CAGGCTGGCC GACGTGGCGA AACCCCGTCT  18780
CTCTGAAAAA TAGAACGATT AGCCGGGCCT GGTGGCGTGG GCTTGGAATC ACGACCGCTC  18840
GGGAGACTGG GGCGGGCGAC TTGTTCCAAC CGGGGAGGCC GAGGCCGCGA TGAGCTGAGA  18900
TCGTGCCGTG GCGATGCGGC CTGGATGACG GAGCGAGACC CCGTCTCGAG AGAATCATGA  18960
TGTTATTATA AGATGAGTTG TGCGCGGTGA TGGCCGCCTG TAGTCGCGGC TACTCGGGAG  19020
GCTGAGACGA GGAGAAGATC ACTTGAGGCC CCACAGGTCG AGGCTTCGGT CGGCCGTGAC  19080
CCACTGTATC CTGGGCAGTC ACCGGTCAAG GAGATATGCC CCTTCCCCGT TTGCTTTTCT  19140
TTTCTTCCCT TCTCTTTTCT TCTTTTTGCT TCTCTTTTCT TTCTTTCTTT CTTTCTTTCT  19200
TTCTTTCTTT CTTTCTTTCT TTTTCTTTTT CTCTCTTCCC CTCTTTCTTT CCTGCCTTCC  19260
TGCCTTTCTT CTTTTCTTCT TTCCTCCCTT CCTCCCTTCC TTCTTTCCTC CCGCCTCAGC  19320
CTCCCAAAGT GCTGGGATGA CTGGCGGGAG GCACCATGCC TGCTTGGCCC AAAGAGACCC  19380
TCTTGGAAAG TGAGACGCAG AGAGCGCCTT CCAGTGATCT CATTGACTGA TTTAGAGACG  19440
GCATCTCGCT CCGTCACCCC GGCAGTGGTG CCGTCGTAAC TCACTCCCTG CAGCGTGGAC  19500
GCTCCTGGAC TCGAGCGATC CTTCCACCTC AGCCTCCAGA GTACAGAGCC TGGGACCGCG  19560
GGCACGCGCC ACTGTGCCCA CACCGTTTTT AATTGTTTTT TTTTCCCCCG AGACAGAGTT  19620
TCACTCTCGT GGCCTAGACT GCAGTGCGGT GGCGCGATCT TGGCTCACCG CAACCTCTGC  19680
CTCCCGGTTT CAAGCGATTC TCCTGCATCG GCCTCCTGAG TAGCCGGGAT TGCGGGCATG  19740
CGCTGCCACG TCTGGCTGAT TTCGTATTTT TAGTGGAGAC GGGGCTTCTC CATGTCGATC  19800
GGGCTGGTTT CGAACTCCCG ACCTCAGGTG ATCCGCCCTC CCCGGCCTCC GGAAGTGCTG  19860
GGATGACAGG CGTGAGCCAC CGCGCCCGGC CTTCATTTTT AAATGTTTTC CCACAGACGG  19920
GGTCTCATCA TTTCTTTGCA ACCCTCCTGC CCGGCGTCTC AAAGTGCTGG CGTGACGGGC  19980
GTGAGCCACT GCGCCTGGAC TCCGGGGAAT GACTCACGAC CACCATCGCT CTACTGATCC  20040
TTTCTTTCTT TCTTTCTTTC TTTCTTTCTT TCTTTCTTTC TTTCTTTCTT TCTTTCTTGA  20100
TGAATTATCT TATGATTTAT TTGTGTACTT ATTTTCAGAC GGAGTCTCGC TCTGGGCGGG  20160
GCGAGGCGAG GCGAGGCACA GCGCATCGCT TTGGAAGCCG CGGCAACGCC TTTCAAAGCC  20220
CCATTCGTAT GCACAGAGCC TTATTCCCTT CCTGGAGTTG GAGCTGATGC CTTCCGTAGC  20280
CTTGGGCTTC TCTCCATTCG GAAGCTTGAC AGGCGCAGGG CCACCCAGAG GCTGGCTGCG  20340
GCTGAGGATT AGGGGGTGTG TTGGGGCTGA AAACTGGGTC CCCTATTTTT GATACCTCAG  20400
CCGACACATC CCCCGACCGC CATCGCTTGC TCGCCCTCTG AGATCCCCCG CCTCCACCGC  20460
CTTGCAGGCT CACCTCTTAC TTTCATTTCT TCCTTTCTTG CGTTTGAGGA GGGGGTGCGG  20520
GAATGAGGGT GTGTGTGGGG AGGGGGTGCG GGGTGGGGAC GGAGGGGAGC GTCCTAAGGG  20580
TCGATTTAGT GTCATGCCTC TTTCACCACC ACCACCACCA CCGAAGATGA CAGCAAGGAT  20640
CGGCTAAATA CCGCGTGTTC TCATCTAGAA GTGGGAACTT ACAGATGACA GTTCTTGCAT  20700
```

GGGCAGAACG AGGGGGACCG GGGACGCGGA AGTCTGCTTG AGGGAGGAGG GGTGGAAGGA 20760
GAGACAGCTT CAGGAAGAAA ACAAAACACG AATACTGTCG GACACAGCAC TGACTACCCG 20820
GGTGATGAAA TCATCTGCAC ACTGAACACC CCCGTCACAA GTTTACCTAT GTCACAATCT 20880
TGCACATGTA TCGCTTGAAC GACAAATAAA AGTTAGGGGG GAGAAGAGAG GAGAGAGAGA 20940
GAGAGAGAGA GACAGAGAGA GACAGAGAGA GAGAGAGAGG AGGGAGAGAG GAAAACGAAA 21000
CACCACCTCC TTGACCTGAG TCAGGGGGTT TCTGGCCTTT TGGGAGAACG TTCAGCGACA 21060
ATGCAGTATT TGGGCCCGTT CTTTTTTTTT CTTCTTCTTT TCTTTCTTTT TTTTTGGACT 21120
GAGTCTCTCT CGCTCTGTCA CCCAGGCTGC GGTCGCGGTG GCGCTCTCTC GGCTCACTGA 21180
AACCTCTGCT TCCCGGGTTC CAGTGATTCT TCTTCGGTAG CTGGGATTAC AGGCGCACAC 21240
CATGACGGCG GGCTCATATT CCTATTTTCA GTAGAGACGG GGTTTCTCCA CGTTGGCCAC 21300
GCTGGTCTCG AACTCCTGAC CTCAAATGAT CCGCCTTCCT GGGCCTCCCA AAGTGCTGGA 21360
AACGACAGGC CTGAGCCGCC GGGATTTCAG CCTTTAAAAG CGCGGCCCTG CCACCTTTCG 21420
CTGTGGCCCT TACGCTCAGA ATGACGTGTC CTCTCTGCCG TAGGTTGACT CCTTGAGTCC 21480
CCTAGGCCAT TGCACTGTAG CCTGGGCAGC AAGAGCCAAA CTCCGNNCCC CCACCTCCTC 21540
GCGCACATAA TAACTAACTA ACAAACTAAC TAACTAACTA AACTAACTAA CTAACTAAAA 21600
TCTCTACACG TCACCCATAA GTGTGTGTTC CCGTGAGAGT GATTTCTAAG AAATGGTACT 21660
GTACACTGAA CGCAGTGGCT CACGTCTGTC ATCCCGAGGT CAGGAGTTCG AGACCAGCCC 21720
GGCCAACGTG GTGAAACCCC GTCTCTACTG AAAATACGAA ATGGAGTCAG GCGCCGTGGG 21780
GCAGGCACCT GTAACCCCAG CTACTCGGGA GGCTGGGGTG GAAGAATTGC TTGAACCTGG 21840
CAGGCGGAGG CTGCAGTGAC CCAAGATCGC ACCACTGCAC TACAGCCTGG GCGACAGAGT 21900
GAGACCCGGT CTCCAGATAA ATACGTACAT AAATAAATAC ACACATACAT ACATACATAC 21960
ATACATACAT ACATACATAC ATCCATGCAT ACAGATATAC AAGAAAGAAA AAAAGAAAAG 22020
AAAAGAAAGA GAAAATGAAA GAAAAGGCAC TGTATTGCTA CTGGGCTAGG GCCTTCTCTC 22080
TGTCTGTTTC TCTCTGTTCG TCTCTGTCTT TCTCTCTGTG TCTCTTTCTC TGTCTGTCTG 22140
TCTCTTTCTT TCTCTCTGTC TCTGTCTCTG TCTTTGTCTC TCTCTCTCCC TCTCTGCCTG 22200
TCTCACTGTG TCTGTCTTCT GTCTTACTCT CTTTCTCTCC CCGTCTGTCT CTCTCTCTCT 22260
CTCTCCCTCC CTGTTTGTTT CTCTCTCTCC CTCCCTGTCT GTTTCTCTCT CTCTCTTTCT 22320
GTCTGTTTCT GTCTCTCTCT GTCTGTCTAT GTCTTTCTCT GTCTGTCTCT TTCTCTGTCT 22380
GTCTGCCTCT CTCTTTCTTT TTCTGTGTCT CTCTGTCGGT CTCTCTCTCT CTGTCTGTCT 22440
GTCTGTCTCT CTCTCTCTCT CTCTGTGCCT ATCTTCTGTC TTACTCTCTT TCTCTGCCTG 22500
TCTGTCTGTC TCTCCCTCCC TTTCTGTTTC TCTCTCTCTC TCTCTCTCTC TCCCCCTCTC 22560
CCTGTCTGTT TCTCTCCGTC TCTCTCTCTT TCTGTCTGTT TCTCACTGTC TCTCTCTGTC 22620
CATCTCTCTC TCTCTCTGTC TGTCTCTTTC GTTCTCTCTG TCTGTCTGTC TCTCTCTCTC 22680
TCTCTCTCTC TCTCTCTCTC TCCCTGTCTG TCTGTTTCTC TCTATCTCTC GCTGTCCATC 22740
TCTGTCTTTC TATGTCTGTC TCTTTCTCTG TCAGTCTGTC AGACACCCCC GTGCCGGGTA 22800
GGGCCCTGCC CCTTCCACGA AAGTGAGAAG CGCGTGCTTC GGTGCTTAGA GAGGCCGAGA 22860
GGAATCTAGA CAGGCGGGCC TTGCTGGGCT TCCCCACTCG GTGTATGATT TCGGGAGGTC 22920
GAGGCCGGGT CCCCGCTTGG ATGCGAGGGG CATTTTCAGA CTTTTCTCTC GGTCACGTGT 22980
GGCGTCCGTA CTTCTCCTAT TTCCCCGATA AGCTCCTCGA CTTCAACATA AACGGCGTCC 23040
TAAGGGTCGA TTTAGTGTCA TGCCTCTTTC ACCGCCACCA CCGAAGATGA AAGCAAAGAT 23100

CGGCTAAATA CCGCGTGTTC TCATCTAGAA GTGGGAACTT ACAGATGACA GTTCTTGCAT 23160

GGGCAGAACG AGGGGGACCG GGNACGCGGA AGCCTGCTTG AGGGRGGAGG GGYGGAAGGA 23220

GAGACAGCTT CAGGAAGAAA ACAAAACACG AATACTGTCG GACACAGCAC TGACTACCCG 23280

GGTGATGAAA TCATCTGCAC ACTGAACACC CCCGTCACAA GTTTACCTAT GTCACAGTCT 23340

TGCTCATGTA TGCTTGAACG ACAAATAAAA GTTCGGGGGG GAGAAGAGAG GAGAGAGAGA 23400

GAGAGACGGG GAGAGAGGGG GGAGAGGGGG GGGGAGAGAG AGAGAGAGAG AGAGAGAGAG 23460

AGAGAGAGAG AGAAAGAGAA GTAAAACCAA CCACCACCTC CTTGACCTGA GTCAGGGGGT 23520

TTCTGGCCTT TTGGGAGAAC GTTCAGCGAC AATGCAGTAT TTGGGCCCGT TCTTTTTTTC 23580

TTCTTCTTCT TTTCTTTCTT TTTTTTTGGA CTGAGTCTCT CTCGCTCTGT CACCCAGGCT 23640

GCGGTGCGGT GGCGCTCTCT CGGCTCACTG AAACCTCTGC TTCCCGGGTT CCAGTGATTC 23700

TTCTTCGGTA GCTGGGATTA CAGGTGCGCA CCATGACGGC CGGCTCATCG TTCTATTTTT 23760

AGTAGAGACG GGGTTTCTCC ACGTTGGCCA CGCTGGTCTC GAACTCCTGA CCACAAATGA 23820

TCCACCTTCC TGGGCCTCCC AAAGTGCTGG AAACGACAGG CCTGAGCCGC CGGGATTTCA 23880

GCCTTTAAAA GCGCGCGGCC CTGCCACCTT TCGCTGCGGC CCTTACGCTC AGAATGACGT 23940

GTCCTCTCTG CCATAGGTTG ACTCCTTGAG TCCCCTAGGC CATTGCACTG TAGCCTGGGC 24000

AGCAAGAGCC AAACTCCGTC CCCCCACCTC CCCGCGCACA TAATAACTAA CTAACTAACT 24060

AACTAACTAA AATCTCTACA CGTCACCCAT AAGTGTGTGT TCCCGTGAGG AGTGATTTCT 24120

AAGAAATGGT ACTGTACACT GAACGCAGGC TTCACGTCTG TCATCCCGAG GTCAGGAGTT 24180

CGAGACCAGC CCGGCCCACG TGGTGAAACC CCCGTCTCTA CTGAAAATAC GAAATGGAGT 24240

CAGGCGCCGT GGGGCAGGCA CCTGTAACCC CAGCTACTCG GGAGGCTGGG GTGGAAGAAT 24300

TGCTTGAACC TGGCAGGCGG AGGCTGCAGT GACCCAAGAT CGCACCACTG CACTACAGCC 24360

TGGGCGACAG AGTGAGACCC GGTCTCCAGA TAAATACGTA CATAAATAAA TACACACATA 24420

CATACATACA TACATACAAC ATACATACAT ACAGATATAC AAGAAAGAAA AAAAGAAAAG 24480

AAAAGAAAGA GAAAATGAAA GAAAAGGCAC TGTATTGCTA CTGGGCTAGG GCCTTCTCTC 24540

TGTCTGTTTC TCTCTGTTCG TCTCTGTCTT TCTCTCTGTG TCTCTTTCTC TGTCTGTCTG 24600

TCTGTCTGTC TGTCTGTCTC TTTCTTTCTT TCTGTCTCTG TCTTTGTCCC TCTCTCTCCC 24660

TCTCTGCCCT GTCTCACTGT GTCTGTCTTC TATCTTACTC TCTTTCTCTC CCCGTCTGTC 24720

TCTCTCTCAC TCCCTCCCTG TCTGTTTCTC TCTCTCTCTC TTTCTGTCTG TTTCTGTCTC 24780

TCTCTGTCTG CCTCTCTCTT TCTCTATCTG TCTCTTTCTC TGTCTGTCTG CCCCTCTCTT 24840

TCTTTTTCTG TGTCTCTCTG TCTGTCTCTC TCTCTCTCTG TGCCTATCTT CTGTCTTACT 24900

CTCTTTCTCT GCCTGTCTGT CTGTCTCTCT CTGTCTCTCC CTCCCTTTCT GCTTCTCTCT 24960

CTCTCTCTCT CTCTNNNCCC TCCCTGTCTG TTTCTCTCTG TCTCCCTCTC TTTCTGTCTG 25020

TTTCTCACTG TCTCTCTCTG TCTGTCTGTT TCATTCTCTC TGTCTCTGTC TCTGTCTCTC 25080

TCTCTCTCTG TCTCTCCCTC TCTGTGTGTA TCTTTTGTCT TACTCTCCTT CTCTGCCTGT 25140

CCGTCTGTCT GTCTGTCTCT CTCTCTCCCT GTCCCTCTCT CTTTCTGTCT GTTTCTCTCT 25200

CTCTCTCTCT CTCTCTCTCT CTGTCTCTGT CTTTCTCTGT CTGTCCCTTT CTCTGTCTGT 25260

CTGCCTCTCT CTTTCTCTTT CTGTGTCTCT CTGTCTCTCT CTCTGTGCCT ATCTTCTGTC 25320

TTACTCTCTT TCTCTGCCTG TCTATCTGTC TGTCTCTCTC TGTCTCTCTC CCTGCCTTTC 25380

TGTTTCTCTC TCTCTCCCTC TCTCGCTCTC TCTGTCTTTC TCTCTTTCTC TCTGTTTCTC 25440

TGTCTCTCTC TGTCCGTCTC TGTCTTTTTC TGTCTGTCTG TCTCTCTCTT TCTTTCTGTC 25500

-continued

GTCTGTCTCT GTCTCTGTCT CTGTCTCTCT CTCTCTCTCT CTCCTTGTCT CTCTCACTGT 25560

GTCTGTCTTC TGTCTTACTC TCCTTCTCTG CCTGTCCATC TGTCTGTCTG TCTCTCTCTC 25620

TCTCTCCCTA CCTTTCTGTT TCTCTCTCGC TAGCTCTCTC TCTCTCTGCC TGTTTCTCTC 25680

TTTCTCTCTC TGTCTTTCTC TGTCTGTCTC TTTCTCTGTC TGTCTGTCTC TTTCTCTCTG 25740

TCTCTGTCTC TGTCTCTCTC TCTCTCTCTC TCTCTCTCTC TGCCTCTCTC ACTGTGTCTG 25800

TCTTCTGTCT TATTCTCTTT CTCTCTCTGT CTCTCTCTCT CTCTCCTTTA CTGTCTGTTT 25860

CTCTCTCTCT CTCTCTCTTT CTGCCTGTTT CTCTCTGTCT GTCTCTGTCT TTCTCTGTCT 25920

GTCTGCCTCT CTCTTTCTTT TTCTGCGTCT CTCTGTCTCT CTCTCTCTCT CTCTGTTCCT 25980

ATCTTCTGTC TTACTCTGTT TCCTTGCCTG CCTGCCTGTC TGTGTGTCTG TCTCTCTCTC 26040

TCTCTCTCTC TCTCTCTCCC TCCCTTTCTC TTTCTCTGTC TCTCTCTCTC TTTCTGGGTG 26100

TTTCTCTCTG TCTCTCTGTC CATCTCTGTC TTTCTATGTC TGTCTCTCTC TTTCTCTCTG 26160

TCTCTGTCTC TGCCTCTCTC TCTCTCTCTC TCTCTCTCTC TCTGTCTGTC TCTCTCACTG 26220

TGTGTGTCTG TCTTCTGTCT TACTCTCCTT CTCTGCCTGT CCGTCTGTCT GTCTGTCTCT 26280

CCCTCTCTCT CCCTCCCTTT CTGTTTCTCT CTCTCTCTCT TTCTGTCTGT TTCTCTCTTT 26340

CTCTCTCTGT CTGTCTCTTT CTCTGTCTGT CTGTCTCTCT CTTTCTTTTT CTCTGTCTCT 26400

CTGTCTCTCT CTGTGTCTGT CTCTCTGTCT GTGCCTATCT TCTGTCTTAC TCTCTTTCTC 26460

TGGCTGTCTG CCTGTCTCTC TCTCTCTCTC TGTCTGTCTC CGTCCCTCTC TCCCTGTCTG 26520

TCTGTTTCTC TCTCTGCCTC TCTCTCTCTC TGTCTGTCTC TTTCTCTGTC TGTCTGTCTC 26580

TCTCTTTCTT TTTCTCTGTC TCTCTGTCTC TCTCTGTGTC TGTCTCTCTT TCTGTGCCTA 26640

TCTTCTGTCT TACTCTCTTT CTCTGGCTGT CTGCCTGTCT CTCTCTCTCT GCCTGTCTCC 26700

GTCCCTCCCT CCCTGTCTGT CTGTTTCTCT CTCTGTCTCT GTCTCTCTGT CCATCTCTGT 26760

CTGTCTCTTT CTCTTTCTCT CTCTCTGTCT CTGTCTCTCT CTCTCTCTGC CTGTCTCTCT 26820

CACTGTGTCT GTCTTCTGTC TTACTCTCTT TCTCTTGCCT GCCTCTCTGT CTGTCTGTCT 26880

CTCTCCCTCC ATGTCTCTCT CTCTCTCTCA CTCACTCTCT CTCCGTCTCT CTCTCTTTCT 26940

GTCTGTTTCT CTCTCTGTCT GTCTCTCTCC CTCCATGTCT CTCTCTCTCT CTCTCACTCA 27000

CTCTCTCTCC GTCTCTCTCT CTCTTTCTGT CTGTTTCTCT CTCTGTCTGT CTCTCTCCCT 27060

CCATGTCTCT CTCTCTCCCT CTCACTCACT CTCTCTCCGT CTCTCTCTCT CTTTCTGTCT 27120

GTTTCTTTGT CTGTCTGTCT GTCTGTCTGT CTGTCTCTCT CTCTCTCTCT CTCTCTCTCT 27180

CTCTCTGTTT GTCTTTCTCC CTCCCTGTCT GTCTGTCTGT CTCTCTCTCT CTGTCTCTGT 27240

CTCTGTCTCT CTCTCTTTCT CTTTCTGTCT GTTTCTCTCT ATCTCTCGCT GTCCATCTCT 27300

GTCTTTCTAT GTCTGTCTCT TTCTCTGTCA GTCTGTCAGA CACACCCGTG CCGGTAGGGC 27360

CCTGCCCTTC CACGAGAGTG AGAAGCGCGT GCTTCGGTGC TTAGAGAGGC CGAGAGGAAT 27420

CTAGACAGGC GGGCCTTGCT GGGCTTCCCC ACTCGGTGTA CGATTTCGGG AGGTCGAGGC 27480

CGGGTCCCCG CTTGGATGCG AGGGGCATTT TCAGACTTTT CTCTCGGTCA CGTGTGGCGT 27540

CCGTACTTCT CCTATTTCCC CGATAAGTCT CCTCGACTTC AACATAAACT GTTAAGGCCG 27600

GACGCCAACA CGGCGAAACC CCGTCTCTAC TAAAAATACA AAGCTGAGTC GGGAGCGGTG 27660

GGGCAGGCCC TGTAATGCCA GCTCCTCGGG AGGCTGAGGC GGGAGAATCG CTTGAACCAG 27720

GGAAGCGGAG GCTGCAGGGA GCCGAGATCG CGCCACTGCA CTACGGCCCA GGCTGTAGAG 27780

TGAGTGAGAC TCGGTCTCTA AATAAATACG GAAATTAATT AATTCATTAA TTCTTTTCCC 27840

TGCTGACGGA CATTTGCAGG CAGGCATCGG TTGTCTTCGG GCATCACCTA GCGGCCACTG 27900

TTATTGAAAG TCGACGTTGA CACGGAGGGA GGTCTCGCCG ACTTCACCGA GCCTGGGGCA 27960
ACGGGTTTCT CTCTCTCCCT TCTGGAGGCC CCTCCCTCTC TCCCTCGTTG CCTAGGGAAC 28020
CTCGCCTAGG GAACCTCCGC CCTGGGGGCC CTATTGTTCT TTGATCGGCG CTTTACTTTT 28080
CTTTGTGTTT TGGCGCCTAG ACTCTTCTAC TTGGGCTTTG GGAAGGGTCA GTTTAATTTT 28140
CAAGTTGCCC CCCGGCTCCC CCCACTACCC ACGTCCCTTC ACCTTAATTT AGTGAGNCGG 28200
TTAGGTGGGT TTCCCCCAAA CCGCCCCCCC CCCCCCGCCT CCCAACACCC TGCTTGGAAA 28260
CCTTCCAGAG CCACCCCGGT GTGCCTCCGT CTTCTCTCCC CTTCCCCCAC CCCTTGCCGG 28320
CGATCTCATT CTTGCCAGGC TGACATTTGC ATCGGTGGGC GTCAGGCCTC ACTCGGGGGC 28380
CACCGTTTTT GAAGATGGGG GCGGCACGGT CCCACTTCCC CGGAGGCAGC TTGGGCCGAT 28440
GGCATAGCCC CTTGACCCGC GTGGGCAAGC GGGCGGGTCT GCAGTTGTGA GGCTTTTCCC 28500
CCCGCTGCTT CCCGCTCAGG CCTCCCTCCC TAGGAAAGCT TCACCCTGGC TGGGTCTCGG 28560
TCACCTTTTA TCACGATGTT TTAGTTTCTC CGCCCTCCGG CCAGCAGAGT TTCACAATGC 28620
GAAGGGCGCC ACGGCTCTAG TCTGGGCCTT CTCAGTACTT GCCCAAAATA GAAACGCTTT 28680
CTGAAAACTA ATAACTTTNC TCACTTAAGA TTTCCAGGGA CGGCGCCTTG GCCCGTGTTT 28740
GTTGGCTTGT TTTGTTTCGT TCTGTTTTGT TTTGTTCGTG TTTTTCCTTT CTCGTATGTC 28800
TTTCTTTTCA GGTGAAGTAG AAATCCCCAG TTTTCAGGAA GACGTCTATT TTCCCCAAGA 28860
CACGTTAGCT GCCGTTTTTT CCTGTTGTGA ACTAGCGCTT TTGTGACTCT CTCAACGCTG 28920
CAGTGAGAGC CGGTTGATGT TTACNATCCT TCATCATGAC ATCTTATTTT CTAGAAATCC 28980
GTAGGCGAAT GCTGCTGCTG CTCTTGTTGC TGTTGTTGTT GTTGTTGTTG TCGTCGTTGC 29040
TGTTGTCGTT GTCGTTGTTG TTGTCGTTGT CGTTGTTTTC AAAGTATACC CCGGCCACCG 29100
TTTATGGGAT CAAAAGCATT ATAAAATATG TGTGATTATT TCTTGAGCAC GCCCTTCCTC 29160
CCCCTCTCTC TGTCTCTCTG TCTGTCTCTG TCTCTCTCTT TCTCTGTCTG TCTTCTCTCT 29220
CTCTCTCTCT CTGTGTCTCT CTCTCTCTGC CTGTCTGTTT CTCTCTCTCT GCCTCTCTCT 29280
CTCTCTCTCT CTCTGCCTGT CTCTCTCACT GTGTCTGTCT TCTGTCTTAC TCCCTTTCTC 29340
TGTCTGTCTG TCGGTCTCTC TCTCTCTCTC TCCCTGTCTG TATGTTTCTC TCTGTCTCTG 29400
TCTCTCTCTC TCTTTCTGTT TCTCTCTCTC CGTCTCTGTC TTTCTCTGAC TGTCTCTCTC 29460
TTTCCTTCTC TCTGTCTCTC TCTGCCTGTC TCTCTCACTC TGTCTTCTGT CTTATCTCTC 29520
TCTCTGCCTG CCTGTCTCTC TCACTCTCTC TCTCTGTGTG TCTCTCTCTC TCTTTCTGTT 29580
TCTCTCTGTC TCTCTGTCCG TCTCTGTCTT TCTCTGTCTG TCTCTTTGTC TGTCTGTCTT 29640
TGTCTTTCCT TCTCTCTGTC TCTGTCTCTC TCACTGTGTC TGTCTTCTGT CTTAGTCTCT 29700
CTCTCTCTCT CTCCCTGTCT GTCTGTCTCT CTCTCTCTCT CCCCCTGTCT GTTTCTCTCT 29760
CTCTCTCTCT CTCTCTCTCT CTCTGTCTTT GTCTTTCTTT CTGTCTCTGT CTCTCTCTCT 29820
CTCTCTGTGT GTCTGTCTTC TGTCTTACTG TCTTTCTCTG CCTGTCTGTC TGTCTGTCTC 29880
TCTCTGTCTG TCTCTCTCTC TCTCTCCCCC TGTCGGCTGT TTCTCTGTCT CTGTCTGTGT 29940
CTCTCTTTCT GTCTGTTTCT CTCTGTCTGT CTTTCTCTCT CTGTCTCTTT CTCTCTGTCT 30000
CTCTGTCTGT CTCTGTCTCT CTCTCTGTCT CTCTCTCTCT GTGGGGGTGT GTGTGTGTGT 30060
GTGTATGTGT GTGTGTGTGT GTGTGTGTGT CTGCCTTCTG TCTTACTCTC TTTCTCTGCC 30120
TGTCTGTCTG CCTGTCTGTT TGTCTCTCTC TCTCTGCCTG TCTCTCTCCC TTCCTGTCTG 30180
TTTCTCTCTC TTTCTGTTTC TCTCTGTCTC TGTCCATCTC TGTCTTTCTC CGTCTGTCTC 30240
TTTATCTGTC TCTCTCCGTC TGTCTCTTTA TCTGTCTCTC TCTCTCTTTC TGTCTTTCTC 30300

TCTCTGTGTA TCGTTGTCTC TCTCTGTCTG TCTCTGTCTC TGTCTCTCTG TCTCTCTCTC 30360
TCTCTCTCTC TCTCTGTCTG TCTGTCCGTC TGTCTGTCTC GGTCTCTGCG TCTCGCTATC 30420
TCCCGCCCTC TCTTTTTTTG CAAAAGAAGC TCAAGTACAT CTAATCTAAT CCCTTACCAA 30480
GGCCTGAATT CTTCACTTCT GACATCCCAG ATTTGATCTC CCTACAGAAT GCTGTACAGA 30540
ACTGGCGAGT TGATTTCTGG ACTTGGATAC CTCATAGAAA CTACATATGA ATAAAGATCC 30600
AATCCTAAAA TCTGGGGTGG CTTCTCCCTC GACTGTCTCG AAAAATCGTA CCTCTGTTCC 30660
CCTAGGATGC CGGAAGAGTT TTCTCAATGT GCATCTGCCC GTGTCCTAAG TGATCTGTGA 30720
CCGAGCCCTG TCCGTCCTGT CTCAAATATG TACGTGCAAA CACTTCTCTC CATTTCCACA 30780
ACTACCCACG GCCCCTTGTG GAACCACTGG CTCTTTGAAA AAAATCCCAG AAGTGGTTTT 30840
GGCTTTTTGG CTAGGAGGCC TAAGCCTGCT GAGAACTTTC CTGCCCAGGA TCCTCGGGAC 30900
CATGCTTGCT AGCGCTGGAT GAGTCTCTGG AAGGACGCAC GGGACTCCGC AAAGCTGACC 30960
TGTCCCACCG AGGTCAAATG GATACCTCTG CATTGGCCCG AGGCCTCCGA AGTACATCAC 31020
CGTCACCAAC CGTCACCGTC AGCATCCTTG TGAGCCTGCC CAAGGCCCCG CCTCCGGGGA 31080
GACTCTTGGG AGCCCGGCCT TCGTCGGCTA AAGTCCAAAG GGATGGTGAC TTCCACCCAC 31140
AAGGTCCCAC TGAACGGCGA AGATGTGGAG CGTAGGTCAG AGAGGGGACC AGGAGGGGAG 31200
ACGTCCCGAC AGGCGACGAG TTCCCAAGGC TCTGGCCACC CCACCCACGC CCCACGCCCC 31260
ACGTCCCGGG CACCCGCGGG ACACCGCCGC TTTATCCCCT CCTCTGTCCA CAGCCGGCCC 31320
CACCCCACCA CGCAACCCAC GCACACACGC TGGAGGTTCC AAAACCACAC GGTGTGACTA 31380
GAGCCTGACG GAGCGAGAGC CCATTTCACG AGGTGGGAGG GGTGGGGGTG GGGTGGGTTG 31440
GGGGTTGTGG GGTCTGTGGC GAGCCCGATT CTCCCTCTTG GGTGGCTACA GGCTAGAAAT 31500
GAATATCGCT TCTTGGGGGG AGGGGCTTCC TTAGGCCATC ACCGCTTGCG GGACTACCTC 31560
TCAAACCCTC CCTTGAGGCC ACAAAATAGA TTCCACCCCA CCCATCGACG TTTCCCCCGG 31620
GTGCTGGATG TATCCTGTCA AGAGACCTGA GCCTGACACC GTCGAATTAA ACACCTTGAC 31680
TGGCTTTGTG TGTTTGTTTG TTTCTGAGAT GGAGTCTTGC TCTGTCCCCC AGGCTGGAGT 31740
GCAGTGGCGT GATCTCAGCT CACTGGAACC TCTGCCTCCT GGGTTCAAGT GATTCTCCTG 31800
TCTCAGCGCC ACCATGGCCG GCTCATTTTT TTTTTTTTTT TTTTTGGTAG ACACGGGGTT 31860
TCACCCTCTT TCATTGGTTT TCACTGGAGA TTCTAGATTC GAGCCACACC TCATTCCGTG 31920
CCACAGAGAG ACTTCTTTTT TTTTTTTTTT TTTTTAAGCG CAACGCAACA TGTCTGCCTT 31980
ATTTGAGTGG CTTCCTATAT CATTATAATT GTGTTATAGA TGAAGAAACG GTATTAAACA 32040
CTGTGCTAAT GATAGTGAAA GTGAAGACAA AAGAAAGGCT ATCTATTTTG TGGTTAGAAT 32100
AAAGTTGCTC AGTATTTAGA AGCTACCTAA ATACGTCAGC ATTTACACTC TTCCTAGTAA 32160
AAGCTGGCCG ATCTGAATAA TCCTCCTTTA AACAAACACA ATTTTTGATA GGGTTAAGAT 32220
TTTTTTAAGA ATGCGACTCC TGCAAAATAG CTGAACAGAC GATACACATT TAAAAAAATA 32280
ACAACACAAG GATCAACCAG ACTTGGGAAA AAATCGAAAA CCACACAAGT CTTATGAAGA 32340
ACTGAGTTCT TAAAATAGGA CGGAGAACGT AGCTATCGGA AGAGAAGGCA GTATTGGCAA 32400
GTTGATTGTT ACGTTGGTCA GCAGTAGCTG GCACTATCTT TTTGGCCATC TTTCGGGCAA 32460
TGTAACTACT ACAGCAAAAT GAGATATGAT CCATTAAACA ACATATTCGC AAATCAAAAA 32520
GTGTTTCAGT AATATAATGC TTCAGATTTA GAAGCAAATC AAATGATAGA ACTCCACTGC 32580
TGTAATAAGT CACCCCAAAG ATCACCGTAT CTGACAAAAT AACTACCACA GGGTTATGAC 32640
TTCAGAATCA TACTTTCTTC TTGATATTTA CTTATGTATT TATTTTTTTT AATTTATTTC 32700

```
TCTTGAGACG CGTCTCGCTC TGTCGCCCAG GCTGGAGTGC GATGGTGTGA TCTCGGCTCA  32760
CTGCAACCGC CACCTCCCTG GGTTCAAGCG ATTCTCCTGC CTCAGCCTCC CGAGTAGCTG  32820
GGACTACAGG TGCCCGCCAC CACGCCCAGC TAATCTTTAT ACTTTTAATA GAGACGGGGT  32880
TTCACCGTGT CGGCCCGGAT GGTCTCGATC TCTTGACCTC GTGACCCGCC CGCCTCGGCC  32940
TCCCAAAGTG CTGGGATGAC AGGCGTGAGC CACTGAGCCC GGCCTTCTCT TGACGTTTAA  33000
ACTATGAAGT CAGTCCAGAG AAACGCAATA AATGTCAACG GTGAGGATGG TGTTGAGGCA  33060
GAAGTAGGAC CACACTTTTT CCTATCTTAT TCAGTTGATA ACAATATGAC CTAGGTAGTA  33120
ATTTCCTATG TGCCTACTTA TACACGAGTA CAAAAGAGTA AAACAGAGAG ACTGCTAAAT  33180
TAAAGGGTAC GTGAAGTTCT TCATAGTAAC TCCGTAAACT GGAACACTGT CAAAAAGCAG  33240
CAGCTAGTGA ATTGTTTCCA TGTATTTTTC TATTATCCAA TAAGTGAACT ATGCTATTCC  33300
TTTCCAGTCT CCCAAGCACT TCTTGTCCCC ATCACCACTT CGGTGCTCGA AGAAAAAGTA  33360
AGCAAATCAA GGAACACAAG CTAAAGAAAC ACACACACAA ACCAAAGACA ACTACAGCGT  33420
CTGCAAAAGT TTGCTAGAAG ACTGAAACTG TTGAGTATAA GGATCTGGTA TTCTACGATC  33480
ATGAGTTCAC TTCAGAGTTT GTTCAAGACA TACGTTTCGT AAGGAAACAT CTTAGTTAGA  33540
AGTTATTCAG CAGTAGGTAC CATCCCTAAG TATTTTTCAC CAAATCCGTG ACAATAAAGA  33600
GCTATCTAAC CAGAAAAATT AGCGAGTACG GGCACCATCC ATAGGGCTTT GTCTTTACGC  33660
TTCATTAGCA CTTACCATGC CTTACAATGT CTAGGATTGA CCCTGATAGC ATTTCGAAAA  33720
CAAGCTAATG CTTTGTCCAG TTCTTCAGTG AAGACAACTC ACGCCCTAAT GCGCTATAGG  33780
CATAAGCATC ATTTGGATCC ACTTCGAGAG TTCTCTGGAA GAATTGAATC GCAATATCGT  33840
GTTCCCGTTT GCAGACCGAA ACAGTTTCCC TGCAGCACAC CAGGCCTCTG GCTGGCGAAT  33900
TTTTATCCAT GTCTGTGAAG TCTTTGGACA GAACTGAAAG AGCAACCTCT TTCGGAGGAT  33960
GCCAAAGTGT TGTAGAGTAG ATCTCCATGC CTTCGACTCT GTAATTCTCA ATCCTCCTAA  34020
CCTCTGAGAA TTGTCTTTCA GCTTGCGTGG ACTCTGAAAG TTTACAATAG GCCNTTTCCG  34080
ATTTGGCACA GTACCCAACC GGTATTGCAG TGGTGAGAAG CTAGATGGCT CAAGATGCTG  34140
ATAGCTTCTT TGCCGTGGTA AGAACACAAA GCTAAATAAC CTTTCCCCCT TTCACGAAGA  34200
AGGCTCATCA AGCCTTCCGC TGCTGCTTTT TGTAGATTAA AAGCCTGAAT CTGAGGCGCG  34260
ATTGCGGCTA TTTTCCCTTC TGAAATGACG GAAGAGTCCA ATTTTGTCAC TTCCAGGCTA  34320
TCACTTATGT TCGGTGGAGT TATTGCTCCT TTATTAGTTT TACTTTTGGT TCTTCTGTTT  34380
GGGATTTTAG GTGGAAACTT CATTTTTAAT TTTCTCCTAA TTCTCCTCGG TTGTGGAGCT  34440
GTCACTAGTC AAGAGTCGTG AATTTCTTCG AGGNCGGTGC ATTTGGGGGA GATGCCATAG  34500
TGGGGCTCAA TACCTGAGGT GTTGCCCTTG TCGGCGGACC AGAACTTTGT GTTTTTGCAA  34560
GGACTGGAGT TACCTTTCGG CTCTTTCCCC TCTGCGAGAA GACAGACGGT GTTCCGGTTT  34620
GGCCGATTCT GGCAACAGGC TTTTCTGAAG GGGCTCCGGT GGATGGCACG TCAGTGACAG  34680
ACGGTGTCTC ATACCAGTGC AGTTTTGTCA ATAGGGTCCG TCTCCGGGAC TTGGGGTTTC  34740
TAATGGCAAA ATGCCAACAC TTGGGGTTAA TGGACTAACA GCTGCTGGTC CTCCTAATAA  34800
ACTTCGACCA GTTTTTGGTT TATGTTGAAC CTGTTTAGAT CATATGGAAG TTCCTGTTCC  34860
CAGTGGGACA GTATCAGGTG AAAGGACAGC TGAATCGATA GAAGACACTG GGGAGTCTGT  34920
ATTCAAGGAG TACTTTGAAT TGGAAGATTC TAAATTCCAT CCGTTTCATT CGACGGTGTC  34980
CTGGGGTGTT TCCGTAAGAA CGGTCTCGGG CTGTCTGTGA CATAAACTAG GACGAGGTCC  35040
AAGTGTTGTG GCGCAACACT TGGACAGGCA GTTGCTAAAG CTCTCTAGAG AGGTGAATCA  35100
```

-continued

```
AAATGTTTGG TCAGGATCTG GCTTTTCCCC CCTATTTCAC ATCATGATTC AAAGGGACAC  35160
CAGAGGAAAG GATTTCAACG AAGGCTCTTT TGGTCACATT CTGATCCTTT GGTAAGCCGA  35220
TCTGTCTTGC AATATACATG TCCCGACGAT GGAAGGGGAA AGCGAGCTGA ATCACCAAAC  35280
TCAGGAACGA TAATATCATC GTGGCTTTTC TGCTTATGAA ACACTCCACC CGATAAGATT  35340
TGATCCCCTT CTGCAAGCTT GCTGAGATCA ACACAACATT TCGCAAGCAG GCATTTGCAT  35400
TGCGGGGTAG TACAACTGTG TCCTTTCAAG AGTCTATATG TTTTATAGGC CTTTCCTGAG  35460
CGGTAAGAAC AGGTCGCCAG TAAGAACAAG GCTTCTTCTG AGTGTACTTC TGCATAAAGG  35520
CGTTCTGCGG GGGAAACCGC ATCTCGGTAG GCATAGTGGT TTAGTGCTTG CCATATAGCA  35580
GCCTGGACGG GTCCCTGCAG CACCGCCATC CTCGAGGCTC AGGCCCACTT TCTGCAGTGC  35640
CACAGGCACC CCCCCCCCCC CATAGCGGCT CCGGCCCGGC CAGCCCCGGC TCATTTAAAG  35700
GCACCAGCCG CCGTTACCGG GGGATGGGGG AGTCCGAGAC AGAATGACTT CTTTATCCTG  35760
CTGACTCTGG AAAGCCCGGC GCCTTGTGAT CCATTGCAAA CCGAGAGTCA CCTCGTGTTT  35820
AGAACACGGA TCCACTCCCA AGTTCAGTGG GGGGATGTGA GGGGTGTGGC AGGTAGGACG  35880
AAGGACTCTC TTCCTTCTGA TTCGGTCTGC ACAGTGGGGC CTAGGGCTGG AGCTCTCTCC  35940
GTGCGGACCG CTGACTCCCT CTACCTTGGG TTCCCTCGGC CCCACCCTGG AACGCCGGGC  36000
CTTGGCAGAT TCTGGCCCTT TCTGGCCCTT CAGTCGCTGT CAGAAACCCC ATCTCATGCT  36060
CGGATGCCCC GAGTGACTGT GGCTCGCACC TCTCCGGAAA CATTGGAAAT CTCTCCTCTA  36120
CGCGCGGCCA CCTGAAACCA CAGGAGCTCG GGACACACGT GCTTTCGGGA GAGAATGCTG  36180
AGAGTCTCTC GCCGACTCTC TCTTGACTTG AGTTCTTCGT GGGTGCGTGG TTAAGACGTA  36240
GTGAGACCAG ATGTATTAAC TCAGGCCGGG TGCTGGTGGC TCACGCCTGT AACCCCAACA  36300
CTTTGGGAGG CCGAGGCCGT AGGATCCCTC GAGGAATCGC CTAACCCTGG GGAGGTTGAG  36360
GTTGCAGTGA GTGAGCCATA GTTGTGTCAC TGTGCTCCAG TCTGGGCGAA AGACAGAATG  36420
AGGCCCTGCC ACAGGCAGGC AGGCAGGCAG GCAGGCAGAA AGACAACAGC TGTATTATGT  36480
TCTTCTCAGG GTAGGAAGCA AAAATAACAG AATACAGCAC TTAATTAATT TTTTTTTTTT  36540
CCTTCGGACG GAGTTTCACT CTTGGTGCCC ACGCTGGAGT GCAGTGGCAC CATCTCGGCT  36600
CACCGCAACC TCCACCTCCC GCGTTCAAGC GATTCTCCTG CCTCAGCCTC CTGAGTAGCT  36660
GGGATTACAG GGAGGAGCCA CCACACCCAG CTGATTTTGT ATTGTTAGTA GAGACGGCAT  36720
TTCTCCATGT GGGTCAGGCT GGTCTCGAAC TGGCGACCCC AGTGGATCTG CCCGCCCCGG  36780
CCTCCCAAAG TGCTGGGGTG ACAGGCGTGA GCCATCGTGA CTGGCCGGCT ACGTTTATTT  36840
ATTTATTTTT TTAATTATTT TACTTTTTTT TAGTTTTCCA TTTTAATCTA TTTATTTATT  36900
TACATTTATT TATTTATTTA TTTATTTACT TATTTATTTA TTTTCGAGAC AGACTCTCGC  36960
TCTGCTGCCC AGGCTGGAGT GCAGCGGCGT GATCTCGGCT CACTGCAACG TCCGCCTCCC  37020
GGGTTCACGC CATTCTCCTG CCTCAGCCTC CCAAGTAGCT GGGACTACAG GCGCCCGCCA  37080
CCGTGCCCGG CTAACTTTTT GTATTTTGAG TAGAGATGGG GTTTCACTGT GGTAGCCAGG  37140
ATGGTCTCGA TCTCCTGACC CCGTGATCCG TCCACCTCGG CCTCCCAAAG TGCTGGGATG  37200
ACAGGCGTGA GCCACCGGCC CCGGCCTATT TATCTATTTA TTAACTTTGA GTCCAGGTTA  37260
TGAAACCAGT TAGTTTTTGT AATTTTTTTT TTTTTTTTTT TTTTTTGAGA CGAGGTTTCA  37320
CCGTGTTGCC AAGGCTTGGA CCGAGGGATC CACCGGCCCT CGGCCTCCCA AAAGTGCGGG  37380
GATGACAGGC GCGAGCCTAC CGCGCCCGGA CCCCCCCTTT CCCCTTCCCC CGCTTGTCTT  37440
CCCGACAGAC AGTTTCACGG CAGAGCGTTT GGCTGGCGTG CTTAAACTCA TTCTAAATAG  37500
```

AAATTTGGGA CGTCAGCTTC TGGCCTCACG GACTCTGAGC CGAGGAGTCC CCTGGTCTGT 37560

CTATCACAGG ACCGTACACG TAAGGAGGAG AAAAATCGTA ACGTTCAAAG TCAGTCATTT 37620

TGTGATACAG AAATACACGG ATTCACCCAA AACACAGAAA CCAGTCTTTT AGAAATGGCC 37680

TTAGCCCTGG TGTCCGTGCC AGTGATTCTT TTCGGTTTGG ACCTTGACTG AGAGGATTCC 37740

CAGTCGGTCT CTCGTCTCTG GACGGAAGTT CCAGATGATC CGATGGGTGG GGGACTTAGG 37800

CTGCGTCCCC CCAGGAGCCC TGGTCGATTA GTTGTGGGGA TCGCCTTGGA GGGCGCGGTG 37860

ACCCACTGTG CTGTGGGAGC CTCCATCCTT CCCCCCACCC CCTCCCCAGG GGGATCCCAA 37920

TTCATTCCGG GCTGACACGC TCACTGGCAG GCGTCGGGCA TCACCTAGCG GTCACTGTTA 37980

CTCTGAAAAC GGAGGCCTCA CAGAGGAAGG GAGCACCAGG CCGCCTGCGC ACAGCCTGGG 38040

GCAACTGTGT CTTCTCCACC GCCCCCGCCC CCACCTCCAA GTTCCTCCCT CCCTTGTTGC 38100

CTAGGAAATC GCCACTTTGA CGACCGGGTC TGATTGACCT TTGATCAGGC AAAAACGAAC 38160

AAACAGATAA ATAAATAAAA TAACACAAAA GTAACTAACT AAATAAAATA AGTCAATACA 38220

ACCCATTACA ATACAATAAG ATACGATACG ATAGGATGCG ATAGGATACG ATAGGATACA 38280

ATACAATAGG ATACGATACA ATACAATACA ATACAATACA ATACAATACA ATACAATACA 38340

ATACAATACA ATACAATACG CCGGGCGCGG TGGCTCATGC CTGTCATCCC GTCACTTTGG 38400

GATGCCGAGG TGGACGCATC ACCTGAAGTC GGGAGTTGGA GACAAGCCCG ACCAACATGG 38460

AGAAATCCCG TCTCAATTGA AAATACAAAA CTAGCCGGGC GCGGTGGCAC ATGCCTATAA 38520

TCCCAGCTGC TAGGAAGGCT GAGGCAGGAG AATCGCTTGA ACCTGGGAAG CGGAGGTTGC 38580

AGTGAGCCGA GATTGCGCCA TCGCACTCCA GTCTGAGCAA CAAGAGCGAA ACTCCGTCTC 38640

AAAAATAAAT ACATAAATAA ATACATACAT ACATACATAC ATACATACAT ACATACATAC 38700

ATAAATTAAA ATAAATAAAT AAAATAAAAT AAATAAATGG GCCCTGCGCG GTGGCTCAAG 38760

CCTGTCATCC CCTCACTTTG GGAGGCCAAG GCCGGTGGAT CAAGAGGCGG TCAGACCAAC 38820

AGGGCCAGTA TGGTGAAACC CCGTCTCTAC TCACAATACA CAACATTAGC CGGGCGCTGT 38880

GCTGTGCTGT ACTGTCTGTA ATCCCAGCTA CTCGGGAGGC CGAGCTGAGG CAGGAGAATC 38940

GCTTGAACCT GGGAGGCGGA GGTTGCAGTG AGCCGAGATC GCGCCACTGC AACCCAGCCT 39000

GGGCGACAGA GCGAGACTCC GTCTCCAAAA AATGAAAATG AAAATGAAAC GCAACAAAAT 39060

AATTAAAAAG TGAGTTTCTG GGGAAAAAGA AGAAAAGAAA AAAGAAAAAA ACAACAAAAC 39120

AGAACAACCC CACCGTGACA TACACGTACG CTTCTCGCCT TTCGAGGCCT CAAACACGTT 39180

AGGAATTATG CGTGATTTCT TTTTTTAACT TCATTTTATG TTATTATCAT GATTGATGTT 39240

TCGAGACGGA GTCTCGGAGG CCCGCCCTCC CTGGTTGCCC AGACAACCCC GGGAGACAGA 39300

CCCTGGCTGG GCCCGATTGT TCTTCTCCTT GGTCAGGGGT TTCCTTGTCT TTCTTCGTGT 39360

CTTTAACCCG CGTGGACTCT TCCGCCTCGG GTTTGACAGA TGGCAGCTCC ACTTTAGGCC 39420

TTGTTGTTGT TGGGGACTTT CCTGATTCTC CCCAGATGTA GTGAAAGCAG GTAGATTGCC 39480

TTGCCTGGCC TTGCCTGGCC TTGCCTTTTC TTTCTTTCTT TCTTTCTTTA TTACTTTCTC 39540

TTTTTCTTCT TCTTCTTCTT CTTTTTTTTG AGACAGAGTT TCACTCTTGT TGCCCAGGCT 39600

AGAGGGCAAT GGCGCGATCT CGGCTCACCG CACCCTCCGC CTCCCAGGTT CAAGCGATTC 39660

TCCTGCCTCA GCCTCCTGAT TAGCTGGGAT TACAGGCATG GGCCACCGTG CTGGCTGATG 39720

TTTGTACTTT TAGTAGAGAC GGTGTTTTTC CATGTTGGTC AGGCTGGTCT CCCACTCCCA 39780

ACCTCAGGTG GTCCGCCTGC CTTAGCCTCC CAAAGTGCTG GGATGACAGG CGTGCAACCG 39840

CGCCCAGCCT CTCTCTCTCT CTCTCTCTCT CTCGCTCGCT TGCTTGCTTG CTTTCGTGCT 39900

-continued

```
TTCTTGCTTT CCCGTTTTCT TGCTTTCTTT CTTTCTTTCG TTTCTTTCAT GCTTGCTTTC  39960
TTGCTTGCTT GCTTGCTTTC GTGCTTTCTT GCTTTCCTGT TTTCTTTCTT TCTTTCTTTC  40020
TTTCTTTCTT TTGTTTCTTT CTTGCTTGCT TTCTTGCTTG CTTGCTTGCT TTCGTGCTTT  40080
CTTGCTTTCC TGTTTTCTTT CTTTCTTTCT TTCTTTTCTT TCTTTCTTGC TTGCTTTCCT  40140
GCTTGCTTGC TTTCGTGCTT TCTTGTTTTC TCGATTTCTT TCTTTCTTTT GTTTCTTTCC  40200
TGCTTGCTTT CTTGCTTGCT TGCTTTCGTG CTTCTTGCTT TCCTGTTTTC TTTCTTTCTT  40260
TCTTTCTTTT GTTTCTTTCT TGCTTGCTTT CTTGCTTGCT TGCTTTCGTG CTGTCTTGTT  40320
TCTCGATTTC TTTCTTTCTT TTGTTTCTTT CCTGCTTGCT TTCTTGCTTG ATTGCTTTCG  40380
TGCTTTCTTG CTTTCTTGTT TTCTTTCTTT CTTTTGTTTC TTTCTTTCTT GCTTCCTTGT  40440
TTTCTTGCTT TCTTGCTTGC TTGCTTTCGT GCTTTCTTGT TTTCTTGCTT TCTTTCTTTT  40500
GTTTCTTTCT TGCTTGCTTT CTTGCTTCCT TGTTTTCTTG CTTTCTTGCT TGCTTGCTTT  40560
CGTGCTTTCT TTCTTGCTTT CTTTTCTTTC TTTCTTTTCT TTTTCTTTCT TTCTTGCTTT  40620
CTTTTCTTTC ATCATCATCT TTCTTTCTTT CCTTTCTTTC TTTCTTTCTT TCTATCTTTC  40680
TTTCTTTCTT TCTTTCTTTC TTTCTTTCTT TCTTTCTGTT TCGTCCTTTT GAGACAGAGT  40740
TTCACTCTTG TTTCCACGGC TAGAGTGCAA TGGCGCGATC TTGGCTCACC GCACCTTCCG  40800
CCTCCCGGGT TCGAGCGCTT CTCCTGCCTC CAGCCTCCCG ATTAGCGGGG ATTGACAGGG  40860
AGGCACCCCC ACGCCTGGCT TGGCTGATGT TTGTGTTTTT AGTAGGCACG CCGTGTCTCT  40920
CCATGTTGCT CAGGCTGGTC TCCAACTCCC GACCTCCTGT GATGCGCCCA CCTCGGCCTC  40980
TCGAAGTGCT GGGATGACGG GCGTGACGAC CGTGCCCGGC CTGTTGACTC ATTTCGCTTT  41040
TTTATTTCTT TCGTTTCCAC GCGTTTACTT ATATGTATTA ATGTAAACGT TTCTGTACGC  41100
TTATATGCAA ACAACGACAA CGTGTATCTC TGCATTGAAT ACTCTTGCGT ATGGTAAATA  41160
CGTATCGGTT GTATGGAAAT AGACTTCTGT ATGATAGATG TAGGTGTCTG TGTTATACAA  41220
ATAAATACAC ATCGCTCTAT AAAGAAGGGA TCGTCGATAA AGACGTTTAT TTTACGTATG  41280
AAAAGCGTCG TATTTATGTG TGTAAATGAA CCGAGCGTAC GTAGTTATCT CTGTTTTCTT  41340
TCTTCCTCTC CTTCGTGTTT TTCTTCCTTC CTTTCTTCCT TTCTCTCCTT CTTTAGGTTT  41400
TTCTTCCTCT CTTCCTTTCC TTCTTTCTCT CTTTCTGTCC TTTTTTCCTT CGTGCTTTAT  41460
TTCTCTTTCG TTCCCTGTGT TTCCTTCTTT TTTCTTTCCT CTCTGTTTCT TTTTCCCTTC  41520
TTTCCTTCGT TTCTTTCCTC ATTCTTTCTC TCTTTTTCGT TGTTTCTTTC CTTCCCGTCT  41580
GTCTTTTAAA AAATTGGAGT GTTTCAGAAG TTTACTTTGT GTATCTACGT TTTCTAAATT  41640
GTCTCTCTTT TCTCCATTTT CTTCCTCCCT CCCTCCCTCC CTCCCTGCTC CCTTCCCTCC  41700
CTCCTTCCCT TTCGCCATCT GTCTCTTTTC CCCACTCCCC TCCCCCCGTC TGTCTCTGCG  41760
TGGATTCCGG AAGAGCCTAC CGATTCTGCC TCTCCGTGTG TCTGCAGCGA CCCCGCGACC  41820
GAGTCCTTGT GTGTTCTTTC TCCCTCCCTC CCTCCCTCCC TCCCTCCCTC CCTCCCTGCT  41880
TCCGAGAGGC ATCTCCAGAG ACCGCGCCGT GGGTTGTCTT CTGACTCTGT CGCGGTCGAG  41940
GCAGAGACGC GTTTTGGGCA CCGTTTGTGT GGGGTTGGGG CAGAGGGGCT GCGTTTTCGG  42000
CCTCGGGAAG AGCTTCTCGA CTCACGGTTT CGCTTTCGCG GTCCACGGGC CGCCCTGCCA  42060
GCCGGATCTG TCTCGCTGAC GTCCGCGGCG GTTGTCGGGC TCCATCTGGC GGCCGCTTTG  42120
AGATCGTGCT CTCGGCTTCC GGAGCTGCGG TGGCAGCTGC CGAGGGAGGG GACCGTCCCC  42180
GCTGTGAGCT AGGCAGAGCT CCGGAAAGCC CGCGGTCGTC AGCCCGGCTG GCCCGGTGGC  42240
GCCAGAGCTG TGGCCGGTCG CTTGTGAGTC ACAGCTCTGG CGTGCAGGTT TATGTGGGGG  42300
```

AGAGGCTGTC GCTGCGCTTC TGGGCCCGCG GCGGGCGTGG GGCTGCCCGG GCCGGTCGAC 42360

CAGCGCGCCG TAGCTCCCGA GGCCCGAGCC GCGACCCGGC GGACCCGCCG CGCGTGGCGG 42420

AGGCTGGGGA CGCCCTTCCC GGCCCGGTCG CGGTCCGCTC ATCCTGGCCG TCTGAGGCGG 42480

CGGCCGAATT CGTTTCCGAG ATCCCCGTGG GGAGCCGGGG ACCGTCCCGC CCCCGTCCCC 42540

CGGGTGCCGG GGAGCGGTCC CCGGGCCGGG CCGCGGTCCC TCTGCCGCGA TCCTTTCTGG 42600

CGAGTCCCCG TGGCCAGTCG GAGAGCGCTC CCTGAGCCGG TGCGGCCCGA GAGGTCGCGC 42660

TGGCCGGCCT TCGGTCCCTC GTGTGTCCCG GTCGTAGGAG GGGCCGGCCG AAAATGCTTC 42720

CGGCTCCCGC TCTGGAGACA CGGGCCGGCC CCTGCGTGTG GCCAGGGCGG CCGGGAGGGC 42780

TCCCCGGCCC GGCGCTGTCC CCGCGTGTGT CCTTGGGTTG ACCAGAGGGA CCCCGGGCGC 42840

TCCGTGTGTG GCTGCGATGG TGGCGTTTTT GGGGACAGGT GTCCGTGTCC GTGTCGCGCG 42900

TCGCCTGGGC CGGCGGCGTG GTCGGTGACG CGACCTCCCG GCCCCGGGGG AGGTATATCT 42960

TTCGCTCCGA GTCGGCAATT TTGGGCCGCC GGGTTATAT 42999

(2) INFORMATION FOR SEQ ID NO: 18:

(i) SEQUENCE CHARACTERISTICS:
(A) LENGTH: 175 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 18:

CTCCCGCGCG GCCCCCGTGT TCGCCGTTCC CGTGGCGCGG ACAATGCGGT TGTGCGTCCA 60

CGTGTGCGTG TCCGTGCAGT GCCGTTGTGG AGTGCCTCGC TCTCCTCCTC CTCCCCGGCA 120

GCGTTCCCAC GGTTGGGGAC CACCGGTGAC CTCGCCCTCT TCGGGCCTGG ATCCG 175

(2) INFORMATION FOR SEQ ID NO: 19:

(i) SEQUENCE CHARACTERISTICS:
(A) LENGTH: 755 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 19:

GGTCTGGTGG GAATTGTTGA CCTCGCTCTC GGGTGCGGCC TTTGGGGAAC GGCGGGGTCG 60

GTCGTGCCCG GCGCCGGACG TGTGTCGGGG CCCACTTCCC GCTCGAGGGT GGCGGTGGCG 120

GCGGCGTTGG TAGTCTCCCG TGTTGCGTCT TCCCGGGCTC TTGGGGGGGG TGCCGTCGTT 180

TTCGGGGCCG GCGTTGCTTG GCTTACGCAG GCTTGGTTTG GGACTGCCTC AGGAGTCGTG 240

GGCGGTGTGA TTCCCGCCGG TTTTGCCTCG CGTCTGCCTG CTTTGCCTCG GGTTTGCTTG 300

GTTCGTGTCT CGGGAGCGGT GGTTTTTTTT TTTTTCGGGT CCCGGGGAGA GGGGTTTTTC 360

CGGGGGACGT TCCCGTCGCC CCCTGCCGCC GGTGGGTTTT CGTTTCGGGC TGTGTTCGTT 420

TCCCCTTCCC CGTTTCGCCG TCGGTTCTCC CCGGTCGGTC GGCCCTCTCC CCGGTCGGTC 480

GCCCGGCCGT GCTGCCGGAC CCCCCCTTCT GGGGGGGATG CCCGGGCACG CACGCGTCCG 540

GGCGGCCACT GTGGTCCGGG AGCTGCTCGG CAGGCGGGTG AGCCAGTTGG AGGGGCGTCA 600

TGCCCCCGCG GGCTCCCGTG GCCGACGCGG CGTGTTCTTT GGGGGGGCCT GTGCGTGCGG 660

GAAGGCTGCG CACGTTGTCG GTCCTTGCGA GGGAAAGAGG CTTTTTTTTT TTAGGGGGTC 720

GTCCTTCGTC GTCCCGTCGG CGGTGGATCC GGCCT 755

(2) INFORMATION FOR SEQ ID NO: 20:

(i) SEQUENCE CHARACTERISTICS:
(A) LENGTH: 463 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 20:

GGCCGAGGTG CGTCTGCGGG TTGGGGCTCG TCCGGCCCCG TCGTCCTCCG GGAAGGCGTT 60

TAGCGGGTAC CGTCGCCGCG CCGAGGTGGG CGCACGTCGG TGAGATAACC CCGAGCGTGT 120

TTCTGGTTGT TGGCGGCGGG GGCTCCGGTC GATGTCTTCC CCTCCCCCTC TCCCCGAGGC 180

CAGGTCAGCC TCCGCCTGTG GGCTTCGTCG GCCGTCTCCC CCCCCCTCAC GTCCCTCGCG 240

AGCGAGCCCG TCCGTTCGAC CTTCCTTCCG CCTTCCCCCC ATCTTTCCGC GCTCCGTTGG 300

CCCCGGGGTT TTCACGGCGC CCCCCACGCT CCTCCGCCTC TCCGCCCGTG GTTTGGACGC 360

CTGGTTCCGG TCTCCCCGCC AAACCCCGGT TGGGTTGGTC TCCGGCCCCG GCTTGCTCTT 420

CGGGTCTCCC AACCCCCGGC CGGAAGGGTT CGGGGGTTCC GGG 463

(2) INFORMATION FOR SEQ ID NO: 21:

(i) SEQUENCE CHARACTERISTICS:
(A) LENGTH: 378 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 21:

GGATTCTTCA GGATTGAAAC CCAAACCGGT TCAGTTTCCT TTCCGGCTCC GGCCGGGGGG 60

GGCGGCCCCG GGCGGTTTGG TGAGTTAGAT AACCTCGGGC CGATCGCACG CCCCCCGTGG 120

CGGCGACGAC CCATTCGAAC GTCTGCCCTA TCAACTTTCG ATGGTAGTCG ATGTGCCTAC 180

CATGGTGACC ACGGGTGACG GGGAATCAGG GTTCGATTCC GGAGAGGGAG CCTGAGAAAC 240

GGCTACCACA TCCAAGGAAG GCAGCAGGCG CGCAAATTAC CCACTCCCGA CCCGGGGAGG 300

TAGTGACGAA AAATAACAAT ACAGGACTCT TTCGAGGCCC TGTAATTGGA ATGAGTCCAC 360

TTTAAATCCT TTAAGCAG 378

(2) INFORMATION FOR SEQ ID NO: 22:

(i) SEQUENCE CHARACTERISTICS:
(A) LENGTH: 378 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 22:

GATCCATTGG AGGGCAAGTC TGGTGCCAGC AGCCGCGGTA ATTCCAGCTC CAATAGCGTA 60

TATTAAAGTT GCTGCAGTTA AAAAGCTCGT AGTTGGATCT TGGGAGCGGG CGGGCGGTCC 120

GCCGCGAGGC GAGTCACCGC CCGTCCCCGC CCCTTGCCTC TCGGCGCCCC CTCGATGCTC 180

TTAGCTGAGT TGTCCCGCGG GGCCCGAAGC GTTTACTTTG AAAAAATTAG AGTTGTTTCA 240

AAGCAGGCCC GAGCCGCCTG GATACCGCCA GCTAGGAAAT AATGGAATAG GACCGCGGTT 300

CCTATTTTGT TTGGTTTTCG GAACTGAGCC CATGATTAAG GGAAACGGCC GGGGGCATTC 360

CCTTATTGCG CCCCCCTA 378

(2) INFORMATION FOR SEQ ID NO: 23:

(i) SEQUENCE CHARACTERISTICS:
(A) LENGTH: 719 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 23:

GGATCTTTCC CGCTCCCCGT TCCTCCCGGC CCCTCCACCC GCGCGTCTCC CCCCTTCTTT 60

TCCCCTCTCC GGAGGGGGGG GAGGTGGGGG CGCGTGGGCG GGGTCGGGGG TGGGGTCGGC 120

GGGGGACCGC CCCCGGCCGG CAAAAGGCCG CCGCCGGGCG CACTTCAACC GTAGCGGTGC 180

GCCGCGACCG GCTACGAGAC GGCTGGGAAG GCCCGACGGG GAATGTGGCT CGGGGGGGGC 240

GGCGCGTCTC AGGGCGCGCC GAACCACCTC ACCCCGAGTG TTACAGCCCT CCGGCCGCGC 300

TTTCGCGGAA TCCCGGGGCC GAGGGGAAGC CCGATACCCG TCGCCGCGCT TTTCCCCTCC 360

CCCCGTCCGC CTCCCGGGCG GGCGTGGGGG TGGGGGCCGG GCCGCCCCTC CCACGCCCGT 420

-continued

GGTTTCTCTC TCTCCCGGTC TCGGCCGGTT TGGGGGGGGG AGCCCGGTTG GGGGCGGGGC 480

GGACTGTCCT CAGTGCGCCC CGGGCGTCGT CGCGCCGTCG GGCCCGGGGG GTTCTCTCGG 540

TCACGCCGCC CCCGACGAAG CCGAGCGCAC GGGGTCGGCG GCGATGTCGG CTACCCACCC 600

GACCCGTCTT GAAACACGGA CCAAGGAGTC TAACGCGTGC GCGAGTCAGG GGCTCGCACG 660

AAAGCCGCCG TGGCGCAATG AAGGTGAAGG GCCCCGTCCG GGGGCCCGAG GTGGGATCC 719

(2) INFORMATION FOR SEQ ID NO: 24:

(i) SEQUENCE CHARACTERISTICS:
(A) LENGTH: 685 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 24:

CGAGGCCTCT CCAGTCCGCC GAGGGCGCAC CACCGGCCCG TCTCGCCCGC CGCGTCGGGG 60

AGGTGGAGCA CGAGCGTACG CGTTAGGACC CGAAAGATGG TGAACTATGC CTGGGCAGGG 120

CGAAGCCAGA GGAAACTCTG GTGGAGGTCC GTAGCGGTCC TGACGTGCAA ATCGGTCGTC 180

CGACCTGGGT ATAGGGGCGA AAGACTAATC GAACCATCTA GTAGCTGGTT CCCTCCGAAG 240

TTTCCCTCAG GATAGCTGGC GCTCTCGCAA CCTTCGGAAG CAGTTTTATC CGGGTAAAGG 300

CGGAATGGAT TAGGAGGTCT TGGGGCCGGA AACGATCTCA AACTATTTCT CAAACTTTAA 360

ATGGGTAAGG AAGCCCGGCT CGCTGGCGTG GAGCCGGGCG TGGAATGCGA GTGCCTAGTG 420

GGCCACTTTT GGTAAGCAGA ACTGGCGCTG CGGGATGAAC CGAACGCCGG GTTAAGGCGC 480

CCGATGCCGA CGCTCATCAG ACCCCAGAAA AGGTGTTGGT TGATATAGAC AGCAGGACGG 540

TGGCCATGGA AGTCGGAATC CGCTAAGGAG TGTGTAACAA CTCACCTGCC GAATCAACTA 600

GCCCTGAAAA TGGATGGCGC TGGAGCGTCG GGCCCATACC CGGCCGTCGC CGGCAGTCGG 660

AACGGGACGG GACGGGAGCG GCCGC 685

(2) INFORMATION FOR SEQ ID NO: 25:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 25:

GAGGAATTCC CCTATCCCTA ATCCAGATTG GTG 33

(2) INFORMATION FOR SEQ ID NO: 26:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 26:

AAACTGCAGG CCGAGCCACC TCTCTTCTGT GTTTG 35

(2) INFORMATION FOR SEQ ID NO: 27:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 27:

AGGAATTCAC AGAAGAGAGG TGGCTCGGCC TGC 33

(2) INFORMATION FOR SEQ ID NO: 28:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 28:

AGCCTGCAGG AAGTCATACC TGGGGAGGTG GCCC 34

(2) INFORMATION FOR SEQ ID NO: 29:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 29:

AAACTGCAGG TTAATTAACC CTAACCCTAA CCCTAACCCT AACCCTAACC CTAACCCTAA 60

CCCTAACCCT AACCCGGGAT 80

(2) INFORMATION FOR SEQ ID NO: 30:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 30:

TTGGGCCCTA GGCTTAAGG 19

(2) INFORMATION FOR SEQ ID NO: 31:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 31:

GCCAGGGTTT TCCCAGTCAC GACGT 25

(2) INFORMATION FOR SEQ ID NO: 32:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 32:

-continued

```
GCTGCAAGGC GATTAAGTTG GGTAAC                                26


(2) INFORMATION FOR SEQ ID NO: 33:

     (i) SEQUENCE CHARACTERISTICS:
          (A) LENGTH: 26 base pairs
          (B) TYPE: nucleic acid
          (C) STRANDEDNESS: single
          (D) TOPOLOGY: linear

    (ii) MOLECULE TYPE: Genomic DNA

   (iii) HYPOTHETICAL: NO

    (iv) ANTI-SENSE: NO

     (v) FRAGMENT TYPE: <Unknown>

    (vi) ORIGINAL SOURCE:

    (xi) SEQUENCE DESCRIPTION: SEQ ID NO: 33:

TATGTTGTGT GGAATTGTGA GCGGAT                                26


(2) INFORMATION FOR SEQ ID NO: 34:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (ii) MOLECULE TYPE: Genomic DNA

   (iii) HYPOTHETICAL: NO

    (iv) ANTI-SENSE: NO

     (v) FRAGMENT TYPE: <Unknown>

    (vi) ORIGINAL SOURCE:

    (xi) SEQUENCE DESCRIPTION: SEQ ID NO: 34:

GGGTTTAAAC AGATCTCTGC A                                     21
```